United States Patent [19]
Oku et al.

[11] Patent Number: 5,750,699
[45] Date of Patent: May 12, 1998

[54] METHOD OF PREPARING CERTAIN 3-HALO-IMIDAZOPYRIDINES

[75] Inventors: Teruo Oku; Hiroshi Kayakiri; Shigeki Satoh, all of Tsukuba; Yoshito Abe, Ibaraki; Yuki Sawada, Tsukuba; Hirokazu Tanaka, Takarazuka, all of Japan

[73] Assignee: Fujisawa Pharmaceutical Co., Ltd., Osaka, Japan

[21] Appl. No.: 662,198

[22] Filed: Jun. 12, 1996

Related U.S. Application Data

[62] Division of Ser. No. 441,786, May 16, 1995, Pat. No. 5,574,042, which is a continuation of Ser. No. 235,632, Apr. 29, 1994, abandoned, which is a continuation-in-part of Ser. No. 142,967, Oct. 29, 1993, abandoned.

[30] Foreign Application Priority Data

Nov. 2, 1992 [GB] United Kingdom .......... 9222947
Mar. 3, 1993 [GB] United Kingdom .......... 9304249

[51] Int. Cl.$^6$ .................................................. C07D 471/02
[52] U.S. Cl. ........................................................ 546/121
[58] Field of Search ............................................ 546/121

[56] References Cited

PUBLICATIONS

Kaminiski et al., J. Med. Chem., vol. 28, pp. 876–892, 1985.

*Primary Examiner*—Bernard Dentz
*Attorney, Agent, or Firm*—Oblon, Spivak, McClelland, Maier & Neustadt, P.C.

[57] ABSTRACT

The invention relates to bradykinin antagonists of the formula:

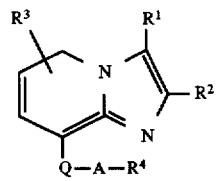

wherein
  $R^1$ is halogen,
  $R^2$ and $R^3$ are each hydrogen, lower alkyl, halo(lower) alkyl or acyl,
  $R^4$ is aryl having suitable substituent(s), or a heterocyclic group optionally having suitable substituent(s),
  Q is O or N—$R^{11}$, in which $R^{11}$ is hydrogen or acyl, and
  A is lower alkylene,
and pharmaceutically acceptable salts thereof.

1 Claim, No Drawings

METHOD OF PREPARING CERTAIN 3-HALO-IMIDAZOPYRIDINES

This is a division of application Ser. No. 08/441,786 filed on May 16, 1995 now U.S. Pat. No. 5,574,042 which is a continuation of application Ser. No. 08/235,632 filed on Apr. 29, 1994 now abandoned, which is a Continuation-in-Part of application Ser. No. 08/142,967 filed on Oct. 29, 1993 now abandoned.

This invention relates to new heterocyclic compounds and pharmaceutically acceptable salts thereof.

More particularly, it relates to new heterocyclic compounds and pharmaceutically acceptable salts thereof which have activities as bradykinin antagonists, to processes for preparation thereof, to a pharmaceutical composition comprising the same, and to methods of using the same therapeutically in the prevention and/or the treatment of bradykinin or its analogues mediated diseases such as allergy, inflammation, autoimmune disease, shock, pain, or the like, in human being or animals.

One object of this invention is to provide new and useful heterocyclic compounds and pharmaceutically acceptable salts thereof which possess activities as bradykinin antagonists.

Another object of this invention is to provide processes for the preparation of said compounds and salts thereof.

A further object of this invention is to provide a pharmaceutical composition comprising, as an active ingredient, said heterocyclic compounds and pharmaceutically acceptable salts thereof.

Still further object of this invention is to provide a therapeutical method for the prevention and/or the treatment of bradykinin or its analogues mediated diseases such as allergy, inflammation, autoimmune disease, shock, pain, or the like, using said heterocyclic compounds and pharmaceutically acceptable salts thereof.

Some heterocyclic compounds have been known as described, for example, in J. Med. Chem., 28, 876–892 (1985). However, it is not known that said compounds have activities as bradykinin antagonists.

The object heterocyclic compounds of this invention are new and can be represented by the following general formula [I]:

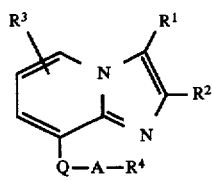

wherein
$R^1$ is halogen,
$R^2$ and $R^3$ are each hydrogen, lower alkyl, halo(lower)alkyl or acyl,
$R^4$ is aryl having suitable substituent(s), or a heterocyclic group optionally having suitable substituent(s),
Q is O or N—$R^{11}$, in which $R^{11}$ is hydrogen or acyl, and
A is lower alkylene.

The object compound [I] or its salt can be prepared by processes as illustrated in the following reaction schemes.

Process 1

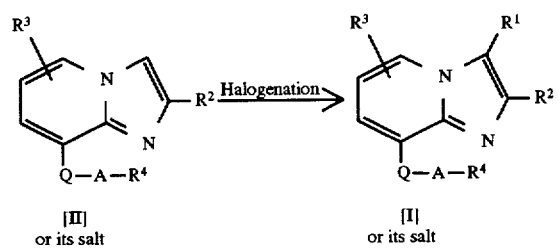

Process 2

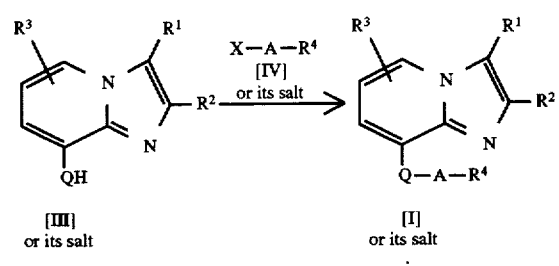

Process 3

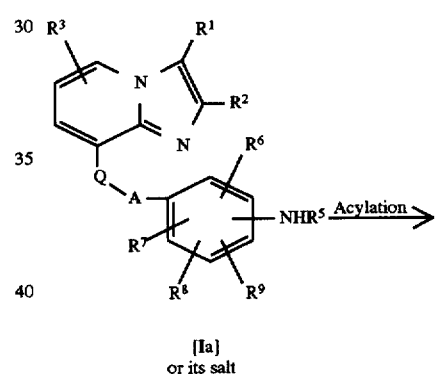

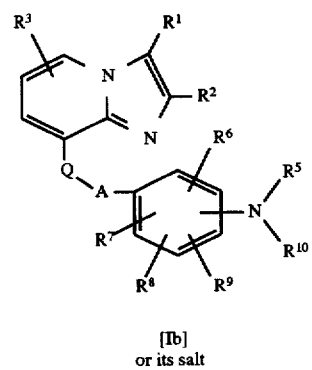

Process 4

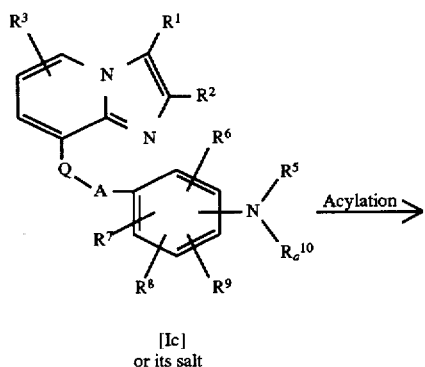

[Ic] or its salt

Acylation →

[Id] or its salt

Process 5

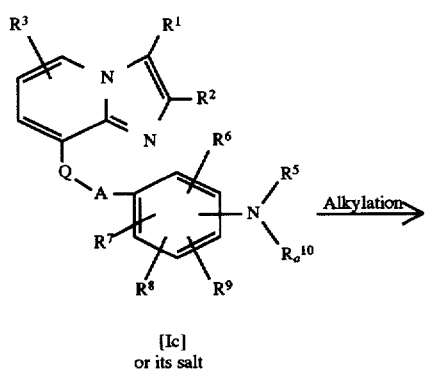

[Ic] or its salt

Alkylation →

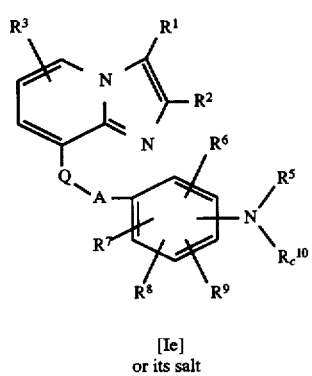

[Ie] or its salt

Process 6

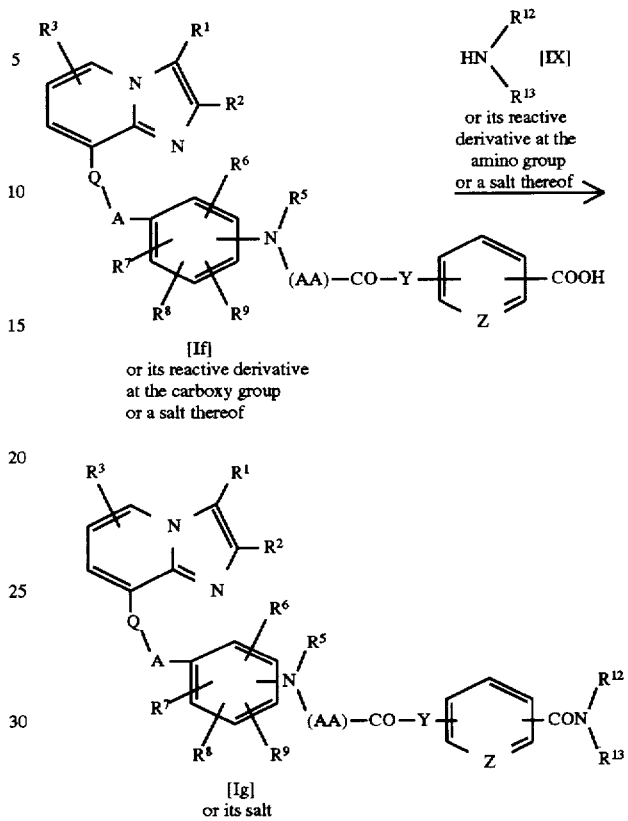

[If] or its reactive derivative at the carboxy group or a salt thereof

[Ig] or its salt wherein $R^5$ is hydrogen or lower alkyl, $R^6$, $R^7$, $R^8$ and $R^9$ are each hydrogen or halogen, $R^{10}$ is acyl, $R_a^{10}$ is acyl having amino, $R_b^{10}$ is acyl having acylamino, $R_c^{10}$ is acyl having lower alkylamino or acyl having ar(lower)alkylamino, $R^{12}$ is hydrogen, lower alkyl, lower alkoxy(lower)alkyl, lower alkylamino(lower)alkyl, heterocyclic(lower)alkyl, a heterocyclic group, lower alkenyl, lower alkynyl, lower alkylcarbamoyl(lower)alkyl, protected or unprotected hydroxy(lower)alkyl or aryl optionally substituted with lower alkylamino, and $R^{13}$ is hydrogen, lower alkyl, lower alkoxy(lower)alkyl or protected or unprotected hydroxy(lower)alkyl, or $R^{12}$ and $R^{13}$ are taken together with the attached nitrogen atom to form a heterocyclic group optionally having suitable substituent(s), (AA) is amino acid residue, X is a leaving group, Y is NH or lower alkenylene, Z is CH or N, and $R^1$, $R^2$, $R^3$, $R^4$, Q and A are each as defined above.

In the above and subsequent description of the present specification, suitable examples of the various definitions to be included within the scope of the invention are explained in detail in the following.

The term "lower" is intended to mean a group having 1 to 6 carbon atom(s), unless otherwise provided.

In this respect, the term "lower" in lower alkenyl moiety, lower alkynyl moiety and ar(lower)alkenyl moiety in the various definitions is intended to mean a group having 2 to 6 carbon atoms.

Further, the term "lower" in lower alkenoyl moiety, lower alkynoyl moiety, cyclo(lower)alkyl moiety, cyclo(lower) alkenyl moiety, ar(lower)alkenoyl moiety, ar(lower) alkynoyl moiety and heterocyclic(lower)alkenoyl moiety in the various definitions is intended to mean a group having 3 to 6 carbon atoms.

Suitable "halogen" may be fluorine, chlorine, bromine and iodine.

Suitable "aryl" may be phenyl, naphthyl, phenyl substituted with lower alkyl [e.g. tolyl, xylyl, mesityl, cumenyl, di(tert-butyl)phenyl, etc.] and the like, in which preferable one is phenyl and tolyl.

Suitable "lower alkyl" and lower alkyl moiety in the terms "heterocyclic(lower)alkyl", and "lower alkylamino" may be straight or branched one such as methyl, ethyl, propyl, isopropyl, butyl, isobutyl, tert-butyl, pentyl, hexyl or the like, in which preferable one is $C_1$–$C_4$ lower alkyl such as methyl, ethyl, propyl, isobutyl or tert-butyl.

Suitable "lower alkylene" may be a straight or branched one such as methylene, ethylene, trimethylene, methylmethylene, tetramethylene, ethylethylene, propylene, pentamethylene, hexamethylene or the like, in which the most preferable one is methylene.

Suitable "halo(lower)alkyl" may be fluoromethyl, difluoromethyl, trifluoromethyl, chloromethyl, dichloromethyl, bromomethyl, fluoroethyl, difluoroethyl, chloroethyl, dichloroethyl, or the like.

Suitable "lower alkenylene" may be a straight or branched $C_2$–$C_6$ alkenylene such as vinylene, methylvinylene, propenylene, 1,3-butadienylene or the like, in which the most preferable one is vinylene.

Suitable "lower alkenyl" may be vinyl, allyl, methylpropenyl, butenyl, pentenyl or the like.

Suitable "lower alkynyl" may be ethynyl, propynyl, butynyl, pentynyl or the like.

Suitable "lower alkylcarbamoyl(lower)alkyl" may be methylcarbamoylmethyl, methylcarbamoylethyl, ethylcarbamoylethyl, dimethylcarbamoylethyl or the like.

Suitable "acyl" may be substituted or unsubstituted alkanoyl such as alkanoyl [e.g. formyl, acetyl, propionyl, butyryl, isobutyryl, valeryl, isovaleryl, pivaloyl, hexanoyl, heptanoyl, 3,3-dimethylbutyryl, etc.], halo(lower)alkanoyl [e.g. chloroacetyl, trifluoroacetyl, bromoacetyl, bromobutyryl, heptafluorobutyryl, etc.], hydroxy(lower) alkanoyl [e.g. glycoloyl, lactoyl, 3-hydroxypropionyl, glyceroyl, etc.], lower alkylsulfonyloxy(lower)alkanoyl [e.g. mesyloxyacetyl, ethylsulfonyloxyacetyl, mesyloxypropionyl, etc.], lower alkoxy(lower)alkanoyl [e.g. methoxyacetyl, ethoxyacetyl, methoxypropionyl, ethoxypropionyl, propoxypropionyl, methoxybutyryl, etc.], lower alkylthio(lower)alkanoyl [e.g. methylthioacetyl, ethylthioacetyl, methylthiopropionyl, ethylthiopropionyl, propylthiopropionyl, methylthiobutyryl, etc.], lower alkanoyloxy(lower)alkanoyl [e.g. acetyloxyacetyl, acetyloxypropionyl, propionyloxyacetyl, etc.], aryloxy (lower)alkanoyl [e.g. phenyloxyacetyl, phenyloxypropionyl, tolyloxyacetyl, naphthyloxyacetyl, etc.], aroyl(lower) alkanoyl [e.g. phenyloxalyl, benzoylacetyl, benzoylpropionyl, etc.], carboxy(lower)alkanoyl [e.g. oxalo, carboxyacetyl, 3-carboxypropionyl, 3-carboxybutyryl, 4-carboxybutyryl, 4-carboxyvaleryl, etc.], esterified carboxy (lower)alkanoyl, for example, lower alkoxycarbonyl(lower) alkanoyl [e.g. methoxycarbonylacetyl, ethoxycarbonylacetyl, methoxycarbonylpropionyl, ethoxycarbonylpropionyl, etc.], carbamoyl(lower)alkanoyl [e.g. carbamoylacetyl, carbamoylpropionyl, etc.], lower alkylcarbamoyl(lower)alkanoyl [e.g. methylcarbamoylacetyl, methylcarbamoylpropionyl, ethylcarbamoylpropionyl, dimethylcarbamoylpropionyl, (N-methyl-N-ethylcarbamoyl)propionyl, etc.], ar(lower) alkanoyl [e.g. phenylacetyl, tolylacetyl, naphthylacetyl, 2-phenylpropionyl, 3-phenylpropionyl, 4-phenylbutyryl, tritylcarbonyl, etc.], optionally substituted heterocyclic (lower)alkanoyl [e.g. morpholinoacetyl, thiomorpholinoacetyl, morpholinopropionyl, thiomorpholinopropionyl, piperidinopropionyl, piperazinylpropionyl, pyridylacetyl, pyrrolidinylpropionyl, imidazolidinylpropionyl, piperidinoacetyl, pyrrolidinylacetyl, hexamethyleneiminoacetyl, hexamethyleneiminopropionyl, imidazolylacetyl, furylacetyl, thienylacetyl, methylpiperazinylacetyl, pyridylpiperazinylacetyl, etc.], heterocyclicthio(lower) alkanoyl [e.g. pyridylthioacetyl, pyrimidinylthioacetyl, imidazolylthiopropionyl, etc.], etc., lower alkenoyl [e.g. acryloyl, crotonoyl, isocrotonoyl, 3-butenoyl, 3-pentenoyl, 4-pentenoyl, methacryloyl, etc.], lower alkynoyl [e.g. propioloyl, 2-butynoyl, 3-butynoyl, etc.], cyclo(lower) alkylcarbonyl [e.g. cyclopropylcarbonyl, cyclobutylcarbonyl, cyclopentylcarbonyl, cyclohexylcarbonyl, etc.], cyclo(lower)alkenylcarbonyl [e.g. cyclopentenylcarbonyl, cyclohexenylcarbonyl, etc.], carboxy, esterified carboxy such as lower alkoxycarbonyl [e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl, etc.], aryloxycarbonyl [e.g. phenoxycarbonyl, etc.], etc., substituted or unsubstituted aroyl such as aroyl [e.g. benzoyl, toluoyl, xyloyl, naphthoyl, etc.], lower alkoxyaroyl [e.g. methoxybenzoyl, etc.], haloaroyl [e.g. chlorobenzoyl, fluorobenzoyl, etc.), acylamoyl, for example, lower alkoxycarbonylaroyl [e.g. methoxycarbonylbenzoyl, etc.], etc., substituted or unsubstituted ar(lower)alkenoyl such as ar(lower)alkenoyl [e.g. cinnamoyl, allocinnamoyl, a-methylcinnamoyl, 4-methylcinnamoyl, etc.], lower alkoxy-ar(lower)alkenoyl [e.g. methoxycinnamoyl, ethoxycinnamoyl, dimethoxycinnamoyl, etc.], lower alkylenedioxy-ar(lower)alkenoyl [e.g. methylenedioxycinnamoyl, ethylenedioxycinnamoyl, etc.], nitro-ar(lower)alkenoyl [e.g. nitrocinnamoyl, etc.], cyano-ar (lower)alkenoyl [e.g. cyanocinnamoyl, etc.], halo-ar(lower) alkenoyl [e.g. chlorocinnamoyl, fluorocinnamoyl, etc.], hydroxy-ar(lower)alkenoyl [e.g. hydroxycinnamoyl, etc.], hydroxy(lower)alkoxy-ar(lower)alkenoyl [e.g. hydroxymethoxycinnamoyl, hydroxyethoxycinnamoyl, etc.], amino(lower)alkoxy-ar(lower)alkenoyl [e.g. aminoethoxycinnamoyl, etc.], lower alkylamino(lower) alkoxy-ar(lower)alkenoyl [e.g. methylaminomethoxycinnamoyl, dimethylaminoethoxycinnamoyl, etc.], heterocyclic(lower) alkoxy-ar(lower)alkenoyl [e.g. pyridylmethoxycinnamoyl, etc.], optionally substituted heterocyclic-ar(lower)alkenoyl [e.g. morpholinocinnamoyl, methylpiperazinylcinnamoyl, pyrrolidinylcinnamoyl, oxopyrrolidinylcinnamoyl, oxopiperidinocinnamoyl, dioxopyrrolidinylcinnamoyl, oxooxazolidinylcinnamoyl, pyrrolylcinnamoyl, tetrazolylcinnamoyl, etc.], amino-ar(lower)alkenoyl [e.g. aminocinnamoyl, etc.], lower alkylamino-ar(lower)alkenoyl [e.g. methylaminocinnamoyl, dimethylaminocinnamoyl, etc.], acylamino-ar(lower)alkenoyl, for example, lower alkanoylamino-ar(lower)alkenoyl [e.g.

acetylaminocinnamoyl, propionylaminocinnamoyl, isobutyrylaminocinnamoyl, etc.], cycloalkyl(lower) alkanoylamino-ar(lower)alkenoyl [e.g. cyclopentylacetylaminocinnamoyl, cyclohexylacetylaminocinnamoyl, adamantylacetylaminocinnamoyl, etc.], cycloalkylcarbonylamino-ar(lower)alkenoyl [e.g. cyclopropylcarbonylaminocinnamoyl, cyclopentylcarbonylaminocinnamoyl, cyclohexylcarbonylaminocinnamoyl, adamantylcarbonylaminocinnamoyl, etc.], lower alkenoylamino-ar(lower)alkenoyl [e.g. acryloylaminocinnamoyl, crotonoylaminocinnamoyl, etc.], lower alkoxycarbonylamino-ar(lower)alkenoyl [e.g. methoxycarbonylaminocinnamoyl, ethoxycarbonylaminocinnamoyl, etc.], hydroxy(lower) alkanoylamino-ar(lower)alkenoyl [e.g. hydroxyacetylaminocinnamoyl, hydroxypropionylaminocinnamoyl, etc.], lower alkoxy(lower)alkanoylamino-ar(lower)alkenoyl [e.g. methoxyacetylaminocinnamoyl, methoxypropionylaminocinnamoyl, etc.], halo(lower) alkanoylamino-ar(lower)alkenoyl [e.g. chloroacetylaminocinnamoyl, bromobutyrylaminocinnamoyl, trifluoroacetylaminocinnamoyl, etc.], amino(lower) alkanoylamino-ar(lower)alkenoyl [e.g. aminoacetylaminocinnamoyl, aminopropionylaminocinnamoyl, etc.], lower alkylamino(lower)alkanoylamino-ar(lower)alkenoyl [e.g. methylaminoacetylaminocinnamoyl, dimethylaminoacetylaminocinnamoyl, etc.], lower alkanoylamino(lower)alkanoylamino-ar(lower)alkenoyl [e.g. acetylaminoacetylaminocinnamoyl, acetylaminopropionylaminocinnamoyl, etc.], carboxy(lower)alkanoylamino-ar(lower)alkenoyl [e.g. carboxyacetylaminocinnamoyl, carboxypropionylaminocinnamoyl, etc.], lower alkoxycarbonyl(lower)alkanoylamino-ar(lower)alkenoyl [e.g. ethoxycarbonylacetylaminocinnamoyl, ethoxycarbonylpropionylaminocinnamoyl, etc.], lower alkoxycarbonyl(lower)alkenoylamino-ar(lower)alkenoyl [e.g. ethoxycarbonylacryloylaminocinnamoyl, etc.], halo(lower)alkoxycarbonylamino-ar(lower)alkenoyl [e.g. chloroethoxycarbonylaminocinnamoyl, etc.], optionally substituted heterocyclic(lower)alkanoylamino-ar(lower) alkenoyl [e.g. pyridylacetylaminocinnamoyl, thienylacetylaminocinnamoyl, methylpyrrolylacetylaminocinnamoyl, etc.], aroylamino-ar(lower)alkenoyl [e.g. benzoylaminocinnamoyl, etc.], optionally substituted heterocycliccarbonylamino-ar(lower)alkenoyl [e.g. pyridylcarbonylaminocinnamoyl, morpholinocarbonylaminocinnamoyl, furylcarbonylaminocinnamoyl, thienylcarbonylaminocinnamoyl, oxazolylcarbonylaminocinnamoyl, methyloxazolylcarbonylaminocinnamoyl, dimethylisoxazolylcarbonylaminocinnamoyl, imidazolylcarbonylaminocinnamoyl, methylimidazolylcarbonylaminocinnamoyl, piperidylcarbonylaminocinnamoyl, ethylpiperidylcarbonylaminocinnamoyl, acetylpiperidylcarbonylaminocinnamoyl, pyrrolidinylcarbonylaminocinnamoyl, acetylpyrrolidinylcarbonylaminocinnamoyl, tert-butoxycarbonylpyrrolidinylcarbonylaminocinnamoyl, etc.], lower alkylsulfonylamino-ar(lower)alkenoyl [e.g. mesylaminocinnamoyl, ethylsulfonylaminocinnamoyl, etc.], etc., N-(lower alkanoyl)-N-(lower alkyl)amino-ar(lower)alkenoyl [e.g. N-acetyl-N-methylaminocinnamoyl, N-acetyl-N-ethylaminocinnamoyl, N-propionyl-N-methylaminocinnamoyl, etc.], N-[lower alkoxy(lower)alkanoyl]-N-(lower alkyl)amino-ar(lower)alkenoyl [e.g. N-methoxyacetyl-N-methylaminocinnamoyl, N-methoxypropionyl-N-methylaminocinnamoyl, etc.], N-(lower alkanoyl)-N-[heterocyclic(lower)alkyl]amino-ar(lower)alkenoyl [e.g. N-acetyl-N-pyridylmethylaminocinnamoyl, etc.], N-(lower alkanoyl)-N-[lower alkoxy(lower)alkyl]amino-ar(lower)alkenoyl [e.g. N-acetyl-N-methoxyethylaminocinnamoyl, N-acetyl-N-methoxymethylaminocinnamoyl, N-propionyl-N-methoxyethylaminocinnamoyl, etc.], N-(lower alkanoyl)-N-[lower alkoxycarbonyl(lower)alkyl]amino-ar(lower)alkenoyl [e.g. N-acetyl-N-tert-butoxycarbonylmethylaminocinnamoyl, N-acetyl-N-tert-butoxycarbonylethylaminocinnamoyl, N-propionyl-N-tert-butoxycarbonylmethylaminocinnamoyl, etc.], N-(lower alkanoyl)-N-[carboxy(lower)alkyl]amino-ar(lower)alkenoyl [e.g. N-acetyl-N-carboxymethylaminocinnamoyl, N-acetyl-N-carboxyethylaminocinnamoyl, N-propionyl-N-carboxymethylaminocinnamoyl, etc.], N-[lower alkoxy(lower)alkanoyl]-N-[heterocyclic(lower)alkyl]amino-ar(lower)alkenoyl [e.g. N-methoxyacetyl-N-pyridylmethylaminocinnamoyl, N-methoxypropionyl-N-pyridylmethylaminocinnamoyl, etc.], N-[heterocycliccarbonyl]-N-[lower alkoxy(lower)alkyl]amino-ar(lower)alkenoyl [e.g. N-pyridylcarbonyl-N-methoxymethylaminocinnamoyl, N-pyridylcarbonyl-N-methoxyethylaminocinnamoyl, N-thienylcarbonyl-N-methoxyethylaminocinnamoyl, etc.], ureido-ar(lower)alkenoyl [e.g. ureidocinnamoyl, etc.], lower alkylureido-ar(lower)alkenoyl [e.g. methylureidocinnamoyl, ethylureidocinnamoyl, dimethylureidocinnanoyl, etc.], heterocyclicureido-ar(lower)alkenoyl [e.g. pyridylureidocinnamoyl, pyrimidinylureidocinnamoyl, thienylureidocinnamoyl, etc.], acyl-ar(lower)alkenoyl, for example, lower alkanoyl-ar(lower)alkenoyl [e.g. formylcinnamoyl, acetylcinnamoyl, propionylcinnamoyl, etc.], carboxy-ar(lower)alkenoyl [e.g. carboxycinnamoyl, etc.], lower alkoxycarbonyl-ar(lower)alkenoyl [e.g. methoxycarbonylcinnamoyl, ethoxycarbonylcinnamoyl, etc.], carbamoyl-ar(lower)alkenoyl [e.g. carbamoylcinnamoyl, etc.], lower alkylcarbamoyl-ar(lower)alkenoyl [e.g. methylcarbamoylcinnamoyl, ethylcarbamoylcinnamoyl, dimethylcarbamoylcinnamoyl, propylcarbamoylcinnamoyl, isopropylcarbamoylcinnamoyl, diethylcarbamoylcinnamoyl, N-methyl-N-ethylcarbamoylcinnamoyl, etc.], hydroxy(lower)alkylcarbamoyl-ar(lower)alkenoyl [e.g. hydroxyethylcarbamoylcinnamoyl, bis(hydroxyethyl)carbamoylcinnamoyl, etc.], N-[hydroxy(lower)alkyl]-N-(lower alkyl)carbamoyl-ar(lower)alkenoyl [e.g. N-hydroxyethyl-N-methylcarbamoylcinnamoyl, etc.], lower alkoxy(lower)alkylcarbamoyl-ar(lower)alkenoyl [e.g. methoxymethylcarbamoylcinnamoyl, methoxyethylcarbamoylcinnamoyl, bis(methoxyethyl)carbamoylcinnamoyl, ethoxyethylcarbamoylcinnamoyl, methoxypropylcarbamoylcinnamoyl, bis(ethoxyethyl)carbamoylcinnamoyl, etc.], N-[lower alkoxy(lower)alkyl]-N-(lower alkyl)carbamoyl-ar(lower)alkenoyl [e.g. N-methoxyethyl-N-methylcarbamoylcinnamoyl, N-ethoxyethyl-N-methylcarbamoylcinnamoyl, etc.], heterocyclic(lower)alkylcarbamoyl-ar(lower)alkenoyl [e.g. pyridylmethylcarbamoylcinnamoyl, furylmethylcarbamoylcinnamoyl, thienylmethylcarbamoylcinnamoyl, etc.], N-[heterocyclic(lower)alkyl]-N-(lower alkyl)carbamoyl-ar(lower)alkenoyl [e.g. N-pyridylmethyl-N-methylcarbamoylcinnamoyl, etc.], heterocycliccarbamoyl-ar(lower)alkenoyl [e.g. morpholinylcarbamoylcinnamoyl, thienylcarbamoylcinnamoyl, pyridylcarbamoylcinnamoyl, pyrimidinylcarbamoylcinnamoyl, tetrazolylcarbamoylcinnamoyl, etc.], optionally substituted heterocycliccarbonyl-ar(lower)alkenoyl [e.g. morpholinocarbonylcinnamoyl, pyrrolidinylcarbonylcinnamoyl, piperidinocarbonylcinnamoyl, tetrahydropyridylcarbonylcinnamoyl, methylpiperazinylcarbonylcinnamoyl, etc.], lower alkenylcarbamoyl-ar(lower)alkenoyl [e.g. vinylcarbamoylcinnamoyl, allylcarbamoylcinnamoyl, methylpropenylcarbamoylcinnamoyl, etc.], lower alkynylcarbamoyl-ar(lower)alkenoyl [e.g. ethynylcarbamoylcinnamoyl, propynylcarbamoylcinnamoyl, etc.], amino(lower)alkylcarbamoyl-ar(lower)alkenoyl [e.g. aminomethylcarbamoylcinnamoyl, aminoethylcarbamoylcinnamoyl, etc.], lower alkylamino(lower)alkylcarbamoyl-ar(lower)alkenoyl [e.g. methylaminomethylcarbamoylcinnamoyl, methylaminoethylcarbamoylcinnamoyl, ethylaminoethylcarbamoylcinnanoyl, dimethylaminoethylcarbamoylcinnamoyl, etc.], lower alkylcarbamoyloxy(lower)alkylcarbamoyl-ar(lower)alkenoyl [e.g. methylcarbamoyloxymethylcarbamoylcinnamoyl, methylcarbamoyloxyethylcarbamoylcinnamoyl, ethylcarbamoyloxyethylcarbamoylcinnamoyl, dimethylcarbamoyloxyethylcarbamoylcinnamoyl, etc.], lower lower alkylcarbamoyl(lower)alkylcarbamoyl-ar(lower)alkenoyl [e.g. methylcarbamoylmethylcarbamoylcinnamoyl, methylcarbamoylethylcarbamoylcinnamoyl, ethylcarbamoylethylcarbamoylcinnamoyl, dimethylcarbamoylethylcarbamoylcinnamoyl, etc.], lower alkoxycarbonyl(lower)alkylcarbamoyl-ar(lower)alkenoyl [e.g. methoxycarbonylmethylcarbamoylcinnamoyl, methoxycarbonylethylcarbamoylcinnamoyl, ethoxycarbonylmethylcarbamoylcinnamoyl, ethoxycarbonylethylcarbamoylcinnamoyl, etc.], carboxy(lower)alkylcarbamoyl-ar(lower)alkenoyl [e.g. carboxymethylcarbamoylcinnamoyl, carboxyethylcarbamoylcinnamoyl, etc.], [lower alkylcarbamoyl-ar(lower)alkyl]carbamoyl-ar(lower)alkenoyl [e.g. (methylcarbamoyl-phenethyl)carbamoylcinnamoyl, (ethylcarbamoyl-phenethyl)carbamoylcinnamoyl, etc.], [lower alkoxycarbonyl-ar(lower)alkyl]carbamoyl-ar(lower)alkenoyl [e.g. (methoxycarbonyl-phenethyl)carbamoylcinnamoyl, (ethoxycarbonyl-phenethyl)carbamoylcinnamoyl, etc.], [carboxy-ar(lower)alkyl]carbamoyl-ar(lower)alkenoyl [e.g. carboxy-phenethyl)carbamoylcinnamoyl, etc.], N-[lower alkylcarbamoyl(lower)alkyl]-N-(lower alkyl)carbamoyl-ar(lower)alkenoyl [e.g. N-(methylcarbamoylmethyl)-N-methylcarbamoylcinnamoyl, N-(methylcarbamoylethyl)-N-methylcarbamoylcinnamoyl, N-(ethylcarbamoylethyl)-N-methylcarbamoylcinnamoyl, N-(dimethylcarbamoylethyl)-N-methylcarbamoylcinnamoyl, etc.], N-[lower alkoxycarbonyl(lower)alkyl]-N-(lower alkyl)carbamoyl-ar(lower)alkenoyl [e.g. N-methoxycarbonylmethyl-N-methylcarbamoylcinnamoyl, N-methoxycarbonylethyl-N-methylcarbamoylcinnamoyl, N-ethoxycarbonylmethyl-N-methylcarbamoylcinnamoyl, N-ethoxycarbonylethyl-N-methylcarbamoylcinnamoyl, etc.], N-[carboxy(lower)alkyl]-N-(lower alkyl)carbamoyl-ar(lower)alkenoyl [e.g. N-carboxymethyl-N-methylcarbamoylcinnamoyl, N-carboxyethyl-N-methylcarbamoylcinnamoyl, etc.], arylcarbamoyl-ar(lower)alkenoyl [e.g. phenylcarbamoylcinnamoyl, naphthylcarbamoylcinnamoyl, etc.], etc., etc., ar(lower)alkynoyl [e.g. phenylpropioloyl, etc.], substituted or unsubstituted heterocyclic(lower)alkenoyl such as heterocyclic(lower)alkenoyl [e.g. morpholinylacryloyl, pyridylacryloyl, thienylacryloyl, etc.], amino-heterocyclic(lower)alkenoyl [e.g. aminopyridylacryloyl, etc.], lower alkylamino-heterocyclic(lower)alkenoyl [e.g. methylaminopyridylacryloyl, dimethylaminopyridylacryloyl, etc.], acylamino-heterocyclic(lower)alkenoyl, for example, lower alkanoylamino-heterocyclic(lower)alkenoyl [e.g. acetylaminopyridylacryloyl, propionylaminopyridylacryloyl, etc.], lower alkenoylamino-heterocyclic(lower)alkenoyl [e.g. acryloylaminopyridylacryloyl, crotonoylaminopyridylacryloyl, etc.], heterocyclic(lower)alkanoylamino-heterocyclic(lower)alkenoyl [e.g. pyridylacetylaminopyridylacryloyl, thienylacetylaminopyridylacryloyl, etc.], heterocycliccarbonylamino-heterocyclic(lower)alkenoyl [e.g. pyridylcarbonylaminopyridylacryloyl, furylcarbonylaminopyridylacryloyl, etc.], lower alkanoylamino(lower)alkanoylamino-heterocyclic(lower)alkenoyl [e.g. acetylaminoacetylaminopyridylacryloyl, acetylaminopropionylaminopyridylacryloyl, etc.], lower alkoxycarbonyl(lower)alkanoylamino-heterocyclic(lower)alkenoyl [e.g. ethoxycarbonylacetylaminopyridylacryloyl, ethoxycarbonylpropionylaminopyridylacryloyl, etc.], lower alkoxy(lower)alkanoylamino-heterocyclic(lower)alkenoyl [e.g. methoxyacetylaminopyridylacryloyl, methoxypropionylaminopyridylacryloyl, ethoxypropionylaminopyridylacryloyl, etc.], etc., lower alkylureido-heterocyclic(lower)alkenoyl [e.g. methylureidopyridylacryloyl, etc.], acyl-heterocyclic(lower)alkenoyl, for example, carboxy-heterocyclic(lower)alkenoyl [e.g. carboxypyridylacryloyl, etc.], lower alkoxycarbonyl-heterocyclic(lower)alkenoyl [e.g. ethoxycarbonylpyridylacryloyl, etc.], lower alkylcarbamoyl-heterocyclic(lower)alkenoyl [e.g. methylcarbamoylpyridylacryloyl, ethylcarbamoylpyridylacryloyl, dimethylcarbamoylpyridylacryloyl, diethylcarbamoylpyridylacryloyl, isopropylcarbamoylpyridylacryloyl, N-ethyl-N-methylcarbamoylpyridylacryloyl, etc.], lower alkoxy(lower)alkylcarbamoyl-heterocyclic(lower)alkenoyl [e.g. methoxymethylcarbamoylpyridylacryloyl, methoxyethylcarbamoylpyridylacryloyl, methoxypropylcarbamoylpyridylacryloyl, ethoxyethylcarbamoylpyridylacryloyl, bis(methoxyethyl)carbamoylpyridylacryloyl, etc.], hydroxy(lower)alkylcarbamoyl-heterocyclic(lower)alkenoyl [e.g. hydroxymethylcarbamoylpyridylacryloyl, hydroxyethylcarbamoylpyridylacryloyl, bis(hydroxyethyl)carbamoylpyridylacryloyl, etc.], heterocycliccarbamoyl-heterocyclic(lower)alkenoyl [e.g. pyridylcarbamoylpyridylacryloyl, morpholinylcarbamoylpyridylacryloyl, thienylcarbamoylpyridylacryloyl, pyrimidinylcarbamoylpyridylacryloyl, etc.], heterocyclic (lower)alkylcarbamoyl-heterocyclic(lower)alkenoyl [e.g. pyridylmethylcarbamoylpyridylacryloyl, furylmethylcarbamoylpyridylacryloyl, thienylmethylcarbamoylpyridylacryloyl, etc.], heterocycliccarbonyl-heterocyclic(lower)alkenoyl [e.g. morpholinocarbonylpyridylacryloyl, pyrrolidinylcarbonylpyridylacryloyl, piperidinocarbonylpyridylacryloyl, etc.3, lower alkenylcarbamoyl-heterocyclic(lower)alkenoyl [e.g. vinylcarbamoylpyridylacryloyl, allylcarbamoylpyridylacryloyl, etc.], lower alkynylcarbamoyl-heterocyclic(lower)alkenoyl [e.g. ethynylcarbamoylpyridylacryloyl, propynylcarbamoylpyridylacryloyl, etc.], etc., etc., heterocycliccarbonyl which may be substituted with substituent [e.g. furoyl, thenoyl, nicotinoyl, isonicotinoyl, morpholinocarbonyl, piperidinocarbonyl, 4-methyl-1-piperazinylcarbonyl, 4-ethyl-1-piperazinylcarbonyl, dimethylaminopiperidinocarbonyl, 4-methylcarbamoyl-1-piperazinylcarbonyl, 1,2,3,6-tetrahydropyridylcarbonyl, pyrrolidinylcarbonyl, indolylcarbonyl, etc.], aryloxycarbonyl which may be substituted with nitro [e.g. phenyloxycarbonyl, nitrophenyloxycarbonyl, etc.], ar(lower)alkoxycarbonyl which may be substituted with nitro [e.g. benzyloxycarbonyl, nitrobenzyloxycarbonyl, etc.], substituted or unsubstituted carbamoyl or thiocarbamoyl such as carbamoyl, lower alkylcarbamoyl [e.g. methylcarbamoyl, ethylcarbamoyl, propylcarbamoyl, isopropylcarbamoyl, butylcarbamoyl, isobutylcarbamoyl, tert-butylcarbamoyl, pentylcarbamoyl, dimethylcarbamoyl, diethylcarbamoyl, N-ethyl-N-methylcarbamoyl, etc.], carboxy(lower)alkylcarbamoyl [e.g. carboxymethylcarbamoyl, carboxyethylcarbamoyl, etc.], esterified carboxy(lower)alkylcarbamoyl, for example, lower alkoxycarbonyl(lower)alkylcarbamoyl [e.g. methoxycarbonylmethylcarbamoyl, ethoxycarbonylmethylcarbamoyl, ethoxycarbonylethylcarbamoyl, etc.], lower alkenylcarbamoyl [e.g. vinylcarbamoyl, allylcarbamoyl, etc.], cyclo(lower)alkylcarbamoyl [e.g. cyclopropylcarbamoyl, cyclobutylcarbamoyl, cyclopentylcarbamoyl, cyclohexylcarbamoyl, etc.], halo(lower)alkanoylcarbamoyl [e.g. trichloroacetylcarbamoyl, etc.], substituted or unsubstituted arylcarbamoyl, for example, arylcarbamoyl [e.g. phenylcarbamoyl, tolylcarbamoyl, xylylcarbamoyl, naphthylcarbamoyl, ethylphenylcarbamoyl, etc.], arylthiocarbamoyl [e.g. phenylthiocarbamoyl, etc.], lower alkoxyarylcarbamoyl [e.g. methoxyphenylcarbamoyl, etc.], haloarylcarbamoyl [e.g. fluorophenylcarbamoyl, chlorophenylcarbamoyl, etc.], halo(lower)alkyl-arylcarbamoyl [e.g. trifluoromethylphenylcarbamoyl, etc.], nitro-arylcarbamoyl [e.g. nitrophenylcarbamoyl, etc.], cyano-arylcarbamoyl [e.g. cyanophenylcarbamoyl, etc.], hydroxy(lower)alkyl-arylcarbamoyl [e.g. hydroxymethylphenylcarbamoyl, hydroxyethylphenylcarbamoyl, etc.], amino-arylcarbamoyl [e.g. aminophenylcarbamoyl, etc.], lower alkylamino-arylcarbamoyl [e.g. methylaminophenylcarbamoyl, ethylaminophenylcarbamoyl, dimethylaminophenylcarbamoyl, etc.], lower alkanoylamino-arylcarbamoyl [e.g. acetylaminophenylcarbamoyl, propionylaminophenylcarbamoyl, etc.], N-(lower alkanoyl)-N-(lower alkyl)amino-arylcarbamoyl [e.g. N-acetyl-N-methylaminophenylcarbamoyl, N-propionyl-N-methylaminophenylcarbamoyl, etc.], lower alkoxy(lower)alkanoylamino-arylcarbamoyl [e.g. methoxyacetylaminophenylcarbamoyl, methoxypropionylaminophenylcarbamoyl, etc.], lower alkoxycarbonyl(lower)alkanoylamino-arylcarbamoyl [e.g. ethoxycarbonylacetylaminophenylcarbamoyl, methoxycarbonylpropionylaminophenylcarbamoyl, etc.], carboxyamino-arylcarbamoyl [e.g. carboxyaminophenylcarbamoyl, etc.], lower alkoxycarbonylamino-arylcarbamoyl [e.g. ethoxycarbonylaminophenylcarbamoyl, etc.], aroylamino-arylcarbamoyl [e.g. benzoylaminophenylcarbamoyl, etc.], heterocycliccarbonylamino-arylcarbamoyl [e.g. pyridylcarbonylaminophenylcarbamoyl, furylcarbonylaminophenylcarbamoyl, morpholinocarbonylaminophenylcarbamoyl, etc.], heterocyclic(lower)alkanoylamino-arylcarbamoyl [e.g. pyridylacetylaminophenylcarbamoyl, thienylacetylaminophenylcarbamoyl, etc.], ureidoarylcarbamoyl [e.g. ureidophenylcarbamoyl, etc.], lower alkylureido-arylcarbamoyl [e.g. methylureidophenylcarbamoyl, ethylureidophenylcarbamoyl, etc.], hydroxyimino(lower)alkyl-arylcarbamoyl [e.g. hydroxyiminoethylphenylcarbamoyl, etc.], lower alkoxyimino(lower)alkyl-arylcarbamoyl [e.g. methoxyiminoethylphenylcarbamoyl, etc.], lower alkylhydrazono(lower)alkyl-arylcarbamoyl [e.g. methylhydrazonoethylphenylcarbamoyl, dimethylhydrazonoethylphenylcarbamoyl, etc.], optionally substituted heterocyclic-arylcarbamoyl [e.g. oxopyrrolidinylphenylcarbamoyl, oxopiperidinophenylcarbamoyl, dioxopyrrolidinylphenylcarbamoyl, oxoooxazolidinylphenylcarbamoyl, pyrrolylphenylcarbamoyl, etc.], acyl-arylcarbamoyl, for example, carboxy-arylcarbamoyl [e.g. carboxyphenylcarbamoyl, etc.], lower alkoxycarbonyl-arylcarbamoyl [e.g. ethoxycarbonylphenylcarbamoyl, etc.], heterocycliccarbonyl-arylcarbamoyl [e.g. morpholinocarbonylphenylcarbamoyl, pyrrolidinylcarbonylphenylcarbamoyl, piperidinocarbonylphenylcarbamoyl, 1,2,3,6-tetrahydropyridylcarbonylphenylcarbamoyl, piperazinylcarbonylphenylcarbamoyl, thiomorpholinocarbonylphenylcarbamoyl, etc.], heterocycliccarbonyl-arylcarbamoyl substituted with lower alkyl [e.g. methylpiperazinylcarbonylphenylcarbamoyl, ethylpiperazinylcarbonylphenylcarbamoyl, etc.], heterocycliccarbonyl-arylcarbamoyl substituted with aryl [e.g. phenylpiperazinylcarbonylphenylcarbamoyl, etc.], heterocycliccarbonyl-arylcarbamoyl substituted with a heterocyclic group [e.g. pyridylpiperazinylcarbonylphenylcarbamoyl, etc.], heterocycliccarbonyl-arylcarbamoyl substituted with lower alkanoyl [e.g. acetylpiperazinylcarbonylphenylcarbamoyl, etc.], heterocycliccarbonyl-arylcarbamoyl substituted with lower alkoxycarbonyl [e.g. ethoxycarbonylpiperazinylcarbonylphenylcarbamoyl, etc.], heterocycliccarbonyl-arylcarbamoyl substituted with lower alkylamino [e.g. methylaminopiperazinylcarbonylphenylcarbamoyl, dimethylaminopiperidinocarbonylphenylcarbamoyl, etc.], heterocycliccarbonyl-arylcarbamoyl substituted with lower alkylcarbamoyl [e.g. methylcarbamoylpiperazinylcarbonylphenylcarbamoyl, etc.], carbamoyl-arylcarbamoyl [e.g. carbamoylphenylcarbamoyl, etc.], lower alkylcarbamoyl-arylcarbamoyl [e.g. methylcarbamoylphenylcarbamoyl, ethylcarbamoylphenylcarbamoyl, propylcarbamoylphenylcarbamoyl, dimethylcarbamoylphenylcarbamoyl, diethylcarbamoylphenylcarbamoyl, N-ethyl-N-methylcarbamoylphenylcarbamoyl, N-isopropyl-N-methylcarbamoylphenylcarbamoyl, etc.], hydroxy(lower)alkylcarbamoyl-arylcarbamoyl [e.g. hydroxymethylcarbamoylphenylcarbamoyl, hydroxyethylcarbamoylphenylcarbamoyl, bis(hydroxyethyl)carbamoylphenylcarbamoyl, etc.], N-[hydroxy(lower)alkyl]-N-(lower alkyl)carbamoyl-arylcarbamoyl [e.g. N-(hydroxyethyl)-N-methylcarbamoylphenylcarbamoyl, etc.], lower alkoxy(lower)alkylcarbamoyl-arylcarbamoyl [e.g. methoxymethylcarbamoylphenylcarbamoyl, methoxyethylcarbamoylphenylcarbamoyl, ethoxyethylcarbamoylphenylcarbamoyl, bis(methoxyethyl)carbamoylphenylcarbamoyl, bis(ethoxyethyl)carbamoylphenylcarbamoyl, etc.], N-[lower alkoxy(lower)alkyl]-N-(lower alkyl)carbamoyl-arylcarbamoyl [e.g. N-(methoxyethyl)-N-methylcarbamoylphenylcarbamoyl, N-(methoxypropyl)-N-methylcarbamoylphenylcarbamoyl, etc.], lower alkylamino(lower)alkylcarbamoyl-arylcarbamoyl [e.g. methylaminoethylcarbamoylphenylcarbamoyl, dimethylaminoethylcarbamoylphenylcarbamoyl, etc.], N-[lower alkylamino(lower)alkyl]-N-(lower alkyl)carbamoyl-arylcarbamoyl [e.g. N-(dimethylaminoethyl)-N-methylcarbamoylphenylcarbamoyl, N-(dimethylaminopropyl)-N-methylcarbamoylphenylcarbamoyl, etc.], heterocycliccarbamoyl-arylcarbamoyl [e.g. morpholinylcarbamoylphenylcarbamoyl, thienylcarbamoylphenylcarbamoyl, pyridylcarbamoylphenylcarbamoyl, pyrimidinylcarbamoylphenylcarbamoyl, etc.], N-(heterocyclic)-N-(lower alkyl)carbamoyl-arylcarbamoyl [e.g. N-pyridyl-N-methylcarbamoylphenylcarbamoyl, etc.], heterocyclic(lower)alkylcarbamoyl-arylcarbamoyl [e.g. pyridylmethylcarbamoylphenylcarbamoyl, pyridylethylcarbamoylphenylcarbamoyl, thienylmethylcarbamoylphenylcarbamoyl, etc.], N-[heterocyclic(lower)alkyl]-N-(lower alkyl)carbamoyl-arylcarbamoyl [e.g. N-pyridylmethyl-N-methylcarbamoylphenylcarbamoyl, etc.], N-[heterocyclic(lower)alkyl]-N-[lower alkoxy(lower)alkyl]carbamoyl-arylcarbamoyl [e.g. N-pyridylmethyl-N-methoxyethylcarbamoylphenylcarbamoyl, etc.] arylcarbamoyl-arylcarbamoyl [e.g. phenylcarbamoylphenylcarbamoyl, etc.], lower alkylamino-arylcarbamoyl-arylcarbamoyl [e.g. dimethylaminophenylcarbamoylphenylcarbamoyl, etc.], lower alkanoyl-arylcarbamoyl [e.g. acetylphenylcarbamoyl, propionylphenylcarbamoyl, etc.], etc., etc., ar(lower)alkylcarbamoyl [e.g. benzylcarbamoyl, phenethylcarbamoyl, etc.], heterocycliccarbamoyl [e.g. furylcarbamoyl, thienylcarbamoyl, pyridylcarbamoyl, quinolylcarbamoyl, isoquinolylcarbamoyl, pyrimidinylcarbamoyl, pyrazolylcarbamoyl, etc.], heterocyclic(lower)alkylcarbamoyl [e.g. pyridylmethylcarbamoyl, pyridylethylcarbamoyl, furylmethylcarbamoyl, thienylmethylcarbamoyl, etc.], arylaminocarbamoyl [e.g. phenylaminocarbamoyl, etc.], aroylcarbamoyl [e.g. benzoylcarbamoyl, etc.], etc., lower alkylsulfonyl [e.g. mesyl, ethylsulfonyl, propylsulfonyl, isopropylsulfonyl, tert-butylsulfonyl, pentylsulfonyl, etc.], arylsulfonyl [e.g. tosyl, phenylsulfonyl, etc.], ar(lower)alkylsulfonyl [e.g. benzylsulfonyl, phenethylsulfonyl, etc.], ar(lower)alkenylsulfonyl [e.g. styrylsulfonyl, cinnamylsulfonyl, etc.], phthaloyl, substituted or unsubstituted amino acid residue mentioned below, or the like.

Suitable "amino acid residue" may include natural or artificial ones, and such amino acid may be glycine, sarcosine, alanine, β-alanine, valine, norvaline, leucine, isoleucine, norleucine, serine, threonine, cysteine, methionine, phenylalanine, phenylglycine, tryptophan, tyrosine, proline, hydroxyproline, glutamic acid, aspartic acid, glutamine, asparagine, lysine, arginine, histidine, ornithine, or the like, in which more preferable one is glycine, sarcosine, alanine, β-alanine and proline, and the most preferable one is glycine. And said amino acid residue may be substituted with suitable substituent(s) such as the above-mentioned lower alkyl, the above-mentioned aryl, the above-mentioned acyl, ar(lower)alkyl [e.g. benzyl, phenethyl, trityl, etc.], cycloalkyl [e.g. cyclopropyl, cyclobutyl, cyclopentyl, cyclohexyl, cycloheptyl, cyclooctyl, adamantyl, etc.], a heterocyclic group mentioned below, heterocyclic(lower)alkyl [e.g. pyridylmethyl, pyridylethyl, imidazolylmethyl, furylmethyl, thienylmethyl, morpholinomethyl, piperidinomethyl, etc.], substituted or unsubstituted amidino [e.g. amidino, methylamidino, N-ethyl-N'-cyanoamidino, etc.], or the like.

Preferred example of said amino acid residue substituted with suitable substituent(s) may be amino acid residue substituted with lower alkyl [e.g. ethylglycyl, isopropylglycyl, dimethylglycyl, diethylglycyl, ethylsarcosyl, isopropylsarcosyl, methylalanyl, methyl-β-alanyl, dimethyl-β-alanyl, etc.], amino acid residue substituted with aryl [e.g. N-phenylglycyl, N-tolylglycyl, N-phenylalanyl, N-phenylsarcosyl, etc.], amino acid residue substituted with ar(lower)alkyl [e.g. benzylglycyl, tritylglycyl, phenethylglycyl, benzylsarcosyl, benzylalanyl, etc.], amino acid residue substituted with a heterocyclic group [e.g. morpholinoglycyl, piperidinoglycyl, pyridylglycyl, etc.], amino acid residue substituted with heterocyclic(lower)alkyl [e.g. pyridylmethylglycyl, imidazolylmethylglycyl, furylmethylglycyl, thienylmethylglycyl, etc.], amino acid residue substituted with cycloalkyl [e.g. cyclopropylglycyl, cyclobutylglycyl, cyclopentylglycyl, cyclohexylglycyl, cycloheptylglycyl, cyclooctylglycyl, adamantylglycyl, cyclohexylsarcosyl, cycloheptylsarcosyl, cyclohexylalanyl, etc.], amino acid residue substituted with optionally substituted amidino [e.g. amidinoglycyl, methylamidinoglycyl, N-ethyl-N'-cyanoamidinoglycyl, etc.], amino acid residue substituted with acyl such as amino acid residue substituted with alkanoyl [e.g. formylglycyl, acetylglycyl, acetylsarcosyl, acetylalanyl, acetyl-β-alanyl, propionylglycyl, butyrylglycyl, isobutyrylglycyl, valerylglycyl, isovalerylglycyl, pivaloylglycyl, hexanoylglycyl, heptanoylglycyl, etc.], amino acid residue substituted with halo(lower)alkanoyl [e.g. trifluoroacetylglycyl, trifluoroacetylsarcosyl, trifluoroacetylalanyl, bromoacetylglycyl, heptafluorobutyrylglycyl, etc.], amino acid residue substituted with hydroxy(lower)alkanoyl [e.g. glycoloylglycyl, glycoloylsarcosyl, lactoylglycyl, lactoylalanyl, etc.], amino acid residue substituted with lower alkylsulfonyloxy(lower)alkanoyl [e.g. mesyloxyacetylglycyl, ethylsulfonyloxyacetylglycyl, mesyloxyacetylsarcosyl, etc.], amino acid residue substituted with lower alkoxy(lower)alkanoyl [e.g. methoxyacetylglycyl, ethoxyacetylglycyl, methoxyacetylsarcosyl, methoxypropionylalanyl, etc.], amino acid residue substituted with aryloxy(lower)alkanoyl

[e.g. phenyloxyacetylglycyl, phenyloxypropionylglycyl, phenyloxyacetylsarcosyl, etc.], amino acid residue substituted with lower alkylthio(lower)alkanoyl [e.g. methylthioacetylglycyl, methylthiopropionylglycyl, etc.], amino acid residue substituted with lower alkylcarbamoyl (lower)alkanoyl [e.g. methylcarbamoylpropionylglycyl, methylcarbamoylpropionylalanyl, etc.], amino acid residue substituted with lower alkanoyloxy(lower)alkanoyl [e.g. acetyloxyacetylglycyl, acetyloxyacetylsarcosyl, propionyloxyacetylglycyl, acetyloxypropionylalanyl, etc.], amino acid residue substituted with carboxy(lower)alkanoyl [e.g. carboxyacetylglycyl, carboxypropionylglycyl, carboxypropionylsarcosyl, carboxyacetylalanyl, etc.], amino acid residue substituted with lower alkoxycarbonyl (lower)alkanoyl [e.g. methoxycarbonylacetylglycyl, ethoxycarbonylpropionylglycyl, methoxycarbonylacetylsarcosyl, etc.], amino acid residue substituted with ar(lower)alkanoyl [e.g. phenylacetylglycyl, phenylacetylsarcosyl, phenylpropionylalanyl, phenylpropionylglycyl, naphthylacetylglycyl, phenylbutyrylglycyl, etc.], amino acid residue substituted with optionally substituted heterocyclic(lower)alkanoyl [e.g. morpholinoacetylglycyl, thiomorpholinoacetylglycyl, its oxide or dioxide, pyridylacetylglycyl, morpholinopropionylalanyl, imidazolylacetylglycyl, piperidinoacetylglycyl, pyrrolidinylacetylglycyl, hexamethyleneiminoacetylglycyl, methylpiperazinylacetylglycyl, pyridylpiperazinylacetylglycyl, etc.], amino acid residue substituted with lower alkenoyl [e.g. acryloylglycyl, crotonoylglycyl, 3-pentenoylglycyl, 3-butenoylglycyl, 4-pentenoylglycyl, 3-butenoylsarcosyl, etc.], amino acid residue substituted with ar(lower)alkenoyl [e.g. cinnamoylglycyl, allocinnamoylglycyl, α-methylcinnamoylglycyl, 4-methylcinnamoylglycyl, cinnamoylsarcosyl, etc.], amino acid residue substituted with lower alkoxy-ar(lower)alkenoyl [e.g. methoxycinnamoylglycyl, ethoxycinnamoylglycyl, dimethoxycinnamoylglycyl, etc.], amino acid residue substituted with lower alkylenedioxy-ar(lower)alkenoyl [e.g. methylenedioxycinnamoylglycyl, ethylenedioxycinnamoylglycyl, etc.], amino acid residue substituted with nitro-ar(lower)alkenoyl [e.g. nitrocinnamoylglycyl, etc.], amino acid residue substituted with cyano-ar(lower)alkenoyl [e.g. cyanocinnamoylglycyl, etc.], amino acid residue substituted with halo-ar(lower) alkenoyl [e.g. chlorocinnamoylglycyl, fluorocinnamoylglycyl, etc.], amino acid residue substituted with hydroxy-ar(lower)alkenoyl [e.g. hydroxycinnamoylglycyl, etc.], amino acid residue substituted with hydroxy(lower)alkoxy-ar(lower)alkenoyl [e.g. hydroxymethoxycinnamoylglycyl, hydroxyethoxycinnamoylglycyl, etc.], amino acid residue substituted with amino(lower)alkoxy-ar(lower)alkenoyl [e.g. aminoethoxycinnamoylglycyl, etc.], amino acid residue substituted with lower alkylamino(lower)alkoxy-ar (lower)alkenoyl [e.g. methylaminomethoxycinnamoylglycyl, dimethylaminoethoxycinnamoylclycyl, etc.], amino acid residue substituted with heterocyclic(lower)alkoxy-ar (lower)alkenoyl [e.g. pyridylmethoxycinnamoylglycyl, etc.], amino acid residue substituted with optionally substituted heterocyclic-ar(lower)alkenoyl [e.g. morpholinocinnamoylglycyl, methylpiperazinylcinnamoylglycyl, pyrrolidinylcinnamoylglycyl, oxopyrrolidinylcinnamoylglycyl, oxopiperidinocinnamoylglycyl, dioxopyrrolidinylcinnamoylglycyl, oxooxazolidinylcinnamoylglycyl, pyrrolylcinnamoylglycyl, tetrazolylcinnamoylglycyl, etc.], amino acid residue substituted with amino-ar(lower)alkenoyl [e.g. aminocinnamoylglycyl, etc.], amino acid residue substituted with lower alkylamino-ar(lower)alkenoyl [e.g. methylaminocinnamoylglycyl, dimethylaminocinnamoylglycyl, etc.], amino acid residue substituted with acylamino-ar(lower)alkenoyl, for example, amino acid residue substituted with lower alkanoylamino-ar(lower)alkenoyl [e.g. acetylaminocinnamoylglycyl, propionylaminocinnamoylglycyl, isobutyrylaminocinnamoylglycyl, etc.], amino acid residue substituted with cycloalkyl(lower)alkanoylamino-ar(lower) alkenoyl (e.g. cyclopentylacetylaminocinnamoylglycyl, cyclohexylacetylaminocinnamoylglycyl, adamantylacetylaminocinnamoylglycyl, etc.], amino acid residue substituted with cycloalkylcarbonylamino-ar(lower) alkenoyl (e.g. cyclopropylcarbonylaminocinnamoylglycyl, cyclopentylcarbonylaminocinnamoylglycyl, cyclohexylcarbonylaminocinnamoylglycyl, adamantylcarbonylaminocinnamoylglycyl, etc.], amino acid residue substituted with lower alkenoylamino-ar(lower) alkenoyl [e.g. acryloylaminocinnamoylglycyl, crotonoylaminocinnamoylglycyl, etc.], amino acid residue substituted with lower alkoxycarbonylamino-ar(lower) alkenoyl [e.g. methoxycarbonylaminocinnamoylglycyl, ethoxycarbonylaminocinnamoylglycyl, etc.], amino acid residue substituted with hydroxy(lower)alkanoylamino-ar (lower)alkenoyl [e.g. hydroxyacetylaminocinnamoylglycyl, hydroxypropionylaminocinnamoylglycyl, etc.], amino acid residue substituted with lower alkoxy(lower) alkanoylamino-ar(lower)alkenoyl [e.g. methoxyacetylaminocinnamoylglycyl, methoxypropionylaminocinnamoylglycyl, etc.], amino acid residue substituted with halo(lower)alkanoylamino-ar (lower)alkenoyl [e.g. chloroacetylaminocinnamoylglycyl, trifluoroacetylaminocinnamoylglycyl, bromobutyrylaminocinnamoylglycyl, etc.], amino acid residue substituted with amino(lower)alkanoylamino-ar(lower) alkenoyl [e.g. aminoacetylaminocinnamoylglycyl, aminopropionylaminocinnamoylglycyl, etc.], amino acid residue substituted with lower alkylamino(lower) alkanoylamino-ar(lower)alkenoyl [e.g. methylaminoacetylaminocinnamoylglycyl, dimethylaminacetylaminocinnamoylglycyl, etc.], amino acid residue substituted with lower alkanoylamino(lower) alkanoylamino-ar(lower)alkenoyl [e.g. acetylaminoacetylaminocinnamoylglycyl, acetylaminopropionylaminocinnamoylglycyl, etc.], amino acid residue substituted with carboxy(lower)alkanoylamino-ar(lower)alkenoyl [e.g. carboxyacetylaminocinnamoylglycyl, carboxypropionylaminocinnamoylglycyl, etc.], amino acid residue substituted with lower alkoxycarbonyl(lower) alkanoylamino-ar(lower)alkenoyl [e.g. ethoxycarbonylacetylaminocinnamoylglycyl, ethoxycarbonylpropionylaminocinnamoylglycyl, etc.], amino acid residue substituted with lower alkoxycarbonyl (lower)alkenoylamino-ar(lower)alkenoyl [e.g. ethoxycarbonylacryloylaminocinnamoylglycyl, etc.], amino acid residue substituted with halo(lower) alkoxycarbonylamino-ar(lower)alkenoyl [e.g. chloroethoxycarbonylaminocinnamoylglycyl, etc.], amino acid residue substituted with optionally substituted heterocyclic(lower)alkanoylamino-ar(lower)alkenoyl [e.g.

pyridylacetylaminocinnamoylglycyl, thienylacetylaminocinnamoylglycyl, methylpyrrolylacetylaminocinnamoylglycyl, etc.], amino acid residue substituted with aroylamino-ar(lower)alkenoyl [e.g. benzoylaminocinnamoylglycyl, etc.], amino acid residue substituted with optionally substituted heterocycliccarbonylamino-ar(lower)alkenoyl [e.g. pyridylcarbonylaminocinnamoylglycyl, morpholinocarbonylaminocinnamoylglycyl, furylcarbonylaminocinnamoylglycyl, thienylcarbonylaminocinnamoylglycyl, oxazolylcarbonylaminocinnamoylglycyl, methyloxazolylcarbonylaminocinnamoylglycyl, dimethylisoxazolylcarbonylaminocinnamoylglycyl, imidazolylcarbonylaminocinnamoylglycyl, methylimidazolylcarbonylaminocinnamoylglycyl, piperidylcarbonylaminocinnamoylglycyl, ethylpiperidylcarbonylaminocinnamoylglycyl, acetylpiperidylcarbonylaminocinnamoylglycyl, pyrrolidinylcarbonylaminocinnamoylglycyl, acetylpyrrolidinylcarbonylaminocinnamoylglycyl, tert-butoxycarbonylpyrrolidinylcarbonylaminocinnamoylglycyl, etc.], amino acid residue substituted with lower alkylsulfonylamino-ar(lower)alkenoyl [e.g. mesylaminocinnamoylglycyl, ethylsulfonylaminocinnamoylglycyl, etc.], etc., amino acid residue substituted with N-(lower alkanoyl)-N-(lower alkyl) amino-ar(lower)alkenoyl [e.g. N-acetyl-N-methylaminocinnamoylglycyl, N-acetyl-N-ethylaminocinnamoylglycyl, N-propionyl-N-methylaminocinnamoylglycyl, etc.], amino acid residue substituted with N-[lower alkoxy(lower)alkanoyl]-N-(lower alkyl)amino-ar(lower)alkenoyl [e.g. N-methoxyacetyl-N-methylaminocinnamoylglycyl, N-methoxypropionyl-N-methylaminocinnamoylglycyl, etc.], amino acid residue substituted with N-(lower alkanoyl)-N-[heterocyclic(lower)alkyl]amino-ar(lower)alkenoyl [e.g. N-acetyl-N-pyridylmethylaminocinnamoylglycyl, etc.], amino acid residue substituted with N-(lower alkanoyl)-N-[lower alkoxy(lower)alkyl]amino-ar(lower)alkenoyl [e.g. N-acetyl-N-methoxyethylaminocinnamoylglycyl, N-acetyl-N-methoxymethylaminocinnamoylglycyl, N-propionyl-N-methoxyethylaminocinnamoylglycyl, etc.], amino acid residue substituted with N-(lower alkanoyl)-N-[lower alkoxycarbonyl(lower)alkyl]amino-ar(lower)alkenoyl [e.g. N-acetyl-N-tert-butoxycarbonylmethylaminocinnamoylglycyl, N-acetyl-N-tert-butoxycarbonylethylaminocinnamoylglycyl, N-propionyl-N-tert-butoxycarbonylmethylaminocinnamoylglycyl, etc.], amino acid residue substituted with N-(lower alkanoyl)-N-[carboxy(lower)alkyl]amino-ar(lower)alkenoyl [e.g. N-acetyl-N-carboxymethylaminocinnamoylglycyl, N-acetyl-N-carboxyethylaminocinnamoylglycyl, N-propionyl-N-carboxymethylaminocinnamoylglycyl, etc.], amino acid residue substituted with N-[lower alkoxy(lower)alkanoyl]-N-[heterocyclic(lower)alkyl]amino-ar(lower)alkenoyl [e.g. N-methoxyacetyl-N-pyridylmethylaminocinnamoylglycyl, N-methoxypropionyl-N-pyridylmethylaminocinnamoylglycyl, etc.], amino acid residue substituted with N-[heterocycliccarbonyl]-N-[lower alkoxy(lower)alkyl]amino-ar(lower)alkenoyl [e.g. N-pyridylcarbonyl-N-methoxymethylaminocinnamoylglycyl, N-pyridylcarbonyl-N-methoxyethylaminocinnamoylglycyl, N-thienylcarbonyl-N-methoxyethylaminocinnamoylglycyl, etc.], amino acid residue substituted with ureido-ar(lower)alkenoyl [e.g. ureidocinnamoylglycyl, etc.], amino acid residue substituted with lower alkylureido-ar(lower)alkenoyl [e.g. methylureidocinnamoylglycyl, ethylureidocinnamoylglycyl, dimethylureidocinnamoylglycyl, etc.], amino acid residue substituted with heterocyclicureido-ar(lower)alkenoyl [e.g. pyridylureidocinnamoylglycyl, pyrimidinylureidocinnamoylglycyl, thienylureidocinnamoylglycyl, etc.], amino acid residue substituted with acyl-ar(lower)alkenoyl, for example, amino acid residue substituted with lower alkanoyl-ar(lower)alkenoyl [e.g. formylcinnamoylglycyl, acetylcinnamoylglycyl, propionylcinnamoylglycyl, etc.], amino acid residue substituted with carboxy-ar(lower)alkenoyl [e.g. carboxycinnamoylglycyl, etc.], amino acid residue substituted with lower alkoxycarbonyl-ar(lower)alkenoyl [e.g. methoxycarbonylcinnamoylglycyl, ethoxycarbonylcinnamoylglycyl, etc.], amino acid residue substituted with carbamoyl-ar(lower)alkenoyl [e.g. carbamoylcinnamoylglycyl, etc.], amino acid residue substituted with lower alkylcarbamoyl-ar(lower)alkenoyl [e.g. methylcarbamoylcinnamoylglycyl, ethylcarbamoylcinnamoylglycyl, dimethylcarbamoylcinnamoylglycyl, propylcarbamoylcinnamoylclycyl, isopropylcarbamoylcinnamoylglycyl, diethylcarbamoylcinnamoylglycyl, N-methyl-N-ethylcarbamoylcinnamoylglycyl, etc.], amino acid residue substituted with hydroxy(lower)alkylcarbamoyl-ar(lower)alkenoyl [e.g. hydroxyethylcarbamoylcinnamoylglycyl, bis(hydroxyethyl)carbamoylcinnamoylglycyl, etc.], amino acid residue substituted with N-[hydroxy(lower)alkyl]-N-(lower alkyl)carbamoyl-ar(lower)alkenoyl [e.g. N-hydroxyethyl-N-methylcarbamoylcinnamoylglycyl, etc.], amino acid residue substituted with lower alkoxy(lower)alkylcarbamoyl-ar(lower)alkenoyl [e.g. methoxymethylcarbamoylcinnamoylglycyl, methoxyethylcarbamoylcinnamoylglycyl, bis(methoxyethyl)carbamoylcinnamoylglycyl, ethoxyethylcarbamoylcinnamoylglycyl, methoxypropylcarbamoylcinnamoylglycyl, bis(ethoxyethyl)carbamoylcinnamoylglycyl, etc.], amino acid residue substituted with N-[lower alkoxy(lower)alkyl]-N-(lower alkyl)carbamoyl-ar(lower)alkenoyl [e.g. N-methoxyethyl-N-methylcarbamoylcinnamoylglycyl, N-ethoxyethyl-N-methylcarbamoylcinnamoylglycyl, etc.], amino acid residue substituted with heterocyclic(lower)alkylcarbamoyl-ar(lower)alkenoyl [e.g. pyridylmethylcarbamoylcinnamoylglycyl, furylmethylcarbamoylcinnamoylglycyl, thienylmethylcarbamoylcinnamoylglycyl, etc.], amino acid residue substituted with N-[heterocyclic(lower)alkyl]-N-(lower alkyl)carbamoyl-ar(lower)alkenoyl [e.g. N-pyridylmethyl-N-methylcarbamoylcinnamoylglycyl, etc.], amino acid residue substituted with heterocycliccarbamoyl-ar(lower)alkenoyl [e.g. morpholinylcarbamoylcinnamoylglycyl, thienylcarbamoylcinnamoylglycyl, pyridylcarbamoylcicinnamoylglycyl, pyrimidinylcarbamoylcinnamoylglycyl, tetrazolylcarbamoylcinnamoylglycyl, etc.], amino acid residue substituted with optionally substituted heterocycliccarbonyl-ar(lower)alkenoyl [e.g. morpholinocarbonylcinnamoylglycyl, pyrrolidinylcarbonylcinnamoylglycyl, piperidinocarbonylcinnamoylglycyl, tetrahydropyridylcarbonylcinnamoylglycyl, methylpiperazinylcarbonylcinnamoylglycyl, etc.], amino acid residue substituted with lower alkenylcarbamoyl-ar(lower)alkenoyl [e.g. vinylcarbamoylcinnamoylglycyl, allylcarbamoylcinnamoylglycyl, methylpropenylcarbamoylcinnamoylglycyl, etc.], amino acid residue substituted with lower alkynylcarbamoyl-ar(lower)alkenoyl [e.g. ethynylcarbamoylcinnamoylglycyl, propynylcarbamoylcinnamoylglycyl, etc.], amino acid residue substituted with amino(lower)alkylcarbamoyl-ar(lower) alkenoyl [e.g. aminomethylcarbamoylcinnamoylglycyl, aminoethylcarbamoylcinnamoylglycyl, etc.], amino acid residue substituted with lower alkylamino(lower) alkylcarbamoyl-ar(lower)alkenoyl [e.g. methylaminomethylcarbamoylcinnamoylglycyl, methylaminoethylcarbamoylcinnamoylglycyl, ethylaminoethylcarbamoylcinnamoylglycyl, dimethylaminoethylcarbamoylcinnamoylglycyl, etc.], amino acid residue substituted with lower alkylcarbamoyloxy(lower)alkylcarbamoyl-ar(lower) alkenoyl [e.g. methylcarbamoyloxymethylcarbamoylcinnamoylglycyl, methylcarbamoyloxyethylcarbamoylcinnamoylglycyl, ethylcarbamoyloxyethylcarbamoylcinnamoylglycyl, dimethylcarbamoyloxyethylcarbamoylcinnamoylglycyl, etc.], amino acid residue substituted with lower alkylcarbamoyl(lower)alkylcarbamoyl-ar(lower)alkenoyl [e.g. methylcarbamoylmethylcarbamoylcinnamoylglycyl, methylcarbamoylethylcarbamoylcinnamoylglycyl, ethylcarbamoylethylcarbamoylcinnamoylglycyl, dimethylcarbamoylethylcarbamoylcinnamoylglycyl, etc.], amino acid residue substituted with lower alkoxycarbonyl (lower)alkylcarbamoyl-ar(lower)alkenoyl [e.g. methoxycarbonylmethylcarbamoylcinnamoylglycyl, methoxycarbonylethylcarbamoylcinnamoylglycyl, ethoxycarbonylmethylcarbamoylcinnamoylglycyl, ethoxycarbonylethylcarbamoylcinnamoylglycyl, etc.], amino acid residue substituted with carboxy(lower) alkylcarbamoyl-ar(lower)alkenoyl [e.g. carboxymethylcarbamoylcinnamoylglycyl, carboxyethylcarbamoylcinnamoylglycyl, etc.], amino acid residue substituted with [lower alkylcarbamoyl-ar(lower)alkyl]carbamoyl-ar(lower)alkenoyl [e.g. (methylcarbamoyl-phenethyl)carbamoylcinnamoylglycyl, (ethylcarbamoyl-phenethyl)carbamoylcinnamoylglycyl, etc.], amino acid residue substituted with [lower alkoxycarbonyl-ar(lower)alkyl]carbamoyl-ar(lower)alkenoyl [e.g. (methoxycarbonyl-phenethyl)carbamoylcinnamoylglycyl, (ethoxycarbonyl-phenethyl)carbamoylcinnamoylglycyl, etc.], amino acid residue substituted with [carboxy-ar(lower)alkyl]carbamoyl-ar(lower)alkenoyl [e.g. (carboxy-phenethyl)carbamoylcinnamoylglycyl, etc.], amino acid residue substituted with N-[lower alkylcarbamoyl(lower)alkyl]-N-(lower alkyl)carbamoyl-ar(lower)alkenoyl [e.g. N-(methylcarbamoylmethyl)-N-methylcarbamoylcinnamoylglycyl, N-(methylcarbamoylethyl)-N-methylcarbamoylcinnamoylglycyl, N-(ethylcarbamoylethyl)-N-methylcarbamoylcinnamoylglycyl, N-(dimethylcarbamoylethyl)-N-methylcarbamoylcinnamoylglycyl, etc.], amino acid residue substituted with N-[lower alkoxycarbonyl(lower)alkyl]-N-(lower alkyl)carbamoyl-ar(lower)alkenoyl [e.g. N-methoxycarbonylmethyl-N-methylcarbamoylcinnamoylglycyl, N-methoxycarbonylethyl-N-methylcarbamoylcinnamoylglycyl, N-ethoxycarbonylmethyl-N-methylcarbamoylcinnamoylglycyl, N-ethoxycarbonylethyl-N-methylcarbamoylcinnamoylglycyl, etc.], amino acid residue substituted with N-[carboxy(lower)alkyl]-N-(lower alkyl)carbamoyl-ar(lower)alkenoyl [e.g. N-carboxymethyl-N-methylcarbamoylcinnamoylglycyl, N-carboxyethyl-N-methylcarbamoylcinnamoylglycyl, etc.], amino acid residue substituted with arylcarbamoyl-ar(lower)alkenoyl [e.g. phenylcarbamoylcinnamoylglycyl, naphthylcarbamoylcinnamoylglycyl, etc.], etc., amino acid residue substituted with ar(lower)alkynoyl [e.g. phenylpropioloylglycyl, etc.], amino acid residue substituted with heterocyclic(lower)alkenoyl [e.g. morpholinylacryloylglycyl, pyridylacryloylglycyl, thienylacryloylglycyl, etc.], amino acid residue substituted with amino-heterocyclic(lower)alkenoyl [e.g. aminopyridylacryloylglycyl, etc.], amino acid residue substituted with lower alkylamino-heterocyclic(lower)alkenoyl [e.g. methylaminopyridylacryloylglycyl, dimethylaminopyridylacryloylglycyl, etc.], amino acid residue substituted with acylamino-heterocyclic(lower) alkenoyl, for example, amino acid residue substituted with lower alkanoylamino-heterocyclic(lower)alkenoyl [e.g. acetylaminopyridylacryloylglycyl, propionylaminopyridylacryloylglycyl, etc.], amino acid residue substituted with lower alkenoylamino-heterocyclic (lower)alkenoyl [e.g. acryloylaminopyridylacryloylglycyl, crotonoylaminopyridylacryloylglycyl, etc.], amino acid residue substituted with heterocyclic(lower)alkanoylamino-heterocyclic(lower)alkenoyl [e.g. pyridylacetylaminopyridylacryloylglycyl, thienylacetylaminopyridylacryloylglycyl, etc.], amino acid residue substituted with heterocycliccarbonylamino-heterocyclic(lower)alkenoyl [e.g. pyridylcarbonylaminopyridylacryloylglycyl, furylcarbamoylaminopyridylacryloylglycyl, etc.], amino acid residue substituted with lower alkanoylamino(lower) alkanoylamino-heterocyclic(lower)alkenoyl [e.g. acetylaminoacetylaminopyridylacryloylglycyl, acetylaminopropionylaminopyridylacryloylglycyl, etc.], amino acid residue substituted with lower alkoxycarbonyl (lower)alkanoylamino-heterocyclic(lower)alkenoyl [e.g. ethoxycarbonylacetylaminopyridylacryloylglycyl, ethoxycarbonylpropionylaminopyridylacryloylglycyl, etc.], amino acid residue substituted with alkoxy(lower) alkanoylamino-heterocyclic(lower)alkenoyl [e.g. methoxyacetylaminopyridylacryloylglycyl, methoxypropionylaminopyridylacryloylglycyl, ethoxypropionylaminopyridylacryloylglycyl, etc.], etc., amino acid residue substituted with lower alkylureido-heterocyclic(lower)alkenoyl [e.g. methylureidopyridylacryloylglycyl, etc.], amino acid residue substituted with acyl-heterocyclic(lower)alkenoyl, for example, amino acid residue substituted with carboxy-heterocyclic(lower)alkenoyl [e.g. carboxypyridylacryloylglycyl, etc.], amino acid residue substituted with lower alkoxycarbonyl-heterocyclic(lower) alkenoyl [e.g. ethoxycarbonylpyridylacryloylglycyl, etc.], amino acid residue substituted with lower alkylcarbamoyl-heterocyclic(lower)alkenoyl [e.g. methylcarbamoylpyridylacryloylglycyl, ethylcarbamoylpyridylacryloylglycyl, dimethylcarbamoylpyridylacryloylglycyl, diethylcarbamoylpyridylacryloylglycyl, isopropylcarbamoylpyridylacryloylglycyl, N-ethyl-N-methylcarbamoylpyridylacryloylglycyl, etc.], amino acid residue substituted with lower alkoxy(lower)
alkylcarbamoyl-heterocyclic(lower)alkenoyl [e.g.
methoxymethylcarbamoylpyridylacryloylglycyl,
methoxyethylcarbamoylpyridylacryloylglycyl,
methoxypropylcarbamoylpyridylacryloylglycyl,
ethoxyethylcarbamoylpyridylacryloylglycyl, bis
(methoxyethyl)carbamoylpyridylacryloylglycyl, etc.],
amino acid residue substituted with hydroxy(lower)
alkylcarbamoyl-heterocyclic(lower)alkenoyl [e.g.
hydroxymethylcarbamoylpyridylacryloylglycyl,
hydroxyethylcarbamoylpyridylacryloylglycyl, bis
(hydroxyethyl)carbamoylpyridylacryloylglycyl, etc.],
amino acid residue substituted with heterocycliccarbamoyl-
heterocyclic(lower)alkenoyl [e.g.
pyridylcarbamoylpyridylacryloylglycyl,
morpholinylcarbamoylpyridylacryloylglycyl,
thienylcarbamoylpyridylacryloylglycyl,
pyrimidinylcarbamoylpyridylacryloylglycyl, etc.], amino
acid residue substituted with heterocyclic(lower)
alkylcarbamoyl-heterocyclic(lower)alkenoyl [e.g.
pyridylmethylcarbamoylpyridylacryloylglycyl,
furylmethylcarbamoylpyridylacryloylglycyl,
thienylmethylcarbamoylpyridylacryloylglycyl, etc.], amino
acid residue substituted with heterocycliccarbonyl-
heterocyclic(lower)alkenoyl [e.g.
morpholinocarbonylpyridylacryloylglycyl,
pyrrolidinylcarbonylpyridylacryloylglycyl,
piperidinocarbonylpyridylacryloylglycyl, etc.], amino acid
residue substituted with lower alkenylcarbamoyl-
heterocyclic(lower)alkenoyl [e.g.
vinylcarbamoylpyridylacryloylglycyl,
allylcarbamoylpyridylacryloylglycyl, etc.], amino acid resi-
due substituted with lower alkynylcarbamoyl-heterocyclic
(lower)alkenoyl [e.g.
ethynylcarbamoylpyridylacryloylglycyl,
propynylcarbamoylpyridylacryloylglycyl, etc.], etc., amino
acid residue substituted with heterocyclicthio(lower)
alkanoyl [e.g. pyridylthioacetylglycyl,
pyrimidinylthioacetylglycyl,
imidazolylthiopropionylglycyl, etc.], amino acid residue
substituted with optionally substituted heterocycliccarbonyl
[e.g. morpholinocarbonylglycyl, indolylcarbonylglycyl,
4-methyl-1-piperazinylcarbonylglycyl, etc.], amino acid
residue substituted with cyclo(lower)alkylcarbonyl [e.g.
cyclopropylcarbonylglycyl, cyclopentylcarbonylglycyl,
cyclohexylcarbonylglycyl, cyclohexylcarbonylsarcosyl,
etc.], amino acid residue substituted with lower alkoxycar-
bonyl [e.g. methoxycarbonylglycyl, tert-
butoxycarbonylglycyl, tert-butoxycarbonylsarcosyl, tert-
butoxycarbonylalanyl, etc.], amino acid residue substituted
with aryloxycarbonyl [e.g. phenoxycarbonylglycyl, etc.],
amino acid residue substituted with aroyl(lower)alkanoyl
[e.g. phenyloxalylglycyl, benzoylpropionylglycyl, etc.],
amino acid residue substituted with aroyl [e.g.
benzoylglycyl, naphthoylglycyl, benzoylsarcosyl,
benzoylalanyl, etc.], amino acid residue substituted with
nitro-aryloxycarbonyl [e.g. nitrophenyloxycarbonylglycyl,
etc.], amino acid residue substituted with carbamoyl [e.g.
carbamoylglycyl, carbamoylalanyl, carbamoylsarcosyl,
carbamoyl-β-alanyl, etc.], amino acid residue substituted
with lower alkylcarbamoyl [e.g. methylcarbamoylglycyl,
ethylcarbamoylglycyl, propylcarbamoylglycyl,
isopropylcarbamoylglycyl, methylcarbamoylsarcosyl,
ethylcarbamoylalanyl, isopropylcarbamoyl-β-alanyl,
pentylcarbamoylglycyl, etc.], amino acid residue substituted
with lower alkoxycarbonyl(lower)alkylcarbamoyl [e.g.
methoxycarbonylmethylcarbamoylglycyl,
ethoxycarbonylmethylcarbamoylglycyl, etc.], amino acid
residue substituted with lower alkenylcarbamoyl [e.g.
vinylcarbamoylglycyl, allylcarbamoylglycyl,
allylcarbamoylsarcosyl, etc.], amino acid residue substituted
with cyclo(lower)alkylcarbamoyl [e.g.
cyclopropylcarbamoylglycyl, cyclohexylcarbamoylglycyl,
cyclohexylcarbamoylsarcosyl, etc.], amino acid residue sub-
stituted with arylcarbamoyl [e.g. phenylcarbamoylglycyl,
naphthylcarbamoylglycyl, tolylcarbamoylglycyl,
ethylphenylcarbamoylglycyl, phenylcarbamoylalanyl,
phenylcarbamoylsarcosyl, etc.], amino acid residue substi-
tuted with lower alkoxy-arylcarbamoyl [e.g.
methoxyphenylcarbamoylglycyl,
ethoxyphenylcarbamoylglycyl,
methoxyphenylcarbamoylalanyl, etc.], amino acid residue
substituted with halo(lower)alkyl-arylcarbamoyl [e.g.
trifluoromethylphenylcarbamoylglycyl,
trifluoromethylphenylcarbamoylalanyl,
trifluoromethylphenylcarbamoylsarcosyl, etc.], amino acid
residue substituted with halo-arylcarbamoyl [e.g.
chlorophenylcarbamoylglycyl,
fluorophenylcarbamoylglycyl,
fluorophenylcarbamoylalanyl, etc.], amino acid residue sub-
stituted with hydroxy(lower)alkyl-arylcarbamoyl [e.g.
hydroxymethylphenylcarbamoylglycyl,
hydroxyethylphenylcarbamoylglycyl,
hydroxyethylphenylcarbamoylalanyl, etc.], amino acid resi-
due substituted with nitro-arylcarbamoyl [e.g.
nitrophenylcarbamoylglycyl, etc.], amino acid residue sub-
stituted with cyano-arylcarbamoyl [e.g.
cyanophenylcarbamoylglycyl, etc.], amino acid residue sub-
stituted with amino-arylcarbamoyl [e.g.
aminophenylcarbamoylglycyl, etc.], amino acid residue sub-
stituted with lower alkylamino-acrylcarbamoyl [e.g.
methylaminophenylcarbamoylglycyl,
ethylaminophenylcarbamoylglycyl,
dimethylaminophenylcarbamoylglycyl, etc.], amino acid
residue substituted with lower alkanoylamino-
arylcarbamoyl [e.g. acetylaminophenylcarbamoylglycyl,
propionylaminophenylcarbamoylglycyl, etc.], amino acid
residue substituted with N-(lower alkanoyl)-N-(lower alkyl)
amino-arylcarbamoyl [e.g. N-acetyl-N-
methylaminophenylcarbamoylglycyl, N-propionyl-N-
methylaminophenylcarbamoylglycyl, etc.], amino acid
residue substituted with lower alkoxy(lower)
alkanoylamino-arylcarbamoyl [e.g.
methoxyacetylaminophenylcarbamoylglycyl,
methoxypropionylaminophenylcarbamoylglycyl, etc.],
amino acid residue substituted with lower alkoxycarbonyl
(lower)alkanoylamino-arylcarbamoyl [e.g.
ethoxycarbonylacetylaminophenylcarbamoylglycyl,
methoxycarbonylpropionylaminophenylcarbamoylglycyl,
etc.], amino acid residue substituted with carboxyamino-
arylcarbamoyl [e.g. carboxyaminophenylcarbamoylglycyl,
etc.], amino acid residue substituted with lower
alkoxycarbonylamino-arylcarbamoyl [e.g.
ethoxycarbonylaminophenylcarbamoylglycyl, etc.], amino
acid residue substituted with aroylamino-arylcarbamoyl
[e.g. benzoylaminophenylcarbamoylglycyl, etc.], amino
acid residue substituted with heterocyclicarbonylamino-
arylcarbamoyl [e.g.
pyridylcarbonylaminophenylcarbamoylglycyl,
furylcarbonylaminophenylcarbamoylglycyl,
morpholinocarbonylaminophenylcarbamoylglycyl, etc.],
amino acid residue substituted with heterocyclic(lower)
alkanoylamino-arylcarbamoyl [e.g.
pyridylacetylaminophenylcarbamoylglycyl, thienylacetylaminophenylcarbamoylglycyl, etc.], amino acid residue substituted with ureido-arylcarbamoyl [e.g. ureidophenylcarbamoylglycyl, etc.], amino acid residue substituted with lower alkylureido-arylcarbamoyl [e.g. methylureidophenylcarbamoylglycyl, ethylureidophenylcarbamoylglycyl, etc.], amino acid residue substituted with hydroxyimino(lower)alkyl-arylcarbamoyl [e.g. hydroxyiminoethylphenylcarbamoylglycyl, etc.], amino acid residue substituted with lower alkoxyimino(lower) alkyl-arylcarbamoyl [e.g. methoxyiminoethylphenylcarbamoylglycyl, etc.], amino acid residue substituted with lower alkylhydrazono(lower) alkyl-arylcarbamoyl [e.g. methylhydrazonoethylphenylcarbamoylglycyl, dimethylhydrazonoethylphenylcarbamoylglycyl, etc.], amino acid residue substituted with optionally substituted heterocyclic-arylcarbamoyl [e.g. oxopyrrolidinylphenylcarbamoylglycyl, oxopiperidinophenylcarbamoylglycyl, dioxopyrrolidinylphenylcarbamoylglycyl, oxooxazolidinylphenylcarbamoylglycyl, pyrrolylphenylcarbamoylglycyl, etc.], amino acid residue substituted with acyl-arylcarbamoyl, for example, amino acid residue substituted with lower alkanoyl-arylcarbamoyl [e.g. acetylphenylcarbamoylglycyl, propionylphenylcarbamoylglycyl, etc.], amino acid residue substituted with heterocyccliccarbonyl-arylcarbamoyl [e.g. morpholinocarbonylphenylcarbamoylglycyl, piperidinocarbonylphenylcarbamoylglycyl, piperazinylcarbonylphenylcarbamoylglycyl, thiomorpholinocarbonylphenylcarbamoylalanyl, pyrrolidinylcarbonylphenylcarbamoylglycyl, 1,2,3,6-tetrahydropyridylcarbonylphenylcarbamoylglycyl, etc.], amino acid residue substituted with carboxy-arylcarbamoyl [e.g. carboxyphenylcarbamoylglycyl, etc.], amino acid residue substituted with lower alkoxycarbonyl-arylcarbamoyl [e.g. methoxycarbonylphenylcarbamoylglycyl, ethoxycarbonylphenylcarbamoylglycyl, etc.], amino acid residue substituted with carbamoyl-arylcarbamoyl [e.g. carbamoylphenylcarbamoylglycyl, etc.], amino acid residue substituted with lower alkylcarbamoyl-arylcarbamoyl [e.g. methylcarbamoylphenylcarbamoylglycyl, ethylcarbamoylphenylcarbamoylglycyl, propylcarbamoylphenylcarbamoylglycyl, dimethylcarbamoylphenylcarbamoylglycyl, diethylcarbamoylphenylcarbamoylglycyl, N-ethyl-N-methylcarbamoylphenylcarbamoylglycyl, N-isopropyl-N-methylcarbamoylphenylcarbamoylglycyl, etc.], amino acid residue substituted with heterocycliccarbonyl-arylcarbamoyl having lower alkyl [e.g. methylpiperazinylcarbonylphenylcarbamoylglycyl, ethylpiperazinylcarbonylphenylcarbamoylglycyl, etc.], amino acid residue substituted with heterocycliccarbonyl-arylcarbamoyl having aryl [e.g. phenylpiperazinylcarbonylphenylcarbamoylglycyl, etc.], amino acid residue substituted with heterocycliccarbonyl-arylcarbamoyl having a heterocyclic group [e.g. pyridylpiperazinylcarbonylphenylcarbamoylglycyl, etc.], amino acid residue substituted with heterocycliccarbonyl-arylcarbamoyl having lower alkanoyl [e.g. acetylpiperazinylcarbonylphenylcarbamoylglycyl, etc.], amino acid residue substituted with heterocycliccarbonyl-arylcarbamoyl having lower alkoxycarbonyl [e.g. ethoxycarbonylpiperazinylcarbonylphenylcarbamoylglycyl, etc.], amino acid residue substituted with heterocycliccarbonyl-arylcarbamoyl having lower alkylamino [e.g. methylaminopiperazinylcarbonylphenylcarbamoylglycyl, dimethylaminopiperidinocarbonylphenylcarbamoylglycyl, etc.], amino acid residue substitued with heterocycliccarbonyl-arylcarbamoyl having lower alkylcarbamoyl [e.g. methylcarbamoylpiperazinylcarbonylphenylcarbamoylglycyl, etc.], amino acid residue substituted with hydroxy(lower) alkylcarbamoyl-arylcarbamoyl [e.g. hydroxymethylcarbamoylphenylcarbamoylglycyl, hydroxyethylcarbamoylphenylcarbamoylglycyl, bis(hydroxyethyl)carbamoylphenylcarbamoylglycyl, etc.], amino acid residue substituted with N-[hydroxy(lower)alkyl]-N-(lower alkyl)carbamoyl-arylcarbamoyl [e.g. N-(hydroxyethyl)-N-methylcarbamoylphenylcarbamoylglycyl, etc.], amino acid residue substituted with lower alkoxy(lower) alkylcarbamoyl-arylcarbamoyl [e.g. methoxymethylcarbamoylphenylcarbamoylglycyl, methoxyethylcarbamoylphenylcarbamoylglycyl, ethoxyethylcarbamoylphenylcarbamoylglycyl, bis(methoxyethyl)carbamoylphenylcarbamoylglycyl, bis(ethoxyethyl)carbamoylphenylcarbamoylglycyl, etc.], amino acid residue substituted with N-[lower alkoxy(lower)alkyl]-N-(lower alkyl)carbamoyl-arylcarbamoyl [e.g. N-(methoxyethyl)-N-methylcarbamoylphenylcarbamoylglycyl, N-(methoxypropyl)-N-methylcarbamoylphenylcarbamoylglycyl, etc.], amino acid residue substituted with lower alkylamino(lower) alkylcarbamoyl-arylcarbamoyl [e.g. methylaminoethylcarbamoylphenylcarbamoylglycyl, dimethylaminoethylcarbamoylphenylcarbamoylglycyl, etc.], amino acid residue substituted with N-[lower alkylamino(lower)alkyl]-N-(lower alkyl)carbamoyl-arylcarbamoyl [e.g. N-(dimethylaminoethyl)-N-methylcarbamoylphenylcarbamoylglycyl, N-(dimethylaminopropyl)-N-methylcarbamoylphenylcarbamoylglycyl, etc.], amino acid residue substituted with heterocycliccarbamoyl-arylcarbamoyl [e.g. morpholinylcarbamoylphenylcarbamoylglycyl, thienylcarbamoylphenylcarbamoylglycyl, pyridylcarbamoylphenylcarbamoylglycyl, pyrimidinylcarbamoylphenylcarbamoylglycyl, etc.], amino acid residue substituted with N-(heterocyclic)-N-(lower alkyl)carbamoyl-arylcarbamoyl [e.g. N-pyridyl-N-methylcarbamoylphenylcarbamoylglycyl, etc.], amino acid residue substituted with heterocyclic(lower)alkylcarbamoyl-arylcarbamoyl [e.g. pyridylmethylcarbamoylphenylcarbamoylglycyl, pyridylethylcarbamoylphenylcarbamoylglycyl, thienylmethylcarbamoylphenylcarbamoylglycyl, etc.], amino acid residue substituted with N-[heterocyclic(lower)alkyl]-N-(lower alkyl)carbamoyl-arylcarbamoyl [e.g. N-pyridylmethyl-N-methylcarbamoylphenylcarbamoylglycyl, etc.], amino acid residue substituted with N-[heterocyclic(lower)alkyl]-N-[lower alkoxy(lower)alkyl]carbamoyl-arylcarbamoyl [e.g. N-pyridylmethyl-N-methoxyethylcarbamoylphenylcarbamoylglycyl, etc.], amino acid residue substituted with arylcarbamoyl-arylcarbamoyl [e.g. phenylcarbamoylphenylcarbamoylglycyl, etc.], amino acid residue substituted with lower alkylaminoarylcarbamoyl-arylcarbamoyl [e.g. dimethylaminophenylcarbamoylphenylcarbamoylglycyl, etc.], etc., amino acid residue substituted with arylthiocarbamoyl [e.g. phenylthiocarbamoylglycyl, naphthylthiocarbamoylglycyl, phenylthiocarbamoylalanyl, phenylthiocarbamoylsarcosyl, etc.], amino acid residue substituted with ar(lower)alkylcarbamoyl [e.g. benzylcarbamoylglycyl, benzylcarbamoylsarcosyl, benzylcarbamoylalanyl, etc.], amino acid residue substituted with aroylcarbamoyl [e.g. benzoylcarbamoylglycyl, etc.], amino acid residue substituted with heterocycliccarbamoyl [e.g. pyridylcarbamoylglycyl, pyridylcarbamoylalanyl, pyridylcarbamoylsarcosyl, thienylcarbamoylglycyl, pyrazolylcarbamoylglycyl, pyrimidinylcarbamoylglycyl, quinolylcarbamoylglycyl, isoguinolylcarbamoylglycyl, etc.], amino acid residue substituted with heterocyclic (lower)alkylcarbamoyl [e.g. pyridylmethylcarbamoylglycyl, pyridylethylcarbamoylglycyl, thienylmethylcarbamoylglycyl, etc.], amino acid residue substituted with arylaminocarbamoyl [e.g. phenylaminocarbamoylglycyl, etc.], amino acid residue substituted with ar(lower)alkenylsulfonyl [e.g. styrylsulfonylglycyl, cinnamoylsulfonylglycyl, etc.], amino acid residue substituted with lower alkylsulfonyl [e.g. mesylglycyl, ethylsulfonylglycyl, mesylsarcosyl, mesylalanyl, etc.], amino acid residue substituted with phthaloyl [e.g. phthaloylglycyl, phthaloylalanyl, phthaloyl-β-alanyl, etc.], amino acid residue having unsubstituted amino acid residue [e.g. glycylglycyl, alanylglycyl, sarcosylglycyl, prolylglycyl, glycylsarcosyl, prolylsarcosyl, etc.], amino acid residue having substituted amino acid residue [e.g. amino acid residue having amino acid residue substituted with lower alkyl (e.g. dimethylglycylglycyl, diethylglycylglycyl, dimethylglycylsarcosyl, ethylsarcosylglycyl, isopropylsarcosylglycyl, ethylglycylglycyl, propylglycylglycyl, isopropylglycylglycyl, ethylglycylalanyl, dimethylglycylalanyl, dimethylalanylglycyl, dimethyl-β-alanylglycyl, etc.), amino acid residue having amino acid residue substituted with a heterocyclic group (e.g. morpholinoglycylglycyl, piperidinoglycylglycyl, pyridylglycylglycyl, piperidinosarcosylglycyl, etc.), amino acid residue having amino acid residue substituted with heterocyclic(lower)alkyl (e.g. pyridylmethylglycylglycyl, imidazolylmethylglycylglycyl, furylmethylglycylglycyl, thienylmethylsarcosylglycyl, etc.), amino acid residue having amino acid residue substituted with cycloalkyl (e.g. cyclopropylglycylglycyl, cyclobutylglycylglycyl, cyclopentylglycylglycyl, cyclohexylglycylglycyl, cycloheptylglycylglycyl, cyclooctylglycylglycyl, adamantylglycylglycyl, cyclohexylsarcosylglycyl, cycloheptylsarcosylglycyl, cyclohexylglycylsarcosyl, cyclohexylglycylalanyl, etc.), amino acid residue having amino acid residue substituted with aryl (e.g. phenylglycylglycyl, phenylsarcosylglycyl, etc.), amino acid residue having amino acid residue substituted with acyl {e.g. amino acid residue having amino acid residue substituted with alkanoyl (e.g. acetylglycylglycyl, acetylprolylglycyl, propionylglycylglycyl, acetylalanylglycyl, etc.), amino acid residue having amino acid residue substituted with lower alkoxycarbonyl (e.g. tert-butoxycarbonylglycylglycyl, tert-butoxycarbonylprolylglycyl, etc.), amino acid residue having amino acid residue substituted with phthaloyl (e.g. phthaloylglycylglycyl, etc.), etc.}, amino acid residue having amino acid residue substituted with ar(lower)alkyl (e.g. benzylglycylglycyl, etc.), etc.], etc., or the like.

Groups of the formulas of the compounds [If] and [Ig]:

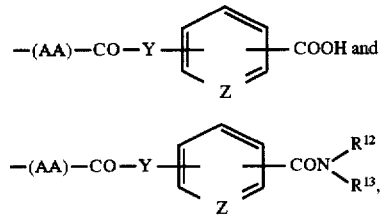

wherein $R^{12}$, $R^{13}$, (AA), Y and Z are each as defined above, are also included within "acyl".

Suitable "acyl having amino" may be unsubstituted amino acid residue, amino acid residue having unsubstituted amino acid residue, or the like, and preferred examples thereof can be referred to those exemplified above.

Suitable "acyl having acylamino" may be amino acid residue substituted with acyl, amino acid residue having amino acid residue substituted with acyl, or the like, and preferred examples thereof can be referred to those exemplified above.

Suitable "protected or unprotected hydroxy(lower)alkyl" may be hydroxymethyl, hydroxyethyl, hydroxypropyl, benzyloxymethyl, tert-butyldiphenylsilyloxyethyl or the like.

Suitable "lower alkoxy(lower)alkyl" may be methoxymethyl, methoxyethyl, methoxypropyl, ethoxymethyl, ethoxyethyl, or the like.

Suitable "lower alkylamino(lower)alkyl" may be methylaminomethyl, methylaminoethyl, methylaminopropyl, dimethylaminomethyl, dimethylaminoethyl, dimethylaminopropyl, diethylaminoethyl, or the like.

Suitable "acyl having lower alkylamino" may be amino acid residue substituted with lower alkyl, amino acid residue having amino acid residue substituted with lower alkyl, or the like, and preferred examples thereof can be referred to those exemplified above.

Suitable "acyl having ar(lower)alkylamino" may be amino acid residue substituted with ar(lower)alkyl, amino acid residue having amino acid residue substituted with ar(lower)alkyl, or the like, and preferred examples thereof can be referred to those exemplified above.

Suitable "heterocyclic group" and heterocyclic moiety in the term "heterocyclic(lower)alkyl" may be saturated or unsaturated, monocyclic or polycyclic heterocyclic group containing at least one hetero-atom such as an oxygen, sulfur and/or nitrogen atom such as:

unsaturated 3 to 8-membered, preferably 5 or 6-membered heteromonocyclic group containing 1 to 4 nitrogen atom(s), for example, pyrrolyl, pyrrolinyl, imidazolyl, pyrazolyl, pyridyl, and its N-oxide, pyrimidinyl, pyrazinyl, pyridazinyl, triazolyl, tetrazolyl, dihydrotriazinyl, etc.;

saturated 3 to 8-membered, preferably 4 or 6-membered heteromonocyclic group containing 1 to 4 nitrogen atom(s), for example, azetidinyl, pyrrolidinyl, imidazolidinyl, piperidyl, pyrazolidinyl, piperazinyl, etc.;

unsaturated condensed 7 to 12-membered heterocyclic group containing 1 to 5 nitrogen atom(s), for example, indolyl, isoindolyl, indolizinyl, benzimidazolyl, quinolyl, isoquinolyl, tetrahydroquinolyl, indazolyl, benzotriazolyl, imidazopyridyl, etc.;

unsaturated 3 to 8-membered, preferably 5 or 6-membered heteromonocyclic group containing an oxygen atom, for example, furyl, etc.;

unsaturated condensed 7 to 12-membered heterocyclic group containing 1 to 2 oxygen atom(s), for example, benzofuryl, piperonyl, etc.;

unsaturated 3 to 8-membered, preferably 5 or 6-membered heteromonocyclic group containing a sulfur atom, for example, thienyl, etc.;

unsaturated condensed 7 to 12-membered heterocyclic group containing 1 to 2 sulfur atom(s), for example, benzothienyl, etc.;

unsaturated 3 to 8-membered, preferably 5 or 6-membered heteromonocyclic group containing 1 to 2 oxygen atom(s) and 1 to 3 nitrogen atom(s), for example, oxazolyl, isoxazolyl, oxadiazolyl, etc.;

saturated 3 to 8-membered, preferably 5 or 6-membered heteromonocyclic group containing 1 to 2 oxygen atom(s) and 1 to 3 nitrogen atom(s), for example, morpholinyl, etc.;

unsaturated condensed 7 to 12-membered heterocyclic group containing 1 to 2 oxygen atom(s) and 1 to 3 nitrogen atom(s), for example, benzoxazolyl, benzoxadiazolyl, etc.;

unsaturated 3 to 8-membered, preferably 5 or 6-membered heteromonocyclic group containing 1 to 2 sulfur atom(s) and 1 to 3 nitrogen atom(s), for example, thiazolyl, isothiazolyl, thiazolinyl, thiadiazolyl, etc.;

saturated 3 to 8-membered, preferably 5 or 6-membered heteromonocyclic group containing 1 to 2 sulfur atom(s) and 1 to 3 nitrogen atom(s), for example, thiazolidinyl, etc.;

unsaturated condensed 7 to 12-membered heterocyclic group containing 1 to 2 sulfur atom(s) and 1 to 3 nitrogen atom(s), for example, benzothiazolyl, benzothiadiazolyl, benzothiazinyl, benzothiazolinyl, etc., or the like.

Suitable substituents in the terms "aryl having suitable substituent(s)" or "heterocyclic group optionally having suitable substituent(s)" may be the above-mentioned halogen; the above-mentioned halo(lower)alkyl; the above-mentioned lower alkyl; the above-mentioned acyl; the above-mentioned aryl; aryl substituted with substituent(s) such as halogen or cyano [e.g. chlorophenyl, cyanophenyl, etc.]; ar(lower)alkyl substituted with hydroxy [e.g. hydroxybenzyl, etc.]; lower alkoxy [e.g. methoxy, ethoxy, propoxy, isopropoxy, butoxy, isobutoxy, tert-butoxy, pentyloxy, hexyloxy, etc.]; oxo; nitro; amino; amino substituted with the above-mentioned lower alkyl, the above-mentioned acyl, ar(lower)alkyl [e.g. benzyl, phenethyl, trityl, etc.], heterocyclic(lower)alkyl [e.g. pyridylmethyl, etc.], carboxy(lower)alkyl [e.g. carboxymethyl, carboxyethyl, etc.], lower alkylaminomethylene [e.g. dimethylaminomethylene, diethylaminomethylene, etc.], N-methylpyrrolidinylidene, etc.; the above-mentioned heterocyclic group; heterocyclic group substituted with oxo [e.g. pyrrolidonyl, etc.]; or the like.

Suitable "heterocyclic group" formed by $R^{12}$, $R^{13}$ and the attached nitrogen atom may be morpholino, thiomorpholino, pyrrolidin-1-yl, piperidino, 1,2,3,6-tetrahydropyridin-1-yl, piperazin-1-yl, or the like. And said heterocyclic group may be substituted with suitable substituent(s) such as the above-mentioned lower alkyl, the above-mentioned heterocyclic group, the above-mentioned acyl, lower alkylamino, the above-mentioned aryl, or the like.

Preferred examples of "heterocyclic(lower)alkyl" may be morpholinomethyl, morpholinoethyl, pyridylmethyl, pyridylethyl, thienylmethyl, piperidinomethyl, imidazolylmethyl, or the like.

Particularly, the preferred embodiments of $R^1$, $R^2$, $R^3$, $R^4$, Q and A are as follows $R^1$ is halogen such as fluorine, chlorine, bromine and iodine;

$R^2$ and $R^3$ are each hydrogen; lower alkyl such as methyl, ethyl, propyl, isopropyl, butyl, isobutyl, tert-butyl, pentyl and hexyl; halo(lower)alkyl such as fluoromethyl, chloromethyl, bromomethyl and trifluoromethyl; or acyl such as carboxy and esterified carboxy, for example, lower alkoxycarbonyl [e.g. methoxycarbonyl, ethoxycarbonyl, tert-butoxycarbonyl, etc.];

$R^4$ is phenyl substituted with substituent(s) such as halogen such as fluorine, chlorine, bromine and iodine, lower alkyl such as methyl, ethyl, propyl and isopropyl, halo(lower)alkyl such as trifluoromethyl, phenyl, cyanophenyl, hydroxybenzyl, lower alkoxy such as methoxy, ethoxy, propoxy and isopropoxy, nitro, a group of the formula:

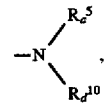

in which $R_a^5$ is hydrogen; lower alkyl such as methyl, ethyl, propyl and butyl; carboxy(lower)alkyl such as carboxymethyl and carboxyethyl; and acyl such as lower alkanoyl [e.g. formyl, acetyl, propionyl, etc.], carboxy and esterified carboxy [e.g. lower alkoxycarbonyl (e.g. methoxycarbonyl, ethoxycarbonyl, tert-butoxycarbonyl, etc.), etc.], $R_d^{10}$ is hydrogen; lower alkyl such as methyl, ethyl, propyl, isopropyl and butyl; ar(lower)alkyl such as benzyl; heterocyclic(lower)alkyl such as pyridyl (lower)alkyl [e.g. pyridylmethyl, pyridylethyl, etc.]; and acyl such as lower alkanoyl [e.g. formyl, acetyl, propionyl, butyryl, isobutyryl, etc.], halo(lower) alkanoyl [e.g. trifluoroacetyl, etc.], carboxy, esterified carboxy [e.g. lower alkoxycarbonyl (e.g. methoxycarbonyl, ethoxycarbonyl, tert-butoxycarbonyl, etc.), etc.], hydroxy(lower)alkanoyl [e.g. glycoloyl, lactoyl, 3-hydroxypropionyl, etc.], lower alkanoyloxy(lower)alkanoyl [e.g. acetyloxyacetyl, acetyloxypropionyl, etc.], lower alkoxy(lower)alkanoyl [e.g. methoxyacetyl, methoxypropionyl, etc.], benzoyl, toluoyl, benzoyl substituted with lower alkoxy [e.g. methoxybenzoyl, etc.], benzoyl substituted with esterified carboxy [e.g. lower alkoxycarbonylbenzoyl (e.g. methoxycarbonylbenzoyl, tert-butoxycarbonylbenzoyl, etc.), etc.], benzoyl substituted with halogen [e.g. chlorobenzoyl, fluorobenzoyl etc.], phenoxycarbonyl optionally substituted with nitro, lower alkylsulfonyl [e.g. mesyl, ethylsulfonyl, etc.], carbamoyl, lower alkylcarbamoyl [e.g. methylcarbamoyl, ethylcarbamoyl, isopropylcarbamoyl, etc.], halo(lower) alkanoylcarbamoyl [e.g. trichloroacetylcarbamoyl, etc.], phenylcarbamoyl, unsubstituted amino acid residue [e.g. glycyl, sarcosyl, alanyl, β-alanyl, etc.] and substituted amino acid residue [e.g. amino acid residue substituted with lower alkyl (e.g. ethylglycyl, isopropylglycyl, dimethylglycyl, diethylglycyl, ethylsarcosyl, isopropylsarcosyl, methylalanyl, methyl-β-alanyl, etc.), amino acid residue substituted with optionally substituted amidino (e.g. amidinoglycyl, N-ethyl-N'-cyanoamidinoglycyl, etc.), amino acid residue substituted with acyl {e.g. amino acid residue substituted with alkanoyl (e.g. formylglycyl, acetylglycyl, acetylsarcosyl, acetylalanyl, acetyl-β-alanyl, propionylglycyl, butyrylglycyl, isobutyrylglycyl, valerylglycyl, isovalerylglycyl, pivaloylglycyl, hexanoylglycyl, heptanoylglycyl, etc.), amino acid residue substituted with halo(lower)alkanoyl (e.g. trifluoroacetylglycyl, trifluoroacetylsarcosyl, trifluoroacetylalanyl, bromoacetylglycyl, heptafluorobutyrylglycyl, etc.), amino acid residue substituted with hydroxy(lower) alkanoyl (e.g. glycoloylglycyl, glycoloylsarcosyl, lactoylglycyl, lactoylalanyl, etc.), amino acid residue substituted with lower alkylsulfonyloxy(lower) alkanoyl (e.g. mesyloxyacetylglycyl, ethylsulfonyloxyacetylglycyl, mesyloxyacetylsarcosyl, etc.), amino acid residue substituted with lower alkoxy (lower)alkanoyl (e.g. methoxyacetylglycyl, ethoxyacetylglycyl, methoxyacetylsarcosyl, methoxypropionylalanyl, etc.), amino acid residue substituted with aryloxy(lower)alkanoyl (e.g. phenyloxyacetylglycyl, phenyloxypropionylglycyl, phenyloxyacetylsarcosyl, etc.), amino acid residue substituted with lower alkylthio(lower)alkanoyl (e.g. methylthioacetylglycyl, methylthiopropionylglycyl, etc.), amino acid residue substituted with lower alkylcarbamoyl(lower)alkanoyl (e.g. methylcarbamoylpropionylglycyl, methylcarbamoylpropionylalanyl, etc.), amino acid residue substituted with lower alkanoyloxy(lower) alkanoyl (e.g. acetyloxyacetylglycyl, acetyloxyacetylsarcosyl, propionyloxyacetylglycyl, acetyloxypropionylalanyl, etc.), amino acid residue substituted with carboxy(lower)alkanoyl (e.g. carboxyacetylglycyl, carboxypropionylglycyl, carboxypropionylsarcosyl, carboxyacetylalanyl, etc.), amino acid residue substituted with lower alkoxycarbonyl(lower)alkanoyl (e.g. methoxycarbonylacetylglycyl, ethoxycarbonylpropionylglycyl, methoxycarbonylacetylsarcosyl, etc.), amino acid residue substituted with ar(lower)alkanoyl (e.g. phenylacetylglycyl, phenylpropionylglycyl, phenylbutyrylglycyl, phenylacetylsarcosyl, phenylpropionylalanyl, naphthylacetylglycyl, etc.), amino acid residue substituted with optionally substituted heterocyclic(lower)alkanoyl (e.g. morpholinoacetylglycyl, pyridylacetylglycyl, morpholinopropionylalanyl, imidazolylacetylglycyl, piperidinoacetylglycyl, pyrrolidinylacetylglycyl, hexamethyleneiminoacetylglycyl, methylpiperazinylacetylglycyl, pyridylpiperazinylacetylglycyl, thiomorpholinoacetylglycyl, its oxide or dioxide, etc.), amino acid residue substituted with lower alkenoyl (e.g. acryloylglycyl, crotonoylglycyl, 3-pentenoylglycyl, 3-butenoylglycyl, 4-pentenoylglycyl, 3-butenoylsarcosyl, etc.), amino acid residue substituted with ar(lower)alkenoyl (e.g. cinnamoylglycyl, α-methylcinnamoylglycyl, 4-methylcinnamoylglycyl, etc.), amino acid residue substituted with lower alkoxy-ar(lower)alkenoyl (e.g. methoxycinnamoylglycyl, ethoxycinnamoylglycyl, dimethoxycinnamoylglycyl, etc.), amino acid residue substituted with lower alkylenedioxy-ar(lower) alkenoyl (e.g. methylenedioxycinnamoylglycyl, ethylenedioxycinnamoylglycyl, etc.), amino acid residue substituted with nitro-ar(lower)alkenoyl (e.g. nitrocinnamoylglycyl, etc.), amino acid residue substituted with cyano-ar(lower)alkenoyl (e.g. cyanocinnamoylglycyl, etc.), amino acid residue substituted with halo-ar(lower)alkenoyl (e.g. chlorocinnamoylglycyl, fluorocinnamoylglycyl, etc.), amino acid residue substituted with hydroxy-ar(lower) alkenoyl (e.g. hydroxycinnamoylglycyl, etc.), amino acid residue substituted with hydroxy(lower)alkoxy-ar(lower)alkenoyl (e.g. hydroxymethoxycinnamoylglycyl, hydroxyethoxycinnamoylglycyl, etc.), amino acid residue substituted with amino(lower)alkoxy-ar(lower) alkenoyl (e.g. aminoethoxycinnamoylglycyl, etc.), amino acid residue substituted with lower alkylamino (lower)alkoxy-ar(lower)alkenoyl (e.g. methylaminomethoxycinnamoylglycyl, dimethylaminoethoxycinnamoylglycyl, etc.), amino acid residue substituted with heterocyclic(lower)alkoxy-ar(lower)alkenoyl (e.g. pyridylmethoxycinnamoylglycyl, etc.), amino acid residue substituted with optionally substituted heterocyclic-ar(lower)alkenoyl (e.g. morpholinocinnamoylglycyl, methylpiperazinylcinnamoylglycyl, pyrrolidinylcinnamoylglycyl, oxopyrrolidinylcinnamoylglycyl, oxopiperidinocinnamoylglycyl, dioxopyrrolidinylcinnamoylglycyl, oxooxazolidinylcinnamoylglycyl, pyrrolylcinnamoylglycyl, tetrazolylcinnamoylglycyl, etc.), amino acid residue substituted with amino-ar(lower)alkenoyl (e.g. aminocinnamoylglycyl, etc.), amino acid residue substituted with lower alkylamino-ar(lower)alkenoyl (e.g. methylaminocinnamoylglycyl, dimethylaminocinnamoylglycyl, etc.), amino acid residue substituted with lower alkanoylamino-ar(lower) alkenoyl (e.g. acetylaminocinnamoylglycyl, propionylaminocinnamoylglycyl, isobutyrylaminocinnamoylglycyl, etc.), amino acid residue substituted with cycloalkyl(lower) alkanoylamino-ar(lower)alkenoyl (e.g. cyclopentylacetylaminocinnamoylglycyl, cyclohexylacetylaminocinnamoylglycyl, adamantylacetylaminocinnamoylglycyl, etc.), amino acid residue substituted with cycloalkylcarbonylamino-ar(lower)alkenoyl (e.g. cyclopropylcarbonylaminocinnamoylglycyl, cyclopentylcarbonylaminocinnamoylglycyl, cyclohexylcarbonylaminocinnamoylglycyl, adamantylcarbonylaminocinnamoylglycyl, etc.), amino acid residue substituted with lower alkenoylamino-ar(lower)alkenoyl (e.g. acryloylaminocinnamoylglycyl, crotonoylaminocinnamoylglycyl, etc.) amino acid residue substituted with lower alkoxycarbonylamino-ar (lower)alkenoyl (e.g. methoxycarbonylaminocinnamoylglycyl, ethoxycarbonylaminocinnamoylglycyl, etc.), amino acid residue substituted with hydroxy(lower) alkanoylamino-ar(lower)alkenoyl (e.g. hydroxyacetylaminocinnamoylglycyl, hydroxypropionylaminocinnamoylglycyl, etc.), amino acid residue substituted with lower alkoxy(lower)alkanoylamino-ar(lower)alkenoyl (e.g. methoxyacetylaminocinnamoylglycyl, methoxypropionylaminocinnamoylglycyl, etc.), amino acid residue substituted with halo(lower)alkanoylamino-ar(lower)alkenoyl (e.g. chloroacetylaminocinnamoylglycyl, trifluoroacetylaminocinnamoylglycyl, bromobutyrylaminocinnamoylglycyl, etc.), amino acid residue substituted with amino(lower)alkanoylamino-ar(lower)alkenoyl (e.g. aminoacetylaminocinnamoylglycyl, aminopropionylaminocinnamoylglycyl, etc.), amino acid residue substituted with lower alkylamino(lower)alkanoylamino-ar(lower)alkenoyl (e.g. methylaminoacetylaminocinnamoylglycyl, dimethylaminoacetylaminocinnamoylglycyl, etc.), amino acid residue substituted with lower alkanoylamino(lower)alkanoylamino-ar(lower)alkenoyl (e.g. acetylaminoacetylaminocinnamoylglycyl, acetylaminopropionylaminocinnamoylglycyl, etc.), amino acid residue substituted with carboxy(lower)alkanoylamino-ar(lower)alkenoyl (e.g. carboxyacetylaminocinnamoylglycyl, carboxypropionylaminocinnamoylglycyl, etc.), amino acid residue substituted with lower alkoxycarbonyl(lower)alkanoylamino-ar(lower)alkenoyl (e.g., ethoxycarbonylacetylaminocinnamoylglycyl, ethoxycarbonylpropionylaminocinnamoylglycyl, etc.), amino acid residue substituted with lower alkoxycarbonyl(lower)alkenoylamino-ar(lower)alkenoyl (e.g. ethoxycarbonylacryloylaminocinnamoylglycyl, etc.), amino acid residue substituted with halo(lower)alkoxycarbonylamino-ar(lower)alkenoyl (e.g. chloroethoxycarbonylaminocinnamoylglycyl, etc.), amino acid residue substituted with optionally substituted heterocyclic(lower)alkanoylamino-ar(lower)alkenoyl (e.g. pyridylacetylaminocinnamoylglycyl, thienylacetylaminocinnamoylglycyl, methylpyrrolylacetylaminocinnamoylglycyl, etc.), amino acid residue substituted with aroylamino-ar(lower)alkenoyl (e.g. benzoylaminocinnamoylglycyl, etc.), amino acid residue substituted with optionally substituted heterocycliccarbonylamino-ar(lower)alkenoyl (e.g. pyridylcarbonylaminocinnamoylglycyl, morpholinocarbonylaminocinnamoylglycyl, furylcarbonylaminocinnamoylglycyl, thienylcarbonylaminocinnamoylglycyl, oxazolylcarbonylaminocinnamoylglycyl, methyloxazolylcarbonylaminocinnamoylglycyl, dimethylisoxazolylcarbonylaminocinnamoylglycyl, imidazolylcarbonylaminocinnamoylglycyl, methylimidazolylcarbonylaminocinnamoylglycyl, piperidylcarbonylaminocinnamoylglycyl, ethylpiperidylcarbonylaminocinnamoylglycyl, acetylpiperidylcarbonylaminocinnamoylglycyl, pyrrolidinylcarbonylaminocinnamoylglycyl, acetylpyrrolidinylcarbonylaminocinnamoylglycyl, tert-butoxycarbonylpyrrolidinylcarbonylaminocinnamoylglycyl, etc.), amino acid residue substituted with lower alkylsulfonylamino-ar(lower)alkenoyl (e.g. mesylaminocinnamoylglycyl, ethylsulfonylaminocinnamoylglycyl, etc.), amino acid residue substituted with N-(lower alkanoyl)-N-(lower alkyl)amino-ar(lower)alkenoyl (e.g. N-acetyl-N-methylaminocinnamoylglyclyl, N-acetyl-N-ethylaminocinnamoylglycyl, N-propionyl-N-methylaminocinnamoylglycyl, etc.), amino acid residue substituted with N-[lower alkoxy(lower)alkanoyl]-N-(lower alkyl)amino-ar(lower)alkenoyl (e.g. N-methoxyacetyl-N-methylaminocinnamoylglycyl, N-methoxypropionyl-N-methylaminocinnamoylglycyl, etc.), amino acid residue substituted with N-(lower alkanoyl)-N-[heterocyclic(lower)alkyl]amino-ar(lower)alkenoyl (e.g. N-acetyl-N-pyridylmethylaminocinnamoylglycyl, etc.), amino acid residue substituted with N-(lower alkanoyl)-N-[lower alkoxy(lower)alkyl]amino-ar(lower)alkenoyl (e.g. N-acetyl-N-methoxyethylaminocinnamoylglycyl, N-acetyl-N-methoxymethylaminocinnamoylglycyl, N-propionyl-N-methoxyethylaminocinnamoylglycyl, etc.), amino acid residue substituted with N-(lower alkanoyl)-N-[lower alkoxycarbonyl(lower)alkyl]amino-ar(lower)alkenoyl (e.g. N-acetyl-N-tert-butoxycarbonylmethylaminocinnamoylglycyl, N-acetyl-N-tert-butoxycarbonylethylaminocinnamoylglycyl, N-propionyl-N-tert-butoxycarbonylmethylaminocinnamoylglycyl, etc.), amino acid residue substituted with N-(lower alkanoyl)-N-[carboxy(lower)alkyl]amino-ar(lower)alkenoyl (e.g. N-acetyl-N-carboxymethylaminocinnamoylglycyl, N-acetyl-N-carboxyethylaminocinnamoylglycyl, N-propionyl-N-carboxymethylaminocinnamoylglycyl, etc.), amino acid residue substituted with N-[lower alkoxy(lower)alkanoyl]-N-[heterocyclic(lower)alkyl]amino-ar(lower)alkenoyl (e.g. N-methoxyacetyl-N-pyridylmethylaminocinnamoylglycyl, N-methoxypropionyl-N-pyridylmethylaminocinnamoylglycyl, etc.), amino acid residue substituted with N-[heterocycliccarbonyl]-N-[lower alkoxy(lower)alkyllamino-ar(lower)alkenoyl (e.g. N-pyridylcarbonyl-N-methoxymethylaminocinnamoylglycyl, N-pyridylcarbonyl-N-methoxyethylaminocinnamoylglycyl, N-thienylcarbonyl-N-methoxyethylaminocinnamoylglycyl, etc.), amino acid residue substituted with ureido-ar(lower)alkenoyl (e.g. ureidocinnamoylglycyl, etc.), amino acid residue substituted with lower alkylureido-ar(lower)alkenoyl (e.g. methylureidocinnamoylglycyl, ethylureidocinnamoylglycyl, dimethylureidocinnamoylglycyl, etc.), amino acid residue substituted with heterocyclicureido-ar(lower)alkenoyl (e.g. pyridylureidocinnamoylglycyl, pyrimidinylureidocinnamoylglycyl, thienylureidocinnamoylglycyl, etc.), amino acid residue substituted with lower alkanoyl-ar(lower)alkenoyl (e.g. formylcinnamoylglycyl, acetylcinnamoylglycyl, propionylcinnamoylglycyl, etc.), amino acid residue substituted with carboxy-ar(lower)alkenoyl (e.g. carboxycinnamoylglycyl, etc.), amino acid residue substituted with lower alkoxycarbonyl-ar(lower)alkenoyl (e.g. methoxycarbonylcinnamoylglycyl, ethoxycarbonylcinnamoylglycyl, etc.), amino acid residue substituted with carbamoyl-ar(lower)alkenoyl (e.g. carbamoylcinnamoylglycyl, etc.), amino acid residue substituted with lower alkylcarbamoyl-ar(lower)

alkenoyl (e.g. methylcarbamoylcinnamoylglycyl, ethylcarbamoylcinnamoylglycyl, dimethylcarbamoylcinnamoylglycyl, propylcarbamoylcinnamoylglycyl, isopropylcarbamoylcinnamoylglycyl, diethylcarbamoylcinnamoylglycyl, N-methyl-N-ethylcarbamoylcinnamoylglycyl, etc.), amino acid residue substituted with hydroxy(lower)alkylcarbamoyl-ar(lower)alkenoyl (e.g. hydroxyethylcarbamoylcinnamoylglycyl, bis(hydroxyethyl)carbamoylcinnamoylglycyl, etc.), amino acid residue substituted with N-[hydroxy(lower)alkyl]-N-(lower alkyl)carbamoyl-ar(lower)alkenoyl (e.g. N-hydroxyethyl-N-methylcarbamoylcinnamoylglycyl, etc.), amino acid residue substituted with lower alkoxy(lower)alkylcarbamoyl-ar(lower)alkenoyl (e.g. methoxymethylcarbamoylcinnamoylglycyl, methoxyethylcarbamoylcinnamoylglycyl, bis(methoxyethyl)carbamoylcinnamoylglycyl, ethoxyethylcarbamoylcinnamoylglycyl, methoxypropylcarbamoylcinnamoylglycyl, bis(ethoxyethyl)carbamoylcinnamoylglycyl, etc.), amino acid residue substituted with N-[lower alkoxy(lower)alkyl]-N-(lower alkyl)carbamoyl-ar(lower)alkenoyl (e.g. N-methoxyethyl-N-methylcarbamoylcinnamoylglycyl, N-ethoxyethyl-N-methylcarbamoylcinnamoylglycyl, etc.), amino acid residue substituted with heterocyclic(lower)alkylcarbamoyl-ar(lower)alkenoyl (e.g. pyridylmethylcarbamoylcinnamoylglycyl, furylmethylcarbamoylcinnamoylglycyl, thienylmethylcarbamoylcinnamoylglycyl, etc.), amino acid residue substituted with N-[heterocyclic(lower)alkyl-N-(lower alkyl)carbamoyl-ar(lower)alkenoyl (e.g. N-pyridylmethyl-N-methylcarbamoylcinnamoylglycyl, etc.), amino acid residue substituted with heterocycliccarbamoyl-ar(lower)alkenoyl (e.g. morpholinylcarbamoylcinnamoylglycyl, thienylcarbamoylcinnamoylglycyl, pyridylcarbamoylcinnamoylglycyl, pyrimidinylcarbamoylcinnamoylglycyl, tetrazolylcarbamoylcinnamoylglycyl, etc.), amino acid residue substituted with optionally substituted heterocycliccarbonyl-ar(lower)alkenoyl (e.g. morpholinocarbonylcinnamoylglycyl, pyrrolidinylcarbonylcinnamoylglycyl, piperidinocarbonylcinnamoylglycyl, tetrahydropyridylcarbonylcinnamoylglycyl, methylpiperazinylcarbonylcinnamoylglycyl, etc.), amino acid residue substituted with lower alkenylcarbamoyl-ar(lower)alkenoyl (e.g. vinylcarbamoylcinnamoylglycyl, allylcarbamoylcinnamoylglycyl, methylpropenylcarbamoylcinnamoylglycyl, etc.), amino acid residue substituted with lower alkynylcarbamoyl-ar(lower)alkenoyl (e.g. ethynylcarbamoylcinnamoylglycyl, propynylcarbamoylcinnamoylglycyl, etc.), amino acid residue substituted with amino(lower)alkylcarbamoyl-ar(lower)alkenoyl (e.g. aminomethylcarbamoylcinnamoylglycyl, aminoethylcarbamoylcinnamoylglycyl, etc.), amino acid residue substituted with lower alkylamino(lower)alkylcarbamoyl-ar(lower)alkenoyl (e.g. methylaminomethylcarbamoylcinnamoylglycyl, methylaminoethylcarbamoylcinnamoylglycyl, ethylaminoethylcarbamoylcinnamoylglycyl, dimethylaminoethylcarbamoylcinnamoylglycyl, etc.), amino acid residue substituted with lower alkylcarbamoyloxy(lower)alkylcarbamoyl-ar(lower)alkenoyl (e.g. methylcarbamoyloxymethylcarbamoylcinnamoylglycyl, methylcarbamoyloxyethylcarbamoylcinnamoylglycyl, ethylcarbamoyloxyethylcarbamoylcinnamoylglycyl, dimethylcarbamoyloxyethylcarbamoylcinnamoylglycyl, etc.), amino acid residue substituted with lower alkylcarbamoyl(lower)alkylcarbamoyl-ar(lower)alkenoyl (e.g. methylcarbamoylmethyl-carbamoylcinnamoylglycyl, methylcarbamoylethylcarbamoylcinnamoylglycyl, ethylcarbamoylethylcarbamoylcinnamoylglycyl, dimethylcarbamoylethylcarbamoylcinnamoylglycyl, etc.), amino acid residue substituted with lower alkoxycarbonyl(lower)alkylcarbamoyl-ar(lower)alkenoyl (e.g. methoxycarbonylmethylcarbamoylcinnamoylglycyl, methoxycarbonylethylcarbamoylcinnamoylglycyl, ethoxycarbonylmethylcarbamoylcinnamoylglycyl, ethoxycarbonylethylcarbamoylcinnamoylglycyl, etc.), amino acid residue substituted with carboxy(lower)alkylcarbamoyl-ar(lower)alkenoyl (e.g. carboxymethylcarbamoylcinnamoylglycyl, carboxyethylcarbamoylcinnamoylglycyl, etc.), amino acid residue substituted with [lower alkylcarbamoyl-ar(lower)alkyl]carbamoyl-ar(lower)alkenoyl (e.g. (methylcarbamoylphenethyl)carbamoylcinnamoylglycyl, (ethylcarbamoylphenethyl)carbamoylcinnamoylglycyl, etc.), amino acid residue substituted with [lower alkoxycarbonyl-ar(lower)alkyl]carbamoyl-ar(lower)alkenoyl (e.g. (methoxycarbonylphenethyl)carbamoylcinnamoylglycyl, (ethoxycarbonylphenethyl)carbamoylcinnamoylglycyl, etc.), amino acid residue substituted with [carboxy-ar(lower)alkyl]carbamoyl-ar(lower)alkenoyl (e.g. (carboxyphenethyl)carbamoylcinnamoylglycyl, etc.), amino acid residue substituted with N-[lower alkylcarbamoyl(lower)alkyl]-N-(lower alkyl)carbamoyl-ar(lower)alkenoyl (e.g. N-(methylcarbamoylmethyl)-N-methylcarbamoylcinnamoylglycyl, N-(methylcarbamoylethyl)-N-methylcarbamoylcinnamoylglycyl, N-(ethylcarbamoylethyl)-N-methylcarbamoylcinnamoylglycyl, N-(dimethylcarbamoylethyl)-N-methylcarbamoylcinnamoylglycyl, etc.), amino acid residue substituted with N-[lower alkoxycarbonyl(lower)alkyl]-N-(lower alkyl)carbamoyl-ar(lower)alkenoyl (e.g. N-methoxycarbonylmethyl-N-methylcarbamoylcinnamoylglycyl, N-methoxycarbonylethyl-N-methylcarbamoylcinnamoylglycyl, N-ethoxycarbonylmethyl-N-methylcarbamoylcinnamoylglycyl, N-ethoxycarbonylethyl-N-methylcarbamoylcinnamoylglycyl, etc.), amino acid residue substituted with N-carboxy(lower)alkyl]-N-(lower alkyl)carbamoyl-ar(lower)alkenoyl (e.g. N-carboxymethyl-N-methylcarbamoylcinnamoylglycyl, N-carboxyethyl-N-methylcarbamoylcinnamoylglycyl, etc.) amino acid residue substituted with arylcarbamoyl-ar(lower)

alkenoyl (e.g. phenylcarbamoylcinnamoylglycyl, naphthylcarbamoylcinnamoylglycyl, etc.), amino acid residue substituted with ar(lower)alkynoyl (e.g. phenylpropioloylglycyl, etc.), amino acid residue substituted with heterocyclic(lower)alkenoyl (e.g. morpholinylacryloylglycyl, pyridylacryloylglycyl, thienylacryloylglycyl, etc.), amino acid residue substituted with amino-heterocyclic(lower)alkenoyl (e.g. aminopyridylacryloylglycyl, etc.), amino acid residue substituted with lower alkylamino-heterocyclic(lower) alkenoyl (e.g. methylaminopyridylacryloylglycyl, dimethylaminopyridylacryloylglycyl, etc.), amino acid residue substituted with lower alkanoylamino-heterocyclic(lower)alkenoyl (e.g. acetylaminopyridylacryloylglycyl, propionylaminopyridylacryloylglycyl, etc.), amino acid residue substituted with lower alkenoylamino-heterocyclic(lower)alkenoyl (e.g. acryloylaminopyridylacryloylglycyl, crotonoylaminopyridylacryloylglycyl, etc.), amino acid residue substituted with heterocyclic(lower) alkanoylamino-heterocyclic(lower)alkenoyl (e.g. pyridylacetylaminopyridylacryloylglycyl, thienylacetylaminopyridylacryloylglycyl, etc.), amino acid residue substituted with heterocycliccarbonylamino-heterocyclic(lower) alkenoyl (e.g. pyridylcarbonylaminopyridylacryloylglycyl, furylcarbonylaminopyridylacryloylglycyl, etc.), amino acid residue substituted with lower alkanoylamino (lower)alkanoylamino-heterocyclic(lower)alkenoyl (e.g. acetylamincacetylaminopyridylacryloylglycyl, acetylaminopropionylaminopyridylacryloylglycyl, etc.), amino acid residue substituted with lower alkoxycarbonyl(lower)alkanoylamino-heterocyclic (lower)alkenoyl (e.g. ethoxycarbonylacetylaminopyridylacryloylglycyl, ethoxycarbonylpropionylaminopyridylacryloylglycyl, etc.), amino acid residue substituted with lower alkoxy (lower)alkanoylamino-heterocyclic(lower)alkenoyl (e.g. methoxyacetylaminopyridylacryloylglycyl, methoxypropionylaminopyridylacryloylglycyl, ethoxypropionylaminopyridylacryloylglycyl, etc.), amino acid residue substituted with lower alkylureido-heterocyclic(lower)alkenoyl (e.g. methylureidopyridylacryloylglycyl, etc.), amino acid residue substituted with carboxy-heterocyclic(lower) alkenoyl (e.g. carboxypyridylacryloylglycyl, etc.), amino acid residue substituted with lower alkoxycarbonyl-heterocyclic(lower)alkenoyl (e.g. ethoxycarbonylpyridylacryloylglycyl, etc.), amino acid residue substituted with lower alkylcarbamoyl-heterocyclic(lower)alkenoyl (e.g. methylcarbamoylpyridylacryloylglycyl, ethylcarbamoylpyridylacryloylglycyl, dimethylcarbamoylpyridylacryloylglycyl, diethylcarbamoylpyridylacryloylglycyl, isopropylcarbamoylpyridylacryloylglycyl, N-ethyl-N-methylcarbamoylpyridylacryloylglycyl, etc.), amino acid residue substituted with lower alkoxy(lower) alkylcarbamoyl-heterocyclic(lower)alkenoyl (e.g. methoxymethylcarbamoylpyridylacryloylglycyl, methoxyethylcarbamoylpyridylacryloylglycyl, methoxypropylcarbamoylpyridylacryloylglycyl, ethoxyethylcarbamoylpyridylacryloylglycyl, bis (methoxyethyl)carbamoylpyridylacryloylglycyl, etc.), amino acid residue substituted with hydroxy(lower) alkylcarbamoyl-heterocyclic(lower)alkenoyl (e.g. hydroxymethylcarbamoylpyridylacryloylglycyl, hydroxyethylcarbamoylpyridylacryloylglycyl, bis (hydroxyethyl)carbamoylpyridylacryloylglycyl, etc.), amino acid residue substituted with heterocycliccarbamoyl-heterocyclic(lower)alkenoyl (e.g. pyridylcarbamoylpyridylacryloylglycyl, morpholinylcarbamoylpyridylacryloylglycyl, thienylcarbamoylpyridylacryloylglycyl, pyrimidinylcarbamoylpyridylacryloylglycyl, etc.), amino acid residue substituted with heterocyclic(lower) alkylcarbamoyl-heterocyclic(lower)alkenoyl (e.g. pyridylmethylcarbamoylpyridylacryloylglycyl, furylmethylcarbamoylpyridylacryloylglycyl, thienylmethylcarbamoylpyridylacryloylglycyl, etc.), amino acid residue substituted with heterocycliccarbonyl-heterocyclic(lower)alkenoyl (e.g. morpholinocarbonylpyridylacryloylglycyl, pyrrolidinylcarbonylpyridylacryloylglycyl, piperidinocarbonylpyridylacryloylglycyl, etc.), amino acid residue substituted with lower alkenylcarbamoyl-heterocyclic(lower)alkenoyl (e.g. vinylcarbamoylpyridylacryloylglycyl, allylcarbamoylpyridylacryloylglycyl, etc.), amino acid residue substituted with lower alkynylcarbamoyl-heterocyclic(lower)alkenoyl (e.g. ethylcarbamoylpyridylacryloylglycyl, propynylcarbamoylpyridylacryloylglycyl, etc.) amino acid residue substituted with heterocyclicthio(lower) alkanoyl (e.g. pyridylthioacetylglycyl, pyrimidinylthioacetylglycyl, imidazolylthiopropionylglycyl, etc.), amino acid residue substituted with optionally substituted heterocyccliccarbonyl (e.g. morpholinocarbonylglycyl, indolylcarbonylglycyl, 4-methyl-1-piperazinylcarbonylglycyl, etc.), amino acid residue substituted with cyclo(lower)alkylcarbonyl (e.g. cyclopropylcarbonylglycyl, cyclopentylcarbonylglycyl, cyclohexylcarbonylglycyl, cyclohexylcarbonylsarcosyl, etc.), amino acid residue substituted with lower alkoxycarbonyl (e.g. methoxycarbonylglycyl, tert-butoxycarbonylglycyl, tert-butoxycarbonylsarcosyl, tert-butoxycarbonylalanyl, etc.), amino acid residue substituted with aryloxycarbonyl (e.g. phenoxycarbonylglycyl, etc.), amino acid residue substituted with aroyl(lower)alkanoyl (e.g. phenyloxalylglycyl, benzoylpropionylglycyl, etc.), amino acid residue substituted with aroyl (e.g. benzoylglycyl, benzoylsarcosyl, naphthoylglycyl, benzoylalanyl, etc.), amino acid residue substituted with nitro-aryloxycarbonyl (e.g. nitrophenyloxycarbonylglycyl, etc.), amino acid residue substituted with carbamoyl (e.g. carbamoylglycyl, carbamoylalanyl, carbamoylsarcosyl, carbamoyl-β-alanyl, etc.), amino acid residue substituted with lower alkylcarbamoyl (e.g. methylcarbamoylglycyl, etylcarbamoylglycyl, propylcarbamoylglycyl, isopropylcarbamoylglycyl, pentylcarbamoylglycyl, methylcarbamoylsarcosyl, ethylcarbamoylalanyl, isopropylcarbamoyl-β-alanyl, etc.), amino acid residue substituted with lower alkoxycarbonyl(lower) alkylcarbamoyl (e.g. methoxycarbonylmethylcarbamoylglycyl, ethoxycarbonylmethylcarbamoylglycyl, etc.), amino acid residue substituted with lower alkenylcarbamoyl (e.g. vinylcarbamoylglycyl, allylcarbamoylglycyl, allylcarbamoylsarcosyl, etc.), amino acid residue substituted with cyclo(lower)alkylcarbamoyl (e.g. cyclopropylcarbamoylglycyl, cyclohexylcarbamoylglycyl, cyclohexylcarbamoylsarcosyl, etc.), amino acid residue substituted with arylcarbamoyl (e.g. phenylcarbamoylglycyl, naphthylcarbamoylglycyl, tolylcarbamoylglycyl, ethylphenylcarbamoylglycyl, phenylcarbamoylalanyl, phenylcarbamoylsarcosyl, etc.), amino acid residue substituted with lower alkoxy-arylcarbamoyl (e.g. methoxyphenylcarbamoylglycyl, ethoxyphenylcarbamoylglycyl, methoxyphenylcarbamoylalanyl, etc.), amino acid residue substituted with halo(lower)alkyl-arylcarbamoyl (e.g. trifluoromethylphenylcarbamoylglycyl, trifluoromethylphenylcarbamoylalanyl, trifluoromethylphenylcarbamoylsarcosyl, etc.), amino acid residue substituted with halo-arylcarbamoyl (e.g. chlorophenylcarbamoylglycyl, fluorophenylcarbamoylglycyl, fluorophenylcarbamoylalanyl, etc.), amino acid residue substituted with lower alkanoyl-arylcarbamoyl (e.g. acetylphenylcarbamoylglycyl, propionylphenylcarbamoylalanyl, etc.), amino acid residue substituted with hydroxy(lower)alkyl-arylcarbamoyl (e.g. hydroxymethylphenylcarbamoylglycyl, hydroxyethylphenylcarbamoylglycyl, hydroxyethylphenylcarbamoylalanyl, etc.), amino acid residue substituted with heterocycliccarbonyl-arylcarbamoyl (e.g. morpholinocarbonylphenylcarbamoylglycyl, piperidinocarbonylphenylcarbamoylglycyl, thiomorpholinocarbonylphenylcarbamoylalanyl, piperazinylcarbonylphenylcarbamoylglycyl, pyrrolidinylcarbonylphenylcarbamoylglycyl, 1,2,3,6-tetrahydropyridylcarbonylphenylcarbamoylglycyl, etc.), amino acid residue substituted with carboxy-arylcarbamoyl (e.g. carboxyphenylcarbamoylglycyl, etc;), amino acid residue substituted with lower alkoxycarbonyl-arylcarbamoyl (e.g. methoxycarbonylphenylcarbamoylglycyl, ethoxycarbonylphenylcarbamoylglycyl, etc.), amino acid residue substituted with carbamoyl-arylcarbamoyl (e.g. carbamoylphenylcarbamoylglycyl, etc.), amino acid residue substituted with lower alkylcarbamoyl-arylcarbamoyl (e.g. methylcarbamoylphenylcarbamoylglycyl, ethylcarbamoylphenylcarbamoylglycyl, propylcarbamoylphenylcarbamoylglycyl, dimethylcarbamoylphenylcarbamoylglycyl, diethylcarbamoylphenylcarbamoylglycyl, N-ethyl-N-methylcarbamoylphenylcarbamoylglycyl, N-isopropyl-N-methylcarbamoylphenylcarbamoylglycyl, etc.), amino acid residue substituted with nitro-arylcarbamoyl (e.g. nitrophenylcarbamoylglycyl, etc.), amino acid residue substituted with cyano-arylcarbamoyl (e.g. cyanophenylcarbamoylglycyl, etc.), amino acid residue substituted with amino-arylcarbamoyl (e.g. aminophenylcarbamoylglycyl, etc.), amino acid residue substituted with lower alkylamino-arylcarbamoyl (e.g. methylaminophenylcarbamoylglycyl, ethylaminophenylcarbamoylglycyl, dimethylaminophenylcarbamoylglycyl, etc.), amino acid residue substituted with lower alkanoylamino-arylcarbamoyl (e.g. acetylaminophenylcarbamoylglycyl, propionylaminophenylcarbamoylglycyl, etc.), amino acid residue substituted with N-(lower alkanoyl)-N-(lower alkyl)amino-arylcarbamoyl (e.g. N-acetyl-N-methylaminophenylcarbamoylglycyl, N-propionyl-N-methylaminophenylcarbamoylglycyl, etc.), amino acid residue substituted with lower alkoxy(lower)alkanoylamino-arylcarbamoyl (e.g. methoxyacetylaminophenylcarbamoylglycyl, methoxypropionylaminophenylcarbamoylglycyl, etc.), amino acid residue substituted with lower alkoxycarbonyl(lower)alkanoylamino-arylcarbamoyl (e.g. ethoxycarbonylacetylaminophenylcarbamoylglycyl, methoxycarbonylpropionylaminophenylcarbamoylglycyl, etc.], amino acid residue substituted with carboxyamino-arylcarbamoyl (e.g. carboxyaminophenylcarbamoylglycyl, etc.), amino acid residue substituted with lower alkoxycarbonylamino-arylcarbamoyl (e.g. ethoxycarbonylaminophenylcarbamoylglycyl, etc.), amino acid residue substituted with aroylamino-arylcarbamoyl (e.g. benzoylaminophenylcarbamoylglycyl, etc.), amino acid residue substituted with heterocycliccarbonylamino-arylcarbamoyl (e.g. pyridylcarbonylaminophenylcarbamoylglycyl, furylcarbonylaminophenylcarbamoylglycyl, morpholinocarbonylaminophenylcarbamoylglycyl, etc.), amino acid residue substituted with heterocyclic (lower)alkanoylamino-arylcarbamoyl (e.g. pyridylacetylaminophenylcarbamoylglycyl, thienylacetylaminophenylcarbamoylglycyl, etc.), amino acid residue substituted with ureido-arylcarbamoyl (e.g. ureidophenylcarbamoylglycyl, etc.), amino acid residue substituted with lower alkylureido-arylcarbamoyl (e.g. methylureidophenylcarbamoylglycyl, ethylureidophenylcarbamoylglycyl, etc.), amino acid residue substituted with hydroxyimino(lower)alkyl-arylcarbamoyl (e.g. hydroxyiminoethylphenylcarbamoylglycyl, etc.), amino acid residue substituted with lower alkoxyimino (lower)alkyl-arylcarbamoyl (e.g. methoxyiminoethylphenylcarbamoylglycyl, etc.), amino acid residue substituted with lower alkylhydrazono(lower)alkyl-arylcarbamoyl (e.g. methylhydrazonoethylphenylcarbamoylglycyl, dimethylhydrazonoethylphenylcarbamoylglycyl, etc.), amino acid residue substituted with optionally substituted heterocyclic-arylcarbamoyl (e.g. oxopyrrolidinylphenylcarbamoylglycyl, oxopiperidinophenylcarbamoylglycyl, dioxopyrrolidinylphenylcarbamoylglycyl, oxcoxazolidinylphenylcarbamoylglycyl, pyrrolylphenylcarbamoylglycyl, etc.), amino acid residue substituted with heterocycliccarbonyl-arylcarbamoyl having lower alkyl (e.g. methylpiperazinylcarbonylphenylcarbamoylglycyl, ethylpiperazinylcarbonylphenylcarbamoylglycyl, etc.), amino acid residue substituted with heterocycliccarbonyl-arylcarbamoyl having aryl (e.g. phenylpiperazinylcarbonylphenylcarbamoylglycyl, etc.), amino acid residue substituted with heterocycliccarbonyl-arylcarbamoyl having a heterocyclic group (e.g. pyridylpiperazinylcarbonylphenylcarbamoylglycyl, etc.), amino acid residue substituted with heterocycliccarbonyl-arylcarbamoyl having lower alkanoyl (e.g. acetylpiperazinylcarbonylphenylcarbamoylglycyl, etc.), amino acid residue substituted with heterocycliccarbonyl-arylcarbamoyl having lower alkoxycarbonyl (e.g. ethoxycarbonylpiperazinylcarbonyl-phenylcarbamoylglycyl, etc.), amino acid residue substituted with heterocycliccarbonyl-arylcarbamoyl having lower alkylamino (e.g. methyl-aminopiperazinylcarbonylphenylcarbamoylglycyl, dimethyl-aminopiperidinocarbonylphenylcarbamoylglycyl, etc.), amino acid residue substituted with heterocycliccarbonyl-arylcarbamoyl having lower alkylcarbamoyl (e.g. methylcarbamoylpiperazinyl-carbonylphenylcarbamoylglycyl, etc.), amino acid residue substituted with hydroxy(lower)alkylcarbamoyl-arylcarbamoyl (e.g. hydroxymethylcarbamoylphenylcarbamoylglycyl, hydroxyethylcarbamoylphenylcarbamoylglycyl, bis(hydroxyethyl)carbamoylphenylcarbamoylglycyl, etc.), amino acid residue substituted with N-[hydroxy(lower)alkyl]-N-(lower alkyl)carbamoyl-arylcarbamoyl (e.g. N-(hydroxyethyl)-N-methylcarbamoylphenylcarbamoylglycyl, etc.), amino acid residue substituted with lower alkoxy(lower)alkylcarbamoyl-arylcarbamoyl (e.g. methoxymethylcarbamoylphenylcarbamoylglycyl, methoxyethylcarbamoylphenylcarbamoylglycyl, ethoxyethylcarbamoylphenylcarbamoylglycyl, bis(methoxyethyl)carbamoylphenylcarbamoylglycyl, bis(ethoxyethyl)carbamoylphenylcarbamoylglycyl etc.), amino acid residue substituted with N-[lower alkoxy(lower)alkyl]-N-(lower alkyl)carbamoyl-arylcarbamoyl (e.g. N-(methoxyethyl)-N-methylcarbamoylphenylcarbamoylglycyl, N-(methoxypropyl)-N-methylcarbamoylphenylcarbamoylglycyl, etc.), amino acid residue substituted with lower alkylamino(lower)alkylcarbamoyl-arylcarbamoyl (e.g. methylaminoethylcarbamoylphenylcarbamoylglycyl, dimethylaminoethylcarbamoylphenylcarbamoylglycyl, etc.), amino acid residue substituted with N-[lower alkylamino(lower)alkyl]-N-(lower alkyl)carbamoyl-arylcarbamoyl (e.g. N-(dimethylaminoethyl)-N-methylcarbamoylphenylcarbamoylglycyl, N-(dimethylaminopropyl)-N-methylcarbamoylphenylcarbamoylglycyl, etc.), amino acid residue substituted with heterocycliccarbamoyl-arylcarbamoyl (e.g. morpholinylcarbamoylphenylcarbamoylglycyl, thienylcarbamoylphenylcarbamoylglycyl, pyridylcarbamoylphenylcarbamoylglycyl, pyrimidinylcarbamoylphenylcarbamoylglycyl, etc.), amino acid residue substituted with N-(heterocyclic)-N-(lower alkyl)carbamoyl-arylcarbamoyl (e.g. N-pyridyl-N-methylcarbamoylphenylcarbamoylglycyl, etc.), amino acid residue substituted with heterocyclic(lower)alkylcarbamoyl-arylcarbamoyl (e.g. pyridylmethylcarbamoylphenylcarbamoylglycyl, pyridylethylcarbamoylphenylcarbamoylglycyl, thienylmethylcarbamoylphenylcarbamoylglycyl, etc.), amino acid residue substituted with N-[heterocyclic(lower)alkyl]-N-(lower alkyl)carbamoyl-arylcarbamoyl (e.g. N-pyridylmethyl-N-methylcarbamoylphenylcarbamoylglycyl, etc.), amino acid residue substituted with N-[heterocyclic(lower)alkyl]-N-[lower alkoxy(lower)alkyl]carbamoyl-arylcarbamoyl (e.g. N-pyridylmethyl-N-methoxyethylcarbamoylphenylcarbamoylglycyl, etc.), amino acid residue substituted with arylcarbamoyl-arylcarbamoyl (e.g. phenylcarbamoylphenylcarbamoylglycyl, etc.), amino acid residue substituted with lower alkylaminoarylcarbamoyl-arylcarbamoyl (e.g. dimethylaminophenylcarbamoylphenyl-carbamoylglycyl, etc.), amino acid residue substituted with arylthiocarbamoyl (e.g. phenylthiocarbamoylglycyl, naphthylthiocarbamoylglycyl, phenylthiocarbamoylalanyl, phenylthiocarbamoylsarcosyl, etc.), amino acid residue substituted with ar(lower)alkylcarbamoyl (e.g. benzylcarbamoylglycyl, benzylcarbamoylsarcosyl, benzylcarbamoylalanyl, etc.), amino acid residue substituted with aroylcarbamoyl (e.g. benzoylcarbamoylglycyl, etc.), amino acid residue substituted with heterocyclicarbamoyl (e.g. pyridylcarbamoylglycyl, pyridylcarbamoylalanyl, pyridylcarbamoylsarcosyl, thienylcarbamoylglycyl, pyrazolylcarbamoylglycyl, pyrimidinylcarbamoylglycyl, quinolylcarbamoylglycyl, isoquinolylcarbamoylglycyl, etc.), amino acid residue substituted with heterocyclic(lower)alkylcarbamoyl (e.g. benzylglycylglycyl, etc.) and amino acid residue having amino acid residue substituted with phthaloyl (e.g. phthaloylglycylglycyl, etc.), etc.}, etc.];

acyl such as carboxy, esterified carboxy [e.g. lower alkoxycarbonyl (e.g. methoxycarbonyl, ethoxycarbonyl, tert-butoxycarbonyl, etc.), etc.], aroyl [e.g. benzoyl, etc.] and heterocycliccarbonyl which may be substituted lower alkyl [e.g. morpholinocarbonyl, 4-methyl-1-piperazinylcarbonyl, etc.], lower alkylaminomethyleneamino such as dimethylaminomethyleneamino and diethylaminomethyleneamino, heterocyclic group such as pyrrolidinyl, heterocyclic group substituted with oxo such as pyrrolidonyl, and/or N-methylpyrrolidinylideneamino; or heterocyclic group such as thienyl, benzofuryl, benzothiazolinyl, benzothiazinyl and piperonyl, each of which may be substituted with substituent(s) such as halogen [e.g. fluorine, chlorine, bromine and iodine], lower alkyl [e.g. methyl, ethyl, propyl, isopropyl, etc.], halo-aryl [e.g. chlorophenyl, etc.] and/or oxo;

Q is O or N—$R^{11}$, in which $R^{11}$ is hydrogen; or acyl such as lower alkanoyl [e.g. formyl, acetyl, propionyl, butyryl, etc.];

A is lower alkylene such as methylene, ethylene, methylmethylene and propylene.

Suitable "a leaving group" may be a conventional acid residue such as halogen [e.g. fluoro, chloro, bromo and iodo], arenesulfonyloxy [e.g. benzenesulfonyloxy, tosyloxy, etc.], alkanesulfonyloxy [e.g. mesyloxy, ethanesulfonyloxy, etc.], and the like.

Suitable pharmaceutically acceptable salts of the object compound [I] are conventional non-toxic salts and include a metal salt such as an alkali metal salt [e.g. sodium salt, potassium salt, etc.] and an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc.], an organic acid addition salt [e.g. formate, acetate, trifluoroacetate, maleate, tartrate, oxalate, methanesulfonate, benzenesulfonate, toluenesulfonate, etc.], an inorganic acid addition salt [e.g. hydrochloride, hydrobromide, sulfate, phosphate, etc.], a salt with an amino acid [e.g. arginine salt, aspartic acid salt, glutamic acid salt, etc.], an intramolecular salt and the like.

With respect to the salts of the compounds [Ia] to [Ig] in the Processes 3 to 6, it is to be noted that these compounds are included within the scope of the compound [I], and accordingly the suitable examples of the salts of these compounds are to be referred to those as exemplified for the object compound [I].

The processes for preparing the object compound [I] are explained in detail in the following.

Process 1

The compound [I] or its salt can be prepared by halogenating a compound [II] or its salt.

Suitable salts of the compound [II] may be the same as those exemplified for the compound [I].

The halogenation is carried out in the presence of a halogenating agent.

Suitable halogenating agents of this reaction may include conventional ones such as N-halosuccinimide [e.g. N-chlorosuccinimide, N-bromosuccinimide, etc.], and the like. These halogenating agents may be selected according to the kind of the starting compound [II] to be used.

This reaction is usually carried out in a conventional solvent such as chloroform, methylene chloride, carbon tetrachloride, dimethylformamide, methanol, ethanol, dioxane, or the like.

The reaction temperature is not critical, and the reaction is usually carried out at ambient temperature or under warming or heating.

Process 2

The object compound [I] or its salt can be prepared by reacting a compound [III] or its salt with a compound [IV] or its salt.

Suitable salts of the compounds [III] and [IV] may be the same as those exemplified for the compound [I].

The reaction is preferably carried out in the presence of a base such as alkali metal [e.g. lithium, sodium, potassium, etc.], the hydroxide or carbonate or bicarbonate thereof [e.g. sodium hydroxide, potassium carbonate, potassium bicarbonate, etc.], alkali metal alkoxide [e.g. sodium methoxide, sodium ethoxide, potassium tert-butoxide, etc.], or the like.

This reaction is usually carried out in a conventional solvent such as tetrahydrofuran, dioxane, N,N-dimethylformamide, acetone, or the like. The reaction temperature is not critical, and the reaction is usually carried out under cooling to heating.

Process 3

The object compound [Ib] or its salt can be prepared by acylating a compound [Ia] or its salt.

The acylation is carried out in the presence of an acylating agent.

Suitable acylating agents are the corresponding carboxylic acid or sulfonic acid compounds, which are represented by the formula: R—OH wherein R is acyl, and reactive derivatives thereof, and the corresponding isocyanate or isothiocyanate compounds.

As suitable said reactive derivatives, there may be mentioned acid halides, acid anhydrides, active amides and active esters. Suitable examples are acid halides such as acid chloride and acid bromide, mixed acid anhydrides with various acids [e.g. substituted phosphoric acid such as dialkyl phosphoric acid, sulfuric acid, aliphatic carboxylic acid, aromatic carboxylic acid, etc.], symmetric acid anhydrides, active amides with various imidazoles, and active esters such as p-nitrophenyl ester and N-hydroxysuccinimide ester. The kind of such reactive derivatives can be selected depending on the kind of acyl group to be introduced.

The reaction is usually carried out in a conventional solvent, such as methylene chloride, chloroform, pyridine, dioxane, tetrahydrofuran, N,N-dimethylformamide, or the like. In case that the acylating agent is liquid, it can also be used as a solvent. In case that the carboxylic acid or sulfonic acid compounds are used as acylating agent in the free acid form or salt form, it is preferable to carry out the reaction in the presence of a conventional condensing agent such as N,N'-dicyclohexylcarbodiimide or the like.

The reaction temperature is not critical and the reaction can be carried out under cooling, at ambient temperature, or under heating.

This reaction is preferably carried out in the presence of a conventional inorganic base or in the presence of a conventional organic base.

Process 4

The object compound [Id] or its salt can be prepared by acylating a compound [Ic] or its salt.

This reaction can be carried out in substantially the same manner as Process 3, and therefore the reaction mode and reaction condition of this reaction are to be referred to those explained in Process 3.

Process 5

The object compound [Ie] or its salt can be prepared by alkylating a compound [Ic] or its salt.

This alkylation is carried out in the presence of an alkylating agent.

Suitable alkylating agents to be used in this reaction may be halide compounds such as lower alkyl halide [e.g. methyl iodide, ethyl iodide, propyl iodide, butyl iodide, etc.] or ar(lower)alkyl halide [e.g. benzylbromide, etc.], aldehyde compounds, ketone compounds, or the like.

When halide compounds are used as alkylating agents, the reaction is usually carried out in the presence of a base such as an alkali metal [e.g. sodium, potassium, etc.], an alkaline earth metal [e.g. magnesium, calcium, etc.], the hydride or hydroxide thereof, alkali metal alkoxide [e.g. sodium methoxide, sodium ethoxide, potassium tert-butoxide, etc.], or the like.

When aldehyde compounds or ketone compounds are used as alkylating agents, the reaction is usually carried out under acidic condition in the presence of reducing agent such as formic acid, sodium cyanoborohydride, or the like.

The reaction of this process is usually carried out in a conventional solvent such as methanol, ethanol, tetrahydrofuran, dioxane, N,N-dimethylformamide, dimethyl sulfoxide, or the like. And in case that the above-mentioned alkylating agent is in liquid, it can be also used as a solvent.

The reaction temperature is not critical, and the reaction is usually carried out under cooling, at ambient temperature or under warming or heating.

Process 6

The object compound [Ig] or its salt can be prepared by reacting a compound [If] or its reactive derivative at the carboxy group or a salt thereof with a comound [IX] or its reactive derivative at the amino group or a salt thereof.

Suitable reactive derivative at the carboxy group of the comopund [If] may include an acid halide, an acid anhydride, an activated amide, an activated ester, and the like. Suitable examples of the reactive derivatives may be an acid chloride; an acid azide; a mixed acid anhydride with an acid such as dialkylphosphoric acid, sulfuric acid aliphatic carboxylic acid or aromatic carboxylic acid; a symmetrical acid anhydride; an activated amide with imidazole; or an activated ester [e.g. p-nitrophenyl ester, etc.]. These reactive derivatives can optionally be selected from them according to the kind of the compound [If] to be used.

Suitable reactive derivative at the amino group of the comopund [IX] may be a silyl derivative formed by the reaction of the compound [IX] with a silyl compound such as bis(trimethylsilyl)acetamide or mono(trimethylsilyl) acetamide, or the like.

Suitable salts of the comound [IX] and its reactive derivative can be referred to the organic or inorganic acid addition salts as exemplified for the comound [I].

This reaction can be carried out in substantially the same manner as Process 3 and therefore the reaction mode and reaction condition of this reaction are to be referred to those explained in Process 3.

The starting compounds [II] or [III] or salts thereof can be prepared by the following reaction schemes.

Process A

[V] or its salt → [II] or its salt

Process B

[VII] or its salt → [V] or its salt

Process C

[VIII] or its salt → [II] or its salt

Process D

[VIII] or its salt → [III] or its salt wherein $R^1$, $R^2$, $R^3$, $R^4$, Q, A and X are each as defined above.

The above-mentioned processes for preparing the starting compounds are explained in detail in the following.

Process A

The compound [II] or its salt can be prepared by reacting a compound [V] or its salt with a compound [VI] or its salt.

Suitable salts of the compounds [V] and [VI] may be the same as those exemplified for the compound [I].

This reaction is usually carried out in a conventional solvent such as methanol, ethanol, acetonitrile, N,N-dimethylformamide, dimethyl sulfoxide or the like.

The reaction temperature is not critical, and the reaction is usually carried out at ambient temperature or under warming or heating.

Process B

The compound [V] or its salt can be prepared by reacting a compound [VII] or its salt with a compound [IV] or its salt.

Suitable salts of the compound [VII] are the same as those exemplified for the compound [I].

This reaction can be carried out in substantially the same manner as Process 2, and therefore the reaction mode and reaction condition of this reaction are to be referred to those explained in Process 2.

Process C

The compound [II] or its salt can be prepared by reacting a compound [VIII] or its salt with a compound [IV] or its salt.

Suitable salts of the compound [VIII] are the same as those exemplified for the compound [I].

This reaction can be carried out in substantially the same manner as Process 2, and therefore the reaction mode and reaction condition of this reaction are to be referred to those explained in Process 2.

Process D

The compound [III] or its salt can be prepared by halogenating a compound [VIII] or its salt.

This reaction can be carried out in substantially the same manner as Process 1, and therefore the reaction mode and reaction condition of this reaction are to be referred to those explained in Process 1.

The object compound [I] and the starting compounds can also be prepared by the methods of Examples and Preparations mentioned below or similar manners thereto or conventional manners.

The compounds obtained by the above processes can be isolated and purified by a conventional method such as pulverization, recrystallization, chromatography, reprecipitation or the like.

It is to be noted that the compound [I] and the other compounds may include one or more stereoisomers and geometrical isomers due to asymmetric carbon atoms and double bonds, and all of such isomers and mixture thereof are included within the scope of this invention.

The object compound [I] and pharmaceutically acceptable salts thereof possess strong activities as bradykinin antagonists, and are useful for the treatment and/or the prevention of bradykinin or its analogues mediated diseases such as allergy, inflammation, autoimmune disease, shock, pain, or the like, and more particularly for the prevention and/or the treatment of asthma, cough, bronchitis, rhinitis, rhinorrhea, obstructive pulmonary disease [e.g. pulmonary emphysema, etc.], expectoration, pneumonitis, systemic inflammatory response syndrome (SIRS), septic shock, endotoxin shock, anaphylactic shock, adult respiratory distress syndrome, disseminated intravascular coagulopathy, arthritis, rheumatism, osteoarthritis, lumbago, inflammation-induced bone resorption, conjunctivitis, vernal conjunctivitis, uveitis, iritis, iridocyclitis, headache, migraine, toothache, backache, superficial pain, cancerous pain, postoperative pain, tenalgia, trauma [e.g. wound, burn, etc.], rash, erythema, eczema or dermatitis [e.g. contact dermatitis, atopic dermatitis, etc.], urticaria, herpes, itching, psoriasis, lichen, inflammatory bowel disease [e.g. ulcerative colitis, Crohn's disease, etc.], diarrhea, hepatitis, pancreatitis, gastritis, esophagitis, food allergy, ulcer, irritable bowel syndrome, nephritis, angina, periodontitis, edema, hereditary angioneurotic edema, cerebral edema, low blood pressure, thrombosis, myocardial infarction, cerebral vasospasm, congestion, coagulation, gout, central nervous system injury, premature labor, arteriosclerosis, postgastrectomy dumping syndrome, carcinoid syndrome, altered sperm mobility, diabetic neuropathy, neuralgia, graft rejection in transplantation, or the like, in human being or animals.

And further, it is known that bradykinin relates to the release of mediators such as prostaglandins, leukotrienes, tachykinins, histamine, thromboxanes, or the like, so the compound [I] is expected to be useful for the prevention and/or the treatment of such mediators mediated diseases.

In order to illustrate the usefulness of the object compound [I], the pharmacological test data of some representative compounds of the compound [I] are shown in the following.

$^3$H-Bradykinin Receptor Binding (i) Test Method
(a) Crude Ileum Membrane Preparation Male Hartly strain guinea pigs were sacrificed by decapitation. The ileum was removed and homogenized in buffer (50 mM trimethylaminoethanesulfonic acid (TES), 1 mM 1,10-phenanthroline pH 6.8). The homogenate was centrifuged (1000×g, 20 minutes) to remove tissue clumps and the supernatant was centrifuges (100,000×g, 60 minutes) to yield a pellet. The pellet was resuspended in buffer (50 mM TES, 1 mM 1,10-phenanthroline, 140 mg/l bacitracin, 1 mM dithiothreiol, 0.1% bovine serum albumin pH 6.8) and homogenized with a glass-teflon homogenizer to yield suspension which was referred to as crude membrane suspension. The obtained membrane suspension was stored at –80° C. until use.

(b) $^3$H-Bradykinin Binding to the Membrane

The frozen crude membrane suspension was thawed. In binding assays, $^3$H-Bradykinin (0.06 nM) and drug ($1\times10^{-5}$M) were incubated with 50 μl of the membrane suspension at room temperature for 60 minutes in a final volume of 250 μl. Separation of receptor-bound from free $^3$H-Bradykinin is achieved by immediate filtration under vacuum and washed three times with 5 ml of ice-cold buffer (50 mM Tris-HCl pH 7.5). Non-specific binding was defined as binding in the presence of 0.1 μM Bradykinin. The radioactivity retained on rinsed filters was determined by a liquid-scintillation counter.

(ii) Test Results

| Test Compound (Example No.) | Inhibition % of $^3$H-Bradykinin binding (concentration: $1\times10^{-5}$M) |
|---|---|
| 35 | 99 |
| 40-(21) | 97 |
| 47 | 100 |
| 49 | 100 |
| 60 | 100 |
| 61-(1) | 95 |
| 61-(5) | 99 |
| 61-(7) | 100 |
| 61-(11) | 98 |
| 61-(13) | 98 |
| 61-(16) | 100 |
| 61-(18) | 97 |
| 61-(23) | 100 |
| 61-(28) | 99 |
| 61-(41) | 100 |
| 61-(51) | 100 |
| 61-(54) | 100 |

The effects of the compound [I] on bradykinin-induced bronchoconstriction and carrageenin-induced paw edema were measured according to similar manners described in British Journal of Pharmacology, 102, 774–777 (1991).

For therapeutic purpose, the compound [I] and a pharmaceutically acceptable salt thereof of the present invention can be used in a form of pharmaceutical preparation containing one of said compounds, as an active ingredient, in admixture with a pharmaceutically acceptable carrier such as an organic or inorganic solid, semi-solid or liquid excipient sutable for oral, parenteral such as intravenous, intramascular, subcutaneous or intraarticular, external such as topical, enteral, intrarectal, transvaginal, inhalant, ophthalmic, nasal or hypoglossal administration. The pharmaceutical preparations may be capsules, tablets, dragees, granules, suppositories, solution, lotion, suspension, emulsion, ointment, gel, cream, or the like. If desired, there may be included in these preparations, auxiliary substances, stabilizing agents, wetting or emulsifying agents, buffers and other commonly used additives.

While the dosage of the compound [I] will vary depending upon the age and condition of the patient, an average single dose of about 0.1 mg, 1 mg, 10 mg, 50 mg, 100 mg, 250 mg, 500 mg and 1000 mg of the compound [I] may be

47 effective for preventing and/or treating the above-mentioned diseases. In general, amounts between 0.1 mg/body and about 1,000 mg/body may be administered per day.

The following Preparations and Examples are given for the purpose of illustrating this invention.

Preparation 1

Concentrated sulfuric acid (2.8 ml) was added dropwise to 70% nitric acid (4.0 ml) in an ice-water bath. This mixture was added to a solution of 2,4,6-trichlorobenzoic acid (5.13 g) in concentrated sulfuric acid (23 ml) dropwise for 20 minutes in an ice-water bath. The mixture was stirred for 16 hours at ambient temperature and poured into ice-water (300 ml) slowly. This mixture was stirred for 1 hour at ambient temperature. The precipitate was collected by vacuum filtration and washed with water to give 2,4,6-trichloro-3-nitrobenzoic acid (5.26 g) as colorless fine crystals.

mp: 162°–164° C. p NMR (CDCl$_3$, δ): 5.72 (1H, br s), 7.60 (1H, s)

Preparation 2

To a solution of 2,6-dichloro-3-nitrotoluene (50 g) in acetic acid (400 ml) and ethanol (200 ml) was added iron (67.8 g) and the mixture was refluxed for 1.5 hours under nitrogen atmosphere. The insoluble material was filtered off and the filtrate was concentrated. To the residue was added a saturated aqueous solution of sodium bicarbonate and the mixture was extracted with ethyl acetate three times. The combined organic layers were washed with a saturated aqueous solution of sodium bicarbonate three times and brine, dried over magnesium sulfate, and concentrated in vacuo to give 2,4-dichloro-3-methylaniline (41 g).

mp: 54°–56° C. p NMR (CDCl$_3$, δ): 2.45 (3H, s), 4.06 (2H, br s), 6.58 (1H, d, J=9Hz), 7.07 (1H, d, J=9Hz)

Preparation 3

(1) To a mixture of 2,4-dichloro-6-mercapto-3-methylaniline (861 mg), sodium hydrogen carbonate (1.16 g), tetrahydrofuran (9 ml) and water (9 ml) was added chloroacetyl chloride (0.36 ml) dropwise under an ice-water bath cooling. The mixture was stirred under an ice-water bath cooling for 15 minutes and then heated under reflux for 1 hour. The reaction mixture was cooled and poured into a mixture of dichloromethane and brine. The aqueous layer and insoluble precipitate was extracted twice with a mixture of dichloromethane and methanol (4:1, V/V). The organic layer and extracts were combined, dried over magnesium sulfate and evaporated in vacuo to give an yellow powder of 2H-5,7-dichloro-6-methyl-1,4-benzothiazin-3(4H)-one (801 mg). This powder was used for the next step without further purification.

(2) To a solution of 2H-5,7-dichloro-6-methyl-1,4-benzothiazin-3(4H)-one (846 mg) in N,N-dimethylformamide (17 ml) was added sodium hydride (40% in oil, 150 mg) under an ice-water bath cooling. The mixture was stirred at ambient temperature for 30 minutes and then, methyl iodide (0.4 ml) was added thereto. After stirring for 30 minutes, the mixture was partitioned between ethyl acetate and brine. The aqueous layer was extracted with ethyl acetate. The organic layers were combined, dried over magnesium sulfate and evaporated in vacuo. The residue was purified by silica gel column chromatography (dichloromethane-n-hexane) followed by crystallization from n-hexane to give 2H-5,7-dichloro-4,6-dimethyl-1,4-benzothiazin-3(4H)-one (590 mg) as pale yellow crystals.

mp: 98°–99° C. p NMR (CDCl$_3$, δ): 2.50 (3H, s), 3.35 (2H, s), 3.40 (3H, s), 7.39 (1H, s)

48

Preparation 4

To a solution of 2,4-dichloro-6-mercapto-3-methylaniline (2.08 g) in dichloromethane (40 ml) was added 1,1'-carbonyldiimidazole (1.78 g) at ambient temperature. The mixture was stirred for one hour at the same temperature. The separated precipitate was collected by filtration, washed with dichloromethane, and dried to give 4,6-dichloro-5-methyl-2-benzothiazolinone (1.40 g).

mp: >250° C. p NMR (DMSO-d$_6$, δ): 2.42 (3H, s), 7.26 (1H, s)

Preparation 5

The following compounds were obtained according to a similar manner to that of Preparation 3-(2).

(1) 4,6-Dichloro-3,5-dimethyl-2-benzothiazolinone mp: 120°–122° C. p NMR (CDCl$_3$, δ): 2.52 (3H, s), 3.87 (3H, s), 7.33 (1H, s)

(2) 4,6-Dichloro-3-ethyl-5-methyl-2-benzothiazolinone mp: 101°–103° C. p NMR (CDCl$_3$, δ): 1.39 (3H, t, J=7.5Hz), 2.53 (3H, s), 4.49 (2H, q, J=7.5Hz), 7.36 (1H, s)

Preparation 6

The following compounds were obtained according to similar manners to those of Example 14 or 15 mentioned below.

(1) 3-Acetylamino-2,6-dichlorotoluene mp: 118°–119° C. p NMR (CDCl$_3$, δ): 2.24 (3H, s), 2.49 (3H, s), 7.29 (1H, d, J=9Hz), 7.63 (1H, br s), 8.20 (1H, d, J=9Hz)

(2) 3-(4-Chlorobutyryl)amino-2,6-dichlorotoluene mp: 103°–105° C. p NMR (CDCl$_3$, δ): 2.23 (2H, m), 2.49 (3H, s), 2.66 (2H, t, J=8Hz), 3.69 (2H, t, J=3Hz), 7.30 (1H, d, J=8Hz), 7.69 (1H, br s), 8.19 (1H, d, J=8Hz)

(3) 3-Acetoxyacetylamino-2,6-dichlorotoluene mp: 111°–112° C. p NMR (CDCl$_3$, δ): 2.25 (3H, s), 2.50 (3H, s), 4.73 (2H, s), 7.31, 8.27 (each 1H, d, J=9Hz), 8.52 1H, br s)

(4) 2,6-Dichloro-3-(phthalimidoacetyl)aminotoluene mp: 245°–246° C. p NMR (CDCl$_3$, δ): 2.48 (3H,, s), 4.59 (2H, s), 7.27 (1H, d, J=9Hz), 7.70–7.96 (4H), 8.00 (1H, br s), 8.12 (1H, d, J=9Hz)

Preparation 7

The following compounds were obtained according to a similar manner to that of Example 23 mentioned below.

(1) 3-(N-Acetyl-N-methylamino)-2,6-dichlorotoluene mp: 118°–119° C. p NMR (CDCl$_3$, δ): 1.80 (3H, s), 2.53 (3H, s), 3.18 (3H, s), 7.10 (1H, d, J=9Hz), 7.38 (1H, d, J=9Hz)

(2) 3-(N-Acetoxyacetyl-N-methylamino)-2,6-dichlorotoluene mp: 107°–108° C. p NMR (CDCl$_3$, δ): 2.13 (3H, s), 2.55 (3H, s), 3.20 (3H, s), 4.16, 4.44 (each 1H, d, J=15Hz), 7.19, 7.40 (each 1H, d, J=9Hz)

(3) 2,6-Dichloro-3-[N-(phthalimidoacetyl)-N-methylamino]toluene mp: 193°–194° C. p NMR (CDCl$_3$, δ): 2.58 (3H, s), 3.21 (3H, s), 4.10 (2H, s), 7.30 (1H, d, J=9Hz), 7.42 (1H, d, J=9Hz), 7.65–7.91 (4H)

Preparation 8

To a solution of 3-(4-chlorobutyryl)amino-2,6-dichlorotoluene (2.80 g) in N,N-dimethylformamide (30 ml) was added sodium hydride (60% oil dispersion, 440 mg) in one portion at 5° C. The mixture was stirred for 10 minutes at 5° C. and then for 2 hours at 60° C. The cooled mixture was poured into ice water. The separated oil was extracted with dichloromethane. The organic layer was washed with water three times, dried, and concentrated in vacuo. The residue was purified by flash chromatography on silica gel to give 1-(2,4-dichloro-3-methylphenyl)-2-pyrrolidinone (1.95 g).

mp: 77°–82° C. p NMR (CDCl$_3$, δ): 2.25 (2H, m), 2.50 (3H, s), 2.58 (2H, t, J=8Hz), 3.75 (2H, t, J=8Hz), 7.08 (1H, d, J=8Hz), 7.33 (1H, d, J=8Hz)

Preparation 9

A mixture of 4,6-dichloro-3,5-dimethyl-2-benzothiazolinone (1.30 g), N-bromosuccinimide (1.03 g), 2,2'-azobis-(2,4-dimethyl-4-methoxyvaleronitrile) (65 mg) and dichloromethane (26 ml) was heated under reflux for 2 hours. N-Bromosuccinimide (500 mg) was added therein and the mixture was heated under reflux for additional 4 hours. The reaction mixture was washed with water twice and brine, dried over magnesium sulfate and evaporated in vacuo. The residue was crystallized from diethyl ether to give 5-bromomethyl-4,6-dichloro-3-methyl-2-benzothiazolinone (1.20 g) as crystals.

mp: 142°–143° C. p NMR (CDCl$_3$, δ): 3.89 (3H, s), 4.82 (2H, s), 7.40 (1H, s)

Preparation 10

The following compounds were obtained according to a similar manner to that of Preparation 9.

(1) 3-Bromomethyl-2,4-dichloro-N-trifluoroacetyl-N-methylaniline

NMR (CDCl$_3$, δ): 3.31 (3H, s), 4.78 (2H, s), 7.23 (1H, d, J=9Hz), 7.43 (1H, d, J=9Hz)

(2) N-Acetyl-3-bromomethyl-2,4-dichloro-N-methylaniline mp: 123° C. (dec.) p NMR (CDCl$_3$, δ): 1.81 (3H, s), 3.19 (3H, s), 4.79 (2H, s), 7.22 (1H, d, J=9Hz), 7.43 (1H, d, J=9Hz)

(3) 1-(3-Bromomethyl-2,4-dichlorophenyl)-2-pyrrolidinone mp: 106°–109° C. p NMR (CDCl$_3$, δ): 2.17–2.38 (2H, m), 2.59 (2H, t, J=8Hz), 3.79 (2H, t, J=6Hz), 4.77 (2H, s), 7.21, 7.40 (each 1H, d, J=9Hz)

(4) N-Acetoxyacetyl-3-bromomethyl-2,4-dichloro-N-methylaniline mp: 92°–93° C. p NMR (CDCl$_3$, δ): 2.12 (3H, s), 3.21 (3H, s), 4.16, 4.44 (each 1H, d, J=15Hz), 4.79 (2H, s) 7.31, 7.48 (each 1H, d, J=9Hz)

(5) 3-Bromomethyl-2,4-dichloro-N-methyl-N-(phthalimidoacetyl)aniline mp: 211° C. (dec.) p NMR (CDCl$_3$, δ): 3.24 (3H, s), 4.09 (2H, s), 4.81 (2H, s), 7.44 (1H, d, J=9Hz), 7.51 (1H, d, J=9Hz), 7.68–7.91 (4H)

(6) N,N-Di-(tert-butoxycarbonyl)-2,4-dichloro-3-bromomethylaniline

NMR (CDCl$_3$, δ): 1.40 (18H, s), 4.79 (2H, s), 7.13 (1H, d, J=9Hz), 7.35 (1H, d, J=9Hz)

(7) 5-Bromomethyl-4,6-dichloro-3-ethyl-2-benzothiazolinone mp: 120°–126° C. p NMR (CDCl$_3$, δ): 1.41 (3H, t, J=7.5Hz), 4.50 (2H, q, J=7.5Hz), 4.85 (2H, s), 7.42 (1H, s)

(8) 2H-6-Bromomethyl-5,7-dichloro-4-methyl-1,4-benzothiazin-3(4H)-one

NMR (CDCl$_3$, δ): 3.38 (2H, s), 3.42 (3H, s), 4.78 (2H, s), 7.44 (1H, s)

Preparation 11

To a solution of 2,4-dichloro-1-isopropoxybenzene (3.53 g) in tetrahydrofuran (35 ml) was added n-butyl lithium solution (1.6 Mol solution in n-hexane, 11 ml) through a syringe at −78° C. After stirring for one hour at −78° C., the mixture was poured into dry diethyl ether (50 ml) containing pulverized dry ice in a few minutes. After warming to ambient temperature, the mixture was concentrated in vacuo. The residue was partitioned between diethyl ether (50 ml) and aqueous 10% sodium hydroxide solution (100 ml). The aqueous layer was adjusted to pH 2 with 10% hydrochloric acid. The separated oil was extracted with dichloromethane. The extract was washed with water, dried, and evaporated under reduced pressure. The residue was crystallized from n-hexane to give 2,6-dichloro-3-isopropoxybenzoic acid (3.0 g).

mp: 133°–138° C. p NMR (CDCl$_3$, δ): 1.39 (6H, d, J=6Hz), 4.55 (1H, m), 6.95 (1H, d, J=10Hz), 7.29 (1H, d, J=10Hz)

Preparation 12

To a solution of 2,6-dichloro-3-isopropoxybenzoic acid (2.49 g) in tetrahydrofuran (30 ml) was added borane-methyl sulfide complex (2 ml, 10 Mol solution) through a syringe at ambient temperature. The mixture was refluxed for half an hour, cooled, and quenched with aqueous saturated ammonium chloride solution. The organic layer was dried and concentrated in vacuo. The residue was purified by flash chromatography on silica gel to give 2,6-dichloro-3-isopropoxybenzyl alcohol as a colorless oil (1.66 g).

NMR (CDCl$_3$, δ): 1.38 (6H, d, J=5Hz), 2.15 (1H, t, J=7.5Hz), 4.52 (1H, m), 4.97 (2H, d, J=7.5Hz), 6.87 (1H, d, J=10Hz), 7.25 (1H, d, J=10Hz)

Preparation 13

The following compounds were obtained according to a similar manner to that of Preparation 12.

(1) 2,6-Dichloro-3-methoxybenzyl alcohol mp: 99°–101° C. p NMR (CDCl$_3$, δ): 2.12 (1H, br s), 3.90 (3H, s), 4.98 (2H, s), 6.86 (1H, d, J=9Hz), 7.30 (1H, d, J=9Hz)

(2) 2,4,6-Trichloro-3-nitrobenzyl alcohol mp: 121°–124° C. p NMR (CDCl$_3$, δ): 2.08 (1H, t, J=6Hz), 4.98 (2H, d, J=6Hz), 7.57 (1H, s)

(3) 2,6-Dichloro-3-nitrobenzyl alcohol mp: 99°–100° C. p NMR (CDCl$_3$, δ): 5.03 (2H, s), 7.50 (1H, d, J=8Hz), 7.72 (1H, d, J=8Hz)

Preparation 14

To a mixture of 2,6-dichloro-3-isopropoxybenzyl alcohol (1.65 g) and triethylamine (808 mg) in dichloromethane was added methanesulfonyl chloride (884 mg) in a few minutes at 5° C. After stirring for half an hour at 5° C., the mixture was washed with diluted hydrochloric acid and then with aqueous sodium bicarbonate solution, dried, and concentrated in vacuo. The residue was crystallized from n-hexane to give 2,6-dichloro-3-isopropoxybenzyl methanesulfonate (2.07 g).

mp: 78°–81° C. p NMR (CDCl$_3$, δ): 1.49 (6H, d, J=5Hz), 3.10 (3H, s), 4.56 (1H, m), 5.54 (2H, s), 6.98 (1H, d, J=10Hz), 7.31 (1H, d, J=10Hz)

Preparation 15

The following compounds were obtained according to a similar manner to that of Preparation 14.

(1) 2,6-Dichloro-3-methoxybenzyl methanesulfonate

NMR (CDCl$_3$, δ): 3.10 (3H, s), 3.91 (3H, s), 5.53 (2H, s), 6.98 (1H, d, J=9Hz), 7.46 (1H, d, J=9Hz)

51

(2) 2,4,6-Trichloro-3-nitrobenzyl methanesulfonate mp: 113°–114° C. p NMR (CDCl₃, δ): 3.12 (3H, s), 5.50 (2H, s), 7.63 (1H, s)

(3) 2,6-Dichloro-3-nitrobenzyl methanesulfonate mp: 78°–80° C. p NMR (CDCl₃, δ): 3.13 (3H, s), 5.60 (2H, s), 7.57 (1H, d, J=8Hz), 7.85 (1H, d, J=8Hz)

Preparation 16

A mixture of 8-hydroxy-2-methylimidazo[1,2-a]pyridine (207 mg), 2,6-dichloro-3-nitrobenzyl bromide (400 mg) and potassium carbonate (580 mg) in N,N-dimethylformamide (8 ml) was stirred for 2 hours at 60° C. The mixture was cooled and diluted with water. The separated oil was extracted with dichloromethane. The organic layer was washed with water, dried, and concentrated in vacuo. The residue was purified by flash chromatography on silica gel to give 8-(2,6-dichloro-3-nitrobenzyloxy)-2-methylimidazo[1,2-a]pyridine (120 mg) as crystals.

mp: 183°–185° C. p NMR (CDCl₃, δ): 2.43 (3H, s), 5.50 (2H, s), 6.59 (1H, d, J=7.5Hz), 6.66 (1H, t, J=7.5Hz), 7.32 (1H, s), 7.52 (1H, d, J=9Hz), 7.75 (1H, d, J=7.5Hz), 7.79 (1H, d, J=9Hz)

Preparation 17

A mixture of 8-hydroxy-2-methylimidazo[1,2-a]pyridine (296 mg), 1,3-dichloro-2-(2-mesyloxyethyl)benzene (645 mg) and potassium carbonate (828 mg) in N,N-dimethylformamide (12 ml) was stirred for 6 hours at 70° C. The mixture was treated according to a similar manner to that of Preparation 16 to give 8-[2-(2,6-dichlorophenyl)ethyloxy]-2-methylimidazo[1,2-a]pyridine (150 mg).

mp: 92°–94° C. p NMR (CDCl₃, δ): 2.48 (3H, s), 3.69 (2H, m), 4.29 (2H, m), 6.49 (1H, d, J=7.5Hz), 6.61 (1H, t, J=7.5Hz), 7.15 (1H, dd, J=7Hz and 5Hz), 7.29–7.35 (3H, m), 7.69 (1H, d, J=7.5Hz)

Preparation 18

The following compounds were obtained according to similar manners to those of Preparation 16 or 17.

(1) 2-Amino-3-(2,6-dichlorobenzyloxy)-6-methylpyridine mp: 140°–141° C. p NMR (CDCl₃, δ): 2.35 (3H, s), 4.61 (2H, br s), 5.28 (2H, s), 6.49 (1H, d, J=8Hz), 7.08 (1H, d, J=8Hz), 7.20–7.41 (3H)

(2) 8-[1-(2,6-Dichlorophenyl)ethoxy]-2-methylimidazo[1,2-a]pyridine mp: 173°–174° C. p NMR (CDCl₃, δ): 1.93 (3H, d, J=7Hz), 2.48 (3H, s), 6.06–6.22 (2H), 6.42 (1H, t, J=7Hz), 7.06–7.32 (4H), 7.59 (1H, d, J=7Hz)

(3) 8-[2,6-Dichloro-3-(N-methyl-N-acetylamino)benzyloxy]-2-methylimidazo[1,2-a]pyridine mp: 159°–161° C. p NMR (CDCl₃, δ): 1.86 (3H, s), 2.44 (3H, s), 3.20 (3H, s), 5.50 (2H, s), 6.55–6.75 (2H), 7.29 (1H, d, J=9Hz), 7.33 (1H, s), 7.46 (1H, d, J=9Hz), 7.74 (1H, d, J=7Hz)

(4) 8-[2,6-Dichloro-3-(N-methyl-N-trifluoroacetylamino)benzyloxy]-2-methylimidazo[1,2-a]pyridine NMR (CDCl₃, δ): 2.42 (3H, s), 3.31 (3H, s), 5.48 (2H, s), 6.57–6.70 (2H, m), 7.30 (1H, d, J=10Hz), 7.33 (1H, s), 7.46 (1H, d, J=10Hz), 7.74 (1H, dd, J=7.5Hz and 2Hz)

(5) 8-[2,6-Dichloro-3-(N-methyl-N-tert-butoxycarbonylamino)benzyloxy]-2-methylimidazol,[1,2-a]pyridine (6) 8-[2,6-Dichloro-3-(N-methyl-N-mesylamino)benzyloxy]-2-methylimidazo[1,2-a]pyridine NMR (CDCl₃, δ): 2.42 (3H, s), 3.04 (3H, s), 3.29 (3H, s), 5.45 (2H, s), 6.58–6.72 (2H, m), 7.32 (1H, s), 7.42 (1H, d, J=10Hz), 7.49 (1H, d, J=10Hz), 7.74 (1H, dd, J=7.5Hz and 1.5Hz)

52

(7) 8-[2,6-Dichloro-3-(2-pyrrolidinon-1-yl)benzyloxy]-2-methylimidazo[1,2-a]pyridine mp: 190°–191° C. p NMR (CDCl₃, δ): 2.13–2.35 (2H, m), 2.42 (3H, s), 2.59 (2H, t, J=9Hz), 3.76 (2H, t, J=9Hz), 5.43 (2H, s), 6.54–6.75 (2H, m), 7.21–7.48 (3H, m), 7.73 (1H, d, J=6Hz)

(8) 8-(2,6-Dichloro-3-methoxybenzyloxy)-2-methylimidazo-[1,2-a]pyridine mp: 179°–180° C.

NMR (CDCl₃, δ): 2.42 (3H, s), 3.91 (3H, s), 5.46 (2H, s), 6.55–6.72 (2H), 6.92 (1H, d, J=9Hz), 7.24–7.36 (2H), 7.71 (1H, d, J=7Hz)

(9) 8-(2,6-Dichloro-3-isopropoxybenzyloxy)-2-methylimidazo[1,2-a]pyridine

NMR (CDCl₃, δ): 1.40 (6H, d, J=5Hz), 2.45 (3H, s), 4.57 (1H, m), 5.45 (2H, s), 6.59–6.70 (2H, m), 6.92 (1H, d, J=10Hz), 7.25–7.31 (2H, m), 7.72 (1H, dd, J=7.5Hz and 1.5Hz)

(10) 8-(2,4,6-Trichloro-3-nitrobenzyloxy)-2-methylimidazo[1,2-a]pyridine mp: 184°–186° C.

NMR (CDCl₃, δ) 2.44 (3H, s), 5.47 (2H, s), 6.57 (1H, d, J=8Hz), 6.67 (1H, t, J=8Hz), 7.33 (1H, s), 7.58 (1H, s), 7.76 (1H, d, J=8Hz)

(11) 8-[2-Chloro-5-(N-methyl-N-acetylamino)benzyloxy]-2-methylimidazo[1,2-a]pyridine NMR (CDCl₃, δ): 2.49 (3H, s), 3.21 (3H, s), 5.43 (2H, s), 6.40 (1H, d, J=7.5Hz), 6.58 (1H, t, J=7.5Hz), 7.10 (1H, dd, J=10Hz and 1.5Hz), 7.37 (1H, s), 7.46 (1H, d, J=10Hz), 7.49 (1H, d, J=1.5Hz), 7.74 (1H, d, J=7.5Hz)

(12) 8-[3-(N-Acetoxyacetyl-N-methylamino)-2,6-dichlorobenzyloxy]-2-methylimidazo[1,2-a]pyridine mp: 118°–119° C.

NMR (CDCl₃, δ): 2.14 (3H, s), 2.42 (3H, s), 3.21 (3H, s), 4.19, 4.48 (each 1H, d, J=15Hz), 5.49 (1H, s), 6.54–6.72 (2H), 7.32 (1H, s), 7.40–7.49 (each 1H, d, J=9Hz), 7.74 (1H, d, J=7Hz)

(13) 8-[2,6-Dichloro-3-(N-methyl-N-phthalimidoacetylamino)benzyloxy]-2-methylimidazo[1,2-a]pyridine mp: 221°–223° C.

NMR (CDCl₃, δ) 2.42 (3H, s), 3.22 (3H, s), 4.11 (2H, s), 5.52 (2H, s), 6.59–6.73 (2H), 7.32 (1H, s), 7.52 (2H, s), 7.67–7.92 (4H)

(14) 2-Methyl-8-(2-trifluoromethylbenzyloxy)imidazo[1,2-a]pyridine mp: 131°–132° C.

NMR (CDCl₃, δ) 2.48 (3H, s), 5.38 (2H, s), 6.35 (1H, d, J=7Hz), 6.55 (1H, t, J=7Hz), 7.32 (1H, s), 7.61 (5H, s), 7.69 (1H, d, J=7Hz)

(15) 8-(2-Methoxycarbonylbenzyloxy)-2-methylimidazo-[1,2-a]pyridine mp: 88°–89° C.

NMR (CDCl₃, δ): 2.49 (3H, s), 3.92 (3H, s), 5.77 (2H, s), 6.38 (1H, d, J=7.5Hz), 6.55 (1H, d, J=7.5Hz), 7.33 (1H, s), 7.37 (1H, t, J=7.5Hz), 7.53 (1H, t, J=7.5Hz), 7.67 (1H, d, J=7.5Hz), 7.88 (1H, d, J=7.5Hz), 8.05 (1H, d, J=7.5Hz)

(16) 8-(2-Phenylbenzyloxy)-2-methylimidazo[1,2-a]pyridine mp: 90°–92° C.

NMR (CDCl₃, δ): 2.48 (3H, s), 5.19 (2H, s), 6.14 (1H, d, J=7.5Hz), 6.48 (1H, t, J=7.5Hz), 7.31–7.45 (9H, m), 7.63 (1H, d, J=7.5Hz), 7.75 (1H, m)

(17) 8-(2,6-Difluorobenzyloxy)-2-methylimidazo[1,2-a]pyridine mp: 114°–116° C.

NMR (CDCl₃, δ): 2.45 (3H, s), 5.31 (2H, s), 6.56–6.67 (2H, m), 6.86–6.99 (2H, m), 7.25–7.41 (1H, m), 7.32 (1H, s), 7.70 (1H, d, J=7.5Hz)

(18) 8-(2,6-Dibromobenzyloxy)-2-methylimidazo[1,2-a]pyridine mp: 159°–162° C.

NMR (CDCl$_3$, δ) 2.43 (3H, s), 5.49 (2H, s), 6.59 (1H, d, J=7Hz), 6.67 (1H, t, J=7Hz), 7.08 (1H, t, J=8Hz), 7.30 (1H, s), 7.58 (2H, d, J=8Hz), 7.71 (1H, d, J=7Hz)

(19) 8-(2-Chloro-6-fluorobenzyloxy)-2-methylimidazo-[1,2-a]pyridine mp: 150°–151° C.

NMR (CDCl$_3$, δ) 2.44 (3H, s), 5.38 (2H, s), 6.59 (1H, d, J=7Hz), 6.63 (1H, t, J=7Hz), 7.02 (1H, t, J=8Hz), 7.20–7.38 (3H), 7.70 (1H, d, J=7Hz)

(20) 8-(4-Bromo-2-fluorobenzyloxy)-2-methylimidazo[1,2-a]pyridine mp: 150°–151° C.

NMR (CDCl$_3$, δ): 2.48 (3H, s), 5.31 (2H, s), 6.42 (1H, d, J=7.5Hz), 6.58 (1H, t, J=7.5Hz), 7.23–7.33 (3H, m), 7.49 (1H, t, J=7.5Hz), 7.69 (1H, d, J=7.5Hz)

(21) 8-(2-Chloro-5-nitrobenzyloxy)-2-methylimidazo[1,2-a]pyridine mp: 134°–135° C.

NMR (CDCl$_3$, δ) 2.49 (3H, s), 5.48 (2H, s), 6.41 (1H, d, J=7Hz), 6.60 (1H, t, J=7Hz), 7.36 (1H, s), 7.60 (1H, d, J=9Hz), 7.74 (1H, d, J=7Hz), 8.16 (1H, dd, J=9Hz and 2Hz), 8.55 (1H, d, J=2Hz)

(22) 8-[2-Chloro-6-(N-methyl-N-acetylamino)benzyloxy]-2-methylimidazo[1,2-a]pyridine NMR (CDCl$_3$, δ) 1.90 (3H, s), 2.41 (3H, s), 3.23 (3H, s), 5.19 (1H, d, J=10Hz), 5.26 (1H, d, J=10Hz), 6.55 (1H, d, J=7.5Hz), 6.67 (1H, t, J=7.5Hz), 7.18 (1H, dd, J=7.5Hz and 2Hz), 7.33 (1H, s), 7.48–7.54 (2H, m), 7.74 (1H, dd, J=7.5Hz and 2Hz)

(23) 8-(2-Chloro-6-nitrobenzyloxy)-2-methylimidazo[1,2-a]pyridine mp: 162°–163° C.

NMR (CDCl$_3$, δ): 2.41 (3H, s), 5.62 (2H, s), 6.51–6.69 (2H), 7.30 (1H, s), 7.48 (1H, t, J=8Hz), 7.63–7.75 (2H), 7.85 (1H, d, J=7Hz).

(24) 8-[3-(N,N-Di-tert-butoxycarbonylamino)-2,6-dichlorobenzyloxy]-2-methylimidazo[1,2-a]pyridine mp: 180°–181° C.

NMR (CDCl$_3$, δ) 1.41 (18H, s), 2.42 (3H, s), 5.53 (2H, s), 6.51–6.68 (2H), 7.20 (1H, d, J=9Hz), 7.30 (1H, s), 7.38 (1H, d, J=9Hz), 7.70 (1H, d, J=7Hz)

(25) 2-Methyl-8-(2,4,6-trichlorobenzyloxy)imidazo[1,2-a]pyridine mp: 187°–189° C.

NMR (CDCl$_3$, δ) 2.42 (3H, s), 5.40 (2H, s), 6.58 (1H, d, J=7Hz), 6.67 (1H, t, J=7Hz), 7.31 (1H, s), 7.49 (2H, s), 7.71 (1H, d, J=7Hz)

(26) 8-(2,3,6-Trichlorobenzyloxy)-2-methylimidazo[1,2-a]pyridine mp: 148°–149° C.

NMR (CDCl$_3$, δ) 2.42 (3H, s), 5.48 (2H, s), 6.52–6.71 (2H), 7.30 (1H, d, J=9Hz), 7.31 (1H, s), 7.45 (1H, d, J=9Hz), 7.72 (1H, d, J=7Hz)

(27) 8-(2,6-Dibromo-4-methoxycarbonylbenzyloxy)-2-methylimidazo[1,2-a]pyridine mp: 153°–154° C.

NMR (CDCl$_3$, δ) 2.42 (3H, s), 3.97 (3H, s), 5.51 (2H, s), 6.58 (1H, d, J=7Hz), 6.68 (1H, t, J=7Hz), 7.31 (1H, s), 7.74 (1H, d, J=7Hz), 8.21 (2H, s)

(28) 8-(4-Benzoyl-2-chlorobenzyloxy)-2-methylimidazo[1,2-a]pyridine

NMR (CDCl$_3$, δ) 2.49 (3H, s), 5.49 (2H, s), 6.40 (1H, d, J=8Hz), 6.60 (1H, d, J=8Hz), 7.35 (1H, s), 7.44–7.88 (9H)

(29) 8-(2,6-Dichloro-4-benzoylbenzyloxy)-2-methylimidazo[1,2-a]pyridine

NMR (CDCl$_3$, δ) 2.45 (3H, s), 5.50 (2H, s), 6.57–6.72 (2H), 7.28–7.92 (9H)

(30) 8-[4-(2-Cyanophenyl)benzyloxy]-2-methylimidazo[1,2-a]pyridine

NMR (CDCl$_3$, δ): 2.49 (3H, s), 5.38 (2H, s), 6.44 (1H, d, J=8Hz), 6.58 (1H, t, J=8Hz), 7.32 (1H, s), 7.38–7.82 (9H)

(31) 8-(6-Chloropiperonyl)methoxy-2-methylimidazo[1,2-a]pyridine mp: 141°–142° C.

NMR (CDCl$_3$, δ) 2.49 (3H, s), 5.31 (2H, s), 5.96 (2H, s), 6.38 (1H, d, J=7Hz), 6.58 (1H, t, J=7Hz), 6.86 (1H, s), 7.11 (1H, s), 7.31 (1H, s), 7.68 (1H, d, J=7Hz)

(32) 8-(2-Bromothiophen-4-yl)methoxy-2-methylimidazo[1,2-a]pyridine mp: 127°–128° C.

NMR (CDCl$_3$, δ): 2.46 (3H, s), 5.42 (2H, s), 6.48 (1H, d, J=7Hz), 6.59 (1H, t, J=7Hz), 7.09 (1H, s), 7.16–7.35 (2H), 7.69 (1H, d, J=7Hz)

(33) 8-(3-Chlorobenzofuran-2-yl)methoxy-2-methylimidazo[1,2-a]pyridine mp: 141°–143° C.

NMR (CDCl$_3$, δ) 2.45 (3H, s), 5.44 (2H, s), 6.56–6.66 (2H, m), 7.29–7.71 (6H, m)

(34) 8-[3-(4-Chlorophenyl)-5-methylbenzofuran-2-yl]methoxy-2-methylimidazo[1,2-a]pyridine mp: 140°–141° C.

NMR (CDCl$_3$, δ) 2.45 (6H, s), 5.33 (2H, s), 6.49 (1H, d, J=7Hz), 6.58 (1H, t, J=7Hz), 7.12–7.56 (8H), 7.70 (1H, d, J=7Hz)

(35) 8-(4,6-Dichloro-3-methyl-2-benzothiazolinon-5-yl)methoxy-2-methylimidazo[1,2-a]pyridine mp: 236°–237° C.

NMR (CDCl$_3$, δ) 2.42 (3H, s), 3.87 (3H, s), 5.50 (2H, s), 6.56–6.72 (2H, m), 7.32 (1H, s), 7.42 (1H, s), 7.72 (1H, d, J=7Hz)

(36) 8-(4,6-Dichloro-3-ethyl-2-benzothiazolinon-5-yl)methoxy-2-methylimidazo[1,2-a]pyridine mp: 202°–205° C.

NMR (CDCl$_3$, δ): 1.41 (3H, t, J=7.5Hz), 2.45 (3H, s), 4.49 (2H, q, J=7.5Hz), 5.53 (2H, s), 6.59–6.72 (2H, m), 7.31 (1H, s), 7.44 (1H, s), 7.74 (1H, dd, J=7.5Hz and 1.5Hz)

(37) 8-(5,7-Dichloro-4-methyl-1,4-benzothiazin-3(4H)-on-6-yl)methoxy-2-methylimidazo[1,2-a]pyridine NMR (CDCl$_3$, δ): 2.44 (3H, s), 3.40 (2H, s), 3.43 (3H, s), 5.45 (2H, s), 6.58 (1H, d, J=8Hz), 6.67 (1H, t, J=8Hz), 7.32 (1H, s), 7.47 (1H, s), 7.73 (1H, d, J=8Hz)

Preparation 19

A mixture of 2-amino-3-(2,6-dichlorobenzyloxy)-pyridine (1.345 g) and 3-bromo-1,1,1-trifluoroacetone (1.147 g) in ethanol (26 ml) was refluxed for 5 hours, cooled, and concentrated in vacuo. The residue was partitioned between ethyl acetate and aqueous sodium bicarbonate solution. The organic layer was washed with water, dried, and concentrated under reduced pressure to give a solid, which was purified by flash chromatography on silica gel to give 8-(2,6-dichlorobenzyloxy)-2-trifluoromethylimidazo[1,2-a]pyridine as a white solid (803 mg).

mp: 184°–185° C.

NMR (CDCl$_3$, δ): 5.50 (2H, s), 6.75 (1H, d, J=7.5Hz), 6.85 (1H, t, J=7.5Hz), 7.23–7.38 (3H, m), 7.83 (1H, d, J=7.5Hz), 7.88 (1H, s)

Preparation 20

The following compounds were obtained according to a similar manner to that of Preparation 19.

(1) 8-(2,6-Dichlorobenzyloxy)-2-ethylimidazo[1,2-a]pyridine mp: 153°–154° C.

NMR (CDCl₃, δ) 1.30 (3H, t, J=7Hz), 2.84 (2H, q, J=7Hz), 5.46 (2H, s), 6.55–6.71 (2H), 7.19–7.42 (4H), 7.73 (1H, d, J=7Hz)

(2) Ethyl 8-(2,6-dichlorobenzyloxy)imidazo[1,2-a]pyridine-2-carboxylate mp: 176°–178° C.

NMR (CDCl₃, δ): 1.40 (3H, t, J=7Hz), 4.42 (2H, q, J=7Hz), 5.49 (2H, s), 6.69 (1H, d, J=7Hz), 6.81 (1H, t, J=7Hz), 7.21–7.43 (3H), 7.81 (1H, d, J=7Hz), 8.18 (1H, s)

(3) 8-(2,6-Dichlorobenzyloxy)-2,5-dimethylimidazo[1,2-a]pyridine mp: 140°–141° C.

NMR (CDCl₃, δ) 2.47 (6H, s), 5.44 (2H, s), 6.45 (1H, d, J=7Hz), 6.60 (1H, d, J=7Hz), 7.15–7.40 (4H)

(4) 8-Amino-2,7-dimethylimidazo[1,2-a]pyridine dihydrochloride mp: >250° C.

NMR (DMSO-d₆, δ): 2.25 (3H, s), 2.46 (3H, s), 6.82 (2H, br s), 7.10 (1H, d, J=7Hz), 7.90 (1H, s), 8.03 (1H, d, J=7Hz)

Preparation 21

8-(2,6-Dichlorophenyl)methylamino-2,7-dimethylimidazo[1,2-a]pyridine (100 mg) was obtained by reacting 8-amino-2,7-dimethylimidazo[1,2-a]pyridine (100 mg) with 2,6-dichlorobenzaldehyde (191 mg) according to a similar manner to that of Example 10 mentioned below.

mp: 87°–88° C.

NMR (CDCl₃, δ) 2.26 (3H, s), 2.40 (3H, s), 4.46 (1H, br s), 4.99 (2H, d, J=5Hz), 6.41 (1H, d, J=7Hz), 7.07–7.40 (4H), 7.53 (1H, d, J=7Hz)

Preparation 22

8-(2,6-Dichlorophenyl)methylamino-2-methylimidazo[1,2-a]pyridine was obtained according to a similar manner to that of Preparation 21.

mp: 119°–121° C.

NMR (CDCl₃, δ): 2.38 (3H, s), 4.69 (2H, d, J=4Hz), 5.19 (1H, t, J=4Hz), 6.29 (1H, d, J=7.5Hz), 6.63 (1H, t, J=7.5Hz), 7.15–7.36 (3H, m), 7.32 (1H, s), 7.47 (1H, d, J=7.5Hz)

Preparation 23

To a suspension of sodium hydride (60% oil dispersion, 17 mg) was added 8-acetylamino-2-methylimidazo[1,2-a]pyridine (73 mg), and the mixture was stirred for 30 minutes. 2,6-dichlorobenzyl bromide (97 mg) was added thereto, and the mixture was stirred for 1 hour. Water was added thereto, and the mixture was extracted with methylene chloride three times. The combined organic layer was washed with water four times and brine, dried over magnesium sulfate, and concentrated in vacuo. The residue was crystallized with diethyl ether to give 8-[N-(2,6-dichlorophenyl)methyl-N-acetylamino]-2-methylimidazo[1,2-a]pyridine (85 mg).

mp: 177°–178° C.

NMR (CDCl₃, δ) 1.95 (3H, s), 2.48 (3H, s), 4.92 (1H, br d, J=15Hz), 6.00 (1H, br d, J=15Hz), 6.36 (1H, d, J=7Hz), 6.45 (1H, t, J=7Hz), 7.00–7.21 (3H), 7.38 (1H, s), 7.98 (1H, d, J=7Hz)

Preparation 24

To a solution of 8-[2,6-dichloro-3-(2-pyrrolidon-1-yl)benzyloxy]-2-methylimidazo[1,2-a]pyridine (120 mg) in tetrahydrofuran (3 ml) was added lithium aluminum hydride (19 mg) under ice-cooling, and the mixture was stirred for 2 hours. A saturated aqueous ammonium chloride solution was added thereto, and insoluble material was filtered off. The filtrate was concentrated, and the residue was purified by preparative thin-layer chromatography (5% solution of methanol in methylene chloride) to give 8-[2,6-dichloro-3-(1-pyrrolidinyl)benzyloxy]-2-methylimidazo[1,2-a]pyridine (23 mg).

NMR (CDCl₃, δ): 1.86–2.01 (4H, m), 2.41 (3H, s), 3.26–3.40 (4H, m), 5.44 (2H, s), 6.57–6.72 (2H, m), 6.90, 7.19 (each 1H, d, J=9Hz), 7.31 (1H, s), 7.72 (1H, d, J=7Hz)

Preparation 25

8-(3-Amino-2,6-dichlorobenzyloxy)-2-methylimidazo[1,2-a]pyridine was obtained according to a similar manner to that of Example 4 mentioned below.

NMR (DMSO-d₆, δ): 2.27 (3H, s), 5.30 (2H, s), 5.70 (2H, s), 6.64–7.00 (3H), 7.24 (1H, d, J=8Hz), 7.65 (1H, s), 8.09 (1H, d, J=7Hz)

Preparation 26

8-(2,6-Dichloro-3-methylaminobenzyloxy)-2-methylimidazo[1,2-a]pyridine was obtained according to a similar manner to that of Example 7 mentioned below.

mp: 167°–168° C.

NMR (CDCl₃, δ): 2.40 (3H, s), 2.91 (3H, d, J=5Hz), 4.41 (1H, br d, J=5Hz), 5.48 (2H, s), 6.56–6.78 (3H), 7.18 (1H, d, J=9Hz), 7.33 (1H, br s), 7.80 (1H, br d, J=6Hz)

Preparation 27

8-[2,6-Dichloro-3-(N-methyl-N-acetylamino)benzyloxy]-2-methylimidazo[1,2-a]pyridine was obtained according to a similar manner to that of Example 14 mentioned below.

mp: 159°–161° C.

NMR (CDCl₃, δ): 1.86 (3H, s), 2.44 (3H, s), 3.20 (3H, s), 5.50 (2H, s), 6.55–6.75 (2H), 7.29 (1H, d, J=9Hz), 7.33 (1H, s), 7.46 (1H, d, J=9Hz), 7.74 (1H, d, J=7Hz)

Preparation 28

8-[2,6-Dichloro-3-(N-methoxycarbonyl-N-methylamino)benzyloxy]-2-methylimidazo[1,2-a]pyridine was obtained according to a similar manner to that of Example 18 mentioned below.

NMR (CDCl₃, δ): 2.40 (3H, s), 3.21 (3H, s), 3.68 (3H, s), 5.45 (2H, s), 6.59–6.82 (2H), 7.21–7.49 (3H), 7.81 (1H, d, J=6Hz)

Preparation 29

Pivaloyl chloride (0.22 ml) was added dropwise to a mixture of acetylsarcosine (264 mg), N-methylmorpholine (0.22 ml) and N-methylpyrrolidone (30 ml) under a dry ice-tetrachloromethane bath cooling. This mixture was stirred for 10 minutes under ice-cooling, and 8-[3-amino-2,6-dichlorobenzyloxy]-2-methylimidazo[1,2-a]pyridine (500 mg) was added thereto under a dry ice-tetrachloromethane bath cooling. The mixture was stirred for 22 hours at ambient temperature. The mixture was partitioned between ethyl acetate and a saturated aqueous sodium bicarbonate solution, and the aqueous layer was extracted with ethyl acetate twice. The combined organic layer was dried over magnesium sulfate and concentrated in vacuo, and the residue was purified by flash column chromatography (methylene chloride:methanol=50:1, V/V) to give 8-[3-

(acetylsarcosylamino)-2,6-dichlorobenzyloxy]-2-methylimidazo[1,2-a]pyridine (260 mg).

NMR (CDCl₃, δ): 2.18 (3H, s), 2.42 (3H, s), 3.09 (0.3H, s), 3.19 (2.7H, s), 4.19 (2H, s), 5.45 (2H, s), 6.55–6.72 (2H), 7.30 (1H, s), 7.34 (1H, d, J=9Hz), 7.72 (1H, d, J=8Hz), 8.38 (1H, d, J=9Hz), 8.81 (1H, br s)

Preparation 30

8-[2,6-Dichloro-3-(N-ethyl-N-methylamino)benzyloxy]-2-methylimidazo[1,2-a]pyridine was obtained according to a similar manner to that of Example 26 mentioned below.

NMR (DMSO-d₆, δ) 1.10 (3H, t, J=7Hz), 2.43 (3H, s), 2.75 (3H, s), 3.05 (2H, q, J=7Hz), 5.59 (2H, s), 7.28–7.62 (3H), 7.71 (1H, d, J=7Hz), 8.16 (1H, br s), 8.55 (1H, d, J=7Hz)

Preparation 31

(1) 3,5'-Dichlorobenzanilide was obtained according to a similar manner to that of Example 15 from 3,5-dichloroaniline and benzoyl chloride.

mp: 148°–149° C.

NMR (CDCl₃, δ): 7.15 (1H, t, J=0.5Hz), 7.44–7.60 (3H, m), 7.51 (2H, d, J=0.5Hz), 7.76–7.97 (3H, m)

(2) 3',5'-Dichloro-N-methylbenzanilide was obtained according to a similar manner to that of Example 23.

NMR (CDCl₃, δ): 3.46 (3H, s), 6.94 (2H, d, J=0.5Hz), 7.13 (1H, t, J=0.5Hz), 7.20–7.41 (5H, m)

(3) To a stirred solution of 3',5'-dichloro-N-methylbenzanilide (2.317 g) in tetrahydrofuran was added lithium aluminum hydride (380 mg) in an ice-bath and the resulting suspension was stirred at the same temperature for one hour. The reaction mixture was quenched with saturated ammonium chloride and filtered through celite pad. The inorganic material on the celite was washed with ethyl acetate.

Methanol was added to the filtrate and stirred at ambient temperature for half an hour. The organic layer was washed with water, dried over anhydrous magnesium sulfate and concentrated in vacuo. The residue was purified by flash chromatography eluting with ethyl acetate-n-hexane (1:9, V/V) to afford 3,5-dichloro-N-methylaniline (1.38 g) as a colorless oil.

NMR (CDCl₃, δ): 2.81 (3H, s), 3.87 (1H, br s), 6.94 (2H, d, J=0.5Hz), 6.66 (1H, t, J=0.5Hz)

(4) The mixture of 3,5-dichloro-N-methylaniline (345 mg) and excess amount of benzyl bromide and triethylamine in acetonitrile (7 ml) was refluxed for 4 hours. The reaction mixture was separated with ethyl acetate and water, and the organic layer was washed with water, dried and concentrated in vacuo to give N-benzyl-3,5-dichloro-N-methylaniline (532 mg).

NMR (CDCl₃, δ): 3.01 (3H, s), 4.50 (2H, s), 6.57 (2H, d, J=0.5Hz), 6.67 (2H, t, J=0.5Hz), 7.10–7.46 (5H, m)

(5) Phosphoryl chloride (12.7 ml) was dropwise added to N,N-dimethylformamide (70 ml), and the mixture was stirred for 30 minutes at ambient temperature. A solution of N-benzyl-3,5-dichloro-N-methylaniline (7.26 g) in N,N-dimethylformamide (30 ml) was dropwise added thereto, and the mixture was stirred for 30 minutes at ambient temperature and then for 30 minutes at 50° C. The reaction mixture was neutralized with 1N aqueous sodium hydroxide solution and extracted with ethyl acetate. The organic solution was washed with water and brine, dried over magnesium sulfate and concentrated in vacuo. The residue was purified by a flash chromatography (ethyl acetate: n-hexane= 1:6, V/V) to give N-benzyl-3,5-dichloro-4-formyl-N-methylaniline (5.70 g).

mp: 66°–70° C.

NMR (CDCl₃, δ): 3.10 (3H, s), 4.60 (2H, s), 6.65 (2H, s), 6.98–7.42 (5H, m), 10.30 (1H, s)

(6) To a solution of N-benzyl-3,5-dichloro-4-formyl-N-methylaniline (820 mg) in ethyl acetate (10 ml) was added palladium hydroxide (80 mg) under nitrogen atmosphere. This mixture was stirred under hydrogen atmosphere under atmospheric pressure at ambient temperature for one and half an hour. The precipitate was dissolved into chloroform and filtered through celite and the filtrate was concentrated in vacuo. The residual solid was suspended in diisopropyl ether and warmed at 90° C. After being stirred and cooled, the solid was collected by filtration to afford 3,5-dichloro-4-formyl-N-methylaniline (470 mg) as a pale brown solid.

mp: 172°–174° C.

NMR (CDCl₃, δ): 2.90 (3H, t, J=5Hz), 4.50 (1H, br s), 6.50 (2H, s), 10.32 (1H, s)

(7) To a solution of 3,5-dichloro-4-formyl-N-methylaniline (242 mg) in methanol (3 ml) and tetrahydrofuran (3 ml) was added sodium borohydride (45 mg) and the mixture was stirred for 30 minutes at ambient temperature. The reaction mixture was quenched with aqueous saturated ammonium chloride solution and ethyl acetate was added thereto. The separated organic layer was washed with aqueous saturated ammonium chloride solution, dried and concentrated in vacuo to give 3,5-dichloro-4-hydroxymethyl-N-methylaniline (246 mg).

mp: 108°–111° C.

NMR (CDCl₃, δ): 1.85 (1H, t, J=6Hz), 2.81 (3H, d, J=5Hz), 3.91 (1H, br s), 4.84 (2H, d, J=6Hz), 6.51 (2H, s)

(8) 3,5-Dichloro-4-hydroxymethyl-N-methylacetanilide was obtained according to a similar manner to that of Example 14.

NMR (CDCl₃, δ) 1.97 (3H, br s), 2.18 (1H, t, J=7Hz), 3.26 (3H, s), 4.96 (2H, d, J=7Hz), 7.23 (2H, s)

(9) 8-[2,6-Dichloro-4-(N-acetyl-N-methylamino)benzyloxy]-2-methylimidazo[1,2-a]pyridine was obtained according to a similar manner to that of Preparation 14 and then Preparation 17.

NMR (CDCl₃, δ) 2.04 (3H, br s), 2.44 (3H, s), 3.27 (3H, s), 5.42 (2H, s), 6.60 (1H, dd, J=7Hz and 0.5Hz), 6.68 (1H, t, J=7Hz), 7.24 (2H, s), 7.33 (1H, s), 7.73 (1H, dd, J=7Hz and 0.5Hz)

Preparation 32

8-[3-(N-Glycyl-N-methylamino)-2,6-dichlorobenzyloxy]-2-methylimidazo[1,2-a]pyridine was obtained according to a similar manner to that of Example 34.

mp: 144°–147° C.

NMR (CDCl₃, δ): 2.42 (3H, s), 3.00 (1H, d, J=17Hz), 3.12 (1H, d, J=17Hz), 3.22 (3H, s), 5.49 (2H, s), 6.56–6.72 (2H), 7.25 (1H, d, J=9Hz), 7.31 (1H, s), 7.45 (1H, d, J=9Hz), 7.72 (1H, d, J=7Hz)

Preparation 33

8-[2,6-Dichloro-3-[N-[N-(N,N-dimethylglycyl)glycyl]-N-methylamino]benzyloxy]-2-methylimidazo[1,2-a]pyridine was obtained according to a similar manner to that of Example 69 mentioned below.

NMR (CDCl₃, δ): 2.31 (6H, s), 2.42 (3H, s), 2.94 (2H, s), 3.25 (3H, s), 3.56 (1H, dd, J=18Hz and 5Hz), 3.86 (1H, dd, J=18Hz and 5Hz), 5.48 (2H, s), 6.59–6.72 (2H), 7.31 (1H, s), 7.33 (1H, d, J=9Hz), 7.49 (1H, d, J=9Hz), 7.72 (1H, d, J=7Hz), 7.89 (1H, br s)

Example 1

To a solution of 8-(2,6-dichloro-3-nitrobenzyloxy)-2-methylimidazo[1,2-a]pyridine (85 mg) in a mixture of ethanol (1 ml) and 1,4-dioxane (1 ml) was added in one portion N-bromosuccinimide (43 mg) at ambient temperature. After stirring for one hour at the same temperature, the mixture was filtered to give 3-bromo-8-(2,6-dichloro-3-nitrobenzyloxy)-2-methylimidazo[1,2-a]pyridine (85 mg) as a yellow solid.

mp: 217°–219° C.

NMR (DMSO-$d_6$, δ): 2.31 (3H, s), 5.50 (2H, s) 7.0–7.04 (2H, m), 7.89–7.98 (2H, m), 8.23 (1H, d, J=9Hz)

Example 2

To a solution of 8-(2,6-dichlorobenzyloxy)-2-methylimidazo[1,2-a]pyridine (100 mg) in ethanol (2 ml) was added in one portion N-chlorosuccinimide (65.3 mg) at ambient temperature. After stirring for 1 hour at the same temperature, water was added thereto, and the mixture was extracted with methylene chloride. The organic layer was washed with brine, dried and concentrated in vacuo. The residue was subjected to a column chromatography on silica gel eluting with 1% solution of methanol in methylene chloride. The desired residue was recrystallized with a mixture of benzene and n-hexane to give 3-chloro-8-(2,6-dichlorobenzyloxy)-2-methylimidazo[1,2-a]pyridine (63 mg).

mp: 185°–186° C.

NMR (CDCl$_3$, δ): 2.43 (3H, s), 5.48 (2H, s), 6.69 (1H, d, J=7Hz), 6.81 (1H, t, J=7Hz), 7.19–7.40 (3H, m), 7.69 (1H, d, J=7Hz)

Example 3

The following compounds were obtained according to similar manners to those of Examples 1 or 2.

(1) 3-Bromo-8-(2,6-dichlorobenzyloxy)-2-methylimidazo[1,2-a]pyridine mp: 173°–174° C.

NMR (CDCl$_3$, δ): 2.44 (3H, s), 5.48 (2H, s), 6.70 (1H, d, J=7Hz), 6.82 (1H, t, J=7Hz), 7.19–7.41 (3H, m), 7.75 (1H, d, J=7Hz)

(2) 3-Chloro-8-(2,6-dichlorobenzyloxy)-2-trifluoromethylimidazo[1,2-a]pyridine mp: 213°–5° C.

NMR (CDCl$_3$—CD$_3$OD, δ): 5.53 (2H, s), 6.98 (1H, d, J=7.5Hz), 7.12 (1H, t, J=7.5Hz), 7.31–7.46 (3H, m), 7.93 (1H, d, J=7.5Hz)

(3) 3-Chloro-8-(2,6-dichlorobenzyloxy)-2-ethylimidazo[1,2-a]pyridine mp: 169°–170° C.

NMR (CDCl$_3$, δ): 1.30 (3H, t, J=7Hz), 2.81 (2H, q, J=7Hz), 5.49 (2H, s), 6.69 (1H, d, J=7Hz), 6.72 (1H, t, J=7Hz), 7.19–7.41 (3H, m), 7.71 (1H, d, J=7Hz)

(4) Ethyl 3-chloro-8-(2,6-dichlorobenzyloxy)imidazo[1,2-a]pyridine-2-carboxylate mp: 207°–208° C.

NMR (CDCl$_3$, δ): 1.41 (3H, t, J=7Hz), 4.47 (2H, q, J=7Hz), 5.50 (2H, s), 6.77 (1H, d, J=7Hz), 6.96 (1H, t, J=7Hz), 7.21–7.44 (3H, m), 7.82 (1H, d, J=7Hz)

(5) 3-Chloro-8-(2,6-dichlorobenzyloxy)-2,5-dimethylimidazo[1,2-a]pyridine mp: 181°–182° C.

NMR (CDCl$_3$, δ) 2.40 (3H, s), 2.89 (3H, s), 5.40 (2H, s), 6.47 (1H, d, J=7Hz), 6.53 (1H, d, J=7Hz), 7.19–7.39 (3H, m)

(6) 3-Bromo-8-[1-(2,6-dichlorophenyl)ethoxy]-2-methylimidazo[1,2-a]pyridine mp: 135°–136° C.

NMR (CDCl$_3$, δ) 1.93 (3H, d, J=7Hz), 2.49 (3H, s), 6.11–6.27 (2H), 6.60 (1H, t, J=7Hz), 7.13 (1H), 7.22–7.32 (2H), 7.61 (1H, d, J=7Hz)

(7) 3-Chloro-8-(2,6-dichlorobenzylamino)-2,7-dimethylimidazo[1,2-a]pyridine mp: 144°–145° C.

NMR (CDCl$_3$, δ) 2.38 (3H, s), 2.40 (3H, s), 4.44 (1H, br s), 5.00 (2H, d, J=5Hz), 6.59 (1H, d, J=7Hz), 7.09–7.42 (3H, m), 7.51 (1H, d, J=7Hz)

(8) 3-Bromo-8-[N-(2,6-dichlorobenzyl)-N-acetylamino]-2-methylimidazo[1,2-a]pyridine mp: 141°–142° C.

NMR (CDCl$_3$, δ) 1.90 (3H, s), 2.49 (3H, s), 4.90 (1H, br d, J=14Hz), 5.99 (1H, br d, J=14Hz), 6.45 (1H, d, J=7Hz), 6.61 (1H, t, J=7Hz), 7.01–7.21 (3H, m), 7.98 (1H, d, J=7Hz)

(9) 3-Chloro-8-[2-(2,6-dichlorophenyl)ethyloxy]-2-methylimidazo[1,2-a]pyridine mp: 131°–134° C.

NMR (CDCl$_3$, δ): 2.48 (3H, s), 3.66 (2H, m), 4.33 (2H, m), 6.58 (1H, d, J=7.5Hz), 6.78 (1H, t, J=7.5Hz), 7.15 (1H, dd, J=7Hz and 5Hz), 7.32 (2H, d, J=7.5Hz), 7.66 (1H, d, J=7.5Hz)

(10) 3-Chloro-8-(2,6-dichloro-3-nitrobenzyloxy)-2-methylimidazo[1,2-a]pyridine mp: 203°–205° C.

NMR (CDCl$_3$, δ): 2.43 (3H, s), 5.55 (2H, s), 6.70 (1H, d, J=7.5Hz), 6.85 (1H, t, J=7.5Hz), 7.54 (1H, d, J=9Hz), 7.74 (1H, d, J=7.5Hz), 7.82 (1H, d, J=9Hz)

(11) 3-Chloro-8-[2,6-dichloro-3-(N-methyl-N-acetylamino)benzyloxy]-2-methylimidazo[1,2-a]pyridine mp: 212°–213° C.

NMR (CDCl$_{31}$ δ): 1.87 (3H, s), 2.48 (3H, s), 3.20 (3H, s), 5.51 (2H, s), 6.74 (1H, br d, J=7Hz), 6.90 (1H, br t, J=7Hz), 7.29 (1H, d, J=9Hz), 7.45 (1H, d, J=9Hz), 7.76 (1H, d, J=7Hz)

(12) 3-Bromo-8-[2,6-dichloro-3-(N-methyl-N-trifluoroacetylamino)benzyloxy]-2-methylimidazo[1,2-a]pyridine mp: 175°–176° C.

NMR (CDCl$_3$, δ) 2.45 (3H, s), 3.33 (3H, s), 5.52 (2H, s), 6.71 (1H, d, J=7.5Hz), 6.85 (1H, t, J=7.5Hz), 7.33 (1H, d, J=8Hz), 7.46 (1H, d, J=8Hz), 7.79 (1H, dd, J=7.5Hz and 1.5Hz)

(13) 3-Bromo-8-[2,6-dichloro-3-(N-methoxycarbonyl-N-methylamino)benzyloxy]-2-methylimidazo[1,2-a]pyridine mp: 178°–179° C.

NMR (CDCl$_3$, δ) 2.48 (3H, s), 3.22 (3H, s), 3.65 (3H, s), 5.49 (2H, s), 6.78 (1H, br d, J=7Hz), 6.90 (1H, br t, J=7Hz), 7.25 (1H, d, J=9Hz), 7.39 (1H, d, J=9Hz), 7.79 (1H, d, J=7Hz)

(14) 3-Bromo-8-[2,6-dichloro-3-(N-methyl-N-tert-butoxycarbonylamino)benzyloxy]-2-methylimidazo[1,2-a]pyridine mp: 122°–123° C.

Mass (M+1): 516

(15) 3-Bromo-8-[2,6-dichloro-3-(N-methyl-N-mesylamino)benzyloxy]-2-methylimidazo[1,2-a]pyridine mp: 161°–164° C.

NMR (CDCl$_3$, δ) 2.45 (3H, s), 3.07 (3H, s), 3.30 (3H, s), 5.48 (2H, m), 6.71 (1H, d, J=7.5Hz), 6.85 (1H, t, J=7.5Hz), 7.52 (1H, d, J=10Hz), 7.60 (1H, d, J=10Hz), 7.77 (1H, d, J=7.5Hz and 1.5Hz)

(16) 3-Bromo-8-[2,6-dichloro-3-(N-ethyl-N-methylamino)benzyloxy]-2-methylimidazo[1,2-a]pyridine dihydrochloride mp: 128°–130° C.

NMR (CDCl$_3$+CD$_3$OD, δ) 1.30 (3H, t, J=7Hz), 2.64 (3H, s), 3.39 (3H, s), 3.80 (2H, q, J=7Hz), 5.69 (2H, s), 7.49 (2H, d, J=4Hz), 7.65 (1H, d, J=9Hz), 8.01–8.21 (2H)

(17) 3-Bromo-8-[2,6-dichloro-3-(2-pyrrolidinon-1-yl)benzyloxy]-2-methylimidazo[1,2-a]pyridine mp: 219°–220° C.

NMR (CDCl₃, δ) 2.16–2.35 (2H, m), 2.42 (3H, S), 2.58 (2H, t, J=8Hz), 3.78 (2H, t, J=7Hz), 5.47 (2H, s), 6.71 (1H, d, J=7Hz), 6.85 (1H, t, J=7Hz), 7.28, 7.42 (each 1H, d, J=9Hz), 7.76 (1H, d, J=7Hz)

(18) 3-Bromo-8-[2,6-dichloro-3-([-pyrrolidinyl)benzyloxy]-2-methylimidazo[1,2-a]pyridine mp: 113°–114° C.

NMR (CDCl₃, δ) 1.88–2.02 (4H, m), 2.42 (3H, s), 3.25–3.41 (4H, m), 5.50 (2H, s), 6.71 (1H, d, J=7Hz), 6.82 (1H, t, J=7Hz), 6.90, 7.20 (each 1H, d, J=9Hz), 7.72 (1H, d, J=7Hz)

(19) 3-Bromo-8-(2,6-dichloro-3-methoxybenzyloxy)-2-methylimidazo[1,2-a]pyridine mp: 175°–176° C.

NMR (CDCl₃, δ) 2.43 (3H, s), 3.91 (3H, s), 5.48 (2H, s), 6.70 (1H, d, J=7Hz), 6.82 (1H, t, J=7Hz), 6.97 (1H, d, J=9Hz), 7.31 (1H, d, J=9Hz), 7.72 (1H, d, J=7Hz)

(20) 3-Bromo-8-(2,6-dichloro-3-isopropoxybenzyloxy)-2-methylimidazo[1,2-a]pyridine mp: 115°–117° C.

NMR (CDCl₃, δ): 1.40 (6H, d, J=5Hz), 2.44 (3H, s), 4.53 (1H, m), 5.45 (2H, s), 6.70 (1H, d, J=7.5Hz), 6.81 (1H, t, J=7.5Hz), 6.93 (1H, d, J=10Hz), 7.27 (1H, d, J=10Hz), 7.73 (1H, dd, J=7.5Hz and 1.5Hz)

(21) 3-Bromo-8-(2,4,6-trichloro-3-nitrobenzyloxy)-2-methylimidazo[1,2-a]pyridine mp: 167°–168° C.

NMR (CDCl₃, δ): 2.45 (3H, s), 5.48 (2H, s), 6.68 (1H, d, J=8Hz), 6.83 (1H, t, J=8Hz), 7.60 (1H, s), 7.78 (1H, d, J=8Hz)

(22) 3-Bromo-8-[2-chloro-5-(N-methyl-N-acetylamino)benzyloxy]-2-methylimidazo[1,2-a]pyridine mp: 141°–145° C.

NMR (CDCl₃, δ) 1.78 (3H, s), 2.50 (3H, s), 3.20 (3H, s), 5.45 (2H, s), 6.50 (1H, d, J=7.5Hz), 6.77 (1H, t, J=7.5Hz), 7.13 (1H, dd, J=10Hz and 1.5Hz), 7.42–7.52 (2H, m), 7.75 (1H, d, J=10Hz)

(23) 3-Bromo-8-[3-(N-acetoxyacetyl-N-methylamino)-2,6-dichlorobenzyloxy]-2-methylimidazo[1,2-a]pyridine NMR (CDCl₃, δ) 2.14 (3H, s), 2.43 (3H, s), 3.21 (2H, s), 4.18, 4.49 (each 1H, d, J=15Hz), 5.50 (2H, s), 6.70 (1H, d, J=7Hz), 6.83 (1H, t, J=7Hz), 7.39, 7.49 (each 1H, d, J=9Hz), 7.78 (1H, d, J=7Hz)

(24) 3-Bromo-8-[2,6-dichloro-3-(N-methyl-M-phthalimidoacetylamino)benzyloxy]-2-methylimidazo[1,2-a]pyridine mp: 229°–230° C.

NMR (CDCl₃, δ): 2.43 (3H, s), 3.26 (3H, s), 4.12 (2H, s), 5.53 (2H, s), 6.72 (1H, d, J=7Hz), 6.87 (1H, d, J=7Hz), 7.52 (2H, s), 7.68–7.92 (5H)

(25) 8-[3-(Acetylsarcosyl)amino-2,6-dichlorobenzyloxy]-3-bromo-2-methylimidazo[1,2-a]pyridine NMR (CDCl₃, δ): 2.20 (3H, s), 2.42 (3H, s), 3.19 (3H, s), 4.19 (2H, s), 5.48 (2H, s), 6.70 (1H, d, J=8Hz), 6.83 (1H, t, J=8Hz), 7.35 (1H, d, J=9Hz), 7.75 (1H, d, J=8Hz), 8.37 (1H, d, J=9Hz), 8.82 (1H, br s)

(26) 3-Chloro-8-(2-trifluromethylbenzyloxy)-2-methylimidazo[1,2-a]pyridine mp: 164°–165° C.

NMR (CDCl₃, δ): 2.48 (3H, s), 5.40 (2H, s), 6.44 (1H, d, J=7Hz), 6.71 (1H, t, J=7Hz), 7.55–7.71 (5H)

(27) 3-Chloro-8-(2-methoxycarbonylbenzyloxy)-2-methylimidazo[1,2-a]pyridine mp: 141°–144° C.

NMR (CDCl₃, δ) 2.48 (3H, s), 3.92 (3H, s), 5.79 (2H, s), 6.49 (1H, d, J=7.5Hz), 6.72 (1H, t, J=7.5Hz), 7.39 (1H, t, J=7.5Hz), 7.55 (1H, t, J=7.5Hz), 7.67 (1H, d, J=7.5Hz), 7.85 (1H, d, J=7.5Hz), 8.08 (1H, d, J=7.5Hz)

(28) 8-(2-Phenylbenzyloxy)-3-chloro-2-methylimidazo[1,2-a]pyridine mp: 121°–122° C.

NMR (CDCl₃, δ) 2.45 (3H, s), 5.19 (2H, s), 6.21 (1H, d, J=7.5Hz), 6.63 (1H, t, J=7.5Hz), 7.30–7.41 (8H, m), 7.61 (1H, d, J=7.5Hz), 7.72 (1H, m)

(29) 3-Chloro-8-(2,6-difluorobenzyloxy)-2-methylimidazo[1,2-a]pyridine mp: 168°–170° C.

NMR (CDCl₃, δ): 2.45 (3H, s), 5.33 (2H, s), 6.68 (1H, d, J=7.5Hz), 6.80 (1H, t, J=7.5Hz), 6.87–7.00 (2H, m), 7.28–7.41 (1H, m), 7.70 (1H, d, J=7.5Hz)

(30) 3-Chloro-8-(2,6-dibromobenzyloxy)-2-methylimidazo[1,2-a]pyridine mp: 157°–158° C.

NMR (CDCl₃, δ): 2.44 (3H, s), 5.51 (2H, s), 6.69 (1H, d, J=7Hz), 6.82 (1H, t, J=7Hz), 7.08 (1H, t, J=8Hz), 7.57 (2H, d, J=8Hz), 7.70 (1H, d, J=7Hz)

(31) 3-Bromo-8-(2-chloro-6-fluorobenzyloxy)-2-methylimidazo[1,2-a]pyridine mp: 130°–131° C.

NMR (CDCl₃, δ) 2.43 (3H, s), 5.38 (2H, s), 6.70 (1H, d, J=7Hz), 6.81 (1H, t, J=7Hz), 7.02 (1H, t, J=8Hz), 7.20–7.38 (2H), 7.73 (1H, d, J=7Hz)

(32) 8-(4-Bromo-2-fluorobenzyloxy)-3-chloro-2-methylimidazo[1,2-a]pyridine mp: 182°–123° C.

NMR (CDCl₃, δ) 2.47 (3H, s), 5.32 (2H, s), 6.51 (1H, d, J=7.5Hz), 6.75 (1H, t, J=7.5Hz), 7.29 (2H, d, J=7.5Hz), 7.48 (1H, t, J=7.5Hz), 7.66 (1H, d, J=7.5Hz)

(33) 3-Bromo-8-(2-chloro-5-nitrobenzyloxy)-2-methylimidazo[1,2-a]pyridine

NMR (CDCl₃, δ): 2.50 (3H, s), 5.48 (2H, s), 6.53 (1H, d, J=7Hz), 6.78 (1H, t, J=7Hz), 7.60 (1H, d, J=7Hz), 7.78 (1H, d, J=7Hz), 8.15 (1H, dd, J=9Hz and 2Hz), 8.52 (1H, d, J=2Hz)

(34) 3-Bromo-8-[2-chloro-6-(N-methyl-N-acetylamino)benzyloxy]-2-methylimidazo[1,2-a]pyridine mp: 135°–136° C.

NMR (CDCl₃, δ) 1.89 (3H, s), 2.41 (3H, s), 3.23 (3H, s), 5.21 (1H, d, J=10Hz), 5.26 (1H, d, J=10Hz), 6.68 (1H, d, J=7.5Hz), 6.82 (1H, t, J=7.5Hz), 7.18 (1H, d, J=7.5Hz), 7.38–7.53 (2H, m), 7.74 (1H, d, J=7.5Hz)

(35) 3-Bromo-8-(2-chloro-6-nitrobenzyloxy)-2-methylimidazo[1,2-a]pyridine mp: 157°–158° C.

NMR (CDCl₃, δ): 2.42 (3H, s), 5.66 (2H, s), 6.67 (1H, d, J=7Hz), 6.82 (1H, t, J=7Hz), 7.49 (1H, t, J=8Hz), 7.72 (2H, t, J=8Hz), 7.85 (1H, d, J=7Hz)

(36) 3-Bromo-8-[3-(N,N-di-tert-butoxycarbonylamino)-2,6-dichlorobenzyloxy]-2-methylimidazo[1,2-a]pyridine mp: 154°–155° C.

NMR (CDCl₆, δ) 1.40 (18H, s), 2.43 (3H, s), 5.58 (2H, s), 6.68 (1H, d, J=7Hz), 6.79 (1H, t, J=7Hz), 7.20 (1H, d, J=8Hz), 7.38 (1H, d, J=8Hz), 7.72 (1H, d, J=7Hz)

(37) 3-Bromo-8-(2,4,6-trichlorobenzyloxy)-2-methylimidazo[1,2-a]pyridine mp: 170°–172° C.

NMR (CDCl₃, δ) 2.44 (3H, s), 5.42 (2H, s), 6.68 (1H, d, J=7Hz), 6.81 (1H, t, J=7Hz), 7.49 (2H, s), 7.76 (1H, d, J=7Hz)

(38) 3-Bromo-8-(2,3,6-trichlorobenzyloxy)-2-methylimidazo-[1,2-a]pyridine mp: 183°–184° C.

NMR (CDCl₃, δ): 2.44 (3H, s), 5.50 (2H, s), 6.70 (1H, d, J=7Hz), 6.83 (1H, t, J=7Hz), 7.31 (1H, d, J=9Hz), 7.46 (1H, d, J=9Hz), 7.76 (1H, d, J=7Hz)

(39) 3-Chloro-8-(2,4,6-trimethylbenzyloxy)-2-methylimidazo[1,2-a]pyridine mp: 154°–155° C.

NMR (CDCl₃, δ): 2.29 (3H, s), 2.38 (6H, s), 2.43 (3H, s), 5.21 (2H, s), 6.63 (1H, d, J=7Hz), 6.75–6.90 (3H), 7.69 (1H, d, J=7Hz)

(40) 3-Bromo-8-(2,6-dibromo-4-methoxycarbonylbenzyloxy)-2-methylimidazo[1,2-a]pyridine mp: 189°–190° C.

NMR (CDCl₃, δ): 2.44 (3H, s), 3.96 (3H, s), 5.52 (2H, s), 6.69 (1H, d, J=7Hz), 6.82 (1H, t, J=7Hz), 7.76 (1H, d, J=7Hz), 8.21 (2H, s)

(41) 3-Bromo-8-(4-benzoyl-2-chlorobenzyloxy)-2-methylimidazo[1,2-a]pyridine

NMR (CDCl₃, δ) 2.50 (3H, s), 5.50 (2H, s), 6.52 (1H, d, J=8Hz), 6.78 (1H, t, J=8Hz), 7.45–7.90 (9H)

(42) 3-Bromo-8-(2,6-dichloro-4-benzoylbenzyloxy)-2-methylimidazo[1,2-a]pyridine mp: 129°–130° C.

NMR (CDCl₃, δ) 2.46 (3H, s), 5.53 (2H, s), 6.71 (1H, d, J=7Hz), 6.83 (1H, t, J=7Hz), 7.34 (1H, d, J=9Hz), 7.42–7.91 (7H)

(43) 3-Bromo-8-[4-(2-cyanophenyl)benzyloxy]-2-methylimidazo[1,2-a]pyridine mp: 138°–140° C.

NMR (CDCl₃, δ) 2.49 (3H, s), 5.40 (2H, s), 6.55 (1H, d, J=8Hz), 6.75 (1H, t, J=8Hz), 7.40–7.81 (9H)

(44) 3-Bromo-8-(6-chloropiperonyl)methoxy-2-methylimidazo[1,2-a]pyridine mp: 185°–186° C.

NMR (CDCl₃, δ) 2.49 (3H, s), 5.32 (2H, s), 5.96 (2H, s), 6.49 (1H, d, J=7Hz), 6.74 (1H, t, J=7Hz), 6.88 (1H, s), 7.09 (1H, s), 7.70 (1H, d, J=7Hz)

(45) 8-(2-Bromothiophen-4-yl)methoxy-3-chloro-2-methylimidazo[1,2-a]pyridine mp: 124°–125° C.

NMR (CDCl₃, δ) 2.48 (3H, s), 5.45 (2H, s), 6.56 (1H, d, J=7Hz), 6.75 (1H, t, J=7Hz), 7.09 (1H, s), 7.20 (1H, s), 7.69 (2H, d, J=7Hz)

(46) 3-Chloro-8-(3-chlorobenzofuran-2-yl)methoxy-2-methylimidazo[1,2-a]pyridine mp: 132°–134° C.

NMR (CDCl₃, δ) 2.46 (3H, s), 5.48 (2H, s), 6.71–6.82 (2H, m), 7.31–7.71 (5H, m)

(47) 3-Bromo-8-[3-(4-chlorophenyl)-5-methylbenzofuran-2-yl]methoxy-2-methylimidazo[1,2-a]pyridine mp: 167°–170° C.

NMR (CDCl₃, δ): 2.44 (6H, s), 5.38 (2H, s), 6.59 (1H, d, J=7Hz), 6.72 (1H, t, J=7Hz), 7.18(1H, br d, J=8Hz), 7.32–7.52 (6H), 7.71 (1H, d, J=7Hz)

(48) 3-Bromo-8-(4,6-dichloro-3-methyl-2-benzothiazolinon-5-yl)methoxy-2-methylimidazo[1,2-a]pyridine mp: 225°–227° C.

NMR (CDCl₃, δ): 2.45 (3H, s), 3.87 (3H, s), 5.51 (2H, s), 6.71 (1H, d, J=7Hz), 6.83 (1H, t, J=7Hz), 7.42 (1H, s), 7.78 (1H, d, J=7Hz)

(49) 3-Bromo-8-(4,6-dichloro-3-ethyl-2-benzothiazolinon-5-yl)methoxy-2-methylimidazo[1,2-a]pyridine mp: 219°–220° C.

NMR (DMSO-d₆, δ): 1.35 (3H, t, J=7.5Hz), 2.35 (3H, s), 4.43 (2H, q, J=7.5Hz), 5.52 (2H, s), 6.93–7.02 (2H, m), 7.83–7.89 (2H, m)

(50) 3-Bromo-8-(5,7-dichloro-4-methyl-1,4-benzothiazin-3 (4H)-on-6-yl)methoxy-2-methylimidazo[1,2-a]pyridine NMR (CDCl₃, δ): 2.44 (3H, s), 3.39 (2H, s), 3.41 (3H, s), 5.47 (2H, s), 6.70 (1H, d, J=8Hz), 6.84 (1H, t, J=8Hz), 7.48 (1H, s), 7.77 (1H, d, J=8Hz)

Example 4

A suspension of 3-bromo-8-(2,6-dichloro-3-nitrobenzyloxy)-2-methylimidazo[1,2-a]pyridine (215 mg) and iron (powder, 84 mg) in a mixture of conc. hydrochloric acid (1 ml) and methanol (1 ml) was refluxed for half an hour. The cooled mixture was poured into an ice water (15 ml). The precipitates were collected and washed with water to give 8-(3-amino-2,6-dichlorobenzyloxy)-3-bromo-2-methylimidazo[1,2-a]pyridine dihydrochloride (140 mg) as an off-white solid.

mp: 181°–183° C.

NMR (DMSO-d₆, δ) 2.42 (3H, s), 5.48 (2H, s), 6.95 (1H, d, J=7.5Hz), 7.24 (1H, d, J=7.5Hz), 7.42 (1H, t, J=7.5Hz), 7.62 (1H, d, J=7.5Hz), 8.25 (1H, d, J=7.5Hz)

Example 5

To a mixture of 3-bromo-8-(2-chloro-6-nitrobenzyloxy)-2-methylimidazo[1,2-a]pyridine (300 mg), nickel(II) chloride hexahydrate (360 mg) and methanol (9 ml) was added sodium borohydride (114 mg) portionwise under an ice-water bath cooling for 20 minutes. After stirring for 30 minutes, the mixture was concentrated in vacuo and diluted with water. The pH value of the mixture was adjusted to 3 and the separated crystals were collected by filtration. The crystals were dissolved in dichloromethane, and the solution was washed with saturated aqueous solution of sodium hydrogencarbonate, dried over magnesium sulfate and evaporated in vacuo. The residue was purified by silica gel column chromatography (3% solution of methanol in dichloromethane) and preparative thin-layer chromatography (3% solution of methanol in dichloromethane) followed by crystallization from diethyl ether to give 8-(2-amino-6-chlorobenzyloxy)-3-bromo-2-methylimidazo[1,2-a]pyridine (40 mg).

mp: 177°–178° C.

NMR (CDCl₃, δ): 2.44 (3H, s), 4.64 (2H, br s), 5.51 (2H, s), 6.57 (1H, d, J=7Hz), 6.71–6.85 (3H), 7.02 (1H, t, J=7Hz), 7.71 (1H, m)

Example 6

The following compounds were obtained according to similar manners to those of Examples 4 or 5.

(1) 8-(3-Amino-2,4,6-trichlorobenzyloxy)-3-bromo-2-methylimidazo[1,2-a]pyridine mp: 217°–219° C.

NMR (DMSO-d₆, δ) 2.30 (3H, s), 5.35 (2H, s), 6.99 (2H, d, J=8Hz), 7.58 (1H, s), 7.92 (1H, t, J=8Hz)

(2) 8-(3-Amino-2,6-dichlorobenzyloxy)-3-bromo-2-methylimidazo[1,2-a]pyridine

NMR (DMSO-d₆, δ): 2.29 (3H, s), 5.31 (2H, s), 5.70 (2H, s, D₂O exchangeable), 6.84–7.04 (3H), 7.23 (1H, d, J=8Hz), 7.90 (1H, d, J=5Hz)

(3) 8-(5-Amino-2-chlorobenzyloxy)-3-bromo-2-methylimidazo[1,2-a]pyridine dihydrochloride mp: >250° C. (dec.)

NMR (DMSO-d₆, δ): 2.45 (3H, s), 4.21 (2H, br s), 5.41 (2H, s), 7.03 (1H, d, J=9Hz), 7.29–7.52 (4H), 8.22 (1H, d, J=6Hz)

Example 7

To a suspension of 3-bromo-8-[2,6-dichloro-3-(N-methyl-N-trifluoroacetylamino)benzyloxy]-2-methylimidazo[1,2-a]pyridine (560 mg) in methanol (6 ml) was added 28% sodium methoxide in methanol (1.93 g). The mixture was refluxed for one hour and cooled. The precipitated solid was filtered, washed with methanol, and dried to give 3-bromo-8-(2,6-dichloro-3-methylaminobenzyloxy)-2-methylimidazo[1,2-a]pyridine (350 mg) as crystals.

mp: 184°–187° C.

NMR (CDCl₃, δ) 2.44 (3H, s), 2.91 (2H, d, J=6Hz), 4.46 (1H, m), 5.46 (2H, s), 6.69 (1H, d, J=8.5Hz), 6.71 (1H, d, J=7.5Hz), 6.83 (1H, t, J=7.5Hz), 7.24 (1H, d, J=8.5Hz), 7.73 (1H, d, J=7.5Hz)

Example 8

The following compounds were obtained according to a similar manner to that of Example 7.

(1) 3-Bromo-8-(2-chloro-5-methylaminobenzyloxy)-2-methylimidazo[1,2-a]pyridine mp: 156°–159° C.

NMR (CDCl₃, δ): 2.48 (3H, s), 2.76 (3H, s), 5.38 (2H, s), 6.43–6.52 (2H, m), 6.73 (1H, t, J=7.5Hz), 6.85 (1H, d, J=2Hz), 7.19 (1H, d, J=9Hz), 7.69 (1H, d, J=7.5Hz)

(2) 3-Chloro-8-(2,6-dichloro-3-methylaminobenzyloxy)-2-methylimidazo[1,2-a]pyridine mp: 187°–188° C.

NMR (CDCl₃, δ): 2.43 (3H, s), 2.90 (3H, d, J=6Hz), 4.46 (1H, br q, J=6Hz), 5.45 (2H, s), 6.62 (1H, d, J=9Hz), 6.68 (1H, d, J=8Hz), 6.82 (1H, t, J=8Hz), 7.24 (1H, d, J=9Hz), 7.69 (1H, d, J=8Hz)

Example 9

A mixture of 8-(3-amino-2,6-dichlorobenzyloxy)-3-bromo-2-methylimidazo[1,2-a]pyridine dihydrochloride (100 mg) and formaldehyde (200 mg, 37% wt % solution in water) in 90% aqueous formic acid (1 ml) was refluxed for 40 minutes. The cooled mixture was concentrated in vacuo. The residue was partitioned between ethyl acetate and aqueous sodium bicarbonate solution. The organic layer was dried and concentrated in vacuo to give an oil, which was purified by preparation thin-layer chromatography on silica gel (ethyl acetate:n-hexane=2:1, V/V) to give 3-bromo-8-(2,6-dichloro-3-dimethylaminobenzyloxy)-2-methylimidazo[1,2-a]pyridine as a white solid (31 mg).

mp: 120°–122° C.

NMR (DMSO-d₆, δ) 2.29 (3H, s), 2.76 (6H, s), 5.41 (2H, s), 6.97–7.03 (2H, m), 7.33 (1H, d, J=9Hz), 7.52 (1H, d, J=9Hz), 7.90 (1H, m)

Example 10

To a mixture of 8-(3-amino-2,6-dichlorobenzyloxy)-3-bromo-2-methylimidazo[1,2-a]pyridine dihydrochloride (100 mg) and acetone (116 mg) in 3M HCl solution in ethanol (2 ml) was added sodium cyanoborohydride (25 mg) in one portion. The mixture was stirred for 2 hours at ambient temperature and then concentrated in vacuo. The residue was partitioned between ethyl acetate and aqueous sodium bicarbonate solution. The organic layer was dried and concentrated in vacuo to give an oil, which was purified by preparative thin-layer chromatography on silica gel (ethyl acetate:n-hexane=1:2, V/V), to give 3-bromo-8-(2,6-dichloro-3-isopropylaminobenzyloxy)-2-methylimidazo[1,2-a]pyridine as a white solid (50 mg).

mp: 133°–134° C.

NMR (CDCl₃, δ) 1.26 (6H, d, J=5Hz), 2.45 (3H, s), 3.66 (1H, m), 4.22 (1H, d, J=7Hz), 5.42 (2H, s), 6.63 (1H, d, J=7.5Hz), 6.70 (1H, d, J=7.5Hz), 6.83 (1H, t, J=7.5Hz), 7.19 (1H, d, J=7.5Hz), 7.73 (1H, d, J=7.5Hz)

Example 11

The following compounds were obtained according to a similar manner to that of Example 10.

(1) 8-(3-Benzylamino-2,6-dichlorobenzyloxy)-3-bromo-2-methylimidazo1,2-a]pyridine mp: 126°–127° C.

NMR (CDCl₃, δ) 2.45 (3H, s), 4.43 (2H, d, J=5Hz), 4.89 (1H, t, J=5Hz), 5.46 (2H, s), 6.58 (1H, d, J=7.5Hz), 6.71 (1H, d, J=7.5Hz), 6.83 (1H, t, J=7.5Hz), 7.15 (1H, d, J=7.5Hz), 7.29–7.43 (5H, m), 7.72 (1H, d, J=7.5Hz)

(2) 3-Bromo-8-[2,6-dichloro-3-(4-pyridylmethyl)aminobenzyloxy]-2-methylimidazo[1,2-a]pyridine mp: 214°–215° C.

NMR (CDCl₃, δ): 2.44 (3H, s), 4.47 (2H, d, J=6Hz), 5.05 (1H, t, J=5Hz), 5.46 (2H, s), 6.41 (1H, d, J=7.5Hz), 6.71 (1H, d, J=7.5Hz), 6.83 (1H, t, J=7.5Hz), 7.12 (1, d, J=7.5Hz), 7.25–7.29 (2H, m), 7.74 (1H, d, J=7.5Hz), 8.59 (2H, m)

Example 12

To a suspension of 8-(3-amino-2,6-dichlorobenzyloxy)-3-bromo-2-methylimidazo[1,2-a]pyridine dihydrochloride (100 mg) in a mixture of pyridine (0.5 ml) and N,N-diethylformamide (1.5 ml) was added methanesulfonyl chloride (27 mg) in one portion. The mixture was stirred at 60°–70° C. for one and half hours, cooled, and poured into ice water. The separated oil was extracted with dichloromethane. The extract was washed with water, dried, and concentrated in vacuo to give a brown oil, which was purified by preparative thin-layer chromatography on silica gel (5% solution of methanol in dichloromethane) to give 3-bromo-8-[2,6-dichloro-3-[(N,N-diethylaminomethylene)amino]benzyloxy]-2-methylimidazo[1,2-a]pyridine (65 mg) as crystals.

mp: 163°–165° C.

NMR (CDCl₃, δ) 1.25 (3H, t, J=7Hz), 2.44 (2H, s), 3.18–3.61 (4H, m), 5.49 (2H, s), 6.68–6.85 (3H, m), 7.23 (1H, d, J=7.5Hz), 7.38 (1H, s), 7.71 (1H, d, J=7.5Hz)

Example 13

The following compounds were obtained according to a similar manner to that of Example 12.

(1) 3-Bromo-8-[2,6-dichloro-3-[(N,N-dimethylaminomethylene)amino]benzyloxy]-2-methylimidazo[1,2-a]pyridine mp: 165°–167° C.

NMR (DMSO-d₆, δ): 2.29 (3H, s), 2.97 (3H, s), 3.06 (3H, s), 5.40 (2H, s), 6.95–7.02 (2H, m), 7.14 (1H, d, J=7.5Hz), 7.40 (1H, d, J=7.5Hz), 7.78 (1H, s), 7.91 (1H, m)

(2) 3-Bromo-8-[2,6-dichloro-3-(1-methyl-2-pyrrolidinylideneamino)benzyloxy]-2-methylimidazo[1,2-a]pyridine mp: 178°–179° C.

NMR (CDCl₃, δ) 1.97 (2H, m), 2.32 (2H, t, J=7.5Hz), 2.45 (3H, s), 2.98 (3H, s), 3.40 (2H, t, J=7.5Hz), 5.47 (2H, s), 6.69–6.82 (2H, m), 6.83 (1H, d, J=7.5Hz), 7.19 (1H, d, J=7.5Hz), 7.72 (1H, d, J=7.5Hz)

Example 14

A mixture of 8-(3-amino-2,6-dichlorobenzyloxy)-3-bromo-2-methylimidazo[1,2-a]pyridine dihydrochloride (100 mg) and acetic anhydride (100 mg) in dry pyridine (2 ml) was stirred at 90° C. for one hour. The cooled mixture was poured into an ice water (10 ml). The precipitated solid was collected, washed with water, and dried under reduced pressure to give 8-(3-acetylamino-2,6-dichlorobenzyloxy)-3-bromo-2-methylimidazo[1,2-a]pyridine (65 mg) as a solid.

mp: 210°–212° C.

NMR (DMSO-d₆, δ) 2.13 (3H, s), 2.29 (3H, s), 5.44 (2H, s), 6.99–7.04 (2H, m), 7.59 (1H, d, J=7.5Hz), 7.84 (1H, d, J=7.5Hz), 7.92 (1H, m), 9.72 (1H, s)

Example 15

To a suspension of 8-(3-amino-2,6-dichlorobenzyloxy)-3-bromo-2-methylimidazo[1,2-a]pyridine dihydrochloride (200 mg), pyridine (1 ml) and N-methylpyrrolidone (3 ml) was added propionyl chloride (78 mg) and the mixture was stirred at 60° C. for 1 hour. To the cooled mixture was added water, and the precipitate was collected by filtration and dissolved in chloroform. This organic solution was washed with water and brine respectively, dried with magnesium sulfate and concentrated in vacuo. The residue was collected by filtration and washed with ethyl acetate to give 3-bromo-8-(2,6-dichloro-3-propionylaminobenzyloxy)-2-methylimidazo [1,2-a]pyridine (158 mg).

mp: 205°–207° C.

NMR (CDCl₃, δ) 1.28 (3H, t, J=7Hz), 2.44 (3H, s), 2.48 (2H, q, J=7Hz), 5.49 (2H, s), 6.70 (1H, d, J=7Hz), 6.82 (1H, t, J=7Hz), 7.37 (1H, d, J=9Hz), 7.69 (1H, br s), 7.76 (1H, d, J=7Hz), 8.42 (1H, d, J=9Hz)

Example 16

The following compounds were obtained according to similar manners to those of Examples 14 or 15.

(1) 3-Bromo-8-[2,6-dichloro-3-(4-methylbenzoylamino) benzyloxy]-2-methylimidazo[1,2-a]pyridine mp: 222°–223° C.

NMR (CDCl₃, δ) 2.43 (6H, s), 5.51 (2H, s), 6.71 (1H, d, J=7Hz), 6.82 (1H, t, J=7Hz), 7.31 (2H, d, J=9Hz), 7.41 (1H, d, J=9Hz), 7.70–7.85 (3H), 8.44 (1H, br s), 8.60 (1H, d, J=9Hz)

(2) 3-Bromo-8-[2,6-dichloro-3-(4-methoxybenzoylamino) benzyloxy]-2-methylimidazo[1,2-a]pyridine mp: 211°–212° C.

NMR (CDCl₃, δ): 2.44 (3H, s), 3.89 (3H, s), 5.51 (2H, s), 6.70 (1H, d, J=7Hz), 6.81 (1H, t, J=7Hz), 7.00 (2H, d, J=9Hz); 7.41 (1H, d, J=9Hz), 7.75 (1H, d, J=7Hz), 7.88 (2H, d, J=9Hz), 8.40 (1H, br s), 8.59 (1H, d, J=9Hz)

(3) 8-(3-Benzoylamino-2,6-dichlorobenzyloxy)-3-bromo-2-methylimidazo[1,2-a]pyridine mp: 208°–210° C.

NMR (CDCl₃, δ): 2.44 (3H, s), 5.52 (2H, s), 6.71 (1H, d, J=7Hz), 6.83 (1H, t, J=7Hz), 7.40–7.66 (4H), 7.75 (1H, d, J=7Hz), 7.87–7.96 (2H), 8.49 (1H, br s), 8.60 (1H, d, J=9Hz)

(4) 3-Bromo-8-[2,6-dichloro-3-(4-methoxycarbonylbenzoylamino)benzyloxy]-2-methylimidazo[1,2-a]pyridine mp: 238°–239° C.

NMR (DMSO-d₆, δ): 2.31 (3H, s), 3.92 (3H, s), 5.49 (2H, s), 6.97–7.08 (2H, m), 7.69 (1H, d, J=8.5Hz), 7.77 (1H, d, J=8.5Hz), 7.95 (1H, dd, J=7.5Hz and 2Hz), 8.13 (4H, s)

(5) 3-Bromo-8-[3-(4-chlorobenzoylamino)-2,6-dichlorobenzyloxy]-2-methylimidazo[1,2-a]pyridine mp: 201°–213° C.

NMR (CDCl₃, δ) 2.45 (3H, s), 5.52 (2H, s), 6.72 (1H, d, J=7.5Hz), 6.84 (1H, t, J=7.5Hz), 7.43 (1H, d, J=8.5Hz), 7.52 (2H, d, J=8.5Hz), 7.76 (1H, d, J=8.5Hz), 7.86 (2H, d, J=8.5Hz), 8.41 (1H, br s), 8.57 (1H, d, J=8.5Hz)

(6) 8-(3-Diacetylamino-2,4,6-trichlorobenzyloxy)-3-bromo-2-methylimidazo[1,2-a]pyridine mp: 141°–142° C.

NMR (CDCl₃, δ) 2.34 (6H, s), 2.45 (3H, s), 5.48 (2H, s), 6.69 (1H, d, J=8Hz), 6.84 (1H, t, J=8Hz), 7.61 (1H, s), 7.77 (1H, d, J=8Hz)

(7) 3-Bromo-8-[2-chloro-5-(N-methyl-N-trifluoroacetylamino)benzyloxy]-2-methylimidazo[1,2-a]pyridine mp: 142°–143° C.

NMR (CDCl₃, δ) 2.50 (3H, s), 3.31 (3H, s), 5.48 (2H, s), 6.46 (1H, d, J=7.5Hz), 6.75 (1H, d, J=7.5Hz), 7.18 (1H, dd, J=9Hz and 2Hz), 7.46–7.53 (1H, m), 7.76 (1H, d, J=7.5Hz)

(8) 3-Bromo-8-[2-chloro-5-(N-methyl-N-propionylamino)benzyloxy]-2-methylimidazo[1,2-a]pyridine mp: 133°–135° C.

NMR (CDCl₃, δ) 0.96 (3H, t, J=7.5Hz), 1.97 (2H, q, J=7.5Hz), 2.50 (3H, s), 3.19 (3H, s), 5.45 (2H, s), 6.50 (1H, d, J=7.5Hz), 6.76 (1H, t, J=7.5Hz), 7.11 (1H, dd, J=9Hz and 2Hz), 7.45 (1H, s), 7.48 (1H, d, J=9Hz), 7.75 (1H, d, J=7.5Hz)

(9) 3-Bromo-8-[2,6-dichloro-3-(phthalimidoacetylamino) benzyloxy]-2-methylimidazo[1,2-a]pyridine mp: 228°–230° C.

NMR (CDCl₃, δ): 2.42 (1.2H, s), 2.46 (1.8H, s), 4.60 (1.8H, s), 4.71 (1.2H, s), 5.47 (1.8Hz), 5.54 (1.2H, s), 6.68 (1H, d, J=8Hz), 6.81 (1H, t, J=8Hz), 7.32 (0.6H, d, J=8Hz), 7.56 (0.4H, d, J=5Hz), 7.70–7.98 (5.6H), 8.28–8.40 (1.4H)

(10) 3-Bromo-8-[2,6-dichloro-3-(2-phthalimidopropionylamino)benzyloxy]-2-methylimidazo[1,2-a]pyridine NMR (DMSO-d₆, δ): 1.62 (3H, d, J=6Hz), 2.28 (3H, s), 5.01 (1H, q, J=6Hz), 5.43 (2H, s), 6.93–7.04 (2H), 7.60 (2H, s), 7.82–7.97 (5H), 9.92 (1H, s)

(11) 3-Bromo-8-[2,6-dichloro-3-(3-phthalimidopropionylamino)benzyloxy]-2-methylimidazo [1,2-a]pyridine mp: 207°–209° C.

NMR (CDCl₃, δ): 2.41 (3H, s), 2.90 (2H, t, J=6Hz), 4.12 (2H, t, J=6Hz), 5.45 (2H, s), 6.69 (1H, d, J=7Hz), 6.82 (1H, t, J=7Hz), 7.35 (1H, d, J=9Hz), 7.61–7.94 (6H), 8.31 (1H, d, J=7Hz)

(12) 3-Chloro-8-[2,6-dichloro-3-[N-methyl-N-(phthalimidoacetyl)amino]benzyloxy]-2-methylimidazo[1,2-a]pyridine mp: 139°–141° C.

NMR (CDCl₃, δ): 2.42 (3H, s), 3.25 (3H, s), 4.12 (2H, s), 5.53 (2H, s), 6.71 (1H, d, J=7Hz), 6.86 (1H, d, J=7Hz), 7.52 (2H, s), 7.68–7.92 (5H)

Example 17

To a solution of 3-bromo-8-(2,6-dichloro-3-methylaminobenzyloxy-2-methylimidazo[1,2-a]pyridine (70 mg) in formic acid (1 ml) was added acetic anhydride (35 mg) at ambient temperature. The mixture was stirred for half an hour at the same temperature and then concentrated in vacuo. The residue was partitioned between aqueous sodium bicarbonate solution and ethyl acetate. The organic layer was dried and evaporated under reduced pressure to give 3-bromo-8-[2,6-dichloro-3-(N-methyl-N-formylamino)benzyloxy]-2-methylimidazo[1,2-a]pyridine (29 mg).

mp: 207°–209° C.

NMR (CDCl₃, δ): 2.45 (3H, s), 3.23 (3H, s), 5.50 (2H, s), 6.71 (1H, d, J=7.5Hz), 6.85 (1H, t, J=7.5Hz), 7.26 (1H, d, J=10Hz), 7.45 (1H, d, J=10Hz), 7.76 (1H, d, J=7.5Hz), 8.15 (1H, s)

Example 18

To a solution of 3-bromo-8-(2,6-dichloro-3-methylaminobenzyloxy)-2-methylimidazo[1,2-a]-pyridine (68 mg) and pyridine (0.5 ml) in dichloromethane (2 ml) was added 4-nitrophenyl chloroformate (40 mg) at ambient temperature. After stirring for 1 hour, the mixture was partitioned between dichloromethane and water. The aqueous layer was extracted with dichloromethane twice. The organic layers were combined, washed with water twice and brine, dried over magnesium sulfate and evaporated in vacuo. The residue was crystallized from diethyl ether to give 3-bromo-8-[2,6-dichloro-3-[N-methyl-N-(4-nitrophenoxycarbonyl)amino]benzyloxy]-2-methylimidazo[1,2-a]pyridine (84 mg) as crystals.

mp: 229°–230° C.

NMR (CDCl$_3$—CD$_3$OD, δ) 2.41 (3H, s), 3.32 (3H, s), 5.49 (1H, d, J=10Hz), 5.57 (1H, d, J=10Hz), 6.73 (1H, d, J=7Hz), 6.88 (1H, t, J=7Hz), 7.19–7.57 (4H), 7.78 (1H, d, J=7Hz), 8.20 (2H, d, J=10Hz)

Example 19

To a solution of 3-bromo-8-(2-chloro-5-methylaminobenzyloxy)- 2-methylimidazo[1,2-a]pyridine (60 mg), pyridine (16 mg) and 4-dimethylaminopyridine (10 mg) in methylene chloride (2 ml) was added mesyl chloride (22 mg) in one portion at 5° C., and the mixture was stirred for 9 hours at ambient temperature. The precipitate was filtered off and the residue was washed with methylene chloride and diethyl ether respectively. The filtrate was concentrated in vacuo and the residue was purified by preparative thin-layer chromatography on silica gel (methanol:methylene chloride=1:10, V/V) to give 3-bromo-8-[2-chloro-5-(N-methyl-N-methylsulfonylamino) benzyloxy]-2-methylimidazo[1,2-a]pyridine (25 mg).

mp: 158°–162° C.

NMR (CDCl$_3$, δ): 2.49 (3H, s), 2.74 (3H, s), 3.26 (3H, s), 5.44 (2H, s), 6.53 (1H, d, J=7.5Hz), 6.78 (1H, t, J=7.5Hz), 7.32–7.46 (2H, m), 7.60 (1H, d, J=2Hz), 7.73 (1H, d, J=7.5Hz)

Example 20

To a mixture of 8-(3-amino-2,6-dichlorobenzyloxy)-3-bromo-2-methylimidazo[1,2-a]pyridine dihydrochloride (100 mg), pyridine (0.5 ml) and N-methylpyrrolidone (1.5 ml) was added ethyl isocyanate (0.10 ml). The mixture was stirred at 60° C. for 6 hours. The insoluble material was filtered off and washed with water. The filtrate and washings were combined and separated precipitate was collected by filtration. The precipitate was purified by preparative thin-layer chromatography (20% solution of methanol in dichloromethane) followed by recrystallization from n-hexane to give 3-bromo-8-[2,6-dichloro-3-(N'-ethylureido)benzyloxy]-2-methylimidazo[1,2-a]pyridine (13 mg) as crystals.

mp: 238°–239° C.

NMR (CDCl$_3$, δ): 1.00 (3H, t, J=7Hz), 2.38 (3H, s), 3.16–3.31 (2H), 5.32 (2H, s), 6.67 (1H, d, J=7Hz), 6.86 (1H, t, J=7Hz), 7.19–7.32 (2H), 7.71 (1H, d, J=7Hz), 7.90 (1H, br s), 8.34 (1H, d, J=9Hz)

Example 21

A mixture of 3-bromo-8-[2,6-dichloro-3-[N-methyl-N-(4-nitrophenyloxycarbonyl)amino]benzyloxy]-2-methylimidazo[1,2-a]pyridine (63 mg) and 30% solution of methylamine in methanol (2 ml) was heated under reflux for 3 hours. After addition of 30% solution of methylamine in methanol (1 ml), the mixture was heated under reflux for additional 1 hour. The mixture was evaporated in vacuo and the residue was extracted with ethyl acetate. The extract was evaporated in vacuo and the residue was purified by preparative thin-layer chromatography (5% solution of methanol in dichloromethane) followed by crystallization from diethyl ether to give 3-bromo-8-[2,6-dichloro-3-(N-methyl-N'-methylureido)benzyloxy]-2-methylimidazo[1,2-a]pyridine (28 mg) as crystals.

mp: 192°–193° C.

NMR (CDCl$_3$, δ): 2.42 (3H, s), 2.79 (3H, d, J=5Hz), 3.20 (3H, s), 4.20 (1H, br d, J=5Hz), 5.49 (2H, s), 6.71 (1H, d, J=7Hz), 6.85 (1H, t, J=7Hz), 7.32 (1H, d, J=9Hz), 7.42 (1H, d, J=9Hz), 7.78 (1H, d, J=7Hz)

Example 22

The following compounds were obtained according to similar manners to those of Examples 20 or 21.

(1) 3-Bromo-8-[2,6-dichloro-3-(N'-phenylureido) benzyloxy]-2-methylimidazo[1,2-a]pyridine mp: >250° C.

NMR (DMSO-d$_6$, δ) 2.30 (3H, s), 5.45 (2H, s), 6.91–7.10 (3H), 7.31 (2H, t, J=9Hz), 7.41–7.62 (3H), 7.92 (1H, m), 8.34 (1H, m), 8.52 (1H, br s), 9.50 (1H, br s)

(2) 3-Bromo-8-[2,6-dichloro-3-(N-methyl-N'-trichloroacetylureido)benzyloxy]-2-methylimidazo[1,2-a]pyridine mp: 160°–164° C. (dec.)

NMR (CDCl$_3$, δ) 2.43 (3H, s), 3.33 (3H, s), 5.54 (2H, s), 6.72 (1H, d, J=7.5Hz), 6.85 (1H, t, J=7.5Hz), 7.41 (1H, d, J=10Hz), 7.52 (1H, d, J=10Hz), 7.81 (1H, d, J=7.5Hz)

Example 23

To a solution of 8-(3-acetylamino-2,6-dichlorobenzyloxy)-3-bromo-2-methylimidazo[1,2-a]pyridine (222 mg) in N,N-dimethylformamide (2 ml) was added sodium hydride (24 mg, 60% oil dispersion) in one portion at ambient temperature. The mixture was stirred for half an hour at the same temperature and iodomethane (142 mg) was added thereto. After stirring for half an hour, the mixture was poured into water. The separated oil was extracted with ethyl acetate. The extracts were washed with water, dried, and evaporated under reduced pressure. The residue was purified by flash chromatography on silica gel to give 3-bromo-8-[2,6-dichloro-3-(N-acetyl-N-methylamino)benzyloxy]-2-methylimidazo[1,2-a]pyridine (135 mg) as a solid.

mp: 201°–204° C.

NMR (CDCl$_3$, δ) 1.88 (3H, s), 2.46 (3H, s), 3.19 (3H, s), 5.52 (2H, s), 6.72 (1H, d, J=7.5Hz), 6.87 (1H, t, J=7.5Hz), 7.31 (1H, d, J=8Hz), 7.48 (1H, d, J=8Hz), 7.80 (1H, d, J=7.5Hz)

Example 24

The following compounds were obtained according to a similar manner to that of Example 23.

(1) 3-Bromo-8-[2,6-dichloro-3-(N-ethyl-N-acetylamino) benzyloxy]-2-methylimidazo[1,2-a]pyridine mp: 161° C.

NMR (CDCl$_3$, δ) 1.15 (3H, t, J=7.5Hz), 1.83 (3H, s), 2.45 (3H, s), 3.30 (1H, m), 4.12 (1H, m), 5.51 (2H, s), 6.71 (1H, d, J=7.5Hz), 6.85 (1H, t, J=7.5Hz), 7.25 (1H, d, J=7.5Hz), 7.46 (1H, d, J=7.5Hz), 7.78 (1H, d, J=7.5Hz)

(2) 3-Bromo-8-[2,6-dichloro-3-(N-propyl-N-acetylamino) benzyloxy]-2-methylimidazo[1,2-a]pyridine mp: 142°–144° C.

NMR (CDCl$_3$, δ) 0.91 (3H, t, J=7Hz), 1.41–1.68 (2), 1.81 (3H, s), 2.45 (3H, s), 3.14 (1H, dt, J=9Hz and 7Hz), 4.03 (1H, dt, J=9Hz and 7Hz), 5.51 (2H, s), 6.70 (1H, d, J=7Hz), 6.85 (1H, t, J=7Hz), 7.24 (1H, d, J=9Hz), 7.44 (1H, d, J=9Hz), 7.79 (1H, d, J=7Hz)

(3) 3-Bromo-8-[2,6-dichloro-3-[N-methyl-N-(4-methoxybenzoyl)amino]benzyloxy]-2-methylimidazo[1,2-a]pyridine mp: 168°–169° C.

NMR (CDCl₃, δ) 2.45 (3H, s), 3.35 (3H, s), 3.78 (3H, s), 5.45 (2H, s), 6.59–6.86 (4H), 7.03–7.40 (4H), 7.76 (1H, d, J=7Hz)

(4) 3-Bromo-8-[2,6-dichloro-3-(N-methyl-N-propionylamino)benzyloxy]-2-methylimidazo[1,2-a]pyridine mp: 170°–171° C.

NMR (CDCl₃, δ) 1.08 (3H, t, J=7Hz), 2.01 (2H, q, J=7Hz), 2.43 (3H, s), 3.20 (3H, s), 5.50 (2H, s), 6.70 (1H, d, J=7Hz), 6.84 (1H, t, J=7Hz), 7.28 (1H, d, J=9Hz), 7.44 (1H, d, J=9Hz), 7.78 (1H, d, J=7Hz)

(5) 3-Bromo-8-[2,4,6-trichloro-3-(N-methyl-N-acetylamino)benzyloxy]-2-methylimidazo[1,2-a]pyridine NMR (CDCl₃, δ): 1.84 (2.7H, s), 2.30 (0.3H, s), 2.44 (3H, s), 3.15 (2.7H, s), 3.28 (0.3H, s), 5.41 (0.2H, s), 5.47 (1.8H, s), 6.70 (1H, d, J=8Hz), 6.84 (1H, t, J=8Hz), 7.53 (0.1H, s), 7.59 (0.9H, s), 7.77 (1H, d, J=8Hz)

(6) 3-Bromo-8-[2,6-dichloro-3-(N-methyl-N-phthalimidoacetylamino)benzyloxy]-2-methylimidazo[1,2-a]pyridine mp: 229°–230° C.

(7) 8-[3-[N-(Acetylsarcosyl)-N-methylamino]-2,6-dichlorobenzyloxy]-3-bromo-2-methylimidazo[1,2-a]pyridine NMR (CDCl₃, δ): 1.98 (0.5H, s), 2.11 (2.5H, s), 2.43 (3H, s), 2.90 (0.5H, s), 3.07 (2.5H, s), 3.21 (2.5H, s), 3.24 (0.5H, s), 3.30 (1H, d, J=16Hz), 4.27 (1H, d, J=16Hz), 5.50 (2H, s), 6.70 (1H, d, J=8Hz), 6.84 (1H, t, J=8Hz), 7.33 (0.17H, d, J=8Hz), 7.48 (1.6H, s), 7.51 (0.17H, d, J=8Hz), 7.78 (1H, d, J=8Hz)

(8) 3-Bromo-8-[2,6-dichloro-3-(N-ethyl-N-(phthalimidoacetylamino)benzyloxy]-2-methylimidazo[1,2-a]pyridine mp: 185°–188° C.

NMR (DMSO-d₆, δ): 1.08 (3H, t, J=7Hz), 2.29 (3H, s), 3.88 (1H, d, J=16Hz), 4.11 (1H, d, J=16Hz), 5.50 (2H, s), 6.95–7.09 (3H), 7.80–8.00 (6H)

(9) 3-Bromo-8-[2,6-dichloro-3-[N-methyl-N-(2-phthalimidopropionyl)amino]benzyloxy]-2-methylimidazo[1,2-a]pyridine NMR (CDCl₃, δ): 1.51–1.65 (6H), 2.41 (0.9H, s), 2.42 (2.1H, s), 3.22 (3H, s), 4.78 (0.3H, d, J=10Hz), 4.83 (1H, q, J=6Hz), 5.17 (0.3H, d, J=10Hz), 5.51 (1.4H, s), 6.46 (0.3H, d, J=8Hz), 6.70–6.90 (1.7H), 7.00 (1H, d, J=8Hz), 7.08 (1H, d, J=8Hz), 7.31 (0.3H, d, J=8Hz), 7.48 (0.3H, d, J=8Hz), 7.67–7.82 (5H)

(10) 3-Bromo-8-[2,6-dichloro-3-[N-methyl-N-(3-phthalimidopropionyl)amino]benzyloxy]-2-methylimidazo[1,2-a]pyridine mp: 213°–215° C.

NMR (CDCl₃, δ) 2.28–2.58 (2H), 2.41 (3H, s), 3.20 (3H, s), 3.82–4.12 (2H), 5.41 (1H, d, J=9Hz), 5.50 (1H, d, J=9Hz), 6.69 (2H, d, J=7Hz), 6.84 (1H, t, J=7Hz) 7.31 (1H, d, J=9Hz), 7.43 (1H, d, J=9Hz), 7.61–7.90 (5H)

Example 25

To a solution of 3-bromo-8-(2,6-dichloro-3-acetylaminobenzyloxy)-2-methylimidazo[1,2-a]pyridine (222 mg) in N,N-dimethylformamide (2 ml) was added sodium hydride (24 mg, 60% oil dispersion) at ambient temperature. The mixture was stirred for half an hour at the same temperature and then ethyl bromoacetate (100 mg) was added thereto in one portion. The mixture was stirred for 2 hours at the same temperature and poured into water. The separated oil was extracted with dichloromethane. The extract was washed with water, dried, and concentrated in vacuo. The residue was purified by flash chromatography on silica gel to give an oil, which was dissolved in a mixture of ethanol (10 ml) and 1N sodium hydroxide solution (2 ml). The solution was refluxed for one and half hour. The organic solvent was removed under reduced pressure. The aqueous layer was adjusted to pH 4 with diluted hydrochloric acid to give 3-bromo-8-[2,6-dichloro-3-(N-carboxymethyl-N-acetylamino)benzyloxy]-2-methylimidazo[1,2-a]pyridine (150 mg) as a white solid.

mp: 225°–227° C. (dec.)

NMR (DMSO-d₆, δ): 1.79 (3H, s), 2.31 (3H, s), 3.78 (1H, d, J=17Hz), 4.64 (1H, d, J=17Hz), 5.45 (2H, s), 6.96–7.06 (2H, m), 7.76 (2H, s), 7.95 (1H, m)

Example 26

To a solution of 3-bromo-8-[2-chloro-6-(N-acetyl-N-methylamino)benzyloxy]-2-methylimidazo[1,2-a]pyridine (103 mg) in tetrahydrofuran (2 ml) was added lithium aluminum hydride (16 mg) in several portions at 5° C. After the addition, the mixture was stirred for 2 hours at 5° C. and then quenched with aqueous saturated ammonium chloride solution. The separated organic layer was washed with aqueous saturated ammonium chloride solution, dried, and concentrated in vacuo. The residue was purified by preparative thin-layer chromatography (ethyl acetate:n-hexane=1:2, V/V) to give 3-bromo-8-[2-chloro-6-(N-ethyl-N-methylamino)benzyloxy]-2-methylimidazo[1,2-a]pyridine (41 mg).

mp: 124°–126° C.

NMR (CDCl₃, δ) 1.02 (3H, t, J=7.5Hz), 2.44 (3H, s), 2.71 (3H, s), 3.03 (2H, q, J=7.5Hz), 5.41 (2H, s), 6.73 (1H, d, J=7.5Hz), 6.81 (1H, t, J=7.5Hz), 7.01–7.28 (3H, m), 7.71 (1H, dd, J=7Hz and 1.5Hz)

Example 27

A mixture of 3-bromo-8-[3-(N-acetoxyacetyl-N-methylamino)-2,6-dichlorobenzyloxy]-2-methylimidazo[1,2-a]pyridine (1.42 g), potassium carbonate (761 mg), methanol (7 ml) and tetrahydrofuran (7 ml) was stirred at ambient temperature for 1 hour. The mixture was partitioned between dichloromethane and water. The aqueous layer was extracted with dichloromethane twice. The combined organic layers were washed with brine, dried over magnesium sulfate and evaporated in vacuo. The residue was crystallized from ethanol to give 3-bromo-8-[2,6-dichloro-3-(N-glycoloyl-N-methylamino)benzyloxy]-2-methylimidazo[1,2-a]pyridine (1.16 g) as crystals.

mp: 217°–218° C.

NMR (CDCl₃, δ) 2.45 (3H, s), 3.19–3.32 (4H), 3.69, 3.82 (each 1H, d, J=15Hz), 5.50 (2H, s), 6.70 (1H, d, J=7Hz), 6.83 (1H, t, J=7Hz), 7.29 (1H, d, J=9Hz), 7.49 (1H, d, J=9Hz), 7.78 (1H, d, J=7Hz)

Example 28

3-Bromo-8-[2,6-dichloro-3-[N-(glycoloylglycyl)-N-methylamino]benzyloxy]-2-methylimidazo[1,2-a]pyridine was obtained according to a similar manner to that of Example 27.

mp: 163°–165° C.

NMR (CDCl₃, δ) 2.40 (3H, s), 3.21 (3H, s), 3.29 (1H, dd, J=17Hz and 4Hz), 3.94 (2H, s), 4.32 (1H, dd, J=17Hz and 9Hz), 5.31 (1H, d, J=10Hz), 5.59 (1H, d, J=10Hz), 6.30 (1H, br s), 6.73 (1H, d, J=7Hz), 6.90 (1H, t, J=7Hz), 7.10 (1H, br s), 7.32 (1H, d, J=9Hz), 7.49 (1H, d, J=9Hz), 7.29 (1H, d, J=7Hz)

Example 29

To a suspension of sodium hydride (60% in oil, 9 mg) in N,N-dimethylformamide (1 ml) was added 3-bromo-8-[2,6-dichloro-3-(N-glycoloyl-N-methylamino)benzyloxy]-2-methylimidazo[1,2-a]pyridine (100 mg). After stirring for 10 minutes, methyl iodide (36 mg) was added thereto and the mixture was stirred at ambient temperature for 1 hour. To this mixture were added methyl iodide (36 mg) and N,N-dimethylformamide (1 ml). The mixture was stirred at 60° C. for additional 2 hours. The reaction mixture was poured into water and extracted with ethyl acetate 3 times. The combined organic layers were washed with water 4 times and brine, dried over magnesium sulfate and evaporated in vacuo. The residue was purified by preparative thin-layer chromatography (dichloromethane: methanol=20:1, V/V) followed by crystallization from ethanol-diethyl ether to give 3-bromo-8-[3-(N-methoxyacetyl-N-methylamino)-2,6-dichlorobenzyloxy]-2-methylimidazo[1,2-a]pyridine (20 mg) as crystals.

mp: 145°–146° C.

NMR (CDCl$_3$, δ): 2.43 (3H, s), 3.21 (3H, s), 3.35 (3H, s), 3.68, 3.32 (each 1H, d, J=15Hz), 5.50 (2H, s), 6.70 (1H, d, J=7Hz), 6.85 (1H, t, J=7Hz), 7.29, 7.46 (each 1H, d, J=9Hz), 7.78 (1H, d, J=7Hz)

Example 30

To a solution of 3-bromo-8-[2,6-dichloro-3-[N-(glycoloylglycyl)-N-methylamino]benzyloxy]-2-methylimidazo[1,2-a]pyridine (200 mg) and triethylamine (76 mg) in methylene chloride (2 ml) was dropwise added mesyl chloride (52 mg) under ice-cooling, and the mixture was stirred for 1 hour at the same temperature. The mixture was washed with water twice and brine, dried over magnesium sulfate and concentrated in vacuo to give 3-bromo-8-[2,6-dichloro-3-[N-(mesyloxyacetylglycyl)-N-methylamino]benzyloxy]-2-methylimidazo[1,2-a]pyridine (221 mg).

NMR (CDCl$_3$, δ): 2.48 (3H, s), 3.19 (3H, s), 3.28 (3H, s), 3.61 (1H, dd, J=17Hz and 5Hz), 4.86 (1H, dd, J=17Hz and 5Hz), 4.18 (2H, s), 5.50 (2H, s), 6.78 (1H, d, J=7Hz), 6.91 (1H, t, J=7Hz), 7.25 (1H, br s), 7.32 (1H, d, J=9Hz), 7.51 (1H, d, J=9Hz), 7.80 (1H, d, J=7Hz)

Example 31

To a solution of 3-bromo-8-[2,6-dichloro-3-[N-(N-mesyloxyacetylglycyl)-N-methylamino]benzyloxy]-2-methylimidazo[1,2-a]pyridine (100 mg) in methanol (2 ml) was added sodium methoxide (317 mg), and the mixture was stirred for 1 hour. Sodium methoxide (200 mg) was added thereto, and the mixture was stirred for 3 hours. To the reaction mixture was added water, and the mixture was extracted with methylene chloride 3 times. The extracts were combined, washed with brine, dried over magnesium sulfate and concentrated in vacuo. The residue was purified by preparative thin-layer chromatography (methylene chloride:methanol=10:1, V/V) to give 3-bromo-8-[2,6-dichloro-3-[N-(methoxyacetylglycyl)-N-methylamino]benzyloxy]-2-methylimidazo[1,2-a]pyridine (60 mg).

NMR (CDCl$_3$, δ): 2.44 (3H, s), 3.27 (3H, s), 3.59 (1H, dd, J=17Hz and 4Hz), 3.78–3.95 (3H), 5.48 (1H, d, J=9Hz), 5.52 (1H, d, J=9Hz), 6.71 (1H, d, J=7Hz), 6.87 (1H, t, J=7Hz), 7.31 (1H, d, J=9Hz), 7.39 (1H, br s), 7.49 (1H, d, J=9Hz), 7.78 (1H, d, J=7Hz)

Example 32

To a solution of 3-bromo-8-[2,6-dichloro-3-(N-glycoloyl-N-methylamino)benzyloxy]-2-methylimidazo[1,2-a]pyridine (700 mg) and triethylamine (269 mg) in methylene chloride (14 ml) was added mesyl chloride (224 mg) under ice-cooling, and the mixture was stirred for 1 hour at ambient temperature. The reaction mixture was washed with water twice and brine, dried over magnesium sulfate and concentrated in vacuo to give the residue of 3-bromo-8-[2,6-dichloro-3-(N-mesyloxyacetyl-N-methylamino)benzyloxy]-2-methylimidazo[1,2-a]pyridine. The residue was dissolved in N,N-dimethylformamide (7 ml) and potassium phthalimide (362 mg) was added thereto at ambient temperature under N$_2$ atmosphere. The mixture was stirred for 1 day, and water was added thereto. The precipitate was collected by filtration and dried to give 3-bromo-8-[2,6-dichloro-3-(N-methyl-N-phthalimidoacetylamino)benzyloxy]-2-methylimidazo[1,2-a]pyridine (629 mg).

mp: 229°–230° C.

NMR (CDCl$_3$, δ) 2.43 (3H, s), 3.26 (3H, s), 4.12 (2H, s), 5.53 (2H, s), 6.72 (1H, d, J=7Hz), 6.87 (1H, t, J=7Hz), 7.52 (2H, s), 7.68–7.92 (5H, m)

Example 33

3-Bromo-8-[2,6-dichloro-3-[N-methyl-N-(phthalimidoacetylglycyl)amino]benzyloxy]-2-methylimidazo[1,2-a]pyridine was obtained according to a similar manner to that of Example 32.

mp: 148°–150° C.

NMR (CDCl$_3$, δ) 2.42 (3H, s), 3.22 (3H, s), 3.53 (1H, dd, J=17Hz and 4Hz), 3.80 (1H, dd, J=17Hz and 5Hz), 4.39 (2H, s), 5.48 (2H, s), 6.70 (1H, d, J=7Hz), 6.78 (1H), 6.84 (1H, t, J=7Hz), 7.29 (1H, d, J=9Hz), 7.45 (1H, d, J=9Hz), 7.62–7.92 (5H)

Example 34

A mixture of 3-bromo-8-[2,6-dichloro-3-(N-methyl-N-phthalimidoacetylamino)benzyloxy]-2-methylimidazo[1,2-a]pyridine (450 mg) and hydrazine hydrate (41 mg) in methanol (5 ml) were refluxed for 30 minutes, and hydrazine hydrate (41 mg) was added thereto, and further, the mixture was refluxed for 1.5 hours. The resulting precipitates were filtered off and the filtrate was concentrated in vacuo. The residue was dissolved in chloroform and the solution was washed with water twice and brine, dried over magnesium sulfate and concentrated in vacuo. The residue was crystallized with diethyl ether to give 8-[3-(N-glycyl-N-methylamino)-2,6-dichlorobenzyloxy]-3-bromo-2-methylimidazo[1,2-a]pyridine (338 mg).

mp: 175°–178° C.

NMR (CDCl$_3$, δ): 2.43 (3H, s), 2.92–3.20 (2H), 3.23 (3H, s), 5.49 (2H, s), 6.70 (1H, d, J=7Hz), 6.83 (1H, t, J=7Hz), 7.29, 7.47 (each 1H, d, J=9Hz), 7.79 (1H, d, J=7Hz)

Example 35

The following compounds were obtained according to a similar manner to that of Example 34.

(1) 8-[3-[N-(Glycylglycyl)-N-methylamino]-2,6-dichlorobenzyloxy]-3-bromo-2-methylimidazo[1,2-a]pyridine NMR (CDCl₃, δ): 2.41 (3H, s), 3.22 (3H, s), 3.41 (3H, s), 3.60 (1H, dd, J=17Hz and 4Hz), 3.84 (1H, dd, J=17Hz and 4Hz), 5.49 (2H, s), 6.71 (1H, d, J=7Hz), 6.87 (1H, t, J=7Hz), 7.34 (1H, d, J=9Hz)

(2) 8-[3-(N-Glycyl-N-ethylamino)-2,6-dichlorobenzyloxy]-3-bromo-2-methylimidazo[1,2-a]pyridine mp: 169°–171° C.

NMR (CDCl₃, δ): 1.16 (3H, t, J=7Hz), 2.45 (3H, s), 2.92–3.40 (3H), 4.18 (1H), 5.50 (2H, s), 6.70 (1H, d, J=7Hz), 6.83 (1H, t, J=7Hz), 7.22 (1H, d, J=9Hz), 7.48 (1H, d, J=9Hz), 7.78 (1H, d, J=7Hz)

(3) 3-Bromo-8-[2,6-dichloro-3-(N-DL-alanyl-N-methylamino)benzyloxy]-2-methylimidazo[1,2-a]pyridine NMR (CDCl₃, δ): 1.11 (1.8H, d, J=6Hz), 1.15 (1.2H, d, J=6Hz), 2.45 (3H, s), 3.20 (0.4H, q, J=6Hz), 3.22 (3H, s), 3.36 (0.6H, q, J=6Hz), 5.43–5.56 (2H), 6.70 (1H, d, J=8Hz), 6.84 (1H, t, J=8Hz), 7.30 (0.6Hz, d, J=8Hz), 7.33 (0.4H, d, J=8Hz), 7.45 (0.4H, d, J=8Hz), 7.48 (0.6H, d, J=8Hz), 7.77 (1H, d, J=8Hz)

(4) 8-[3-(N-β-Alanyl-N-methylamino)-2,6-dichlorobenzyloxy]-3-bromo-2-methylimidazo[1,2-a]pyridine mp: 163°–165° C.

NMR (CDCl₃, δ) 2.10–2.25 (2H), 2.41 (3H, s), 2.85–2.99 (2H), 3.20 (3H, s), 5.50 (2H, s), 6.72 (1H, d, J=7Hz), 6.88 (1H, t, J=7Hz), 7.32 (1H, d, J=9Hz), 7.49 (1H, d, J=9Hz), 7.78 (1H, d, J=7Hz)

(5) 3-Chloro-8-[2,6-dichloro-3-(N-glycyl-N-methylamino)benzyloxy]-2-methylimidazo[1,2-a]pyridine mp: 184°–186° C.

NMR (CDCl₃, δ): 2.43 (3H, s), 3.01 (1H, d, J=17Hz), 3.12 (1H, d, J=17Hz), 3.22 (3H, s), 5.50 (2H, s), 6.70 (1H, d, J=7Hz) 6.86 (1H, t, J=7Hz), 7.29 (1H, d, J=9Hz), 7.46 (1H, d, J=9Hz), 7.72 (1H, d, J=7Hz)

Example 36

To a solution of 3-bromo-8-[2,6-dichloro-3-(N-glycyl-N-methylamino)benzyloxy]-2-methylimidazo[1,2-a]pyridine (100 mg) in methylene chloride (2 ml) were added pyridine (17 mg), 4-dimethylaminopyridine (10 mg) and acetic anhydride (32 mg), and the mixture was stirred for 1.5 hours. The mixture was washed with water twice and brine, dried over magnesium sulfate and concentrated in vacuo. The residue was purified by silica gel column chromatography (methylene chloride:methanol=5:1, V/V) to give 8-[3-[N-(acetylglycyl)-N-methylamino]-2,6-dichlorobenzyloxy]-3-bromo-2-methylimidazo[1,2-a]pyridine (74 mg).

mp: 187°–189° C.

NMR (CDCl₃, δ): 2.01 (3H, s), 2.43 (3H, s), 3.24 (3H, s), 3.51, 3.78 (each 1H, dd, J=17Hz and 4Hz), 5.49 (2H, s), 6.45 (1H, br s), 6.71 (1H, d, J=7Hz), 6.87 (1H, t, J=7Hz), 7.30, 7.49 (each 1H, d, J=9Hz), 7.77 (1H, d, J=7Hz)

Example 37

To a mixture of 3-bromo-8-[2,6-dichloro-3-(N-glycyl-N-methylamino)benzyloxy]-2-methylimidazo[1,2-a]pyridine (100 mg), pyridine (25 mg) and methylene chloride (2 ml) was added propionyl chloride (0.02 ml) at ambient temperature and the mixture was stirred at the same temperature for 30 minutes. The mixture was partitioned between methylene chloride and water, and the organic layer was washed with water, dried over magnesium sulfate and concentrated in vacuo to give 3-bromo-8-[2,6-dichloro-3-[N-methyl-N-(propionylglycyl)amino]benzyloxy]-2-methylimidazo[1,2-a]pyridine (111 mg).

NMR (CDCl₃, δ): 1.25 (3H, t, J=6Hz), 2.27 (2H, q, J=6Hz), 2.43 (2.8H, s), 3.30 (0.2H, s), 3.52 (1H, dd, J=17Hz and 4Hz), 3.80 (1H, dd, J=17Hz and 4Hz), 5.48 (2H, s), 6.43 (1H, t like), 6.73 (1H, d, J=7Hz), 6.87 (1H, t, J=7Hz), 7.30 (1H, d, J=8Hz), 7.47 (1H, d, J=8Hz), 7.76 (1H, d, J=7Hz)

Example 38

Pivaloyl chloride (0.04 ml) was added dropwise to a mixture of tert-butoxycarbonyl-L-proline (77 mg), N-methylmorpholine (0.04 ml) and dichloromethane (3 ml) under a dry ice-tetrachloromethane bath cooling. This mixture was stirred for 5 minutes under an ice-water bath cooling and cooled under a dry ice-tetrachloromethane bath cooling. To the mixture was added a solution of 8-[3-(N-glycyl-N-methylamino)-2,6-dichlorobenzyloxy]-3-bromo-2-methylimidazo[1,2-a]pyridine (139 mg) in dichloromethane (4 ml). The mixture was stirred for 30 minutes at ambient temperature and washed with saturated aqueous solution of sodium hydrogen carbonate and water. The organic layer was dried over magnesium sulfate and evaporated in vacuo. The residue was purified by preparative thin-layer chromatography (dichloromethane:methanol= 19:1, V/V) to give 3-bromo-8-[3-[N-(tert-butoxycarbonyl-L-prolylglycyl)-N-methylamino]-2,6-dichlorobenzyloxy]-2-methylimidazo[1,2-a]pyridine (72 mg) (Compound A), and 3-bromo-8-[2,6-dichloro-3-(N-methyl-N-pivaloylglycylamino)benzyloxy]-2-methylimidazo[1,2-a]pyridine (93 mg) (Compound B).

Compound A:

p NMR (CDCl₃, δ): 1.45 (9H, br s), 1.78–2.22 (4H), 2.43 (3H, s), 3.23 (3H, s), 3.32–3.90 (4H), 4.25 (1H, m), 5.48 (2H, s), 6.72 (1H, d, J=8Hz), 6.86 (1H, t, J=8Hz), 7.31 (1H, d, J=9Hz), 7.47 (1H, d, J=9Hz), 7.77 (1H, d, J=8Hz)

Compound B

NMR (CDCl₃, δ) 1.20 (9H, s), 2.44 (3H, s), 3.26 (3H, s), 3.49 (1H, dd, J=16Hz and 4Hz), 3.77 (1H, dd, J=16Hz and 4Hz), 5.48 (2H, s), 6.64 (1H, t, like), 6.72 (1H, d, J=8Hz), 6.85 (1H, t, J=8Hz), 7.31 (1H, d, J=9Hz), 7.47 (1H, d, J=9Hz), 7.77 (1H, d, J=8Hz)

Example 39

A mixture of 3-bromo-8-[2,6-dichloro-3-(N-glycyl-N-methylamino)benzyloxy]-2-methylimidazo[1,2-a]pyridine (150 mg), 4-pentenoic acid (33 mg), N-ethyl-N'-(3-dimethylaminopropyl)carbodiimide hydrochloride (77 mg), 1-hydroxybenzotriazole (64 mg) and N,N-dimethylformamide (1.5 ml) was stirred for 2 hours at ambient temperature. Water was added thereto, and the mixture was extracted with methylene chloride three times. The organic layers were combined, washed with water four times and brine, dried over magnesium sulfate and concentrated in vacuo. The residue was purified by silica gel column chromatography (methylene chloride:methanol= 30:1, V/V) to give 3-bromo-8-[2,6-dichloro-3-[N-(4-pentenoylglycyl)-N-methylamino]benzyloxy]-2-methylimidazo[1,2-a]pyridine (172 mg).

NMR (CDCl₃, δ): 2.24–2.42 (4H), 2.44 (3H, s), 3.26 (3H, s), 3.52 (1H, dd, J=17Hz and 4Hz), 3.80 (1H, dd, J=17 and 4Hz), 4.96–5.16 (2H), 5.49 (2H, s), 5.70–5.92 (1H, m), 6.46 (1H, br s), 6.72 (1H, d, J=7Hz), 6.88 (1H, t, J=7Hz), 7.31 (1H, d, J=9Hz), 7.49 (1H, d, J=9Hz), 7.78 (1H, d, J=7Hz)

Example 40

The following compounds were obtained according to similar manner to those of Examples 36 to 39.

(1) 3-Bromo-8-[3-[N-(butyrylglycyl)-N-methylamino]-2,6-dichlorobenzyloxy]-2-methylimidazo[1,2-a]pyridine NMR (CDCl₃, δ): 0.94 (3H, t, J=7Hz), 1.65 (2H, m), 2.20 (2H, t, J=7Hz), 2.44 (3H, s), 3.26 (3H, s), 3.52 (1H, dd, J=16Hz and 4Hz), 3.80 (1H, dd, J=16Hz and 4Hz), 5.49 (2H, s), 6.41 (1H, t like), 6.72 (1H, d, J=8Hz), 6.86 (1H, t, J=8Hz), 7.31 (1H, d, J=9Hz), 7.48 (1H, d, J=9Hz), 7.77 (1H, d, J=8Hz)

(2) 3-Bromo-8-[3-[N-(isobutyrylglycyl)-N-methylamino]-2,6-dichlorobenzyloxy]-2-methylimidazo[1,2-a]pyridine NMR (CDCl$_3$, δ): 1.14 (6H, d, J=6Hz), 2.42 (1H, m), 2.44 (3H, s), 3.25 (3H, s), 3.50 (1H, dd, J=16Hz and 4Hz), 3.79 (1H, dd, J=16Hz and 5Hz), 5.48 (2H, s), 6.45 (1H, t like), 6.72 (1H, d, J=8Hz), 6.86 (1H, t, J=8Hz), 7.31 (1H, d, J=9Hz), 7.48 (1H, d, J=9Hz), 7.77 (1H, d, J=8Hz)

(3) 3-Bromo-8-[2,6-dichloro-3-[N-(cyclopropylcarbonylglycyl)-N-methylamino]benzyloxy]-2-methylimidazo-[1,2-a]pyridine NMR (CDCl$_3$, δ) 0.70–1.00 (4H), 1.47 (1H, m), 2.44 (3H, s), 3.25 (3H, s), 3.54 (1H, dd, J=16Hz and 4Hz), 3.81 (1H, dd, J=16Hz and 4Hz), 5.48 (2H, s), 6.58 (1H, t like), 6.7 (1H, d, J=8Hz), 6.86 (1H, t, J=8Hz), 7.30 (1H, d, J=9Hz), 7.46 (1H, d, J=9Hz), 7.77 (1H, d, J=8Hz)

(4) 3-Bromo-8-[2,6-dichloro-3-[N-(trifluoroacetylglycyl)-N-methylamino]benzyloxy]-2-methylimidazo[1,2-a]pyridine NMR (CDCl$_3$, δ) 2.42 (3H, s), 3.29 (3H, s), 3.61 (1H, dd, J=18Hz and 4Hz), 3.83 (1H, dd, J=18Hz and 4Hz), 5.48 (1H, d, J=7Hz), 5.53 (1H, d, J=7Hz), 6.71 (1H, d, J=7Hz), 6.88 (1H, t, J=7Hz), 7.31 (1H, d, J=9Hz), 7.41 (1H, br s), 7.50 (1H, d, J=9Hz), 7.78 (1H, d, J=7Hz)

(5) 8-[3-[N-(Benzoylglycyl)-N-methylamino]-2,6-dichlorobenzyloxy]-3-bromo-2-methylimidazo[1,2-a]pyridine mp: 126° C. (dec.)

NMR (CDCl$_3$, δ): 2.44 (3H, s), 3.29 (3H, s), 3.73 (1H, dd, J=18Hz and 4Hz), 3.99 (1H, dd, J=18Hz and 4Hz), 5.48 (1H, d, J=7Hz), 5.54 (1H, d, J=7Hz), 6.73 (1H, d, J=7Hz), 6.88 (1H, t, J=7Hz), 7.18 (1H, br s), 7.31–7.59 (5H), 7.72–7.88 (3H)

(6) 3-Bromo-8-[2,6-dichloro-3-[N-(cyclohexylcarbonylglycyl)-N-methylamino]benzyloxy]-2-methylimidazo[1,2-a]pyridine NMR (CDCl$_3$, δ) 1.14–1.94 (10H), 2.14 (1H, m), 2.44 (3H, s), 3.26 (3H, s), 3.50 (1H, dd, J=18Hz and 4Hz), 3.78 (1H, dd, J=18Hz and 5Hz), 5.48 (2H, s), 6.43 (1H, t like), 6.72 (1H, d, J=8Hz), 6.86 (1H, t, J=8Hz), 7.32 (1H, d, J=8Hz), 7.48 (1H, d, J=8Hz), 7.77 (1H, d, J=8Hz)

(7) 3-Bromo-8-[2,6-dichloro-3-[N-(phenylacetylglycyl)-N-methylamino]benzyloxy]-2-methylimidazo[1,2-a]pyridine NMR (CDCl$_3$, δ): 2.43 (3H, s), 3.21 (3H, s), 3.49 (1H, dd, J=17Hz and 4Hz), 3.59 (2H, s), 3.75 (1H, dd, J=17Hz and 5Hz), 5.48 (2H, s), 6.40 (1H, t like), 6.72 (1H, d, J=8Hz), 6.86 (1H, t, J=8Hz), 7.21–7.43 (6H), 7.46 (1H, d, J=8Hz), 7.77 (1H, d, J=8Hz)

(8) 3-Bromo-8-[3-[N-(tert-butoxycarbonyl-D-prolylglycyl)-N-methylamino]-2,6-dichlorobenzyloxy]-2-methylimidazo[1,2-a]pyridine NMR (CDCl$_3$, δ) 1.45 (9H, br s), 1.78–2.22 (4H), 2.43 (3H, s), 3.23 (3H, s), 3.32–3.90 (4H), 4.25 (1H, m), 5.48 (2H, s), 6.72 (1H, d, J=8Hz), 6.86 (1H, t, J=8Hz), 7.31 (1H, d, J=9Hz), 7.47 (1H, d, J=9Hz), 7.77 (1H, d, J=8Hz)

(9) 8-[3-[N-(Acetoxyacetylglycyl)-N-methylamino]-2,6-dichlorobenzyloxy]-3-bromo-2-methylimidazo[1,2-a]pyridine NMR (CDCl$_3$, δ) 2.20 (3H, s), 2.44 (3H, s), 3.26 (3H, s), 3.59 (1H, dd, J=17Hz and 4Hz), 3.82 (1H, dd, J=17Hz and 4Hz), 4.59 (2H, s), 5.46 (1H, d, J=10Hz), 5.52 (1H, d, J=10Hz), 6.71 (1H, d, J=7Hz), 6.87 (1H, t, J=7Hz), 7.11 (1H, br s), 7.31 (1H, d, J=9Hz), 7.49 (1H, d, J=9Hz), 7.78 (1H, d, J=7Hz)

(10) 8-[3-[N-(Acetylglycyl)-N-ethylamino]-2,6-dichlorobenzyloxy]-3-bromo-2-methylimidazo[1,2-a]pyridine NMR (CDCl$_3$, δ): 1.19 (3H, t, J=7Hz), 2.00 (3H, s), 2.42 (3H, s), 3.29 (1H), 3.48 (1H, dd, J=17Hz and 5Hz), 3.72 (1H, dd, J=17Hz and 5Hz), 4.21 (1H), 5.49 (2H, s), 6.46 (1H, br s), 6.71 (1H, d, J=7Hz), 6.87 (1H, t, J=7Hz), 7.22 (1H, d, J=9Hz), 7.48 (1H, d, J=9Hz), 7.78 (1H, d, J=7Hz)

(11) 8-[3-[N-(Acetyl-DL-alanyl)-N-methylamino]-2,6-dichlorobenzyloxy]-3-bromo-2-methylimidazo[1,2-a]pyridine NMR (CDCl$_3$, δ): 1.18 (1.5H, d, J=6Hz), 1.20 (1.5H, d, J=6Hz), 1.95 (1.5H, s), 1.99 (1.5H, s), 2.43 (3H, s), 3.22 (3H, s), 4.26–4.51 (1H), 5.47 (1H, s), 5.51 (1H, s), 6.15 (0.5H, d, J=8Hz), 6.43 (1H, d, J=8Hz), 6.65–6.90 (2H), 7.30 (0.5H, d, J=8Hz), 7.47 (0.5H, d, J=8Hz), 7.50 (1H, s), 7.76 (1H, d, J=8Hz)

(12) 8-[3-[N-(Acetyl-5-alanyl)-N-methylamino]-2,6-dichlorobenzyloxy]-3-bromo-2-methylimidazo[1,2-a]pyridine NMR (CDCl$_3$, δ) 1.94 (3H, s), 2.10–2.30 (2H), 2.42 (3H, s), 3.20 (3H, s), 3.39–3.56 (2H), 5.49 (2H, s), 6.39 (1H, br s), 6.70 (1H, d, J=7Hz), 6.85 (1H, t, J=7Hz), 7.26 (1H, d, J=9Hz), 7.45 (1H, d, J=9Hz), 7.78 (1H, d, J=7Hz)

(13) 3-Bromo-8-[2,6-dichloro-3-[N-(methoxycarbonylglycyl)-N-methylamino]benzyloxy]-2-methylimidazo[1,2-a]pyridine NMR (CDCl$_3$, δ) 2.42 (3H, s), 3.22 (3H, s), 3.49 (1H, dd, J=17Hz and 5Hz), 3.67 (3H, s), 3.72 (1H, dd, J=17Hz and 5Hz), 5.48 (2H, s), 5.54 (1H, br s), 6.71 (1H, d, J=7Hz), 6.82 (1H, t, J=7Hz), 7.31 (1H, d, J-9Hz), 7.49 (1H, d, J=9Hz), 7.78 (1H, d, J=7Hz)

(14) 3-Bromo-8-[2,6-dichloro-3-[N-(valerylglycyl)-N-methylamino]benzyloxy]-2-methylimidazo[1,2-a]pyridine NMR (CDCl$_3$, δ): 0.91 (3H, t, J=7Hz), 1.34 (2H, m), 1.61 (2H, m), 2.22 (2H, t, J=7Hz), 2.45 (3H, s), 3.26 (3H, s), 3.52 (1H, dd, J=16Hz and 4Hz), 3.80 (1H, dd, J=16Hz and 4Hz), 5.48 (2H, s), 6.41 (1H, t like), 6.71 (1H, d, J=8Hz), 6.86 (1H, dd, J=8Hz and 7Hz), 7.30 (1H, d, J=9Hz), 7.48 (1H, d, J=9Hz), 7.77 (1H, d, J=7Hz)

(15) 3-Bromo-8-[2,6-dichloro-3-[N-(isovalerylglycyl)-N-methylamino]benzyloxy]-2-methylimidazo[1,2-a]pyridine NMR (CDCl$_3$, δ): 0.90 (6H, d, J=7Hz), 2.02–2.17 (3H), 2.44 (3H, s), 3.26 (3H, s), 3.52 (1H, dd, J=16Hz and 4Hz), 3.80 (1H, dd, J=16Hz and 4Hz), 5.49 (2H, s), 6.39 (1H, t like), 6.72 (1H, d, J=8Hz), 6.86 (1H, dd, J=8Hz and 7Hz), 7.30 (1H, d, J=9Hz), 7.48 (1H, d, J=9Hz), 7.77 (1H, d, J=7Hz)

(16) 3-Bromo-8-[2,6-dichloro-3-[N-(2-pyridylacetylglycyl)-N-methylamino]benzyloxy]-2-methylimidazo[1,2-a]pyridine NMR (CDCl$_3$, δ): 2.45 (3H, s), 3.22 (3H, s), 3.54 (1H, dd, J=18Hz and 5Hz), 3.76 (2H, s), 3.81 (1H, dd, J=18Hz and 5Hz), 5.48 (2H, s), 6.71 (1H, d, J=7Hz), 6.85 (1H, t, J=7Hz), 7.16–7.32 (3H), 7.47 (1H, d, J=9Hz), 7.68 (1H, t, J=7Hz), 7.77 (1H, d, J=7Hz), 7.93 (1H, br t, J=5Hz)

(17) 3-Bromo-8-[2,6-dichloro-3-[N-(3-pyridylacetylglycyl)-N-methylamino]benzyloxy]-2-methylimidazo[1,2-a]pyridine NMR (CDCl$_3$, δ): 2.43 (3H, s), 3.22 (3H, s), 3.51 (1H, dd, J=17Hz and 5Hz), 3.58 (2H, s), 3.79 (1H, dd, J=17Hz and 5Hz), 5.48 (2H, s), 6.50 (1H, br t, J=5Hz), 6.70 (1H, d, J=7Hz), 6.85 (1H, t, J=7Hz), 7.21–7.32 (2H), 7.48 (1H, d, J=9Hz), 7.66 (1H, d, J=8Hz), 7.78 (1H, d, J=7Hz), 8.49–8.59 (2H)

(18) 3-Bromo-8-[2,6-dichloro-3-[N-(3-ethoxycarbonylpropionylglycyl)-N-methylamino]benzyloxy]-2-methylimidazo[1,2-a]pyridine NMR (CDCl₃, δ): 1.26 (3H, t, J=7Hz), 2.44 (3H, s), 2.49–2.69 (4H), 3.25 (3H, s), 3.53 (1H, dd, J=16Hz and 4Hz), 3.79 (1H, dd, J=16Hz and 4Hz), 4.13 (2H, q, J=7Hz), 5.50 (2H, s), 6.56 (1H, t like), 6.71 (1H, d, J=8Hz), 6.86 (1H, dd, J=8Hz and 6Hz), 7.30 (1H, d, J=10Hz), 7.48 (1H, d, J=10Hz), 7.77 (1H, d, J=6Hz)

(19) 3-Bromo-8-[2,6-dichloro-3-[N-(bromoacetylglycyl)-N-methylamino]benzyloxy]-2-methylimidazo[1,2-a]pyridine NMR (CDCl₃, δ): 2.44 (3H, s), 3.28 (3H, s), 3.57 (1H, dd, J=18Hz and 4Hz), 3.80 (1H, dd, J=18Hz and 4Hz), 3.88 (2H, s), 5.49 (2H, s), 6.71 (1H, d, J=7Hz), 6.88 (1H, t, J=7Hz), 7.31 (1H, d, J=9Hz), 7.39 (1H, br t, J=4Hz), 7.50 (1H, d, J=9Hz), 7.78 (1H, d, J=7Hz)

(20) 3-Bromo-8-[2,6-dichloro-3-[N-(phthalimidoacetylglycyl)-N-methylamino]benzyloxy]-2-methylimidazo[1,2-a]pyridine mp: 211°–213° C.

NMR (CDCl₃, δ) 2.43 (3H, s), 3.22 (3H, s), 3.56 (1H, dd, J=18Hz and 5Hz), 3.82 (1H, dd, J=18Hz and 5Hz), 4.40 (2H, s), 5.49 (2H, s), 6.69 (1H, d, J=7Hz), 6.78 (1H, br t, J=5Hz), 6.82 (1H, t, J=7Hz), 7.29 (1H, d, J=9Hz), 7.47 (1H, d, J=7Hz), 7.69–7.80 (3H), 7.82–7.92 (2H)

(21) 3-Bromo-8-[2,6-dichloro-3-[N-(4-nitrophenoxycarbonylglycyl)-N-methylamino]benzyloxy]-2-methylimidazo-[1,2-a]pyridine mp: 166°–168° C.

NMR (CDCl₃, δ): 2.43 (3H, s), 3.29 (3H, s), 3.60 (1H, dd, J=17Hz and 5Hz), 3.81 (1H, dd, J=17Hz and 5Hz), 5.50 (2H, s), 6.05 (1H, br t, J=5Hz), 6.71 (1H, d, J=7Hz), 6.87 (1H, t, J=7Hz), 7.22–7.38 (3H), 7.49 (1H, d, J=9Hz), 7.79 (1H, d, J=7Hz), 8.22 (2H, d, J=9Hz)

(22) 3-Chloro-8-[2,6-dichloro-3-[N-(phenylacetylgylcyl)-N-methylamino]benzyloxy]-2-methylimidazo[1,2-a]pyridine mp: 198°–200° C.

NMR (CDCl₃, δ): 2.42 (3H, s), 3.21 (3H, s), 3.49 (1H, dd, J=15Hz and 4Hz), 3.60 (2H, s), 3.76 (1H, dd, J=15Hz and 4Hz), 5.46 (2H, s), 6.40 (1H, t like), 6.69 (1H, d, J=8Hz), 6.84 (1H, dd, J=8Hz and 7Hz), 7.20–7.50 (7H), 7.71 (1H, d, J=6Hz)

(23) 3-Chloro-8-[2,6-dichloro-3-[N-(butyrylglycyl)-N-methylamino]benzyloxy]-2-methylimidazo[1,2-a]pyridine mp: 103°–104° C.

NMR (CDCl₃, δ): 0.93 (3H, t, J=7Hz), 1.54–1.77 (2H), 2.20 (2H, t, J=7Hz), 2.42 (3H, s), 3.23 (3H, s), 3.51 (1H, dd, J=17Hz and 4Hz), 3.79 (1H, dd, J=17Hz and 4Hz), 5.49 (2H, s), 6.41 (1H, br t, J=4Hz), 6.70 (1H, d, J=7Hz), 6.86 (1H, t, J=7Hz), 7.31 (1H, d, J=9Hz), 7.47 (1H, d, J=9Hz), 7.71 (1H, d, J=7Hz)

Example 41

To a suspension of 3-bromo-8-[2,6-dichloro-3-(N-glycyl-N-methylamino)benzyloxy]-2-methylimidazo[1,2-a]pyridine (150 mg) in formic acid (1 ml) was added acetic anhydride (65 mg), and the mixture was stirred for 1.5 hours. Acetic anhydride (40 mg) was added thereto, and the mixture was stirred for 3 hours. The mixture was concentrated in vacuo, and a saturated aqueous solution of sodium bicarbonate was added thereto, and the mixture was extracted with methylene chloride three times. The organic layers were combined, washed with brine, dried over magnesium sulfate, and concentrated in vacuo. The residue was purified by preparative thin-layer chromatography (methylene chloride:methanol=5:1, V/V) to give 3-bromo-8-[2,6-dichloro-3-[N-(formylglycyl)-N-methylamino]benzyloxy]-2-methylimidazo[1,2-a]pyridine (102 mg).

mp: 211°–212° C.

NMR (CDCl₃, δ) 2.43 (3H, s), 3.26 (3H, s), 3.58 (1H, dd, J=17Hz and 5Hz), 3.82 (1H, dd, J=17Hz and 5Hz), 5.47 (1H, d, J=7Hz), 5.52 (1H, d, J=7Hz), 6.61 (1H, br s), 6.71 (1H, d, J=7Hz), 6.87 (1H, t, J=7Hz), 7.31 (1H, d, J=9Hz), 7.50 (1H, d, J=9Hz), 7.78 (1H, d, J=7Hz), 8.20 (1H, s)

Example 42

To a solution of 3-bromo-8-[2,6-dichloro-3-(N-glycyl-N-methylamino)benzyloxy]-2-methylimidazo[1,2-a]pyridine (98 mg) in methylene chloride (2 ml) was added methyl isocyanate (0.02 ml), and the mixture was stirred for 1 hour at ambient temperature. The mixture was concentrated in vacuo to give 3-bromo-8-[2,6-dichloro-3-[N-methyl-N-(N'-methylureidoacetyl)amino]benzyloxy]-2-methylimidazo[1,2-a]pyridine (9.5 mg).

NMR (CDCl₃, δ) 2.44 (3H, s), 2.74 (3H, d, J=5Hz), 3.23 (3H, s), 3.58 (1H, dd, J=16Hz and 5Hz), 4.76 (1H, br s), 5.35 (1H, t like), 5.49 (2H, s), 6.74 (1H, d, J=8Hz), 6.88 (1H, t, J=8Hz), 7.35 (1H, d, J=8Hz), 7.48 (1H, d, J=8Hz), 7.78 (1H, d, J=8Hz)

Example 43

A mixture of 3-bromo-8-[2,6-dichloro-3-[N-(4-nitrophenoxycarbonylglycyl)-N-methylamino]benzyloxy]-2-methylimidazo[1,2-a]pyridine (100 mg), 3-aminopyridine (18 mg) and dioxane (1 ml) was refluxed for 1.5 hours under nitrogen atmosphere. The reaction mixture was washed with water four times and brine, dried over magnesium sulfate, and concentrated in vacuo. The residue was purified by preparative thin-layer chromatography (methylene chloride:methanol=10:1, V/V) to give 3-bromo-8-[2,6-dichloro-3-[N-[N'-(3-pyridyl)ureidoacetyl]-N-methylamino]benzyloxy]-2-methylimidazo[1,2-a]pyridine (58 mg).

NMR (CDCl₃, δ): 2.40 (3H, s), 3.22 (3H, s), 3.82 (2H, d, J=5Hz), 5.42 (1H, d, J=10Hz), 5.52 (1H, d, J=10Hz), 6.07 (1H, br t, J=5Hz), 6.72 (1H, d, J=7Hz), 6.89 (1H, t, J=7Hz), 7.11 (1H, dd, J=9Hz and 5Hz), 7.34 (1H, d, J=9Hz), 7.41 (1H, d, J=9Hz), 7.79 (1H, d, J=7Hz), 7.86 (1H, d, J=9Hz), 8.18 (1H, d, J=5Hz), 8.31 (1H, br s), 8.41 (1H, br s)

Example 44

The following compounds were obtained according to similar manners to those of Examples 42 or 43.

(1) 3-Bromo-8-[2,6-dichloro-3-[N-(N'-ethylureidoacetyl)-N-methylamino]benzyloxy]-2-methylimidazo[1,2-a]pyridine mp: 126°–127° C.

NMR (CDCl₃, δ): 1.20 (3H, t, J=7Hz), 2.42 (3H, s), 3.09–3.33 (5H), 3.56 (1H, dd, J=17Hz and 5Hz), 3.80 (1H, dd, J=17Hz and 5Hz), 4.71 (1H, br t, J=5Hz), 5.32 (1H, br t, J=5Hz), 5.49 (2H, s), 6.71 (1H, d, J=7Hz), 6.88 (1H, t, J=7Hz), 7.31 (1H, d, J=9Hz), 7.46 (1H, d, J=9Hz), 7.78 (1H, d, J=7Hz)

(2) 3-Bromo-8-[2,6-dichloro-3-[N-methyl-(N'-phenylureidoacetyl)amino]benzyloxy]-2-methylimidazo[1,2-a]pyridine mp: 144°–147° C.

NMR (CDCl₃, δ) 2.42 (3H, s), 3.22 (3H, s), 3.70 (1H, dd, J=17Hz and 4Hz), 3.86 (1H, dd, J=17Hz and 4Hz), 5.49 (2H, s), 5.79 (1H, br t, J=4Hz), 6.71 (1H, d, J=7Hz), 6.86 (1H, t, J=7Hz), 7.02 (1H), 7.19–7.30 (5H), 7.32 (1H, d, J=9Hz), 7.42 (1H, d, J=9Hz), 7.78 (1H, d, J=7Hz)

(3) 3-Bromo-8-[2,6-dichloro-3-[N-(N'-cyclohexylureidoacetyl)-N-methylamino]benzyloxy]-2-methylimidazo[1,2-a]pyridine NMR (CDCl$_3$, δ) 0.98–2.01 (10H), 2.43 (3H, s), 3.22 (3H, s), 3.42 (1H, m), 3.52 (1H, dd, J=17Hz and 5Hz), 3.80 (1H, dd, J=17Hz and 5Hz), 4.56 (1H, d, J=8Hz), 5.26 (1H, br t, J=5Hz), 5.48 (2H, s), 6.71 (1H, d, J=8Hz), 6.87 (1H, t, J=8Hz), 7.32 (1H, d, J=9Hz), 7.48 (1H, d, J=9Hz), 7.78 (1H, d, J=8Hz)

(4) 3-Bromo-8-[2,6-dichloro-3-[N-[N'-(α-naphthyl)ureidoacetyl]-N-methylamino]benzyloxy]-2-methylimidazo[1,2-a]pyridine mp: 148°–151° C.

NMR (CDCl$_3$, δ): 2.41 (3H, S), 3.16 (3H, s), 3.61 (1H, dd, J=18Hz and 4Hz), 3.87 (1H, dd, J=18Hz and 4Hz), 5.42 (2H, s), 6.01 (1H, br t, J=4Hz), 6.69 (1H, d, J=8Hz), 6.85 (1H, t, J=8Hz), 7.18 (1H, br s), 7.25 (1H, d, J=9Hz), 7.40 (1H, d, J=9Hz), 7.42–7.56 (4H), 7.62–7.92 (3H), 7.99–8.10 (1H, m)

(5) 3-Bromo-8-[2,6-dichloro-3-[N-(N'-benzylureidoacetyl)-N-methylamino]benzyloxy]-2-methylimidazo[1,2-a]pyridine NMR (CDCl$_3$, δ): 2.42 (3H, s), 3.11 (3H, s), 3.57 (1H, dd, J=17Hz and 5Hz), 3.82 (1H, dd, J=17Hz and 5Hz), 4.32 (2H, d, J=5Hz), 5.30 (1H, br t, J=5Hz), 5.48 (2H, s), 5.58 (1H, br t, J=5Hz), 6.71 (1H, d, J=7Hz), 6.86 (1H, t, J=7Hz), 7.18–7.39 (6H), 7.46 (1H, d, J=9Hz), 7.78 (1H, d, J=7Hz)

(6) 3-Bromo-8-[2,6-dichloro-3-[N-[N'-(m-tolyl)ureidoacetyl]-N-methylamino]benzyloxy]-2-methylimidazo[1,2-a]pyridine NMR (CDCl$_3$, δ): 2.29 (3H, s), 2.42 (3H, s), 3.22 (3H, s), 3.65 (1H, dd, J=17Hz and 5Hz), 3.85 (1H, dd, J=17Hz and 5Hz), 5.47 (2H, s), 5.96 (1H, br t, J=5Hz), 6.71 (1H, d, J=7Hz), 6.80–6.91 (2H), 7.00–7.39 (4H), 7.32 (1H, d, J=9Hz), 7.43 (1H, d, J=9Hz), 7.78 (1H, d, J=7Hz)

(7) 3-Bromo-8-[2,6-dichloro-3-[N-[N'-(p-tolyl)ureidoacetyl]-N-methylamino]benzyloxy]-2-methylimidazo[1,2-a]pyridine NMR (CDCl$_3$, δ): 2.30 (3H, s), 2.42 (3H, s), 3.21 (3H, s), 3.62 (1H, dd, J=17Hz and 5Hz), 3.85 (1H, dd, J=17Hz and 5Hz), 5.47 (2H, s), 5.91 (1H, br t, J=5Hz), 6.71 (1H, d, J=7Hz), 6.86 (1H, t, J=7Hz), 7.01–7.21 (5H), 7.31 (1H, d, J=9Hz), 7.43 (1H, d, J=9Hz), 7.78 (1H, d, J=7Hz)

(8) 3-Bromo-8-[2,6-dichloro-3-[N-[N'-(4-methoxyphenyl)ureidoacetyl]-N-methylamino]benzyloxy]-2-methylimidazo[1,2-a]pyridine NMR (CDCl$_3$, δ): 2.42 (3H, s), 3.21 (3H, s), 3.62 (1H, dd, J=17Hz and 5Hz), 3.78 (3H, s), 3.83 (1H, dd, J=17Hz and 5Hz), 5.48 (2H, s), 5.78 (1H, br t, J=5Hz), 6.68–6.96 (5H), 7.12–7.25 (2H), 7.32 (1H, d, J=9Hz), 7.45 (1H, d, J=9Hz), 7.78 (1H, d, J=7Hz)

(9) 3-Bromo-8-[2,6-dichloro-3-[N-[N'-(4-trifluoromethylphenyl)ureidoacetyl]-N-methylamino]benzyloxy]-2-methylimidazo[1,2-a]pyridine NMR (CDCl$_3$, δ): 2.41 (3H, s), 3.22 (3H, s), 3.72 (1H, dd, J=17Hz and 5Hz), 3.86 (1H, dd, J=17Hz and 5Hz), 5.43 (1H, d, J=9Hz), 5.51 (1H, d, J=9Hz), 6.18 (1H, br t, J=5Hz), 6.72 (1H, d, J=7Hz), 6.89 (1H, t, J=7Hz), 7.26–7.45 (6H), 7.79 (1H, d, J=7Hz), 8.42 (1H, br s)

(10) 3-Bromo-8-[2,6-dichloro-3-[N-[N'-(4-fluorophenyl)ureidoacetyl]-N-methylamino]benzyloxy]-2-methylimidazo[1,2-a]pyridine NMR (CDCl$_3$, δ): 2.42 (3H, s), 3.21 (3H, s), 3.69 (1H, dd, J=17Hz and 5Hz), 3.83 (1H, dd, J=17Hz and 5Hz), 5.48 (2H, s), 5.91 (1H, br t, J=5Hz), 6.71 (1H, d, J=7Hz), 6.81–7.00 (3H), 7.16–7.29 (2H), 7.34 (1H, d, J=9Hz), 7.42 (1H, d, J=9Hz), 7.58 (1H, br s), 7.78 (1H, d, J=7Hz)

(11) 3-Bromo-8-[2,6-dichloro-3-[N-(N'-n-propylureidoacetyl)-N-methylamino]benzyloxy]-2-methylimidazo[1,2-a]pyridine NMR (CDCl$_3$, δ) 0.90 (3H, t, J=7Hz), 1.39–1.59 (2H), 2.43 (3H, s), 3.10 (2H, q, J=6Hz), 3.22 (3H, s), 3.54 (1H, dd, J=17Hz and 4Hz), 3.80 (1H, dd, J=17Hz and 4Hz), 4.73 (1H, br t, J=6Hz), 5.32 (1H, br t, J=4Hz), 5.49 (2H, s), 6.71 (1H, d, J=7Hz), 6.88 (1H, t, J=7Hz), 7.32 (1H, d, J=9Hz), 7.48 (1H, d, J=9Hz), 7.77 (1H, d, J=7Hz)

(12) 3-Bromo-8-[2,6-dichloro-3-[N-(N'-isopropylureidoacetyl)-N-methylamino]benzyloxy]-2-methylimidazo[1,2-a]pyridine NMR (CDCl$_3$, δ) 1.12 (6H, d, J=7Hz), 2.45 (3H, s), 3.52 (1H, dd, J=17Hz and 4Hz), 3.70–3.88 (2H), 4.51 (1H, br d, J=7Hz), 5.23 (1H, br t, J=4Hz), 5.49 (2H, s), 6.71 (1H, d, J=7Hz), 6.87 (1H, t, J=7Hz), 7.32 (1H, d, J=9Hz), 7.48 (1H, d, J=9Hz), 7.78 (1H, d, J=7Hz)

(13) 3-Bromo-8-[2,6-dichloro-3-[N-(N'-allylureidoacetyl)-N-methylamino]benzyloxy]-2-methylimidazo[1,2-a]pyridine NMR (CDCl$_3$, δ): 2.43 (3H, s), 3.22 (3H, s), 3.57 (1H, dd, J=17Hz and 5Hz), 3.70–3.89 (3H), 4.94 (1H, br t, J=5Hz), 5.04–5.28 (2H), 5.42–5.55 (3H), 5.83 (1H, m), 6.71 (1H, d, J=7Hz), 6.87 (1H, t, J=7Hz), 7.31 (1H, d, J=9Hz), 7.48 (1H, d, J=9Hz), 7.78 (1H, d, J=7Hz)

(14) 3-Bromo-8-[2,6-dichloro-3-[N-[N'-(4-pyridyl)ureidoacetyl]-N-methylamino]benzyloxy]-2-methylimidazo[1,2-a]pyridine NMR (CDCl$_3$, δ) 2.41 (3H, s), 3.20 (3H, s), 3.80 (2H, d, J=5Hz), 5.41 (1H, d, J=10Hz), 5.51 (1H, d, J=10Hz), 6.19 (1H, br t, J=5Hz), 6.76 (1H, d, J=7Hz), 6.90 (1H, t, J=7Hz), 7.19 (2H, d, J=6Hz), 7.32 (1H, d, J=9Hz), 7.40 (1H, d, J=9Hz), 7.79 (1H, d, J=7Hz), 8.28 (2H, d, J=6Hz), 8.95 (1H, br s)

(15) 3-Chloro-8-[2,6-dichloro-3-[N-(N'-phenylureidoacetyl)-N-methylamino]benzyloxy]-2-methylimidazo[1,2-a]pyridine mp: 230°–231° C.

NMR (CDCl$_3$, δ): 2.42 (3H, s), 3.23 (3H, s), 3.69 (1H, dd, J=16Hz and 4Hz), 3.85 (1H, dd, J=16Hz and 4Hz), 5.49 (2H, s), 5.93 (1H, t like), 6.71 (1H, d, J=8Hz), 6.86 (1H, dd, J=8Hz and 7Hz), 7.20–7.37 (7H), 7.44 (1H, d, J=9Hz), 7.74 (1H, d, J=7Hz)

(16) 3-Chloro-8-[2,6-dichloro-3-[N-(N'-cyclohexylureidoacetyl)-N-methylamino]benzyloxy]-2-methylimidazo[1,2-a]pyridine mp: 137°–140° C.

NMR (CDCl$_3$, δ): 0.98–1.47 (6H), 1.50–1.78 (2H), 1.81–2.00 (2H), 2.43 (3H, s), 3.23 (3H, s), 3.43 (1H, m), 3.52 (1H, dd, J=16Hz and 4Hz), 3.79 (1H, dd, J=16Hz and 4Hz), 4.50 (1H, d, J=10Hz), 5.21 (1H, t like), 5.48 (2H, s), 6.70 (1H, d, J=8Hz), 6.86 (1H, dd, J=8Hz and 7Hz), 7.34 (1H, d, J=8Hz), 7.47 (1H, d, J=8Hz), 7.72 (1H, d, J=7Hz)

(17) 3-Chloro-8-[2,6-dichloro-3-[N-(N'-ethylureidoacetyl)-N-methylamino]benzyloxy]-2-methylimidazo[1,2-a]pyridine NMR (CDCl$_3$, δ) 1.11 (3H, t, J=6Hz), 2.42 (3H, s), 3.09–3.28 (5H), 3.53 (1H, dd, J=17Hz and 5Hz), 3.80 (1H, dd, J=17Hz and 5Hz), 4.70 (1H, br t, J=5Hz), 5.32 (1H, br t, J=5Hz), 5.49 (2H, s), 6.70 (1H, d, J=7Hz), 6.87 (1H, t, J=7Hz), 7.32 (1H, d, J=9Hz), 7.48 (1H, d, J=9Hz), 7.71 (1H, d, J=7Hz)

Example 45

To a mixture of 8-[3-(N-glycyl-N-methylamino)-2,6-dichlorobenzyloxy]-3-bromo-2-methylimidazo[1,2-a]pyridine (100 mg), acetic acid (0.5 ml) and water (1.0 ml) was added an aqueous solution (1 ml) of sodium cyanate (138 mg) at 40° C. The mixture was stirred at the same temperature for 1 hour and evaporated in vacuo. The residue was partitioned into dichloromethane and a saturated aqueous solution of sodium hydrogen carbonate and the organic layer was separated. The aqueous layer was extracted with dichloromethane twice. The combined organic layers were washed with brine, dried over magnesium sulfate and evaporated in vacuo. The residue was purified by preparative thin-layer chromatography (dichloromethane:methanol= 10:1, V/V) followed by crystallization from ethyl acetate-diethyl ether to give 3-bromo-8-[2,6-dichloro-3-[N-methyl-N-(ureidoacetyl)amino]benzyloxy]-2-methylimidazo[1,2-a]pyridine (72 mg) as crystals.

mp: 147°–149° C.

NMR (CDCl$_3$, δ): 2.44 (3H, s), 3.23 (3H, s), 3.52 (1H, dd, J=17Hz and 5Hz), 3.80 (1H, dd, J=17Hz and 5Hz), 4.76 (2H, br s), 5.49 (2H, s), 5.82 (1H, t, J=5Hz), 6.71 (1H, d, J=7Hz), 6.87 (1H, t, J=7Hz), 7.33 (1H, d, J=9Hz), 7.49 (1H, d, J=9Hz), 7.79 (1H, d, J=7Hz)

Example 46

To a solution of 3-bromo-8-[2,6-dichloro-3-(N-glycyl-N-methylamino)benzyloxy]-2-methylimidazo[1,2-a]pyridine (150 mg) in methylene chloride (3 ml) was added phenylisothiocyanate (86 mg), and the mixture was refluxed for 1 hour under nitrogen atmosphere. The mixture was concentrated in vacuo, and the residue was purified by silica gel column chromatography (methylene chloride:methanol= 40:1, V/V) to give 3-bromo-8-[2,6-dichloro-3-[N-(N'-phenylthioureidoacetyl)-N-methylamino]benzyloxy]-2-methylimidazo[1,2-a]pyridine (190 mg).

NMR (CDCl$_3$, δ): 2.42 (3H, s), 3.21 (3H, s), 3.82 (1H, dd, J=18Hz and 4Hz), 4.21 (1H, dd, J=18Hz and 5Hz), 5.49 (2H, s), 6.71 (1H, d, J=8Hz), 6.88 (1H, t, J=8Hz), 7.16 (1H, br s), 7.21–7.56 (7H), 7.71–7.87 (2H)

Example 47

3-Chloro-8-[2,6-dichloro-3-[N-(N'-phenylthioureidoacetyl)-N-methylamino]benzyloxy]-2-methylimidazo[1,2-a]pyridine was obtained according to a similar manner to that of Example 46.

mp: 135°–137° C.

NMR (CDCl$_3$, δ): 2.43 (3H, s), 3.22 (3H, s), 3.85 (1H, dd, J=16Hz and 4Hz), 4.22 (1H, dd, J=16Hz and 4Hz), 5.51 (2H, s), 6.70 (1H, d, J=8Hz), 6.87 (1H, dd, J=8Hz and 7Hz), 7.16 (1H, t like), 7.21–7.54 (6H), 7.68–7.80 (2H)

Example 48

3-Bromo-8-[3-[N-(tert-butoxycarbonyl-L-prolylglycyl)-N-methylamino]-2,6-dichlorobenzyloxy]-2-methylimidazo[1,2-a]pyridine (67 mg) was dissolved in 4N solution of hydrogen chloride in ethyl acetate (3 ml). The solution was evaporated in vacuo to give 3-bromo-8-[2,6-dichloro-3-[N-(L-prolylglycyl)-N-methylamino]benzyloxy]-2-methylimidazo[1,2-a]pyridine dihydrochloride (64 mg) as colorless glass.

NMR (CDCl$_3$—CD$_3$OD, δ) 2.00–2.20 (4H), 2.56 (3H, s), 3.26 (2.5H, s), 3.31–3.97 (4.5H), 4.38 (1H, t like), 5.70 (2H, s), 7.41–7.71 (4H), 8.23 (1H, d, J=8Hz)

Example 49

3-Bromo-8-[2,6-dichloro-3-[N-(D-prolylglycyl)-N-methylamino]benzyloxy]-2-methylimidazo[1,2-a]pyridine dihydrochloride was obtained according to a similar manner to that of Example 48.

NMR (CDCl$_3$—CD$_3$OD, δ): 2.00–2.20 (4H), 2.54 (3H, s), 3.26 (2.5H, s), 3.31–3.95 (4.5H), 4.38 (1H, t like), 5.72 (2H, s), 7.49–7.71 (4H), 8.29 (1H, d, J=8Hz)

Example 50

A mixture of 3-bromo-8-[2,6-dichloro-3-[N-(L-prolylglycyl)-N-methylamino]benzyloxy]-2-methylimidazo[1,2-a]pyridine dihydrochloride (40 mg), acetic anhydride (0.01 ml), pyridine (0.03 ml) and methylene chloride (2 ml) was stirred for 2 hours at ambient temperature. The mixture was washed with water twice, dried over magnesium sulfate, and concentrated in vacuo to give 8-[3-[N-(acetyl-L-prolylglycyl)-N-methylamino]-2,6-dichlorobenzyloxy]-3-bromo-2-methylimidazo[1,2-a]pyridine (31 mg).

NMR (CDCl$_3$, δ): 1.82–2.37 (7H), 2.44 (3H, s), 3.24 (3H, s), 3.34–3.89 (4H), 4.58 (1H, br s), 5.48 (2H, s), 6.71 (1H, d, J=8Hz), 6.85 (1H, t, J=8Hz), 7.29–7.53 (2H), 7.77 (1H, d, J=8Hz)

Example 51

The following compounds were obtained according to a similar manner to that of Example 50.

(1) 8-[3-[N-(Acetyl-D-prolylglycyl)-N-methylamino]-2,6-dichlorobenzyloxy]-3-bromo-2-methylimidazo[1,2-a]pyridine NMR (CDCl$_3$, δ) 1.82–2.37 (7H), 2.44 (3H, s), 3.24 (3H, s), 3.34–3.89 (4H), 4.58 (1H, br s), 5.48 (2H, s), 6.71 (1H, d, J=8Hz), 6.85 (1H, t, J=8Hz), 7.29–7.53 (2H), 7.77 (1H, d, J=8Hz)

(2) 8-[3-[N-(Acetylglycylglycyl)-N-methylamino]-2,6-dichlorobenzyloxy]-3-bromo-2-methylimidazo[1,2-a]pyridine mp: 220°–222° C.

NMR (CDCl$_3$, δ) 2.04 (3H, s), 2.41 (3H, s), 3.22 (3H, s), 3.53 (1H, dd, J=17Hz and 5Hz), 3.84 (1H, dd, J=17Hz and 5Hz), 3.38–4.00 (2H), 5.51 (2H, s) 6.72 (1H, d, J=7Hz), 6.90 (11H, t, J=7Hz), 7.40 (1H, d, J=9Hz), 7.52 (1H, d, J=9Hz), 7.79 (1H, d, J=7Hz)

Example 52

The following compounds were obtained according to similar manners to those of Examples 9 or 10.

(1) 3-Bromo-8-[2,6-dichloro-3-[N-(N,N-dimethylglycyl)-N-methylamino]benzyloxy]-2-methylimidazo[1,2-a]pyridine NMR (CDCl$_3$, δ): 2.27 (6H, s), 2.45 (3H, s), 2.72 (1H, d, J=15Hz), 2.91 (1H, d, J=15Hz), 3.20 (3H, s), 5.49 (1H, d, J=7Hz), 5.55 (1H, d, J=7Hz), 6.71 (1H, d, J=7Hz), 6.85 (1H, t, J=7Hz), 7.79 (1H, d, J=9Hz), 7.45 (1H, d, J=9Hz), 7.78 (1H, d, J=7Hz)

(2) 3-Bromo-8-[2,6-dichloro-3-[N-(isopropylglycyl)-N-methylamino]benzyloxy]-2-methylimidazo[1,2-a]pyridine NMR (CDCl$_3$, δ): 0.98–1.09 (6H), 2.43 (3H, s), 2.72 (1H), 3.00 (1H, d, J=16Hz), 3.18 (1H, d, J=16Hz), 3.22 (3H, s), 5.51 (2H, s), 6.71 (1H, d, J=7Hz), 6.85 (1H, t, J=7Hz), 7.30 (1H, d, J=9Hz), 7.48 (1H, d, J=9Hz), 7.78 (1H, d, J=7Hz)

(3) 3-Bromo-8-[2,6-dichloro-3-[N-(isopropylglycylglycyl)-N-methylamino]benzyloxy]-2-methylimidazo[1,2-a]pyridine NMR (CDCl$_3$, δ) 1.10 (6H, d, J=6Hz), 2.43 (3H, s), 3.26 (3H, s), 3.29 (2H, s), 3.56 (1H, dd, J=17Hz and 5Hz), 3.82 (1H, dd, J=17Hz and 5Hz), 5.49 (2H, s), 6.71 (1H, d, J=7Hz), 6.86 (1H, t, J=7Hz), 7.32 (1H, d, J=9Hz), 7.48 (1H, d, J=9Hz), 7.76 (1H, d, J=7Hz); 8.08 (1H, br t, (4) 3-Bromo-8-[2,6-dichloro-3-[N-[(N,N-dimethylglycyl)glycyl]-N-methylamino]benzyloxy]-2-methylimidazo[1,2-a]pyridine NMR (CDCl$_3$, δ): 2.32 (6H, s), 2.43 (3H, s), 2.96 (2H, s), 3.25 (3H, s), 3.55 (1H, dd, J=18Hz and 4Hz), 3.85 (1H, dd, J=18Hz and 4Hz), 5.50 (2H, s), 6.71 (1H, d, J=7Hz), 6.86 (1H, t, J=7Hz), 7.32 (1H, d, J=9Hz), 7.49 (1H, d, J=9Hz), 7.78 (1H, d, J=7Hz), 7.89 (1H, br t, J=4Hz)

(5) 3-Bromo-8-[2,6-dichloro-3-[N-(benzylglycylglycyl)-N-methylamino]benzyloxy]-2-methylimidazo[1,2-a]pyridine NMR (CDCl$_3$, δ) 2.43 (3H, s), 3.28 (3H, s), 3.31 (2H, s), 3.58 (1H, dd, J=17Hz and 5Hz), 3.80 (2H, s), 3.84 (1H, dd, J=17Hz and 5Hz), 5.50 (2H, s), 6.71 (1H, d, J=7Hz), 6.86 (1H, t, J=7Hz), 7.19–7.40 (7H), 7.48 (1H, d, J=9Hz), 7.27 (1H, d, J=7Hz), 7.97 (1H, br t, J=5Hz)

Example 53

A mixture of 3-bromo-8-[2,6-dichloro-3-[N-(bromoacetylglycyl)-N-methylamino]benzyloxy]-2-methylimidazo[1,2-a]pyridine (150 mg) and 30% solution of methylamine in methanol (2 ml) was stirred for 1 hour at ambient temperature. The mixture was concentrated in vacuo, and the residue was purified by silica gel column chromatography (methylene chloride:methanol=10:1, V/V) to give 3-bromo-8-[2,6-dichloro-3-[N-(sarcosylglycyl)-N-methylamino]benzyloxy]-2-methylimidazo[1,2-a]pyridine (103 mg).

NMR (CDCl$_3$, δ) 2.45 (3H, s), 2.48 (3H, s), 3.26 (5H, s), 3.59 (1H, dd, J=17Hz and 5Hz), 3.83 (1H, dd, J=17.5Hz), 5.49 (2H, s), 6.71 (1H, d, J=7Hz), 6.86 (1H, t, J=7Hz), 7.32 (1H, d, J=9Hz), 7.49 (1H, d, J=9Hz), 7.78 (1H, d, J=7Hz), 7.89 (1H, br t, J=5Hz)

Example 54

The following compounds were obtained according to a similar manner to that of Example 53.

(1) 3-Bromo-8-[2,6-dichloro-3-[N-(ethylglycylglycyl)-N-methylamino]benzyloxy]-2-methylimidazo[1,2-a]pyridine NMR (CDCl$_3$, δ): 1.12 (3H, t, J=6Hz), 2.43 (3H, s-), 2.69 (2H, q, J=6Hz), 3.26 (3H, s), 3.30 (2H, s), 3.58 (1H, dd, J=17Hz and 5Hz), 3.82 (1H, dd, J=17Hz and 5Hz), 5.49 (2H, s), 6.71 (1H, d, J=7Hz), 6.86 (1H, t, J=7Hz), 7.32 (1H, d, J=9Hz), 7.49 (1H, d, J=9Hz), 7.78 (1H, d, J=7Hz), 7.99 (1H, br t, J=5Hz)

(2) 3-Bromo-8-[2,6-dichloro-3-[N-[(N-phenylglycyl)glycyl]-N-methylamino]benzyloxy]-2-methylimidazo[1,2-a]pyridine NMR (CDCl$_3$, δ) 2.42 (3H, s), 3.21 (3H, s), 3.60 (1H, dd, J=18Hz and 5Hz), 3.80 (2H, s), 3.83 (1H, dd, J=18Hz and 5Hz), 4.39 (1H, br s), 5.49 (2H, s), 6.60 (2H, d, J=6Hz), 6.68–6.90 (3H), 7.12–7.41 (4H), 7.48 (1H, d, J=9Hz), 7.78 (1H, d, J=7Hz)

(3) 3-Bromo-8-[2,6-dichloro-3-[N-(morpholinoacetylglycyl)-N-methylamino]benzyloxy]-2-methylimidazo-[1,2-a]pyridine NMR (CDCl$_3$, δ) 2.45 (3H, s), 2.50–2.62 (4H), 3.02 (2H, s), 3.26 (3H, s), 3.57 (1H, dd, J=18Hz and 5Hz), 3.70–3.92 (5H), 5.50 (2H, s), 6.71 (1H, d, J=7Hz), 6.87 (1H, t, J=7Hz), 7.32 (1H, d, J=9Hz), 7.49 (1H, d, J=9Hz), 7.78 (1H, d, J=7Hz), 7.92 (1H, br t, J=5Hz)

Example 55

To a mixture of 3-bromo-8-(2,6-dichloro-4-benzoylbenzyloxy)-2-methylimidazo[1,2-a]pyridine (80 mg), sodium borohydride (18.5 mg) and ethanol (2 ml) was stirred at ambient temperature for 1 hour. The reaction mixture was partitioned between dichloromethane and water and the aqueous layer was extracted with dichloromethane twice. The combined organic layers were washed with brine, dried over magnesium sulfate and evaporated in vacuo. The residue was crystallized from diethyl ether to give 3-bromo-8-[2,6-dichloro-4-(α-hydroxybenzyl)benzyloxy]-2-methylimidazo[1,2-a]pyridine (73 mg) as crystals.

mp: 178°–179° C.

NMR (CDCl$_3$, δ): 2.40 (3H, s), 2.73 (1H, br s), 5.45 (2H, dd, J=10Hz and 9Hz), 6.28 (1H, s), 6.69 (1H, d, J=7Hz), 6.80 (1H, t, J=7Hz), 7.23–7.48 (6H), 7.60–7.80 (2H)

Example 56

3-Bromo-8-[2,6-dichloro-3-[N-(mesylglycyl)-N-methylamino]benzyloxy]-2-methylimidazo[1,2-a]pyridine was obtained according to a similar manner to that of Example 19.

NMR (CDCl$_3$, δ) 2.45 (3H, s), 2.97 (2.7Hz, s), 3.02 (0.3H, s), 3.27 (2.7H, s), 3.30 (0.3H, s), 3.50 (1H, dd, J=16Hz and 5Hz), 3.67 (1H, dd, J=16Hz and 5Hz), 3.18 (1H, t like), 5.51 (2H, s), 6.71 (1H, d, J=8Hz), 6.87 (1H, t, J=8Hz), 7.32 (1H, d, J=8Hz), 7.51 (1H, d, J=8Hz), 7.78 (1H, d, J=8Hz)

Example 57

To a mixture of 3-bromo-8-(2,6-dibromo-4-methoxycarbonylbenzyloxy)-2-methylimidazo[1,2-a]pyridine (550 mg), methanol (10 ml) and tetrahydrofuran (5 ml) was added 1N aqueous solution of sodium hydroxide (1.135 ml), and the mixture was stirred for 1 hour at 60° C. The reaction mixture was adjusted pH 4 with 1N hydrochloric acid, and water was added thereto. The precipitate was collected by filtration to give 3-bromo-8-(2,6-dibromo-4-carboxybenzyloxy)-2-methylimidazo[1,2-a]pyridine (518 mg).

mp: 241°–242° C.

NMR (DMSO-d$_6$, δ): 2.41 (3H, s), 5.62 (2H, s), 7.54 (1H, t, J=7Hz), 7.78 (1H, d, J=7Hz), 8.19 (2H, s), 8.32 (1H, d, J=7Hz)

Example 58

The following compounds were obtained according to a similar manner to that of Example 57.

(1) 3-Chloro-8-(2,6-dichlorobenzyloxyimidazo[1,2-a]pyridine-2-carboxylic acid mp: 212°–213° C.

NMR (CDCl$_3$+CD$_3$OD, δ): 5.50 (2H, s), 6.82 (1H, d, J=7Hz), 7.02 (1H, t, J=7Hz), 7.22–7.48 (3H), 7.86 (1H, d, J=7Hz)

(2) 3-Bromo-8-[2,6-dichloro-3-[N-(3-carboxypropionylglycyl)-N-methylamino]benzyloxy]-2-methylimidazo[1,2-a]pyridine NMR (CDCl$_3$—CD$_3$OD, δ): 2.30 (3H, s), 2.44 (4H, s), 3.12 (3H, s), 3.68–3.86 (2H), 5.40 (2H, s), 6.69 (1H, d, J=8Hz), 6.81 (1H, dd, J=8Hz and 6Hz), 7.46 (2H, s), 7.69 (1H, d, J=6Hz)

Example 59

To a mixture of 3-bromo-8-(2,6-dibromo-4-carboxybenzyloxy)-2-methylimidazo[1,2-a]pyridine (100 mg), methylene chloride (2 ml) and N,N-dimethylformamide (1 drop) was added oxalyl chloride (49 mg), and the mixture was stirred for 30 minutes and evaporated. The residue was dissolved in methylene chloride, triethylamine (0.5 ml) and 1-methylpiperazine (23 mg) were added thereto, and the mixture was stirred for 1 hour. Water was added thereto, the mixture was extracted with methylene chloride 3 times. The combined organic layer was washed with brine, dried over magnesium sulfate, and concentrated in vacuo. The residue was purified by silica gel column chromatography (5% solution of methanol in methylene chloride) to give 3-bromo-8-[2,6-dibromo-4-(N-methylpiperazinylcarbonyl)benzyloxy]-2-methylimidazo[1,2-a]pyridine (102 mg).

mp: 188°–190° C.

NMR (CDCl₃, δ): 2.45 (3H, s), 2.48 (3H, s), 2.49–2.79 (4H), 3.56–4.02 (4H), 5.50 (2H, s), 6.70 (1H, d, J=7Hz), 6.85 (1H, t, J=7Hz), 7.61 (2H, s), 7.77 (1H, d, J=7Hz)

Example 60

To a suspension of 3-bromo-8-(2,6-dichloro-3-nitrobenzyloxy)-2-methylimidazo[1,2-a]pyridine (200 mg) in ethanol (2 ml) was added hydrogen chloride in ethanol (3.5 Mol solution, 1 ml). The solution was concentrated to half volume under reduced pressure. The separated precipitates were collected by filtration and washed with ethanol to give 3-bromo-8-(2,6-dichloro-3-nitrobenzyloxy)-2-methylimidazo[1,2-a]pyridine hydrochloride (175 mg) as an off-white solid.

mp: 195°–197° C.

NMR (DMSO-d₆, δ): 2.39 (3H, s), 5.60 (2H, s), 7.39 (1H, t, J=7.5Hz), 7.56 (1H, d, J=7.5Hz), 7.92 (1H, d, J=7.5Hz), 8.25 (2H, d, J=7.5Hz)

Example 61

The following compounds were obtained according to a similar manner to that of Example 60.
(1) 3-Bromo-8-[2,6-dichloro-3-(N-acetyl-N-methylamino) benzyloxy]-2-methylimidazo[1,2-a]pyridine hydrochloride
 mp: 148°–150° C.
 NMR (CDCl₃+CD₃OD, δ) 1.88 (3H, s), 2.68 (3H, s), 3.22 (3H, s), 5.62 (1H, d, J=9Hz), 5.70 (1H, d, J=9Hz), 7.32–7.61 (4H), 8.09 (1H, d, J=6Hz)
(2) 3-Chloro-8-[2,6-dichloro-3-(N-acetyl-N-methylamino) benzyloxy]-2-methylimidazo [1,2-a]pyridine hydrochloride
 mp: 145°–149° C.
 NMR (CDCl₃+CD30D, δ): 1.89 (3H, s), 2.70 (3H, s), 3.22 (3H, s), 5.61 (1H, d, J=10Hz), 5.70 (1H, d, J=10Hz), 7.25–7.59 (4H), 8.01 (1H, d, J=7Hz)
(3) 3-Bromo-8-[2,6-dichloro-3-(N-propionyl-N-methylamino)benzyloxy]-2-methylimidazo[1,2-a]pyridine hydrochloride
 mp: 146°–148° C.
 NMR (CDCl₃, δ) 1.08 (3H, t, J=7Hz), 2.09 (2H, q, J=7Hz), 2.74 (3H, s), 3.26 (3H, s), 5.66 (2H, br t, J=12Hz), 7.16–7.58 (4H), 8.00 (1H)
(4) 3-Bromo-8-[2,4,6-trichloro-3-(N-acetyl-N-methylamino)benzyloxy]-2-methylimidazo[1,2-a]pyridine hydrochloride
 mp: 116°–120° C.
 NMR (CDCl₃, δ): 1.90 (2.6H, s), 2.29 (0.4H, s), 2.70 (2.6H, s), 2.72 (0.4H, s), 3.22 (2.6H, s), 3.43 (0.4H, s), 5.50–5.70 (2H), 7.18 (1H, d, J=8Hz), 7.36 (1H, t, J=8Hz), 7.52 (0.13H, s), 7.62 (0.87H, s), 7.98 (1H, d, J=8Hz)
(5) 8-[3-[N-(Acetylglycyl)-N-methylamino]-2,6-dichlorobenzyloxy]-3-bromo-2-methylimidazo[1,2-a]pyridine hydrochloride
 mp: 175°–176° C.
 NMR (DMSO-d₆, δ): 1.83, 2.40, 3.12 (each 3H, s), 3.37, 3.67 (each 1H, dd, J=16Hz and 5Hz), 5.59 (2H, s), 7.31–7.83 (4H), 8.10 (1H, t, J=5Hz), 8.25 (1H, d, J=7Hz)
(6) 3-Bromo-8-[2,6-dichloro-3-[N-methyl-N-(propionylglycyl)amino]benzyloxy]-2-methylimidazo[1,2-a]pyridine hydrochloride
 NMR (CDCl₃, δ): 1.13 (3H, t, J=6Hz), 2.23 (2H, q, J=6Hz), 2.71 (3H, s), 3.33 (2.8H, s), 3.47 (0.2H, s), 3.66 (1H, dd, J=16Hz and 4Hz), 3.80 (1H, dd, J=16Hz and 4Hz), 5.61 (1H, d, J=10Hz), 5.68 (1H, d, J=10Hz), 6.74 (1H, t like), 7.20–7.44 (3H), 7.50 (1H, d, J=8Hz), 8.00 (1H, d, J=7Hz)
(7) 3-Bromo-8-[3-[N-(butyrylglycyl)-N-methylamino]-2,6-dichlorobenzyloxy]-2-methylimidazo[1,2-a]pyridine hydrochloride
 NMR (DMSO-d₆, δ) 0.84 (3H, t, J=7Hz), 1.49 (2H, m), 2.10 (2H, t, J=7Hz), 2.40 (3H, s), 3.13 (2.4H, s), 3.30 (0.6H, s), 3.36 (1H, dd, J=16Hz and 5Hz), 3.68 (1H, dd, J=16Hz and 5Hz), 5.60 (2H, s), 7.37–7.86 (4H), 8.03 (1H, t like), 8.28 (1H, d, J=6Hz)
(8) 3-Bromo-8-[3-[N-(isobutyrylglycyl)-N-methylamino]-2,6-dichlorobenzyloxy]-2-methylimidazo[1,2-a]pyridine hydrochloride
 NMR (DMSO-d₆, δ): 0.97 (6H, d, J=6Hz), 2.40 (3H, s), 2.45 (1H, m), 3.12 (2.3H, s), 3.28 (0.7H, s), 3.34 (1H, dd, J=16Hz and 5Hz), 3.67 (1H, dd, J=16Hz and 5Hz), 5.58 (2H, s), 7.36–7.84 (4H), 7.99 (1H, t like), 8.27 (1H, d, J=7Hz)
(9) 3-Bromo-8-[2,6-dichloro-3-[N-(cyclopropylcarbonylglycyl)-N-methylamino]benzyloxy]-2-methylimidazo[1,2-a]pyridine hydrochloride
 NMR (DMSO-d₆, δ): 0.53–0.72 (4H), 1.68 (1H, m), 2.39 (3H, s), 3.12 (2.5H, s), 3.28 (0.5H, s), 3.40 (1H, dd, J=16Hz and 5Hz), 3.70 (1H, dd, J=16Hz and 5Hz), 5.59 (2H, s), 7.33–7.89 (4H), 8.26 (1H, d, J=7Hz), 8.34 (1H, t, J=6Hz)
(10) 3-Bromo-8-[2,6-dichloro-3-[N-(trifluoroacetylglycyl)-N-methylamino]benzyloxy]-2-methylimidazo[1,2-a] pyridine hydrochloride
 mp: 194°–195° C.
 NMR (DMSO-d₆, δ) 2.39 (3H, s), 3.14 (3H, s), 3.51 (1H, dd, J=17Hz and 5Hz), 3.78 (1H, dd, J=17Hz and 5Hz), 5.58 (2H, s), 7.39 (1H, t, J=6Hz), 7.59 (1H), 7.81 (2H, s), 8.25 (1H, d, J=6Hz), 9.71 (1H, t, J=6Hz)
(11) 8-[3-[N-(Benzoylglycyl)-N-methylamino]-2,6-dichlorobenzyloxy]-3-bromo-2-methylimidazo[1,2-a] pyridine hydrochloride
 mp: 138° C. (dec.)
 NMR (DMSO-d₆, δ): 2.39 (3H, s), 3.15 (3H, s), 3.58 (1H, dd, J=16Hz and 6Hz), 3.89 (1H, dd, J=16Hz and 6Hz), 5.59 (2H, s), 7.34–7.64 (5H), 7.77–7.93 (4H), 8.28 (1H, d, J=6Hz), 8.72 (1H, t, J=6Hz)
(12) 3-Bromo-8-[2,6-dichloro-3-[N-(cyclohexylcarbonylglycyl)-N-methylamino]benzyloxy]-2-methylimidazo[1,2-a]pyridine hydrochloride
 NMR (DMSO-d₆, δ): 1.02–1.79 (1OH), 2.18 (1H, m), 2.39 (3H, s), 3.11 (2.6H, s), 3.27 (0.4H, s), 3.31 (1H, dd, J=16Hz and 5Hz), 3.65 (1H, dd, J=16Hz and 5Hz), 5.58 (2H, s), 7.31–7.82 (4H), 7.92 (1H, t, J=5Hz), 8.26 (1H, d, J=7Hz)
(13) 3-Bromo-8-[2,6-dichloro-3-[N-(phenylacetylglycyl)-N-methylamino]benzyloxy]-2-methylimidazo[1,2-a] pyridine hydrochloride
 NMR (DMSO-d₆, δ) 2.38 (3H, s), 3.13 (2.5H, s), 3.27 (0.5H, s), 3.30–3.76 (4H), 5.56 (2H, s), 7.14–7.85 (9H), 8.24 (1H, d, J=7Hz), 8.32 (1H, t, J=5Hz)
(14) 8-[3-[N-(Acetoxyacetylglycyl)-N-methylamino]-2,6-dichlorobenzyloxy]-3-bromo-2-methylimidazo[1,2-a] pyridine hydrochloride
 NMR (CDCl₃—CD₃OD, δ) 2.21 (3H, s), 2.61 (3H, s), 3.25 (3H, s), 3.59–3.88 (2H), 4.09 (1H, br s), 4.59 (1H, br s), 5.69 (2H, br s), 7.35–7.68 (4H), 8.11 (1H, br s)
(15) 3-Bromo-8-[2,6-dichloro-3-[N-(glycoloylglycyl)-N-methylamino]benzyloxy]-2-methylimidazo[1,2-a]pyridine hydrochloride
 NMR (CDCl₃—CD₃OD, δ): 2.59 (3H, s), 3.28 (3H, s), 3.78 (2H, s), 4.09 (2H, s), 5.54–5.81 (2H), 7.47–7.68 (4H), 8.14 (1H, br s)

(16) 3-Bromo-8-[2,6-dichloro-3-[N-(methoxyacetylglycyl)acetyl-N-methylamino]benzyloxy]-2-methylimidazo[1,2-a]pyridine hydrochloride mp: 175°–177° C.

NMR (DMSO-d₆, δ): 2.40 (3H, s), 3.12 (3H, s), 3.32 (3H, s), 3.42 (1H, dd, J=17Hz and 5Hz), 3.70 (1H, dd, J=17Hz and 5Hz), 3.82 (2H, s), 5.59 (2H, s), 7.34–7.79 (5H), 8.26 (1H, d, J=7Hz)

(17) 3-Bromo-8-[2,6-dichloro-3-[N-methyl-N-(phthalimidoacetylglycyl)amino]benzyloxy]-2-methylimidazo-[1,2-a]pyridine hydrochloride NMR (CDCl₃—CD₃OD, δ) 2.57 (3H, s), 3.26 (3H, s), 3.65 (1H, d, J=15Hz), 3.78 (1H, d, J=15Hz), 4.32 (1H, d, J=15Hz), 4.46 (1H, d, J=15Hz), 5.66 (2H, s), 7.35–7.64 (4H), 7.70–7.92 (4H), 8.08 (1H, d, J=5Hz)

(18) 8-[3-[N-(Acetylglycylglycyl)-N-methylamino]-2,6-dichlorobenzyloxy]-3-bromo-2-methylimidazo[1,2-a]pyridine hydrochloride NMR (CDCl₃+CD₃OD, δ) 2.01 (3H, s), 2.52 (3H, s), 3.22 (3H, s), 3.56–3.70 (2H), 3.84 (2H, s), 5.70 (2H, br s), 7.51–7.72 (5H), 8.29 (1H, d, J=6Hz)

(19) 8-[3-[N-(Acetylglycyl)-N-ethylamino]-2,6-dichlorobenzyloxy]-3-bromo-2-methylimidazo[1,2-a]pyridine hydrochloride NMR (CDCl₃, δ) 1.20 (3H, t, J=7Hz), 2.00 (3H, s), 2.71 (3H, s), 3.43–3.88 (3H), 4.14 (1H), 5.68 (2H, s), 6.88 (1H, br s), 7.18–7.58 (3H), 8.00 (1H, br s)

(20) 8-[3-[N-(Acetyl-DL-alanyl)-N-methylamino]-2,6-dichlorobenzyloxy]-3-bromo-2-methylimidazo[1,2-a]pyridine hydrochloride NMR (CDCl₃, δ) 1.11 (3H, d, J=6Hz), 1.94 (3H, s), 2.68 (3H, s), 3.30 (3H, s), 4.36 (1H, m), 5.53–5.76 (2H), 6.60–6.80 (1H), 7.13–7.60 (4H), 7.93–8.06 (1H)

(21) 8-[3-[N-(Acetyl-β-alanyl)-N-methylamino]-2,6-dichlorobenzyloxy]-3-bromo-2-methylimidazo[1,2-a]pyridine hydrochloride mp: 188°–190° C.

NMR (CDCl₃+CD3OD, δ) 2.01 (3H, s), 2.12–2.72 (2H), 3.63 (3H, s), 3.20 (3H, s), 3.30–3.68 (2H), 5.58 (1H, d, J=10Hz), 5.73 (1H, d, J=10Hz), 7.32–7.61 (4H), 8.11 (1H, d, J=5Hz)

(22) 3-Bromo-8-[2,6-dichloro-3-[N-(N,N-dimethylglycyl)-N-methylamino]benzyloxy]-2-methylimidazo[1,2-a]pyridine dihydrochloride mp: 162°–164° C.

NMR (CDCl₃+CD₃OD, δ): 2.66 (3H, s), 3.00–3.19 (6H), 3.28 (3H, s), 4.01 (1H, d, J=17Hz), 4.36 (1H, d, J=17Hz), 5.49 (1H, d, J=9Hz), 5.75 (1H, d, J=9Hz), 7.32–7.56 (2H), 7.61 (1H, d, J=9Hz), 7.15 (1H, d, J=9Hz), 8.09 (1H, d, J=5Hz)

(23) 3-Bromo-8-[2,6-dichloro-3-[N-(isopropylglycyl)-N-methylamino]benzyloxy]-2-methylimidazo[1,2-a]pyridine dihydrochloride NMR (CDCl₃+CD₃OD, δ) 1.41 (6H, br s), 2.67 (3H, br s), 3.29 (3H, br s), 3.60–3.98 (3H), 5.51 (1H, br s), 5.76 (1H, br s), 7.32–8.14 (5H)

(24) 3-Bromo-8-[2,6-dichloro-3-[N-(methoxycarbonylglycyl)-N-methylamino]benzyloxy]-2-methylimidazo[1,2-a]pyridine hydrochloride mp: 176°–177° C.

NMR (CDCl₃+CD₃OD, δ): 2.68 (3H, s), 3.29 (3H, s), 3.50–3.79 (5H), 5.68 (2H, s) 7.31–7.60 (4H), 8.02 (1H, d, J=6Hz)

(25) 3-Bromo-8-[2,6-dichloro-3-[N-(mesylglycyl)-N-methylamino]benzyloxy]-2-methylimidazo[1,2-a]pyridine hydrochloride mp: 174°–176° C.

NMR (CDCl₃—CD₃OD, δ): 2.63 (3H, s), 3.03 (3H, s), 3.27 (3H, s), 3.60 (1H, d, J=16Hz), 3.70 (1H, d, J=16Hz), 5.62 (1H, d, J=12Hz), 5.70 (1H, d, J=12Hz), 7.33–7.51 (3H), 7.58 (1H, d, J=8Hz), 8.06 (1H, d, J=6Hz)

(26) 3-Bromo-8-[2,6-dichloro-3-[N-methyl-N-(ureidoacetyl)amino]benzyloxy]-2-methylimidazo[1,2-a]pyridine hydrochloride NMR (DMSO-d₆, δ) 2.40 (3H, s), 3.12 (3H, s), 3.39 (1H, d, J=17Hz), 3.61 (1H, d, J=17Hz), 5.57 (1H, d, J=8Hz), 5.67 (1H, d, J=8Hz), 7.49 (1H, t, J=7Hz), 7.69 (1H, d, J=7Hz), 7.81 (2H, s), 8.31 (1H, d, J=7Hz)

(27) 3-Bromo-8-[2,6-dichloro-3-[N-methyl-N-(N'-methylureidoacetyl)amino]benzyloxy]-2-methylimidazo[1,2-a]pyridine hydrochloride mp: 153°–155° C.

NMR (CDCl₃, δ) 2.63 (3H, s), 2.74 (3H, s), 3.23 (3H, s), 3.85 (1H, d, J=16Hz), 3.98 (1H, d, J=16Hz), 5.57 (1H, d, J=10Hz), 5.67 (1H, d, J=10Hz), 7.30–7.60 (4H), 8.04 (1H, d, J=7Hz)

(28) 3-Bromo-8-[2,6-dichloro-3-[N-(N'-ethylureidoacetyl)-N-methylamino]benzyloxy]-2-methylimidazo[1,2-a]pyridine hydrochloride NMR (DMSO-d₆, δ): 0.96 (3H, t, J=7Hz), 2.41 (3H, s), 2.98 (2H, q, J=7Hz), 3.11 (3H, s), 3.30 (1H, d, J=17Hz), 3.61 (1H, d, J=17Hz), 5.56 (1H, d, J=9Hz), 5.67 (1H, d, J=9Hz), 7.50 (1H, t, J=7Hz), 7.70 (1H, d, J=7Hz), 7.81 (2H, s), 8.31 (1H, d, J=7Hz) its dihydrochloride mp: 173°–175° C.

(29) 3-Bromo-8-[2,6-dichloro-3-[N-methyl-N-(N'-phenylureidoacetyl)amino]benzyloxy]-2-methylimidazo[1,2-a]pyridine hydrochloride NMR (DMSO-d₆, δ): 2.38 (3H, s), 3.16 (2.5H, s), 3.29 (0.5H, s), 3.42 (1H, d, J=16Hz), 3.70 (1H, d, J=16Hz), 5.58 (2H, s), 6.45 (1H, br s), 6.89 (1H, t, J=7Hz), 7.13–7.90 (8H), 8.26 (1H, d, J=7Hz), 8.97 (1H, s)

(30) 3-Bromo-8-[2,6-dichloro-3-[N-(4-pentenoylglycyl)-N-methylamino]benzyloxy]-2-methylimidazo[1,2-a]pyridine hydrochloride NMR (CDCl₃—CD₃OD, δ) 2.20–2.32 (4H), 2.46 (3H, s), 3.17 (3H, s), 3.56 (1H, s), 3.59 (1H, s), 4.83–5.06 (2H), 5.56–5.84 (3H), 7.42–7.62 (4H), 8.19 (1H, d, J=6Hz)

(31) 3-Bromo-8-[2,6-dichloro-3-[N-(valerylglycyl)-N-methylamino]benzyloxy]-2-methylimidazo[1,2-a]pyridine hydrochloride NMR (CDCl₃, δ) 0.90 (3H, t, J=7Hz), 1.32 (2H, m), 1.60 (2H, m), 2.22 (2H, t, J=7Hz), 2.72 (3H, s), 3.33 (3H, s), 3.58–3.87 (2H), 5.60 (1H, d, J=11Hz), 5.68 (1H, d, J=11Hz), 6.76 (1H, br s), 7.21–7.45 (3H), 7.50 (1H, d, J=9Hz), 8.00 (1H, d, J=6Hz)

(32) 3-Bromo-8-[2,6-dichloro-3-[N-(isovalerylglycyl)-N-methylamino]benzyloxy]-2-methylimidazo[1,2-a]pyridine hydrochloride NMR (CDCl₃, δ) 0.93 (6H, d, J=6Hz), 2.00–2.20 (3H), 2.73 (3H, s), 3.33 (3H, s), 3.60–3.88 (2H), 5.65 (2H, s), 6.77 (1H, br s), 7.30–7.44 (3H), 7.50 (1H, d, J=9Hz), 8.00 (1H, d, J=6Hz)

(33) 3-Bromo-8-[2,6-dichloro-3-[N-(2-pyridylacetylglycyl)-N-methylamino]benzyloxy]-2-methylimidazo[1,2-a]pyridine dihydrochloride NMR (CDCl₃—CD₃OD, δ): 2.53 (3H, s), 3.25 (3H, s), 3.35 (2H, s), 3.62 (1H, d, J=17Hz), 3.82 (1H, d, J=17Hz), 5.72 (2H, s), 7.48–7.72 (4H), 7.87–8.03 (2H), 8.29 (1H, d, J=6Hz), 8.48 (1H, t, J=7Hz), 8.75 (1H, d, J=6Hz)

(34) 3-Bromo-8-[2,6-dichloro-3-[N-(3-pyridylacetylglycyl)-N-methylamino]benzyloxy]-2-methylimidazo[1,2-a]pyridine dihydrochloride NMR (CDCl₃—CD₃OD, δ): 2.56 (3H, s), 3.25 (3H, s), 3.60 (1H, d, J=17Hz), 3.80 (1H, d, J=17Hz), 3.93 (2H, s), 5.72 (2H, s), 7.52–7.73 (4H), 8.07 (1H, dd, J=7Hz and 5Hz), 8.29 (1H, d, J=7Hz), 8.60 (1H, d, J=7Hz), 8.75 (1H, d, J=5Hz), 8.89 (1H, br s)

(35) 3-Bromo-8-[2,6-dichloro-3-[N-[(3-ethoxycarbonylpropionyl)glycyl]-N-methylamino]benzyloxy]-2-methylimidazo[1,2-a]pyridine hydrochloride NMR (CDCl₃, δ): 1.23 (3H, t, J=7Hz), 2.44–2.66 (4H), 2.70 (3H, s), 3.30 (3H, s), 3.63 (1H, dd, J=15Hz and 4Hz), 3.79 (1H, dd, J=15Hz and 4Hz), 4.10 (2H, q, J=7Hz), 5.58 (1H, d, J=11Hz), 5.67 (1H, d, J=11Hz), 6.89 (1H, br s), 7.09–7.43 (3H), 7.51 (1H, d, J=9Hz), 7.96 (1H, d, J=5Hz)

(36) 3-Bromo-8-[2,6-dichloro-3-[N-(sarcosylglycyl)-N-methylamino]benzyloxy]-2-methylimidazo[1,2-a]pyridine dihydrochloride NMR (CDCl₃—CD₃OD, δ) 2.28 (3H, s), 2.46 (3H, s), 2.98 (3H, s), 3.34 (1H, d, J=16Hz), 3.52 (2H, s), 3.59 (1H, d, J=16Hz), 5.43 (2H, s), 7.22–7.42 (4H), 8.00 (1H, d, J=6Hz)

(37) 3-Bromo-8-[2,6-dichloro-3-[N-[(ethylglycyl)glycyl]-N-methylamino]benzyloxy]-2-methylimidazo[1,2-a]pyridine dihydrochloride NMR (CDCl₃—CD₃OD, δ) 1.38 (3H, t, J=6Hz), 2.56 (3H, s), 3.10 (2H, q, J=6Hz), 3.27 (3H, s), 3.61 (1H, d, J=16Hz), 3.82 (2H, s), 3.88 (1H, d, J=16Hz), 5.72 (2H, s), 7.50–7.74 (4H), 8.29 (1H, d, J=6Hz)

(38) 3-Bromo-8-[2,6-dichloro-3-[N-[(N-phenylglycyl)glycyl]-N-methylamino]benzyloxy]-2-methylimidazo[1,2-a]pyridine dihydrochloride NMR (CDCl₃—CD₃OD, δ): 2.59 (3H, s), 3.26 (3H, s), 3.61–3.78 (2H), 4.00 (2H, s), 5.71 (2H, br s), 7.02–7.20 (3H), 7.30–7.41 (2H), 7.53–7.70 (4H), 8.26 (1H, d, J=6Hz)

(39) 3-Bromo-8-[2,6-dichloro-3-[N-(morpholinoacetylglycyl)-N-methylamino]benzyloxy]-2-methylimidazo[1,2-a]pyridine dihydrochloride NMR (CDCl₃—CD₃OD, δ): 2.53 (3H, s), 3.21 (3H, s), 3.30–3.48 (4H), 3.59 (1H, d, J=16Hz), 3.81 (1H, d, J=16Hz), 3.85–4.07 (6H), 5.69 (2H, s), 7.50–7.69 (4H), 8.24 (1H, d, J=6Hz)

(40) 3-Bromo-8-[2,6-dichloro-3-[N-(isopropylglycylglycyl)-N-methylamino]benzyloxy]-2-methylimidazo[1,2-a]pyridine dihydrochloride NMR (CDCl₃—CD₃OD, δ): 1.38 (6H, d, J=6Hz), 2.56 (3H, s), 3.28 (3H, s), 3.81–3.48 (3H), 3.82 (2H, s), 5.72 (2H, s), 7.49–7.73 (4H), 8.30 (1H, d, J=6Hz)

(41) 3-Bromo-8-[2,6-dichloro-3-[N-[(N,N-dimethylglycyl)glycyl]-N-methylamino]benzyloxy]-2-methylimidazo[1,2-a]pyridine dihydrochloride NMR (CDCl₃—CD3OD, δ): 2.29 (3H, s), 2.68 (6H, s), 2.97 (3H, s), 3.35 (1H, d, J=17Hz), 3.58 (1H, d, J=17Hz), 3.71 (2H, s), 5.42 (2H, s), 7.25–7.44 (4H), 7.99 (1H, d, J=6Hz)

(42) 3-Bromo-8-[2,6-dichloro-3-[N-(benzylglycylglycyl)-N-methylamino]benzyloxy]-2-methylimidazo[1,2-a]pyridine dihydrochloride NMR (CDCl₃—CD₃OD, δ) 2.58 (3H, s), 3.25 (3H, s), 3.62 (1H, d, J=17Hz), 3.70–3.92 (3H), 4.22 (2H, s), 5.72 (2H, s), 7.40–7.75 (9H), 8.30 (1H, d, J=6Hz)

(43) 3-Bromo-8-[2,6-dichloro-3-[N-(N'-cyclohexylureidoacetyl)-N-methylamino]benzyloxy]-2-methylimidazo[1,2-a]pyridine hydrochloride NMR (CDCl₃—CD3OD, δ): 1.03–1.92 (10H), 2.58 (3H, s), 3.27 (3H, s), 3.44 (1H, m), 3.60 (1H, d, J=17Hz), 3.71 (1H, d, J=17Hz), 5.68 (1H, d, J=10Hz), 5.79 (1H, d, J=10Hz), 7.53–7.72 (4H), 8.79 (1H, d, J=6Hz)

(44) 3-Bromo-8-[2,6-dichloro-3-[N-[N'-(α-naphthyl)ureidoacetyl]-N-methylamino]benzyloxy]-2-methylimidazo[1,2-a]pyridine hydrochloride NMR (CDCl₃—CD₃OD, δ): 1.99 (3H, s), 3.00 (3H, s), 3.45 (1H, d, J=17Hz), 3.62 (1H, d, J=17Hz), 5.40 (2H, s), 7.02–7.50 (10H), 7.69 (1H, d, J=9Hz), 7.91 (1H, d, J=5Hz)

(45) 3-Bromo-8-[2,6-dichloro-3-[N-(N'-benzylureidoacetyl)-N-methylamino]benzyloxy]-2-methylimidazo[1,2-a]pyridine hydrochloride NMR (CDCl₃—CD₃OD, δ): 2.48 (3H, s), 3.28 (3H, s), 3.70 (2H, s), 4.30 (2H, s), 5.68 (1H, d, J=10Hz), 6.79 (1H, d, J=10Hz), 7.16–7.35 (5H), 7.54–7.72 (4H), 8.29 (1H, d, J=6Hz)

(46) 3-Bromo-8-[2,6-dichloro-3-[N-[N'-(m-tolyl)ureidoacetyl]-N-methylamino]benzyloxy]-2-methylimidazo[1,2-a]pyridine hydrochloride NMR (CDCl₃—CD₃OD, δ): 2.30 (3H, s), 2.52 (3H, s), 3.29 (3H, s), 3.72 (2H, s), 5.67 (1H, d, J=10Hz), 5.79 (1H, d, J=10Hz), 6.82 (1H, m), 7.09–7.19 (3H), 7.51–7.71 (4H), 8.26 (1H, d, J=5Hz)

(47) 3-Bromo-8-[2,6-dichloro-3-[N-[N'-(p-tolyl)ureidoacetyl]-N-methylamino]benzyloxy]-2-methylimidazo[1,2-a]pyridine hydrochloride NMR (CDCl₃—CD₃OD, δ): 2.18 (3H, s), 2.42 (3H, s), 3.19 (3H, s), 3.62 (2H, s), 5.59 (1H, br d, J=10Hz), 5.69 (1H, br d, J=10Hz), 6.93 (2H, d, J=9Hz), 7.10 (2H, d, J=9Hz), 7.43–7.62 (4H), 8.18 (1H, d, J=6Hz)

(48) 3-Bromo-8-[2,6-dichloro-3-[N-[N'-(4-methoxyphenyl)ureidoacetyl]-N-methylamino]benzyloxy]-2-methylimidazo[1,2-a]pyridine hydrochloride NMR (CDCl₃—CD₃OD, δ): 2.52 (3H, s), 3.29 (3H, s), 372 (2H, s), 3.79 (3H, s), 5.69 (1H, d, J=10Hz), 5.79 (1H, d, J=10Hz), 6.80 (2H, d, J=10Hz), 7.22 (2H, d, J=10Hz), 7.52–7.73 (4H), 8.29 (1H, d, J=6Hz)

(49) 3-Bromo-8-[2,6-dichloro-3-[N-[N'-(4-trifluoromethylphenyl)ureidoacetyl]-N-methylamino]benzyloxy]-2-methylimidazo[1,2-a]pyridine hydrochloride NMR (CDCl₃—CD₃OD, δ): 2.54 (3H, s), 3.29 (3H, s), 3.66 (1H, d, J=17Hz), 3.76 (1H, d, J=17Hz), 5.68 (1H, d, J=10Hz), 5.76 (1H, d, J=10Hz), 7.49–7.71 (8H), 8.28 (1H, d, J=6Hz)

(50) 3-Bromo-8-[2,6-dichloro-3-[N-[N'-(4-fluorophenyl)ureidoacetyl]-N-methylamino]benzyloxy]-2-methylimidazo[1,2-a]pyridine hydrochloride NMR (CDCl₃—CD₃OD, δ): 2.52 (3H, s), 3.28 (3H, s), 3.68 (1H, d, J=16Hz), 3.78 (1H, d, J=16Hz), 5.70 (1H, d, J=10Hz), 5.79 (1H, d, J=10Hz), 6.89–7.02 (2H), 7.22–7.36 (2H), 7.55–7.75 (4H), 8.80 (1H, d, J=5Hz)

(51) 3-Bromo-8-[2, 6-dichloro-3-[N-(N'-n-propylureidoacetyl)-N-methylamino]benzyloxy]-2-methylimidazo[1,2-a]pyridine hydrochloride
mp: 168°–171° C.

NMR (CDCl₃—CD3OD, δ) 0.92 (3H, t, J=7Hz), 1.40–1.60 (2H), 2.55 (3H, s), 3.08 (2H, t, J=6Hz), 3.22 (3H, s), 3.58 (1H, d, J=17Hz), 3.71 (1H, d, J=17Hz), 5.69 (1H, d, J=10Hz), 5.79 (1H, d, J=10Hz), 7.53–7.77 (4H), 8.31 (1H, d, J=6Hz)

(52) 3-Bromo-8-[2,6-dichloro-3-[N-(N'-isopropylureidoacetyl)-N-methylamino]benzyloxy]-2-methylimidazo[1,2-a]pyridine hydrochloride NMR (CDCl₃,CD₃OD, δ): 1.12 (6H, d, J=6Hz), 2.56 (3H, s), 3.25 (3H, s), 3.57–3.32 (3H), 5.65 (1H, d, J=10Hz), 5.78 (1H, d, J=10Hz), 7.51–7.71 (4H), 8.28 (1H, d, J=6Hz)

(53) 3-Bromo-8-[2,6-dichloro-3-[N-(N'-allylureidoacetyl)-N-methylamino]benzyloxy]-2-methylimidazo[1,2-a]pyridine hydrochloride NMR (CDCl₃—CD₃OD, δ): 2.51 (3H, s), 3.20 (3H, s), 3.57–3.79 (4H), 5.00–5.21 (2H), 5.57–2.90 (3H), 7.50–7.68 (4H), 8.22 (1H, d, J=6Hz)

(54) 3-Bromo-8-[2,6-dichloro-3-[N-[N'-(3-pyridyl)ureidoacetyl]-N-methylamino]benzyloxy]-2-methylimidazo[1,2-a]pyridine dihydrochloride NMR (CDCl$_3$—CD$_3$OD, δ): 2.48 (3H, s), 3.19 (3H, s), 3.52 (1H, d, J=17Hz), 3.73 (1H, d, J=17Hz), 5.62 (2H, s), 7.44–7.62 (4H), 7.81 (1H, m), 8.15–8.29 (3H), 9.12 (1H, s)
(55) 3-Bromo-8-[2,6-dichloro-3-[N-[N'-(4-pyridyl) ureidoacetyl]-N-methylamino]benzyloxy]-2-methylimidazo [1,2-a]pyridine dihydrochloride NMR (CDCl$_3$—CD$_3$OD, δ): 2.55 (3H, s), 3.28 (3H, s), 3.62 (1H, d, J=17Hz), 3.84 (1H, d, J=17Hz), 5.72 (2H, s), 7.50–7.72 (4H), 7.98 (2H, d, J=6Hz), 8.26 (1H, d, J=6Hz), 8.39 (2H, d, J=6Hz)
(56) 3-Bromo-8-[2,6-dichloro-3-[N-(N'-phenylthioureidoacetyl)-N-methylamino]benzyloxy]-2-methylimidazo[1,2-a]pyridine hydrochloride NMR (CDCl$_3$—CD$_3$OD, δ): 2.58 (3H, s), 3.26 (3H, s), 3.92 (1H, d, J=17Hz), 4.18 (1H, d, J=17Hz), 5.74 (2H, s), 7.20–7.72 (9H), 8.27 (1H, d, J=6Hz)
(57) 3-Chloro-8-[2,6-dichloro-3-[N-(N'-phenylureidoacetyl)-N-methylamino]benzyloxy]-2-methylimidazo[1,2-a]pyridine hydrochloride
mp: 157°–162° C.

NMR (DMSO-d$_6$, δ) 2.40 (3H, s), 3.16 (3H, s), 3.42 (1H, d, J=16Hz), 3.70 (1H, d, J=16Hz), 5.60 (2H, s), 6.48 (1H, br s), 6.89 (1H, t, J=8Hz), 7.12–7.90 (8H), 8.29 (1H, d, J=6Hz), 9.00 (1H, s)
(58) 3-Chloro-8-[2,6-dichloro-3-[N-(N'-cyclohexylureidoacetyl)-N-methylamino]benzyloxy]-2-methylimidazo[1,2-a]pyridine hydrochloride
mp: 170°–172° C.

NMR (DMSO-d$_6$, δ) 0.91–1.80 (10H), 2.43 (3H, s), 3.12 (3H, s), 3.20–3.40 (2H), 3.62 (1H, d, J=16Hz), 5.58 (1H, d, J=10Hz), 5.66 (1H, dd, J=10Hz), 7.45–7.85 (4H), 8.37 (1H, d, J=6Hz)
(59) 3-Chloro-8-[2,6-dichloro-3-[N-(N'-ethylureidoacetyl)-N-methylamino]benzyloxy]-2-methylimidazo[1,2-a]pyridine hydrochloride NMR (CDCl$_3$—CD$_3$OD, δ): 1.10 (3H, t, J=6Hz), 2.57 (3H, s), 3.15 (2H, q, J=6Hz), 3.27 (3H, s), 3.66 (2H, s), 5.68 (1H, d, J=10Hz), 5.79 (1H, d, J=10Hz), 7.54–7.72 (4H), 8.29 (1H, d, J=6Hz)
(60) 3-Chloro-8-[2,6-dichloro-3-[N-(phenylacetylglycyl)-N-methylamino]benzyloxy]-2-methylimidazo[1,2-a]pyridine hydrochloride NMR (DMSO-d$_6$, δ): 2.39 (3H, s), 3.12 (2.2H, s), 3.27 (0.8H, s), 3.48 (1H, dd, J=16Hz and 6Hz), 3.47 (2H, s), 3.69 (1H, dd, J=16Hz and 6Hz), 5.58 (2H, s), 7.14–7.84 (9H), 8.23–8.37 (2H)
(61) 3-Chloro-8-[2,6-dichloro-3-[N-(butyrylglycyl)-N-methylamino]benzyloxy]-2-methylimidazo[1,2-a]pyridine hydrochloride NMR (CDCl$_3$—CD$_3$OD, δ): 0.98 (3H, t, J=6Hz), 1.53–1.75 (2H), 2.23 (2H, t, J=6Hz), 2.57 (3H, s), 3.27 (3H, s), 3.68 (1H, s), 3.70 (1H, s), 5.70 (1H, d, J=10Hz), 5.78 (1H, d, J=10Hz), 7.56–7.75 (4H), 8.30 (1H, d, J=6Hz)
(62) 3-Chloro-8-[2,6-dichloro-3-[N-(N'-phenylthioureidoacetyl)-N-methylamino]benzyloxy]-2-methylimidazo-[1,2-a]pyridine hydrochloride
mp: 150°–155° C.

NMR (DMSO-d$_6$, δ): 2.40 (3H, s), 3.18 (3H, s), 3.80 (1H, dd, J=16Hz and 4Hz), 4.23 (1H, dd, J=16Hz and 4Hz), 5.61 (2H, s), 7.11 (1H, t, J=8Hz), 7.27–7.92 (8H), 7.97 (1H, br s), 8.28 (1H, d, J=6Hz), 10.15 (1H, br s)
(63) 3-Bromo-8-[2,6-dichloro-3-[N-(glycylglycyl)-N-methylamino]benzyloxy]-2-methylimidazo[1,2-a]pyridine dihydrochloride NMR (CDCl$_3$—CD$_3$OD, δ): 2.56 (3H, s), 3.25 (3H, s), 3.69 (1H, d, J=17Hz), 3.72 (2H, s), 3.86 (1H, d, J=17Hz), 5.72 (2H, s), 7.50–7.78 (4H), 8.31 (1H, d, J=6Hz)

Example 62

The following compounds were obtained according to similar manners to those of Examples 1 or 2 using N-iodosuccinimide instead of N-bromosuccinimide or N-chlorosuccinimide.

(1) 8-[2,6-Dichloro-3-[N-[N-(N,N-dimethylglycyl)glycyl]-N-methylamino]benzyloxy]-3-iodo-2-methylimidazo[1,2-a] pyridine NMR (CDCl$_3$, δ): 2.31 (6H, s), 2.48 (3H, s), 2.96 (2H, s), 3.25 (3H, s), 3.55 (1H, dd, J=18Hz and 5Hz), 3.85 (1H, dd, J=18Hz and 5Hz), 5.50 (2H, s), 6.72 (1H, d, J=7Hz), 6.86 (1H, t, J=7Hz), 7.32 (1H, d, J=9Hz), 7.48 (1H, d, J=9Hz), 7.79 (1H, d, J=7Hz), 7.89 (1H, br s)
(2) 8-[2,6-Dichloro-3-(N-acetyl-N-methylamino) benzyloxy]-3-iodo-2-methylimidazo[1,2-a]pyridine
mp: 190°–192° C.

NMR (CDCl$_3$, δ) 1.84 (3H, s), 2.49 (3H, s), 3.20 (3H, s), 5.50 (2H, s), 6.71 (1H, d, J=7Hz), 6.86 (1H, t, J=7Hz), 7.30 (1H, d, J=9Hz), 7.47 (1H, d, J=9Hz), 7.80 (1H, d, J=7Hz)

Example 63

The following compounds were obtained according to similar manners to those of Example 1 or 2.

(1) 3-Bromo-8-[2,6-dichloro-4-(N-acetyl-N-methylamino) benzyloxy]-2-methylimidazo[1,2-a]pyridine
mp: 82°–88° C.

NMR (CDCl$_3$, δ): 2.06 (3H, br s), 2.45 (3H, s), 3.28 (3H, s), 5.45 (2H, s), 6.73 (1H, d, J=7.5Hz), 6.86 (1H, t, J=7.5Hz), 7.25 (2H, s), 7.77 (1H, d, J=7.5Hz)
(2) 3-Chloro-8-[2,6-dichloro-4-(N-acetyl-N-methylamino) benzyloxy]-2-methylimidazo[1,2-a]pyridine
mp: 74°–78° C.

NMR (CDCl$_3$, δ) 2.04 (3H, br s), 2.44 (3H, s), 3.28 (3H, s), 5.45 (2H, s), 6.70 (1H, d, J=7Hz), 6.84 (1H, t, J=7.0Hz), 7.25 (2H, s), 7.71 (1H, d, J=7Hz)

Example 64

The following compounds were obtained according to similar manners to those of Example 42 or 43.

(1) 3-Bromo-8-[2,6-dichloro-3-[N-[N'-(3-methoxyphenyl) ureidoacetyl]-N-methylamino]benzyloxy]-2-methylimidazo [1,2-a]pyridine NMR (CDCl$_3$, δ) 2.41 (3H, s), 3.22 (3H, S), 3.61–3.91 (5H), 5.47 (2H, S), 5.95 (1H, br t, J=4Hz), 6.58 (1H, dd, J=7Hz and 1Hz), 6.58–6.91 (3H), 7.01 (1H, t, J=1Hz), 7.13 (1H, t, J=7Hz), 7.32 (1H, d, J=9Hz), 7.42 (1H, d, J=9Hz), 7.78 (1H, d, J=7Hz)
(2) 3-Bromo-8-[3-[N-[N'-(3-chlorophenyl)ureidoacetyl]-N-methylamino]-2,6-dichlorobenzyloxy]-2-methylimidazo[1,2-a]pyridine
mp: 151°–152° C.

NMR (CDCl$_3$, δ) 2.42 (3H, s), 3.21 (3H, s), 3.88 (1H, dd, J=18Hz and 4Hz), 4.21 (1H, dd, J=18Hz and 4Hz), 5.50 (2H, s), 6.71 (1H, d, J=7Hz), 6.88 (1H, t, J=7Hz), 7.18–7.42 (6H), 7.50 (1H, d, J=9Hz), 7.78 (1H, d, J=7Hz), 8.01 (1H, br s)
(3) 3-Bromo-8-[2,6-dichloro-3-[N-[N'-(3-trifluoromethylphenyl)ureidoacetyl]-N-methylamino] benzyloxy]-2-methylimidazo[1,2-a]pyridine NMR (CDCl$_3$, δ): 2.40 (3H, s), 3.22 (3H, s), 3.82 (2H, br d, J=5Hz), 5.42 (1H, d, J=10Hz), 5.52 (1H, d, J=10Hz), 6.07 (1H, br t, J=5Hz), 6.73 (1H, d, J=7Hz), 6.89 (1H, t, J=7Hz), 7.11–7.46 (5H), 7.65 (1H, br s), 7.79 (1H, d, J=7Hz), 8.22 (1H, br s)
(4) 5-[3-[N-[N'-(3-Acetylphenyl)ureidoacetyl]-N-methylamino]-2,6-dichlorobenzyloxy]-3-bromo-2-methylimidazo[1,2-a]pyridine NMR (CDCl₃, δ): 2.40 (3H, s), 2.54 (3H, s), 3.37 (3H, s), 3.76 (1H, dd, J=18Hz and 5Hz), 3.89 (1H, dd, J=18Hz and 5Hz), 5.44 (1H, d, J=10Hz), 5.52 (1H, d, J=10Hz), 6.09 (1H, br t, J=5Hz), 6.72 (1H, d, J=7Hz), 6.88 (1H, t, J=7Hz), 7.28 (1H, t, J=7Hz), 7.39 (1H, d, J=9Hz), 7.43 (1H, d, J=9Hz), 7.54 (2H, d, J=7Hz), 7.79 (1H, d, J=7Hz), 7.86 (1H, br s), 8.00 (1H, br s)

(5) 3-Bromo-8-[3-[N-[N'-(3-cyanophenyl)ureidoacetyl]-N-methylamino]-2,6-dichlorobenzyloxy]-2-methylimidazo[1,2-a]pyridine NMR (CDCl₃, δ) 2.40 (3H, s), 3.21 (3H, s), 3.81 (2H, d, J=5Hz), 5.42 (1H, d, J=10Hz), 5.53 (1H, d, J=10Hz), 6.08 (1H, br t, J=5Hz), 6.76 (1H, d, J=7Hz), 6.90 (1H, t, J=7Hz), 7.11–7.26 (2H), 7.31–7.42 (3H), 7.66 (1H, br s), 7.80 (1H, d, J=7Hz), 8.63 (1H, br s)

(6) 3-Bromo-8-[2,6-dichloro-3-[N-[N'-(o-tolyl)ureidoacetyl]-N-methylamino]benzyloxy]-2-methylimidazo[1,2-a]pyridine NMR (CDCl₃, δ): 2.25 (3H, s), 2.42 (3H, s), 3.21 (3H, s), 3.58 (1H, dd, J=18Hz and 4Hz), 3.85 (1H, dd, J=18Hz and 5Hz), 5.48 (2H, s), 5.72 (1H, br s), 6.37 (1H, br s), 6.71 (1H, d, J=7Hz), 6.87 (1H, t, J=7Hz), 7.05–7.51 (6H), 7.78 (1H, d, J=7Hz)

(7) 3-Bromo-8-[2,6-dichloro-3-[N-[N'-(3-fluorophenyl)ureidoacetyl]-N-methylamino]benzyloxy]-2-methylimidazo[1,2-a]pyridine NMR (CDCl₃, δ): 2.41 (3H, s), 3.21 (3H, s), 3.79 (2H, br t, J=5Hz), 5.43 (1H, d, J=10Hz), 5.51 (1H, d, J=10Hz), 6.02 (1H, br t, J=5Hz), 6.58–6.94 (4H), 7.03–7.28 (2H), 7.34 (1H, d, J=9Hz), 7.41 (1H, d, J=9Hz), 7.78 (1H, d, J=7Hz), 7.98 (1H, br s)

(8) 3-Bromo-8-[3-[N-[N'-(3-ethylphenyl)ureidoacetyl]-N-methylamino]-2,6-dichlorobenzyloxy]-2-methylimidazo[1,2-a]pyridine NMR (CDCl₃, δ): 1.20 (3H, t, J=7Hz), 2.42 (3H, s), 2.60 (2H, q, J=7Hz), 3.22 (3H, s), 3.68 (1H, dd, J=18Hz and 5Hz), 3.87 (1H, dd, J=18Hz and 5Hz), 5.48 (2H, s), 5.91 (1H, br t, J=5Hz), 6.71 (1H, d, J=7Hz), 6.88 (1H, t, J=7Hz), 7.01–7.26 (4H), 7.32 (1H, d, J=9Hz), 7.45 (1H, d, J=9Hz), 7.78 (1H, d, J=7Hz)

(9) 8-[3-[N-(N'-Benzoylureidoacetyl)-N-methylamino]-2,6-dichlorobenzyloxy]-3-bromo-2-methylimidazo[1,2-a]pyridine mp: 187°–190° C. (dec.)

NMR (CDCl₃, δ): 2.42 (3H, s), 3.28 (3H, s), 3.71 (1H, dd, J=18Hz and 5Hz), 3.96 (1H, dd, J=18Hz and 5Hz), 5.50 (2H, s), 6.71 (1H, d, J=7Hz), 6.86 (1H, t, J=7Hz), 7.36 (1H, d, J=9Hz), 7.40–7.62 (4H), 7.77 (1H, d, J=7Hz), 7.83 (2H, d, J=8Hz), 8.45 (1H, br s), 9.23 (1H, br t, J=5Hz)

(10) 3-Bromo-8-[2,6-dichloro-3-[N-methyl-N-[N'-(3-nitrophenyl)ureidoacetyl]amino]benzyloxy]-2-methylimidazo[1,2-a]pyridine mp: 160°–168° C. (dec.)

NMR (CDCl₃, δ): 2.40 (3H, s), 3.25 (3H, s), 3.83 (2H, d, J=5Hz), 5.42 (1H, d, J=10Hz), 5.52 (1H, d, J=10Hz), 6.16 (1H, br t, J=5Hz), 6.77 (1H, d, J=7Hz), 6.90 (1H, t, J=7Hz), 7.23 (1H, t, J=8Hz), 7.40 (2H, s), 7.52 (1H, d, J=8Hz), 7.70 (1H, dd, J=8Hz and 1Hz), 7.79 (1H, d, J=7Hz), 8.14 (1H, t, J=1Hz), 8.79 (1H, s)

(11) 3-Bromo-8-[2,6-dichloro-3-[N-[N'-(3-ethoxycarbonylphenyl)ureidoacetyl]-N-methylamino]benzyloxy]-2-methylimidazo[1,2-a]pyridine NMR (CDCl₃, δ): 1.35 (3H, t., J=7Hz), 2.41 (3H, s), 3.25 (3H, s), 3.80 (2H, dd, J=7Hz and 5Hz), 4.32 (2H, q, J=7Hz), 5.44 (1H, d, J=10Hz), 5.51 (1H, d, J=10Hz), 6.01 (1H, br t, J=5Hz), 6.72 (1H, d, J=7Hz), 6.88 (1H, t, J=7Hz), 7.36 (1H, d, J=9Hz), 7.42 (1H, d, J=9Hz), 7.56–7.69 (2H), 7.72–7.89 (3H)

(12) 3-Bromo-8-[2,6-dichloro-3-[N-(N'-ethoxycarbonylmethylureidoacetyl)-N-methylamino]benzyloxy]-2-methylimidazo[1,2-a]pyridine mp: 194°–196° C.

NMR (CDCl₃, δ): 1.28 (3H, t, J=7Hz), 2.42 (3H, s), 3.22 (3H, s), 3.57 (1H, dd, J=18Hz and 5Hz), 3.80 (1H, dd, J=18Hz and 5Hz), 3.92 (2H, d, J=5Hz), 4.20 (2H, q, J=7Hz), 5.38 (1H, br t, J=5Hz), 5.49 (2H, s), 5.62 (1H, br t, J=5Hz), 6.71 (1H, d, J=7Hz), 6.86 (1H, t, J=7Hz), 7.32 (1H, d, J=9Hz), 7.47 (1H, d, J=9Hz), 7.78 (1H, d, J=7Hz)

Example 65

A mixture of 2-thiophenecarboxylic acid (60 mg), triethylamine (52 mg) and diphenylphosphoryl azide (135 mg) in dry toluene (0.6 ml) was refluxed. After 1 hour, to the cooled mixture was added a solution of 8-[3-(N-glycyl-N-methylamino)-2,6-dichlorobenzyloxy]-3-bromo-2-methylimidazo[1,2-a]pyridine (200 mg) in dry dichloromethane (1 ml), and the mixture was stirred at ambient temperature. After 1 hour, to the mixture was added 2-thiophenecarboxylic acid (60 mg), triethylamine (52 mg) and diphenylphosphoryl azide (135 mg). The mixture was refluxed for 1 hour. The reaction mixture was washed with water twice and brine. The organic layer was dried over magnesium sulfate and evaporated in vacuo. The residue was purified by silica gel column chromatography (ethyl acetate:methanol=50:1, V/V) followed by preparative thin layer chromatography (dichloromethane: methanol=10:1, V/V) to give 3-bromo-8-[2,6-dichloro-3-[N-[N'-(2-thienyl)ureidoacetyl]-N-methylamino]benzyloxy]-2-methylimidazo[1,2-a]pyridine (201 mg) as amorphous.

NMR (CDCl₃, δ): 2.42 (3H, s), 3.29 (3H, s), 3.71 (1H, dd, J=18Hz and 4Hz), 3.97 (1H, dd, J=18Hz and 5Hz), 5.50 (2H, s), 6.71 (1H, d, J=7Hz), 6.88 (1H, t, J=7Hz), 7.00 (1H, br s), 7.09 (1H, dd, J=5Hz and 4Hz), 7.34 (1H, d, J=9Hz), 7.42–7.60 (3H), 7.78 (1H, d, J=7Hz)

Example 66

3-Bromo-8-[3-[N-[N'-(3-carboxyphenyl)ureidoacetyl]-N-methylamino]-2,6-dichlorobenzyloxy]-2-methylimidazo[1,2-a]pyridine was obtained according to a similar manner to that of Example 57.

mp: 248°–250° C.

NMR (DMSO-d₆, δ): 2.30 (3H, s), 3.18 (3H, s), 3.43 (1H, dd, J=18Hz and 5Hz), 3.69 (1H, dd, J=18Hz and 5Hz), 5.49 (2H, s), 6.42 (1H, br t, J=5Hz), 6.94–7.07 (2H), 7.32 (1H, t, J=7Hz), 7.42–7.62 (2H), 7.30 (2H, s), 7.93 (1H, m), 8.02 (1H, br s), 9.09 (1H, s)

Example 67

To a solution of 3-bromo-8-[3-[N-[N'-(3-carboxyphenyl)ureidoacetyl]-N-methylamino]-2,6-dichlorobenzyloxy]-2-methylimidazo[1,2-a]pyridine (200 mg) and dimethylamine hydrochloride (31 mg) in N,N-dimethylformamide (2 ml) were added N-ethyl-N'-(3-dimethylaminopropyl)carbodiimide (64 mg) and 1-hydroxybenzotriazole (64 mg), and the mixture was stirred for 1 hour at ambient temperature. Water was added thereto, and the mixture was extracted with ethyl acetate three times. The organic layer was washed with water for times and brine, dried over magnesium sulfate and concentrated in vacuo. The residue was purified by a silica gel column chromatography (methylene chloride:methanol=20:1, V/V) to give 3-bromo-8-[3-[N-[N'-[3-(N,N-dimethylcarbamoyl)phenyl]ureidoacetyl]-N-methylamino]-2,6-dichlorobenzyloxy]-2-methylimidazo[1,2-a]pyridine (189 mg).

97

NMR (CDCl₃, δ): 2.41 (3H, s), 2.95 (3H, br s), 3.09 (3H, br s), 3.22 (3H, s), 3.64 (1H, dd, J=17Hz and 5Hz), 3.82 (1H, dd, J=17Hz and 5Hz), 5.48 (2H, s), 6.06 (1H, br t, J=5Hz), 6.72 (1H, d, 7Hz), 6.88 (1H, t, J=7Hz), 6.99 (1H, d, J=8Hz), 7.20 (1H, t, J=8Hz), 7.30–7.49 (4H), 7.78 (1H, d, J=7Hz), 8.11 (1H, s)

Example 68

3-Bromo-8-[2,6-dichloro-3-[N-[N-[3-(N-methylcarbamoyl)propionyl]glycyl]-N-methylamino]benzyloxy]-2-methylimidazo[1,2-a]pyridine was obtained according to a similar manner to that of Example 67.

NMR (CDCl₃, δ): 2.40–2.63 (7H), 2.79 (3H, d, J=5Hz), 3.25 (3H, s), 3.52, 3.80 (each 1H, dd, J=18Hz and 5Hz), 5.48 (2H, s), 6.01 (1H, br s), 6.62–6.76 (2H), 6.86 (1H, t, J=7Hz), 7.31, 7.48 (each 1H, d, J=9Hz), 7.78 (1H, d, J=7Hz)

Example 69

To a mixture of 8-[3-(N-glycyl-N-methylamino)-2,6-dichlorobenzyloxy]-3-chloro-2-methylimidazo[1,2-a]pyridine (200 mg), triethylamine (0.1 ml) and dichloromethane (2 ml) was added bromoacetyl chloride (0.042 ml) in a dry ice-acetone bath. After 20 minutes, to the mixture was added 50% aqueous solution of dimethylamine (0.42 ml). The mixture was stirred for 1 hour at ambient temperature. The reaction mixture was washed with aqueous sodium bicarbonate solution, water and brine. The organic layer was dried over magnesium sulfate and evaporated in vacuo. The residue was purified by a silica gel column chromatography (dichloromethane:methanol=20:1, V/V) to yield colorless crystals (191 mg) of 3-chloro-8-[2,6-dichloro-3-[N-[N-(N,N-dimethylglycyl)glycyl]-N-methylamino]benzyloxy]-2-methylimidazo[1,2-a]pyridine.

mp: 171°–172° C.

NMR (CDCl₃, δ): 2.31 (6H, s), 2.44 (3H, s), 2.96 (2H, s), 3.23 (3H, s), 3.56 (1H, dd, J=18Hz, and 4Hz), 3.85 (1H, dd, J=18Hz and 4Hz), 5.49 (2H, s), 6.70 (1H, d, J=7Hz), 6.86 (1H, t, J=7Hz), 7.32 (1H, d, J=9Hz), 7.49 (1H, d, J=9Hz), 7.72 (1H, d, J=7Hz), 7.89 (1H, br s)

Example 70

The following compounds were obtained according to similar manners to those of Examples 53 or 69.

(1) 3-Bromo-8-[2,6-dichloro-3-[N-[N-(N-ethyl-N-methylglycyl)glycyl]-N-methylamino]benzyloxy]-2-methylimidazo[1,2-a]pyridine mp: 168°–170° C.

NMR (CDCl₃, δ) 1.09 (3H, t, J=7Hz), 2.30 (3H, s), 2.43 (3H, s), 2.50 (2H, q, J=7Hz), 2.99 (2H, s), 3.25 (3H, s), 3.56 (1H, dd, J=17Hz and 5Hz), 3.85 (1H, dd, J=17Hz and 5Hz), 5.49 (2H, s), 6.71 (1H, d, J=7Hz), 6.87 (1H, t, J=7Hz), 7.32 (1H, d, J=9Hz), 7.48 (1H, d, J=9Hz), 7.78 (1H, d, J=7Hz), 8.01 (1H, br s)

(2) 3-Bromo-8-[3-[N-[N-(N-cyclopropylglycyl)glycyl]-N-methylamino]-2,6-dichlorobenzyloxy]-2-methylimidazo[1,2-a]pyridine NMR (CDCl₃, δ): 0.39–0.53 (4H), 2.22 (1H, m), 2.42 (3H), 3.25 (3H, s), 3.38 (2H, s), 3.55 (1H, dd, J=18Hz and 4Hz), 3.82 (1H, dd, J=18Hz and 4Hz), 5.49 (2H, s), 6.71 (1H, d, J=7Hz), 6.87 (1H, t, J=7Hz), 7.31 (1H, d, J=9Hz), 7.49 (1H, d, J=9Hz), 7.68 (1H, br s), 7.78 (1H, d, J=7Hz)

(3) 3-Bromo-8-[3-[N-[N-(N-cyclohexylglycyl)glycyl]-N-methylamino]-2,6-dichlorobenzyloxy]-2-methylimidazo[1,2-a]pyridine mp: 182°–184° C.

98

NMR (CDCl₃, δ) 0.98–1.31 (5H), 1.52–1.95 (5H), 2.39 (1H, m), 2.43 (3H, s), 3.24 (3H, s), 3.30 (2H, s), 3.56 (1H, dd, J=18Hz and 4Hz), 3.82 (1H, dd, J=18Hz and 4Hz), 5.49 (2H, s), 6.71 (1H, d, J=7Hz), 6.86 (1H, t, J=7Hz), 7.31 (1H, d, J=9Hz), 7.47 (1H, d, J=9Hz), 7.78 (1H, d, J=7Hz), 8.11 (1H, br s)

(4) 3-Bromo-8-[2,6-dichloro-3-[N-methyl-N-[N-(1-pyrrolidinylacetyl)glycyl]amino]benzyloxy]-2-methylimidazo[1,2-a]pyridine NMR (CDCl₃, δ): 1.72–1.90 (4H), 2.42 (3H, s), 2.57–2.70 (4H), 3.16 (2H, s3), 3.25 (3H, s), 3.57 (1H, dd, J=18Hz and 5Hz), 3.87 (1H, dd, J=18Hz and 5Hz), 5.50 (2H, s), 6.71 (1H, d, J=7Hz), 6.87 (1H, t, J=7Hz), 7.32 (1H, d, J=9Hz), 7.49 (1H, d, J=9Hz), 7.78 (1H, d, J=7Hz), 7.89 (1H, br s)

(5) 3-Bromo-8-[2,6-dichloro-3-[N-methyl-N-[N-(piperidinoacetyl)glycyl]amino]benzyloxy]-2-methylimidazo[1,2-a]pyridine NMR (CDCl₃, δ) 1.38–1.72 (6H), 2.39–2.55 (7H), 2.94 (2H, s), 3.27 (3H, s), 3.55 (1H, dd, J=18Hz and 4Hz), 3.83 (1H, dd, J=18Hz and 4Hz), 5.50 (2H, s), 6.71 (1H, d, J=7Hz), 6.87 (1H, t, J=7Hz), 7.31 (1H, d, J=9Hz), 7.49 (1H, d, J=9Hz), 7.78 (1H, d, J=7Hz), 8.08 (1H, br s)

(6) 3-Bromo-8-[2,6-dichloro-3-[N-methyl-N-[N-[[4-(4-pyridyl)-1-piperazinyl]acetyl]glycyl]amino]benzyloxy]-2-methylimidazo[1,2-a]pyridine NMR (CDCl₃, δ): 2.43 (3H, s), 2.61–2.78 (4H), 3.09 (2H, s), 3.26 (3H, s), 3.34–3.49 (4H), 3.58 (1H, dd, J=18Hz and 4Hz), 3.88 (1H, dd, J=18Hz and 4Hz), 5.48 (1H, d, J=10Hz), 5.52 (1H, d, J=10Hz), 6.61–6.78 (3H), 6.86 (1H, t, J=7Hz), 7.32 (1H, d, J=9Hz), 7.50 (1H, d, J=9Hz), 7.78 (1H, d, J=7Hz), 7.92 (1H, br t, J=4Hz), 8.29 (2H, br d, J=6Hz)

(7) 3-Bromo-8-[2,6-dichloro-3-[N-[N-(N-isopropyl-N-methylglycyl)glycyl]-N-methylamino]benzyloxy]-2-methylimidazo[1,2-a]pyridine mp: 150°–151° C.

NMR (CDCl₃, δ) 1.02 (6H, d, J=6Hz), 2.38 (3H, S), 2.42 (3H, s), 2.85 (1H, m), 3.00 (2H, s), 3.25 (3H, s), 3.55 (1H, dd, J=18Hz and 5Hz), 3.85 (1H, dd, J=18Hz and 5Hz), 5.49 (2H, s), 6.71 (1H, d, J=7Hz), 6.86 (1H, t, J=7Hz), 7.32 (1H, d, J=9Hz), 7.49 (1H, d, J=9Hz), 7.76 (1H, d, J=7Hz), 8.12 (1H, br s)

(8) 3-Bromo-8-[3-[N-[N-(N-cyclohexyl-N-methylglycyl)glycyl]-N-methylamino]-2,6-dichlorobenzyloxy]-2-methylimidazo[1,2-a]pyridine NMR (CDCl₃, δ): 1.00–1.33 (6H), 1.70–1.90 (4H), 2.31 (3H, s), 2.38 (1H, m), 2.42 (3H, s), 3.02 (2H, s), 3.25 (3H, s), 3.56 (1H, dd, J=18Hz and 5Hz), 3.83 (1H, dd, J=18Hz and 5Hz), 5.49 (2H, s), 6.71 (1H, d, J=7Hz), 6.86 (1H, t, J=7Hz), 7.32 (1H, d, J=9Hz), 7.48 (1H, d, J=9Hz), 7.78 (1H, d, J=7Hz), 8.19 (1H, br s)

(9) 3-Bromo-8-[3-[N-[N-(N-cycloheptylglycyl)glycyl]-N-methylamino]-2,6-dichlorobenzyloxy]-2-methylimidazo[1,2-a]pyridine NMR (CDCl₃, δ) 1.29–1.92 (12H), 2.43 (3H, s), 2.62 (1H, m), 3.24 (3H, s), 3.28 (2H, s), 3.58 (1H, dd, J=18Hz and 5Hz), 3.82 (1H, dd, J=18Hz and 5Hz), 5.49 (2H, s), 6.71 (1H, d, J=7Hz), 6.86 (1H, t, J=7Hz), 7.31 (1H, d, J=9Hz), 7.48 (1H, d, J=9Hz), 7.78 (1H, d, J=7Hz), 8.10 (1H, br s)

(10) 3-Bromo-8-[3-[N-[N-(N-cyclopentylglycyl)glycyl]-N-methylamino]-2,6-dichlorobenzyloxy]-2-methylimidazo[1,2-a]pyridine NMR (CDCl₃, δ) 1.23–1.90 (8H), 2.42 (3H, s), 3.09 (1H, m), 3.24 (3H, s), 3.28 (2H, s), 3.56 (1H, dd, J=18Hz and 5Hz), 3.82 (1H, dd, J=18Hz and 5Hz), 5.49 (2H, s), 6.72 (1H, d, J=7Hz), 6.86 (1H, t, J=7Hz), 7.31 (1H, d, J=9Hz), 7.49 (1H, d, J=9Hz), 7.78 (1H, d, J=7Hz), 8.00 (1H, br s)

(11) 3-Bromo-8-[3-[N-[N-(N-cyclooctylglycyl)glycyl]-N-methylamino]-2,6-dichlobenzyloxy]-2-methylimidazo-[1,2-a]pyridine NMR (CDCl$_3$, δ): 1.35–1.85 (14H), 2.42 (3H, s), 2.65 (1H, m), 3.27 (5H, s), 3.58 (1H, dd, J=18Hz and 5Hz), 3.82 (1H, dd, J=18Hz and 5Hz), 5.50 (2H, s), 6.71 (1H, d, J=7Hz), 6.88 (1H, t, J=7Hz), 7.32 (1H, d, J=9Hz), 7.49 (1H, d, J=9Hz), 7.79 (1H, d, J=7Hz), 8.10 (1H, br s)

(12) 3-Bromo-8-[3-[N-[N-(N-cycloheptyl-N-methylglycyl)glycyl]-N-methylamino]-2,6-dichlorobenzyloxy]-2-methylimidazo[1,2-a]pyridine NMR (CDCl$_3$, δ): 1.28–1.92 (12H), 2.29 (3H, s), 2.15 (3H, s), 2.60 (1H, m), 3.01 (2H, s), 3.25 (3H, s), 3.56 (1H, dd, J=18Hz and 5Hz), 3.85 (1H, dd, J=18Hz and 5Hz), 5.50 (2H, s), 6.72 (1H, d, J=7Hz), 6.88 (1H, t, J=7Hz), 7.32 (1H, d, J=9Hz), 7.49 (1H, d, J=9Hz), 7.79 (1H, d, J=7Hz), 8.18 (1H, br s)

(13) 3-Bromo-8-[2,6-dichloro-3-[N-[N-(hexamethyleneiminoacetyl)glycyl]-N-methylamino]benzyloxy]-2-methylimidazo[1,2-a]pyridine NMR (CDCl$_3$, δ): 1.58–1.78 (8H), 2.42 (3H, s), 2.63–2.73 (4H), 3.13 (2H, s), 3.28 (3H, s), 3.58 (1H, dd, J=18Hz and 5Hz), 3.83 (1H, dd, J=18Hz and 5Hz), 5.50 (2H, s), 6.71 (1H, d, J=7Hz), 6.86 (1H, t, J=7Hz), 7.32 (1H, d, J=9Hz), 7.49 (1H, d, J=9Hz), 7.78 (1H, d, J=7Hz), 8.12 (1H, br s)

(14) 8-[3-[N-[N-[N-(1-Adamantyl)glycyl]glycyl]-N-methylamino]-2,6-dichlorobenzyloxy]-3-bromo-2-methylimidazo[1,2-a]pyridine NMR (CDCl$_3$, δ): 1.49–1.74 (12H), 1.99–2.12 (3H), 2.43 (3H, s), 3.25 (5H, s), 3.56 (1H, dd, J=18Hz and 5Hz), 3.82 (1H, dd, J=18Hz and 5Hz), 5.50 (2H, s), 6.71 (1H, d, J=7Hz), 6.86 (1H, t, J=7Hz), 7.32 (1H, d, J=9Hz), 7.49 (1H, d, J=9Hz), 7.78 (1H, d, J=7Hz), 8.25 (1H, br s)

(15) 3-Bromo-8-[2,6-dichloro-3-[N-methyl-N-[N-[N-(piperidino)glycyl]glycyl]amino]benzyloxy]-2-methylimidazo[1,2-a]pyridine mp: 242°–243° C.

NMR (CDCl$_3$—CD$_3$OD, δ): 1.50–1.90 (4H), 2.06–2.34 (2H), 2.42 (3H, s), 2.66 (1H, m), 3.22 (3H, s, 3.52–3.87 (5H), 4.53 (2H, s), 5.50 (2H, s), 6.73 (1H, d, J=7Hz), 6.89 (1H, t, J=7Hz), 7.44 (1H, d, J=9Hz), 7.52 (1H, d, J=9Hz), 7.79 (1H, d, J=7Hz)

(16) 3-Bromo-8-[2,6-dichloro-3-[N-[N-[N-(2-furylmethyl)glycyl]glycyl]-N-methylamino]benzyloxy]-2-methylimidazo[1,2-a]pyridine NMR (CDCl$_3$, δ): 2.42 (3H, s), 3.25 (3H, s), 3.30 (2H, s), 3.56 (1H, dd, J=18Hz and 5Hz), 3.72–3.91 (3H), 5.50 (2H, s), 6.20 (1H, d, J=2Hz), 6.30 (1H, m), 6.71 (1H, d, J=7Hz), 6.86 (1H, t, J=7Hz), 7.29–7.39 (2H), 7.48 (1H, d, J=9Hz), 7.77 (1H, d, J=7Hz), 7.88 (1H, br s)

(17) 3-Bromo-8-[2,6-dichloro-3-[N-[N-(N,N-diethylglycyl)glycyl]-N-methylamino]benzyloxy]-2-methylimidazo-[1,2-a]pyridine mp: 159°–160° C.

NMR (CDCl$_3$, δ): 1.06 (6H, t, J=7Hz), 2.43 (3H, s), 2.58 (4H, , J=7Hz), 3.02 (2H, s), 3.26 (3H, s), 3.55 (1H, dd, J=18Hz and 4Hz), 3.84 (1H, dd, J=18Hz and 4Hz), 5.49 (2H, s), 6.71 (1H, d, J=7Hz), 6.86 (1H, t, J=7Hz), 7.31 (1H, d, J=9Hz), 7.48 (1H, d, J=9Hz), 7.76 (1H, d, J=7Hz), 8.18 (1H, br s)

(18) 3-Bromo-8-[2,6-dichloro-3-[N-[N-(1-imidazolylacetyl)glycyl]-N-methylamino]benzyloxy]-2-methylimidazo-[1,2-a]pyridine NMR (CDCl$_3$, δ) 2.42 (3H, s), 3.21 (3H, s), 3.52 (1H, dd, J=18Hz and 4Hz), 3.79 (1H, dd, J=18Hz and 5Hz), 4.68 (2H, s), 5.49 (2H, s), 6.49 (1H, br s), 6.71 (1H, d, J=7Hz), 6.86 (1H, t, J=7Hz), 7.00 (1H, s), 7.19 (1H, s), 7.30 (1H, d, J=9Hz), 7.49 (1H, d, J=9Hz), 7.55 (1H, s), 7.78 (1H, d, J=7Hz)

Example 71

To a solution of 3-bromo-8-[2,6-dichloro-3-[N-(N-bromoacetylglycyl)-N-methylamino]benzyloxy]-2-methylimidazo[1,2-a]pyridine (200 mg) in N,N-dimethylformamide (2 ml) was added sodium methanethiolate (35 mg), and the mixture was stirred for 5 hours at ambient temperature under nitrogen atmosphere. The reaction mixture was concentrated in vacuo, the residue was dissolved in methylene chloride. The solution was washed with water four times and brine, dried over magnesium sulfate and concentrated in vacuo. The residue was purified by a silica gel column chromatography (methylene chloride:methanol=40:1, V/V) to give 3-bromo-8-[2,6-dichloro-3-[N-methyl-N-[N-(methylthioacetyl)glycyl]amino]benzyloxy]-2-methylimidazo[1,2-a]pyridine (105 mg).

NMR (CDCl$_3$, δ): 2.19 (3H, s), 2.43 (3H, s), 3.21 (2H, s), 3.28 (3H, s), 3.59 (1H, dd, J=18Hz and 4Hz), 3.84 (1H, dd, J=18Hz and 5Hz), 5.50 (2H, s), 6.72 (1H, d, J=7Hz), 6.86 (1H, t, J=7Hz), 7.32 (1H, d, J=9Hz), 7.49 (1H, d, J=9Hz), 7.61 (1H, br s), 7.78 (1H, d, J=7Hz)

Example 72

The following compounds were obtained according to similar manners to those of Examples 36 to 39.

(1) 3-Bromo-8-[2,6-dichloro-3-[N-(N-hexanoylglycyl)-N-methylamino]benzyloxy]-2-methylimidazo[1,2-a]-pyridine mp: 131°–132° C.

NMR (CDCl$_3$, δ) 0.89 (3H, t, J=6Hz), 1.19–1.40 (4H), 1.51–1.71, (2.20 (2H, t, J=6Hz), 2.42 (3H, s), 3.25 (3H, s), 3.51 (1H, dd, J=18Hz and 4Hz), 3.79 (1H, dd, J=18Hz and 5Hz), 5.49 (2H, s), 6.40 (1H, br s), 6.71 (1H, d, J=7Hz), 6.86 (1H, t, J=7Hz), 7.30 (1H, d, J=9Hz), 7.48 (1H, d, J=9Hz), 7.78 (1H, d, J=7Hz)

(2) 3-Bromo-8-[2,6-dichloro-3-[N-methyl-N-[N-(3-phenylpropionyl)glycyl]amino]benzyloxy]-2-methylimidazo-[1,2-a]pyridine NMR (CDCl$_3$, δ): 2.42 (3H, s), 2.88–3.02 (4H), 3.23 (3H, s), 3.50 (1H, dd, J=18Hz and 4Hz), 3.79 (1H, dd, J=18Hz and 5Hz), 5.49 (2H, s), 6.45 (1H, br s), 6.71 (1H, d, J=7Hz), 6.88 (1H, t, J=7Hz), 7.11–7.33 (5H), 7.46 (1H, d, J=9Hz), 7.78 (1H, d, J=7Hz)

(3) 3-Bromo-8-[2,6-dichloro-3-[N-[N-(N-methyl-N-phenylglycyl)glycyl]-N-methylamino]benzyloxy]-2-methylimidazo[1,2-a]pyridine NMR (CDCl$_3$, δ): 2.43 (3H, s), 3.08 (3H, s), 3.22 (3H, s), 3.56 (1H, dd, J=18 Hz and 5 Hz), 3.82 (1H, dd, J=18 Hz and 5 Hz), 3.90 (2H, s), 5.50 (2H, s), 6.69–6.91 (5H), 7.20–7.40 (3H), 7.48 (1H, d, J=9 Hz), 7.78 (1H, d, J=7 Hz)

Example 73

The following compounds were obtained according to a similar manner to that of Example 60.

(1) 3-Bromo-8-[2,6-dichloro-3-[N-methyl-N-[N-(metylthioacetyl)glycyl]amino]benzyloxy]-2-methylimidazo[1,2-a]pyridine hydrochloride NMR (CDCl$_3$—CD$_3$OD, δ): 2.19 (3H, s), 2.53 (3H, s), 3.21 (2H, s), 3.27 (3H, s), 3.66 (1H, d, J=18 Hz), 3.79 (1H, d, J=18 Hz), 5.72 (2H, s), 7.49–7.73 (4H), 8.29 (1H, d, J=6 Hz)

(2) 3-Bromo-8-[2,6-dichloro-3-[N-[N-(1-imidazolylacetyl)glycyl]-N-methylamino]benzyloxy]-2-methylimidazo-[1,2-a]pyridine dihydrochloride NMR (CDCl$_3$—CD$_3$OD, δ): 2.52 (3H, s), 3.26 (3H, s), 3.63 (1H, d, J=18 Hz), 3.83 (1H, d, J=18 Hz), 5.12 (2H, s), 5.71 (2H, s), 7.48–7.72 (6H), 8.29 (1H, d, J=6 Hz), 9.00 (1H, s)

(3) 3-Bromo-8-[2,6-dichloro-3-[N-(N-hexanoylglycyl)-N-methylamino]benzyloxy]-2-methylimidazo[1,2-a]pyridine hydrochloride NMR (CDCl₃—CD₃OD, δ): 0.90 (3H, t, J=6 Hz), 1.21–1.42 (4H), 1.52–1.71 (2H), 2.25 (2H, t, J=6 Hz), 2.56 (3H, s), 3.27 (3H, s), 3.62 (1H, d, J=16 Hz), 3.74 (1H, d, J=16 Hz), 5.70 (1H, d, J=10 Hz), 5.78 (1H, d, J=10 Hz), 7.53–7.76 (4H), 8.30 (1H, d, J=6 Hz)

(4) 3-Bromo-8-[2,6-dichloro-3-[N-methyl-N-[N-(3-phenylpropionyl)glycyl]amino]benzyloxy]-2-methylimidazo-[1,2-a]pyridine hydrochloride NMR (CDCl₃—CD₃OD, δ): 2.53 (3H, s), 2.83–3.00 (4H), 3.22 (3H, s), 3.18 (2H, s), 5.71 (2H, s), 7.10–7.30 (5H), 7.55–7.76 (4H), 8.30 (1H, d, J=6 Hz)

(5) 3-Bromo-8-[2,6-dichloro-3-[N-[N-(N,N-diethylglycyl)glycyl]-N-methylamino]benzyloxy]-2-methylimidazo-[1,2-a]pyridine dihydrochloride NMR (CDCl₃—CD₃OD, δ): 1.40 (6H, t, J=7 Hz), 2.63 (3H, s), 3.25 (3H, s), 3.28–3.49 (4H), 3.60–4.09 (4H), 5.61 (1H, d, J=10 Hz), 5.70 (1H, d, J=10 Hz), 7.40–7.62 (4H), 8.11 (1H, d, J=6 Hz)

(6) 3-Bromo-8-[2,6-dichloro-3-[N-[N-(N-ethyl-N-methylglycyl)glycyl]-N-methylamino]benzyloxy]-2-methylimidazo[1,2-a]pyridine dihydrochloride NMR (CDCl₃—CD₃OD, δ): 1.40 (3H, t, J=7 Hz), 2.45–2.90 (5H), 2.95 (3H, s), 3.21 (3H s), 3.61–4.01 (4H), 5.63 (3H, br s), 7.38–7.64 (4H), 8.08 (1H, d, J=6 Hz)

(7) 3-Bromo-8-[3-[N-[N-(N-cyclopropylglycyl)glycyl]-N-methylamino]-2,6-dichlorobenzyloxy]-2-methylimidazo-[1,2-a]pyridine dihydrochloride NMR (CDCl₃—CD₃OD, δ): 0.84–1.03 (4H), 2.59 (3H, s), 2.79 (1H, m), 3.25 (3H, s), 3.58–3.71 (2H), 3.80–4.00 (3H), 5.73 (2H, s), 7.56–7.75 (4H), 8.30 (1H, d, J=6 Hz)

(8) 3-Bromo-8-[3-[N-[N-(N-cyclohexylglycyl)glycyl]-N-methylamino]-2,6-dichlorobenzyloxy]-2-methylimidazo-[1,2-a]pyridine dihydrochloride NMR (CDCl₃—CD₃OD, δ): 1.16–1.51 (5H), 1.68–2.20 (5H), 2.58 (3H, s), 3.08 (1H, m), 3.26 (3H, s), 3.56–3.71 (2H), 3.80–3.92 (3H), 5.72 (2H, s), 7.48–7.74 (4H), 8.30 (1H, d, J=6 Hz)

(9) 3-Bromo-8-[2,6-dichloro-3-[N-methyl-N-[N-(1-pyrrolidinylacetyl)glycyl]amino]benzyloxy]-2-methylimidazo[1,2-a]pyridine dihydrochloride NMR (CDCl₃—CD₃OD, δ): 1.97–2.29 (4H), 2.58 (3H, s), 3.09–3.30 (5H), 3.53–3.91 (4H), 4.09 (2H, s), 5.71 (2H, s), 7.53–7.76 (4H), 8.30 (1H, d, J=6 Hz)

(10) 3-Bromo-8-[2,6-dichloro-3-[N-methyl-N-[N-(piperidinoacetyl)glycyl]amino]benzyloxy]-2-methylimidazo-[1,2-a]pyridine dihydrochloride NMR (CDCl₃—CD₃OD, δ): 1.42–2.09 (6H), 2.58 (3H, s), 2.98–3.19 (2H), 3.28 (3H, s), 3.50–3.71 (4H), 3.80–4.04 (2H), 5.72 (2H, s), 7.55–7.76 (4H), 8.30 (1H, d, J=6 Hz)

(11) 3-Bromo-8-[2,6-dichloro-3-[N-methyl-N-[N-[[4-(4-pyridyl)-1-piperazinyl]acetyl]glycyl]amino]-benzyloxy]-2-methylimidazo[1,2-a]pyridine tetrahydrochloride NMR (CDCl₃—CD₃OD, δ): 2.59 (3H, s), 3.28 (3H, s), 3.58–3.72 (5H), 3.89 (1H, d, J=18 Hz), 4.02–4.25 (4H), 5.72 (2H, s), 7.30 (2H, d, J=7 Hz), 7.55–7.76 (4H), 8.21 (2H, d, J=7 Hz), 8.30 (1H, d, J=6 Hz)

(12) 3-Bromo-8-[2,6-dichloro-3-[N-[N-(N-isopropyl-N-methylglycyl)glycyl]-N-methylamino]benzyloxy]-2-methylimidazo[1,2-a]pyridine dihydrochloride NMR (CDCl₃—CD₃OD, δ): 1.40 (6H, d, J=6 Hz), 2.56 (3H, s), 2.85 (3H, s), 3.25 (3H, s), 3.59–3.71 (3H), 3.90 (1H, d, J=18 Hz), 4.01 (1H, m), 5.72 (2H, s), 7.48–7.78 (4H), 8.30 (1H, d, J=6 Hz)

(13) 3-Bromo-8-[3-[N-[N-(N-cyclohexyl-N-methylglycyl)glycyl]-N-methylamino]-2,6-dichlorobenzyloxy]-2-methylimidazo[1,2-a]pyridine dihydrochloride NMR (CDCl₃—CD₃OD, δ): 1.43–1.90 (8H), 2.01–2.19 (2H), 2.56 (3H, s), 3.26 (3H, s), 3.31–3.41 (4H), 3.62 (1H, d, J=18 Hz), 3.80–3.96 (3H), 5.72 (2H, s), 7.50–7.72 (4H), 8.29 (1H, d, J=6 Hz)

(14) 3-Bromo-8-[3-[N-[N-(N-cycloheptylglycyl)glycyl]-N-methylamino]-2,6-dichlorobenzyloxy]-2-methylimidazo[1,2-a]pyridine dihydrochloride NMR (CDCl₃—CD₃OD, δ): 1.25–2.20 (12H), 2.59 (3H, s), 2.89 (3H, s), 3.26 (3H, s), 3.31–3.41 (2H), 3.62 (1H, d, J=18 Hz), 3.90 (1H, d, J=18 Hz), 4.09 (1H, m), 5.73 (2H, s), 7.56–7.75 (4H), 8.30 (1H, d, J=6 Hz)

(15) 3-Bromo-8-[3-[N-[N-(N-cyclopentylglycyl)glycyl]-N-methylamino]-2,6-dichlorobenzyloxy]-2-methylimidazo-[1,2-a]pyridine dihydrochloride NMR (CDCl₃—CD₃OD, δ): 1.59–1.93 (6H), 2.00–2.23 (2H), 2.56 (3H, s), 3.26 (3H, s), 3.49–3.67 (2H), 3.80–3.92 (3H), 5.72 (2H, s), 7.50–7.74 (4H), 8.30 (1H, d, J=6 Hz)

(16) 3-Bromo-8-[3[N-[N-(N-cyclooctylglycyl)glycyl]-N-methylamino]-2,6-dichlorobenzyloxy]-2-methylimidazo-[1,2-a]pyridine dihydrochloride NMR (CDCl₃—CD₃OD, δ): 1.31–2.10 (14H), 2.63 (3H, s), 3.23 (3H, s), 3.30 (1H, m), 3.71 (1H, d, J=18 Hz), 3.81 (2H, s), 3.90 (1H, d, J=18 Hz), 5.65 (2H, s), 7.40–7.66 (4H), 8.09 (1H, d, J=6 Hz)

(17) 3-Bromo-8-[3-[N-[N-(N-cycloheptyl-N-methylglycyl)glycyl]-N-methylamino]-2,6-dichlorobenzyloxy]-2-methylimidazo[1,2-a]pyridine dihydrochloride NMR (CDCl₃—CD₃OD, δ): 1.42–1.90 (10H), 2.05–2.30 (2H), 2.65 (3H, s), 2.88 (3H, s), 3.24 (3H, s), 3.50–3.72 (2H), 3.80–4.10 (3H), 5.61 (1H, d, J=10 Hz), 5.71 (1H, d, J=10 Hz), 7.42–7.62 (4H), 8.10 (1H, d, J=6 Hz)

(18) 3-Bromo-8-[2,6-dichloro-3-[N-[N-(hexamethyleneiminoacetyl)glycyl]-N-methylamino]benzyloxy]-2-methylimidazo[1,2-a]pyridine dihydrochloride NMR (CDCl₃—CD₃OD, δ): 1.42–2.20 (8H), 2.66 (3H, s), 3.22 (3H, s), 3.30–3.82 (6H), 3.90–4.08 (2H), 5.56 (1H, d, J=10 Hz), 5.69 (1H, d, J=10 Hz), 7.20–7.50 (3H), 7.59 (1H, d, J=9 Hz), 8.00 (1H, d, J=6 Hz)

(19) 8-[3-[N-[N-[N-(1-Adamantyl)glycyl]glycyl]-N-methylamino]-2,6-dichlorobenzyloxy]-3-bromo-2-methylimidazo[1,2-a]pyridine dihydrochloride NMR (CDCl₃—CD₃OD, δ): 1.56–2.35 (15H), 2.65 (3H, s), 3.22 (3H, s), 3.66–3.99 (4H), 5.60 (1H, d, J=10 Hz), 5.70 (1H, d, J=10 Hz), 7.31–7.54 (3H), 7.62 (1H, d, J=9 Hz), 8.02 (1H, d, J=6 Hz)

(20) 3-Bromo-8-[2,6-dichloro-3-[N-methyl-N-[N-[N-(piperidino)glycyl]glycyl]amino]benzyloxy]-2-methylimidazo[1,2-a]pyridine trihydrochloride NMR (CDCl₃—CD₃OD, δ): 1.52–2.40 (6H), 2.68 (3H, s), 3.22 (3H, s), 3.51–3.99 (6H), 4.59 (1H, d, J=11 Hz), 4.70 (1H, d, J=11 Hz), 5.67 (2H, s), 7.31–7.50 (2H), 7.55 (1H, d, J=9 Hz), 7.67 (1H, d, J=9 Hz), 8.06 (1H, d, J=6 Hz)

(21) 3-Bromo-8-[2,6-dichloro-3-[N-[N-[N-(2-furylmethyl)glycyl]glycyl]-N-methylamino]benzyloxy]-2-methylimidazo[1,2-a]pyridine dihydrochloride NMR (CDCl₃—CD₃OD, δ): 2.62 (3H, s), 3.22 (3H, s), 3.70–3.99 (4H), 4.30 (2H, s), 5.60 (1H, d, J=10 Hz), 5.70 (1H, d, J=10 Hz), 6.39 (1H, m), 6.69 (1H, d, J=3 Hz), 7.37–7.62 (5H), 8.08 (1H, d, J=6 Hz)

(22) 3-Bromo-8-[2,6-dichloro-3-[N-[N'-(3-methoxyphenyl)ureidoacetyl]-N-methylamino]benzyloxy]-2-methylimidazo[1,2-a]pyridine hydrochloride NMR (CDCl₃—CD₃OD, δ): 2.51 (3H, s), 3.28 (3H, s), 3.71 (2H, s), 3.76 (3H, s), 5.70 (1H, d, J=10 Hz), 5.79 (1H, d, J=10 Hz), 6.56 (1H, dd, J=9 Hz and 1 Hz), 6.81 (1H, dd, J=9 Hz and 1 Hz), 7.06 (1H, t, J=1 Hz), 7.12 (1H, t, J=9 Hz), 7.50–7.78 (4H), 8.30 (1H, d, J=6 Hz)

(23) 3-Bromo-8-[3-[N-[N'-(3-chlorophenyl)ureidoacetyl]-N-methylamino]-2,6-dichlorobenzyloxy]-2-methylimidazo[1,2-a]pyridine hydrochloride NMR (CDCl₃—CD₃OD, δ): 2.55 (3H, s), 3.29 (3H, s), 3.95 (1H, d, J=18 Hz), 4.16 (1H, d, J=18 Hz), 5.77 (2H, s), 7.18 (1H, m), 7.31 (2H, d, J=5 Hz), 7.50–7.72 (5H), 8.29 (1H, d, J=6 Hz)

(24) 3-Bromo-8-[2,6-dichloro-3-[N-[N'-(3-trifluoromethylphenyl)ureidoacetyl]-N-methylamino]benzyloxy]-2-methylimidazo[1,2-a]pyridine hydrochloride NMR (CDCl₃—CD₃OD, δ): 2.52 (3H, s), 3.30 (3H, s), 3.72 (2H, s), 5.69 (1H, d, J=10 Hz), 5.79 (1H, d, J=10 Hz), 7.23 (1H, m), 7.39 (2H, d, J=5 Hz), 7.50–7.73 (4H), 7.89 (1H, br s), 8.28 (1H, d, J=6 Hz)

(25) 8-[3-[N-[N'-(3-Acetylphenyl)ureidoacetyl]-N-methylamino]-2,6-dichlorobenzyloxy]-3-bromo-2-methylimidazo[1,2-a]pyridine hydrochloride NMR (CDCl₃—CD₃OD, δ): 2.54 (3H, s), 2.60 (3H, s), 3.30 (3H, s), 3.72 (2H, br s), 5.70 (1H, d, J=10 Hz), 5.80 (1H, d, J=10 Hz), 7.38 (1H, t, J=9 Hz), 7.49–7.72 (6H), 8.04 (1H, br s), 8.29 (1H, d, J=6 Hz)

(26) 3-Bromo-8-[3-[N-[N'-(3-cyanophenyl)ureidoacetyl]-N-methylamino]-2,6-dichlorobenzyloxy]-2-methylimidazo-[1,2-a]pyridine hydrochloride NMR (CDCl₃—CD₃OD, δ): 2.58 (3H, s), 3.29 (3H, s), 3.72 (2H, s), 5.69 (1H, d, J=10 Hz), 5.79 (1H, d, J=10 Hz), 7.25–7.72 (7H), 7.97 (1H, br s), 8.28 (1H, d, J=7 Hz)

(27) 3-Bromo-8-[2,6-dichloro-3-[N-[N'-(o-tolyl)ureidoacetyl]-N-methylamino]benzyloxy]-2-methylimidazo-1,2-a]pyridine hydrochloride NMR (CDCl₃—CD₃OD, δ): 2.25 (3H, s), 2.49 (3H, s), 3.28 (3H, s), 3.73 (2H, s), 5.68 (1H, d, J=10 Hz), 5.78 (1H, d, J=10 Hz), 6.95–7.20 (3H), 7.40–7.71 (5H), 8.29 (1H, d, J=6 Hz)

(28) 3-Bromo-8-[3-[N-[N'-(3-fluorophenyl)ureidoacetyl]-N-methylamino]-2,6-dichlorobenzyloxy]-2-methylimidazo-[1,2-a]pyridine hydrochloride NMR (CDCl₃—CD₃OD, δ): 2.55 (3H, s), 3.29 (3H, s), 3.71 (2H, s), 5.67 (1H, d, J=10 Hz), 5.78 (1H, d, J=10 Hz), 6.68 (1H, dt, J=8 Hz and 1 Hz), 6.93 (1H, br d, J=8 Hz), 7.20 (1H, dt, J=8 Hz and 6 Hz), 7.32 (1H, dt, J=10 Hz and 1 Hz), 7.48–7.71 (4H), 8.24 (1H, d, J=6 Hz)

(29) 3-Bromo-8-[3-[N-[N'-(3-ethylphenyl)ureidoacetyl]-N-methylamino]-2,6-dichlorobenzyloxy]-2-methylimidazo-[1,2-a]pyridine hydrochloride NMR (CDCl₃—CD₃OD, δ): 1.21 (3H, t, J=7 Hz), 2.52 (3H, s), 2.60 (2H, q, J=7 Hz), 3.28 (3H, s), 3.71 (2H, s), 5.65 (1H, d, J=10 Hz), 5.79 (1H, d, J=10 Hz), 6.87 (1H, m), 7.10–7.22 (3H), 7.52–7.71 (4H), 8.25 (1H, d, J=6 Hz)

(30) 8-[3-[N-(N'-Benzoylureidoacetyl)-N-methylamino]-2,6-dichlorobenzyloxy]-3-bromo-2-methylimidazo[1,2-a]pyridine hydrochloride NMR (CDCl₃—CD₃OD, δ): 2.62 (3H, s), 3.30 (3H, s), 3.75 (1H, d, J=18 Hz), 3.95 (1H, d, J=18 Hz), 5.68 (2H, s), 7.38–7.66 (7H), 7.89 (2H, d, J=8 Hz), 8.09 (1H, d, J=6 Hz)

(31) 3-Bromo-8-[2,6-dichloro-3-[N-methyl-N-[N'-(3-nitrophenyl)ureidoacetyl]amino]benzyloxy]-2-methylimidazo[1,2-a]pyridine hydrochloride NMR (CDCl₃—CD₃OD, δ): 2.63 (3H, s), 3.25 (3H, s), 3.92 (2H, s), 5.59 (1H, d, J=10 Hz), 5.68 (1H, d, J=10 Hz), 7.29–7.58 (5H), 7.70 (1H, dd, J=7 Hz and 1 Hz), 7.79 (1H, d, J=7 Hz), 8.10 (1H, d, J=6 Hz), 8.19 (1H, br s)

(32) 3-Bromo-8-[2,6-dichloro-3-[N-[N'-(3-ethoxycarbonylphenyl)ureidoacetyl]-N-methylamino]benzyloxy]-2-methylimidazo[1,2-a]pyridine hydrochloride NMR (CDCl₃—CD₃OD, δ): 1.30 (3H, t, J=7 Hz), 2.62 (3H, s), 3.21 (3H, s), 3.99 (2H, s), 4.20 (2H, q, J=7 Hz), 5.58 (2H, s), 7.12–7.52 (6H), 7.62–7.80 (2H), 8.01 (1H, d, J=6 Hz)

(33) 3-Bromo-8-[2,6-dichloro-3-[N-(N'-ethoxycarbonylmethylureidoacetyl)-N-methylamino]benzyloxy]-2-methylimidazo[1,2-a]pyridine hydrochloride NMR (CDCl₃, δ): 2.57 (3H, s), 3.28 (3H, s), 3.68 (2H, s), 3.89 (2H, s), 5.68 (1H, d, J=10 Hz), 5.78 (1H, d, J=10 Hz), 7.57–7.72 (4H), 8.29 (1H, d, J=6 Hz)

(34) 3-Bromo-8-[3-[N-[N'-[3-(N,N-dimethylcarbamoyl)phenyl]ureidoacetyl]-N-methylamino]-2,6-dichlorobenzyloxy2-methylimidazo[1,2-a]pyridine hydrochloride NMR (CDCl₃—CD₃OD, δ): 2.56 (3H, s), 3.01 (3H, br s), 3.11 (3H, br s), 3.30 (3H, s), 3.73 (2H, s), 5.68 (1H, d, J=10 Hz), 5.79 (1H, d, J=10 Hz), 7.00 (1H, d, J=8 Hz), 7.30 (1H, t, J=8 Hz), 7.38–7.70 (6H), 8.24 (1H, d, J=6 Hz)

(35) 3-Bromo-8-[2,6-dichloro-3-[N-[N-[3-(N-methylcarbamoyl)propionyl]glycyl]-N-methylamino]benzyloxy]-2-methylimidazo[1,2-a]pyridine hydrochloride NMR (CDCl₃—CD₃OD, δ): 2.25–2.70 (5H), 2.80 (3H, s), 3.26 (3H, s), 3.72 (1H, d, J=18 Hz), 3.89 (1H, d, J=18 Hz), 5.60 (1H, d, J=10 Hz), 5.70 (1H, d, J=10 Hz), 7.38–7.61 (4H), 8.09 (1H, d, J=6 Hz)

(36) 3-Bromo-8-[2,6-dichloro-3-[N-[N-(N-methyl-N-phenylglycyl)glycyl]-N-methylamino]benzyloxy]-2-methylimidazo[1,2-a]pyridine dihydrochloride NMR (CDCl₃—CD₃OD, δ): 2.69 (3H, s), 3.21 (3H, s), 3.29 (3H, s), 3.64 (1H, d, J=17 Hz), 3.81 (1H, d, J=17 Hz), 4.20 (1H, d, J=16 Hz), 4.32 (1H, d, J=16 Hz), 5.62 (2H, s), 7.20–7.61 (9H), 8.06 (1H, d, J=6 Hz)

(37) 3-Bromo-8-[2,6-dichloro-3-[N-[N'-(2-thienyl)ureidoacetyl]-N-methylamino]benzyloxy]-2-methylimidazo-[1,2-a]pyridine hydrochloride NMR (CDCl₃—CD₃CD, δ): 2.63 (3H, s), 3.30 (3H, s), 3.81 (1H, d, J=17 Hz), 3.93 (1H, d, J=17 Hz), 5.62 (1H, d, J=10 Hz), 5.72 (1H, d, J=10 Hz), 7.09 (1H, dd, J=5 Hz and 4 Hz), 7.45–7.59 (5H), 7.69 (1H, d, J=4 Hz), 8.09 (1H, dd, J=5 Hz and 1 Hz)

(38) 3-Bromo-8-[3-[N-[N'-(3-carboxyphenyl)ureidoacetyl]-N-methylamino]-2,6-dichlorobenzyloxy]-2-methylimidazo-[1,2-a]pyridine hydrochloride NMR (CDCl₃—CD₃OD, δ): 2.52 (3H, s), 3.29 (3H, s), 3.75 (2H, s), 5.68 (1H, d, J=10 Hz), 5.79 (1H, d, J=10 Hz), 7.32 (1H, t, J=8 Hz), 7.49–7.72 (6H), 8.05 (1H, br s), 8.28 (1H, d, J=6 Hz)

(39) 3-Chloro-8-[2,6-dichloro-3-[N-[N-(N,N-dimethylglycyl)glycyl]-N-methylamino]benzyloxy]-2-methylimidazo[1,2-a]pyridine dihydrochloride NMR (CDCl₃—CD₃OD, δ): 2.65 (3H, s), 2.96 (3H, s), 2.99 (3H, s), 3.22 (3H, s), 3.62–4.04 (4H), 5.68 (2H, s), 7.38–7.68 (4H), 8.08 (1H, d, J=6 Hz)

(40) 8-[2,6-Dichloro-3-[N-[N-(N,N-dimethylglycyl)glycyl]-N-methylamino]benzyloxy]-3-iodo-2-methylimidazo-[1,2-a]pyridine dihydrochloride NMR (CDCl₃—CD₃OD, δ): 2.58 (3H, s), 2.97 (6H, s), 3.27 (3H, s), 3.61 (1H, d, J=18 Hz), 3.88 (1H, d, J=18 Hz), 4.01 (2H, s), 5.72 (2H, s), 7.50–7.75 (4H), 8.28 (1H, d, J=6 Hz)

(41) 3-Bromo-8-[2,6-dichloro-4-(N-acetyl-N-methylamino)benzyloxy]-2-methylimidazo[1,2-a]pyridine hydrochloride mp: 118°–121° C.

NMR (DMSO-d₆, δ): 2.03 (3H, br s), 2.38 (3H, s), 3.25 (3H, s), 5.51 (2H, s), 7.36 (1H, t, J=7 Hz), 7.50 (1H, d, J=7 Hz), 7.71 (2H, s), 8.20 (1H, d, J=7 Hz)

(42) 3-Chloro-8-[2,6-dichloro-4-(N-acetyl-N-methylamino)benzyloxy]-2-methylimidazo[1,2-a]pyridine hydrochloride NMR (DMSO-d₆, δ): 2.01 (3H, br s), 2.38 (3H, s), 3.25 (3H, s), 5.50 (2H, s), 7.35 (1H, t, J=7 Hz), 7.50 (1H, d, J=7 Hz), 7.72 (2H, s), 8.22 (1H, d, J=7 Hz)

Preparation 34

To a stirred two-phase solution of 3-nitrobenzoyl chloride (9.3 g) in a mixture of diethyl ether (50 ml) and saturated sodium bicarbonate solution (50 ml) was added 3-aminomethylpyridine (5.4 g) in an ice-cooled bath. The mixture was stirred vigorously at ambient temperature for 30 minutes. The reaction mixture was filtered, and the resulting solid was washed with water. The solid was further solidified with diisopropyl alcohol-water to afford 3-nitro-N-(3-pyridylmethyl)benzamide (5.91 g) as a pale yellow amorphous solid.

p NMR (CDCl$_3$, δ): 4.70 (2H, d, J=5 Hz), 7.05 (1H, br s), 7.30 (1H, dd, J=7, 5 Hz), 7.68 (1H, t, J=9 Hz), 7.76 (1H, dt, J=8, 0.5 Hz), 8.22 (1H, d, J=8 Hz), 8.39 (1H, m), 8.54 (1H, dd, J=5, 0.5 Hz), 8.60 (1H, d, J=0.5 Hz), 8.65 (1H, t, J=0.5 Hz)

Preparation 35

To a solution of N,N-bis(2-methoxyethyl)amine (2.40 g) and triethylamine (2.27 g) in dichloromethane (30 ml) was added 3-nitrobenzoyl chloride (2.78 g) in an ice-water bath. The mixture was stirred at ambient temperature for 1 hour. The reaction mixture was washed with saturated sodium bicarbonate solution, water and brine, dried over anhydrous magnesium sulfate, and evaporated in vacuo. The residue was purified with column chromatography eluting with dichloromethane-methanol to give N,N-bis(2-methoxyethyl)-3-nitrobenzamide (4.12 g) as an oil.

p NMR (CDCl$_3$, δ): 3.22–3.88 (14H), 7.59 (1H, t, J=8 Hz), 7.80 (1H, dt, J=8, 1 Hz), 8.26 (1H, dt, J=8, 1 Hz), 8.39 (1H, t, J=1 Hz)

Preparation 36

The following compounds were obtained according to similar manners to those of Preparations 34 or 35.

(1) 3-Nitro-N-(4-pyridyl)benzamide
mp: >250° C.
NMR (DMSO-d$_6$, δ): 7.80 (2H, d, J=6 Hz), 7.89 (1H, t, J=7 Hz), 8.38–8.58 (4H), 8.80 (1 Hz t, J=1 Hz)

(2) 4-Methyl-1-(3-nitrobenzoyl)piperazine
mp: 97°–98° C.
NMR (CDCl$_3$, δ): 2.31–2.66 (7H), 3.38–3.97 (4H), 7.62 (1H, dt, J=8, 1 Hz), 7.78 (1H, dt, J=1, 8 Hz), 8.25–8.34 (2H)

(3) 1-(3-Nitrobenzoyl)pyrrolidine
mp: 67° C.
NMR (CDCl$_3$, δ): 1.85–2.10 (4H, m), 3.45 (2H, t, J=6 Hz), 3.69 (2H, t, J=6 Hz), 7.61 (1H, t, J=8 Hz), 7.89 (1H, dif-ddd, J=8 Hz), 8.29 (1H, dif-ddd, J=8 Hz), 8.40 (1H, dif-dd)

Preparation 37

To a stirred solution of 3-nitro-N-(3-pyridylmethyl)benzamide (2.00 g) in tetrahydrofuran (40 ml) was added potassium tert-butoxide (917 mg) in one portion in an ice-cooled bath. The stirring was continued for 40 minutes and then iodomethane (0.53 ml) was added thereto. The reaction mixture was stirred at 0° C. for one hour, then at ambient temperature for five hours. Saturated sodium bicarbonate solution was added thereto and the mixture was extracted with ethyl acetate. The organic layer was washed with water and saturated sodium chloride solution. After dried over anhydrous magnesium sulfate and filtered, the solvent was removed in vacuo and the residue was purified by flash chromatography (methanol-chloroform 3%, V/V) to afford 3-nitro-N-methyl-N-(3-pyridylmethyl)benzamide (1.8 g) as an yellow oil.

p NMR (CDCl$_3$, δ): 2.80–3.22 (3H, m), 4.40–4.93 (2H, m), 7.30–7.42 (1H, m), 7.44–7.90 (3H, m), 8.24–8.37 (2H, m), 8.40–8.75 (2H, m)

Preparation 38

Ethyl 4-[N-(3-pyridylmethyl)acetamido]cinnamate was obtained by reacting ethyl 4-acetamidocinnamate with 3-pyridylmethyl chloride according to a similar manner to that of Preparation 37.

p NMR (CDCl$_3$, δ): 1.34 (3H, t, J=7 Hz), 1.92 (3H, s), 4.29 (2H, q, J=7 Hz), 4.90 (2H, s), 6.41 (1H, d, J=15 Hz), 7.02 (2H, d, J=7 Hz), 7.24 (1H, m), 7.51 (2H, d, J=7 Hz), 7.60–7.70 (2H), 8.38 (1H, br s), 8.51 (1H, d, J=3 Hz)

Preparation 39

A mixture of N,N-bis(2-methoxyethyl)-3-nitrobenzamide (4.11 g) and palladium on charcoal (411 mg) in ethyl acetate (41 ml) was hydrogenated under 1 atmospheric pressure of hydrogen for 1 hour at ambient temperature. The catalyst was removed by filtration and washed with ethyl acetate, and the volatiles were removed in vacuo. The residue was purified with column chromatography eluting with dichloromethane-methanol to give 3-amino-N,N-bis(2-methoxyethyl)benzamide (3.62 g) as an oil.

p NMR (CDCl$_3$, δ): 3.19–3.86 (16H), 6.62–6.79 (3H), 7.16 (1H, dt, J=8, 1 Hz)

Preparation 40

The following compounds were obtained according to a similar manner to that of Preparation 39.

(1) 3-Amino-N-methyl-N-(3-pyridylmethyl)benzamide
NMR (CDCl$_3$, δ): 2.87 (3H, br s), 3.75 (1H, or 2H, br s), 4.41–4.88 (2H, m), 6.55–6.84 (3H, m), 7.03–7.40 (2H, m), 7.42–7.84 (1H, m), 8.35–8.70 (2H, m)

(2) 3-Amino-N-(4-pyridyl)benzamide
mp: 232°–234° C.
NMR (DMSO-d$_6$, δ): 5.39 (2H, br s), 6.79 (1H, br d, J=8 Hz), 7.02–7.11 (2H), 7.19 (1H, t, J=8 Hz), 7.78 (2H, d, J=7 Hz), 8.46 (2H, d, J=7 Hz)

(3) 1-(3-Aminobenzoyl)-4-methylpiperazine
mp: 114°–116° C.
NMR (CDCl$_3$, δ): 2.28–2.60 (7H), 3.38–3.90 (6H), 6.68–6.79 (3H), 7.68 (1H, t, J=8 Hz)

(4) 1-(3-Aminobenzoyl)pyrrolidine
NMR (CDCl$_3$, δ): 1.75–2.05 (4H, m), 3.40 (2H, t, J=6 Hz), 3.60 (2H, t, J=6 Hz, 3.72 (2H, br s), 6.71 (1H, dif-ddd, J=8 Hz), 6.78–6.89 (2H, m), 7.10 (1H, t, J=8 Hz)

(5) 3-Amino-N-(3-pyridylmethyl)benzamide
NMR (CDCl$_3$—CD$_3$OD, δ): 4.60 (2H, s), 6.82 (1H, dt, J=8, 1 Hz), 7.10–7.39 (4H), 7.79 (1H, dt, J=9, 1 Hz), 8.45 (1H, dd, J=5, 1 Hz), 8.52 (1H, d, J=1 Hz)

Preparation 41

To a stirred solution of 3-amino-N,N-bis(2-methoxyethyl)benzamide (1.01 g) in 1,4-dioxane (10 ml) was added 1N sodium hydroxide solution (5.2 ml) and phenyl chloroformate (0.55 ml) successively in an ice-cooled bath. The bath was removed and the reaction mixture was stirred vigorously for 1 hour, during which time phenyl chloroformate (0.25 ml) was further added. The mixture was extracted with dichloromethane and the organic layer was washed with water twice and brine, dried over anhydrous magnesium sulfate, and evaporated in vacuo. The residue was crystallized from diisopropyl ether to give phenyl 3[N,N-bis(2-methoxyethyl)carbamoyl]phenylcarbamate (1.30 g) as a colorless powder.

mp: 116°–118° C.

p NMR (CDCl$_3$, δ): 3.19–3.82 (14H), 7.10–7.57 (10H)

Preparation 42

The following compounds were obtained according to a similar manner to that of Preparation 41.

(1) Phenyl 3-[N-(4-pyridyl)carbamoyl]phenylcarbamate
mp: 204°–206° C.

NMR (DMSO-d$_6$, δ): 5.39 (1H, br s), 6.71–6.82 (2H), 7.02–7.33 (4H), 7.40–7.81 (4H), 8.09 (1H,. br s), 8.41–8.51 (2H), 9.32 (1H, br s)

(2) Phenyl 3-(4-methyl-1-piperazinylcarbonyl) phenylcarbamate
mp 152°–154° C.
mp: 152°–154° C.

NMR (CDCl$_3$, δ): 2.27–2.56 (7H), 3.38–3.91 (4H), 7.10–7.60 (9H)

(3) Phenyl 3-(1-pyrrolidinylcarbonyl)phenylcarbamate
mp: 135°–140° C.

NMR (CDCl$_3$, δ): 1.74–2.00 (4H, m), 3.45 (2H, t, J=6 Hz), 3.63 (2H, t, J=6 Hz), 7.07–7.53 (9H, m), 7.72 (1H, br s)

(4) Phenyl 3-[N-methyl-N-(3-pyridylmethyl)carbamoyl]-phenylcarbamate

NMR (CDCl$_3$, δ): 2.90–3.08 (3H), 4.58 (0.5H, br s), 4.76 (1.5H, br s), 7.15–7.80 (13H), 8.58 (1H, d, J=5 Hz)

(5) Phenyl 3-[N-(3-pyridylmethyl)carbamoyl] phenylcarbamate
mp: 185°–188° C.

NMR (CDCl$_3$—CD$_3$OD, δ): 4.62 (2H, s), 7.11–7.49 (7H), 7.56 (1H, dt, J=8, 1 Hz), 7.63–7.80 (2H), 7.84 (1H, t, J=1 Hz), 8.49 (1H, dd, J=5, 1 Hz), 8.55 (1H, d, J=1 Hz)

(6) Phenyl 3-(N,N-dimethylamino)phenylcarbamate
mp: 226°–228° C.

NMR (CDCl$_3$, δ): 2.93 (6H, s), 6.49 (1H, d, J=7 Hz), 6.65 (1H, d, J=7 Hz), 6.87 (1H, br s), 7.03 (1H, br s), 7.12–7.29 (4H), 7.32–7.42 (2H)

Preparation 43

(1) Ethyl 4-(phenoxycarbonylamino)cinnamate was obtained by reacting ethyl 4-aminocinnamate with phenyl chloroformate according to a similar manner to that of Preparation 42.
mp: 136°–138° C.

NMR (CDCl$_3$, δ): 1.33 (3H, t, J=7 Hz), 4.27 (2H, q, J=7 Hz), 6.39 (1H, d, J=15 Hz), 7.09 (1H, br s), 7.15–7.58 (9H), 7.65 (1H, d, J=15 Hz)

(2) A solution of ethyl 4-(phenoxycarbonylamino)cinnamate (500 mg) 3-aminopyridine (154 mg) and triethylamine (325 mg) in N,N-dimethylformamide (5 ml) was stirred for 2 hours at 80° C. Water was added thereto, and the resulting precipitate was collected by filtration to give ethyl 4-[3-(3-pyridyl)ureido]cinnamate (307 mg) as a colorless powder.
mp: 188°–189° C.

NMR (DMSO-d$_6$, δ): 1.26 (3H, t, J=7 Hz), 4.19 (2H, q, J=7 Hz), 6.50 (1H, d, J=15 Hz), 7.34 (1H, dd, J=9, 5 Hz), 7.46–7.72 (5H), 7.96 (1H, dt, J=9, 1 Hz), 8.21 (1H, dd, J=9, 1 Hz), 8.62 (1H, d, J=1 Hz), 8.98 (1H, br s), 9.10 (1H, m)

Preparation 44

To a mixture of ethyl 4-aminocinnamate (300 mg), triethylamine (167 mg) and dichloromethane (3 ml) was added a solution of propionyl chloride (182 mg) in dichloromethane (1 ml) in an ice-water bath, and the mixture was stirred for 1 hour at the same temperature. To the reaction mixture was added 4 drops of N,N-dimethylpropanediamine, and the mixture was further stirred for 5 minutes. The reaction mixture was washed with water, dried over magnesium sulfate, and evaporated in vacuo. The residue was crystallized from diisopropyl ether to give ethyl 4-propionamidocinnamate (341 mg) as a colorless powder.
mp 138° C.

p NMR (CDCl$_3$, δ): 1.26 (3H, t, J=8 Hz), 1.34 (3H, t, J=8 Hz), 2.42 (2H, q, J=8 Hz), 4.26 (2H, q, J=8 Hz), 6.37 (1H, d, J=16 Hz), 7.21 (1H, br s), 7.49 (2H, d, J=8 Hz), 7.58 (2H, d, J=8 Hz), 7.68 (1H, d, J=16 Hz)

Preparation 45

To a solution of ethyl 4-aminocinnamate (2.00 g) and methoxyacetic acid (1.04 ml) in N,N-dimethylformamide (20 ml) were added 1-ethyl-3-(3-dimethylaminopropyl)carbodiimide hydrochloride (2.61 g) and 1-hydroxybenzotriazole (2.12 g) at ambient temperature, and the mixture was stirred for 1 hour at the same temperature. The reaction mixture was poured into water, and extracted with dichloromethane. The organic layer was washed with aqueous sodium bicarbonate solution and water, dried over magnesium sulfate, and evaporated in vacuo. The residue was crystallized from diisopropyl ether to give ethyl 4-(methoxyacetamido)cinnamate (2.34 g) as a pale yellow powder.
mp: 92.2° C.

p NMR (CDCl$_3$, δ): 1.34 (3H, t, J=7.5 Hz), 3.52 (3H, s), 4.03 (2H, s), 4.26 (2H, q, J=7.5 Hz), 6.88 (1H, d, J=16 Hz), 7.50 (2H, d, J=9 Hz), 7.62 (2H, d, J=9 Hz), 7.65 (1H, d, J=16 Hz), 8.34 (1H, br s)

Preparation 46

The following compounds were obtained according to similar manners to those of Preparations 44 or 45.

(1) Ethyl 4-(4-bromobutyramido)cinnamate
mp: 119°–124° C.

NMR (CDCl$_3$, δ): 1.32 (3H, t, J=7.5 Hz), 2.21 (2H, quint, J=6 Hz), 2.59 (2H, t, J=6 Hz), 3.66 (22H, t, J=6 Hz), 4.25 (2H, q, J=7.5 Hz), 6.34 (1H, d, J=16 Hz), 7.47 (2H, d, J=8 Hz), 7.55 (2H, d, J=8 Hz), 7.61 (1H, d, J=16 Hz)

(2) Ethyl 4-(methoxyacetamido)cinnamate
mp: 87°–92° C.

NMR (CDCl$_3$, δ): 1.34 (3H, t, J=7.5 Hz), 3.53 (3H, s), 4.03 (2H, s), 4.26 (2H, q, J=7.5 Hz), 6.37 (1H, d, J=16 Hz), 7.50 (2H, d, J=8 Hz), 7.63 (2H, d, J=8 Hz), 7.65 (1H, d, J=16 Hz), 8.35 (1H, br s)

(3) Ethyl 4-(isonicotinoylamino)cinnamate
mp: 179°–188° C.

NMR (CDCl$_3$, δ): 1.34 (3H, t, J=7.5 Hz), 4.26 (2H, q, J=7.5 Hz), 6.40 (1H, d, J=16 Hz), 7.52 (2H, d, J=9 Hz), 7.57 (1H, d, J=16 Hz), 7.65–7.78 (4H), 8.19 (1H, br s), 8.31 (2H, dd, J=6, 0.5 Hz)

(4) Ethyl 4-(morpholinocarbonylamino)cinnamate
mp: 170°–173° C.

NMR (CDCl$_3$, δ): 1.33 (3H, t, J=7 Hz), 3.43–3.56 (4H), 3.70–3.81 (4H), 4.28 (2H, q, J=7 Hz), 6.35 (1H, d, J=15 Hz), 6.49 (1H, br s), 7.40 (2H, d, J=9 Hz), 7.48 (2H, d, J=9 Hz), 7.63 (1H, d, J=15 Hz)

(5) Ethyl 4-(5-bromovaleramido)cinnamate
mp: 124.0° C.–134.7° C.

NMR (CDCl$_3$, δ): 1.33 (3H, t, J=7.5 Hz), 1.79–2.06 (4H, m), 2.42 (2H, t, J=6 Hz), 3.44 (2H, t, J=6 Hz), 4.26 (2H, q, J=7.5 Hz), 6.36 (1H, d, J=16 Hz), 7.30 (1H, br s), 7.49 (2H, d, J=8 Hz), 7.57 (2H, d, J=8 Hz), 7.64 (1H, d, J=16 Hz)

Preparation 47

To a solution of methyl 4-carboxycinnamate (160 mg) in methylene chloride was added methylamine hydrochloride (58 mg) and 1-ethyl-3-(3-dimethylaminopropyl) carbodiimide (140 mg) at ambient temperature, and the mixture was stirred for 2 hours. To this suspension was added 1-hydroxybenzotriazole (137 mg) and dimethylformamide (2 ml), and the mixture was stirred for 14 hours at same temperature. The reaction mixture was poured into water, and extracted with dichloromethane. The organic layer was washed with aqueous sodium bicarbonate solution and water, dried over magnesium sulfate, and evaporated in vacuo. The residue was crystallized from diisopropyl ether to give methyl 4-(methylcarbamoyl)cinnamate (82 mg) as a colorless powder.

mp: 210.5° C.

NMR (DMSO-$d_6$, $\delta$): 2.79 (3H, d, J=5 Hz), 3.74 (3H, s), 6.74 (1H, d, J=16 Hz), 7.69 (1H, d, J=16 Hz), 7.80 (2H, d, J=8 Hz), 7.87 (2H, d, J=8 Hz), 8.51 (1H, q-like)

Preparation 48

To a stirred suspension of methyl 4-carboxycinnamate (400 mg) in thionyl chloride (1.4 ml) was added one drop or N,N-dimethylformamide. The mixture was refluxed for 20 minutes. The solvent was removed in vacuo. To the residue was added toluene (2 ml) and the mixture was evaporated in vacuo twice. The residue was dissolved with dichloromethane (4 ml), and 4-aminopyridine (201 mg) and triethylamine (0.81 ml) were added thereto in an ice-water-bath. After 10 minutes the mixture was stirred at ambient temperature. After 3 hours, to the reaction mixture was added water and the mixture was extracted with dichloromethane-methanol (5:1, V/V). The organic layer was washed with saturated sodium bicarbonate solution, water and brine, and dried over anhydrous magnesium sulfate. The solvent was evaporated in vacuo. The residue was crystallized from ethyl acetate to give methyl 4-[N-(4-pyridyl)carbamoyl]cinnamate (555 mg) as a colorless powder.

mp: 209°–211° C.

p NMR (DMSO-$d_6$, $\delta$): 3.76 (3H, s), 6.82 (1H, d, J=15 Hz), 7.69–7.83 (3H), 7.92 (2H, d, J=9 Hz), 8.01 (2H, d, J=9 Hz), 8.50 (2H, d, J=7 Hz)

Preparation 49

The following compounds were obtained according to similar manners to those of Preparations 47 or 48.

(1) Methyl 4-(N,N-dimethylcarbamoyl)cinnamate
mp: 130° C.
NMR (CDCl$_3$, $\delta$): 3.00 (3H, s), 3.12 (3H, s), 3.83 (3H, s), 6.49 (1H, d, J=16 Hz), 7.45 (2H, d, J=8 Hz), 7.58 (2H, d, J=8 Hz), 7.70 (1H, d, J=16 Hz)

(2) Methyl 4-[N-(2-methoxyethyl)carbamoyl]cinnamate
mp: 122°–124° C.
NMR (CDCl$_3$, $\delta$): 3.40 (3H, s), 3.53–3.72 (4H), 3.83 (3H, s), 6.45–6.60 (3H), 7.58 (2H, d, J=8 Hz), 7.71 (1H, d, J=15 Hz), 7.80 (2H, d, J=8 Hz)

(3) Methyl 4-[N,N-bis(2-methoxyethyl)carbamoyl]cinnamate
NMR (CDCl$_3$, $\delta$): 3.21–3.86 (17H), 6.48 (1H, d, J=15 Hz), 7.44 (1H, d, J=9 Hz), 7.57 (1H, d, J=9 Hz), 7.70 (1H, d, J=15 Hz)

Preparation 50

To a solution of ethyl 4-aminocinnamate (150 mg) in methylene chloride were added methyl isocyanate (0.06 ml) under nitrogen atmosphere at ambient temperature, and the mixture was stirred for 2 hours at the same temperature. The reaction mixture was poured into the mixture of ethyl acetate and water. The organic layer was washed with water twice, dried over magnesium sulfate, and concentrated in vacuo. The residue was crystallized from diisopropyl ether to give ethyl 4-(3-methylureido)cinnamate (136 mg).

mp: 166° C.

p NMR (DMSO-$d_6$, $\delta$): 1.25 (3H, t, J=7.5 Hz), 2.64 (3H, d, J=5 Hz), 4.17 (2H, q, J=7.5 Hz), 6.12 (1H, q, J=5 Hz), 6.43 (1H, d, J=16 Hz), 7.45 (2H, d, J=8 Hz), 7.56 (1H, d, J=16 Hz), 7.59 (2H, d, J=8 Hz), 8.81 (1H, s)

Preparation 51

To a stirred solution of ethyl 4-(4-bromobutyramido) cinnamate (420 mg) in N,N-dimethylformamide (5 ml) was added potassium carbonate (552 mg) at ambient temperature and the resulting mixture was warmed at 50° C. for three hours. The reaction mixture was diluted with ethyl acetate and washed with water and brine. The organic phase was dried over anhydrous magnesium sulfate, and concentrated in vacuo. The residue was purified by flash column chromatography eluting with chloroform to afford ethyl 4-(2-oxo-1-pyrrolidinyl)cinnamate (281 mg) as a pale yellow solid.

mp: 134° C.

p NMR (CDCl$_3$, $\delta$): 1.34 (3H, t, J=7.7 Hz), 2.19 (2H, quint, J=7.7 Hz), 2.63 (2H, t, J=7.7 Hz), 3.88 (2H, t, J=7.7 Hz), 4.26 (2H, q, J=7.7 Hz), 6.38 (7H, d, J=16 Hz), 7.53 (2H, d, J=8 Hz), 7.64 (1H, d, J=16 Hz), 7.68 (2H, d, J=8 Hz)

Preparation 52

Ethyl 4-(2-oxopiperidino)cinnamate was obtained according to a similar manner to that of Preparation 51.

mp: 120.2° C.

p NMR (CDCl$_3$, $\delta$): 1.34 (3H, t, J=7.5 Hz), 1.83–2.05 (4H, ad ), 2.56 (2H, dif-t), 3.65 (2H dif-d), 4.26 (2H, g, J=7.5 Hz), 6.40 (1H, d, J=16 Hz), 7.29 (2H, d, J=8 Hz), 7.54 (2H, d, J=8 Hz), 7.65 (1H, d, J=16 Hz)

Preparation 53

A solution of ethyl 4-aminocinnamate (1 g) and 2,5-dimethoxytetrahydrofuran (0.677 ml) in toluene (3 ml) and acetic acid (3 ml) was refluxed for 5 hours with removing methane. After cooling, the mixture was washed with water twice and saturated sodium bicarbonate solution, dried over anhydrous magnesium sulfate. The solvent was evaporated in vacuo. The residue was purified with column chromatography eluting with n-hexane-ethyl acetate to give ethyl 4-(1-pyrrolyl)cinnamate (740 mg) as colorless crystals.

mp: 86°–87° C.

NMR (CDCl$_3$, $\delta$): 1.37 (3H, t, J=7 Hz), 4.29 (2H, q, J=7 Hz), 6.32–6.49 (2H), 7.12 (2H, t, J=1 Hz), 7.41 (2H, d, J=9 Hz), 7.60 (2H, d, J=9 Hz), 7.69 (1H, d, J=16 Hz)

Preparation 54

Ethyl 4-(N-methyl-2-methoxyacetamido)cinnamate was obtained according to a similar manner to that of Preparation 37.

p NMR (CDCl$_3$, $\delta$): 1.35 (3H, t, J=7.5 Hz), 3.29 (3H, s), 3.35 (3H, s), 3.85 (2H, br s), 4.27 (2H, q, J=7.5 Hz), 6.46 (1H, d, J=16 Hz), 7.24 (2H, d, J=8 Hz), 7.57 (2H, d, J=8 Hz), 7.67 (1H, d, J=16 Hz)

Preparation 55

To a solution of ethyl 4-propionamidocinnamate (160 mg) in ethanol (5 ml) was added 1N aqueous sodium hydroxide solution (1.5 ml) at ambient temperature. The mixture was stirred at same temperature for 14 hours, and then at 40° C. for 2 hours. 1N-hydrochloric acid (1.5 ml) was added to the reaction mixture and evaporated in vacuo. The residue was diluted with 10% methanol-dichloromethane, washed with water, dried over magnesium sulfate and evaporated in vacuo. The residue was crystallized from diisopropyl ether to give 4-propionamidocinnamic acid (115 mg) as a colorless powder.

mp: 243° C.

p NMR (DMSO-$d_6$, δ): 1.08 (3H, t, J=8 Hz), 2.34 (2H, q, J=8 Hz), 6.39 (1H, d, J=16 Hz), 7.51 (1H, d, J=16 Hz), 7.62 (4H, s-like), 10.07 (1H, s)

Preparation 56

The following compounds were obtained according to a similar manner to that of Preparation 55.

(1) 4-(Methylcarbamoyl)cinnamic acid
mp: >250° C.

NMR (DMSO-$d_6$, δ): 2.78 (3H, d, J=5 Hz), 6.62 (1H, d, J=16 Hz), 7.61 (1H, d, J=16 Hz), 7.77 (2H, d, J=8 Hz), 7.85 (2H, d, J=8 Hz), 8.51 (1H, q-like)

(2) 4-(N,N-Dimethylcarbamoyl)cinnamic acid
mp: 82° C.

NMR (DMSO-$d_6$, δ): 2.93 (3H, s), 2.97 (3H, s), 6.59 (1H, d, J=16 Hz), 7.43 (2H, d, J=8 Hz), 7.61 (1H, d, J=16 Hz), 7.75 (2H, d, J=8 Hz)

(3) 4-(3-Methylureido)cinnamic acid
mp: 234° C.

NMR (DMSO-$d_6$, δ): 2.64 (3H, d, J=5 Hz), 6.12 (1H, q, J=5 Hz), 6.33 (1H, d, J=16 Hz), 7.44 (2H, d, J=8 Hz), 7.51 (1H, d, J=16 Hz), 7.55 (2H, d, J=8 Hz), 8.78 (1H, s)

(4) 4-[N-(2-Methoxyethyl)carbamoyl]cinnamic acid
mp: 207°–209° C.

NMR (DMSO-$d_6$, δ): 3.20–3.50 (7H), 6.63 (1H, d, J=15 Hz), 7.62 (1H, d, J=15 Hz), 7.79 (2H, d, J=8 Hz), 7.89 (2H, d, J=8 Hz), 8.61 (1H, br s)

(5) 4-[N,N-Bis(2-methoxyethyl)carbamoyl]cinnamic acid

NMR (CDCl$_3$, δ): 3.21–3.86 (17H), 6.48 (1H, d, J=15 Hz), 7.44 (2H, d, J=9 Hz), 7.57 (2H, d, J=9 Hz), 7.70 (1H, d, J=15 Hz)

(6) 4-[N-(4-Pyridyl)carbamoylcinnamic acid
mp: >250° C.

NMR (DMSO-$d_6$, δ): 6.69 (1H, d, J=16 Hz), 7.52–8.08 (7H), 8.49 (2H, d, J=6 Hz)

(7) 4-(2-Oxo-1-pyrrolidinyl)cinnamic acid
mp: >250° C.

NMR (DMSO-$d_6$, δ): 2.06 (2H, quint, J=8 Hz), 3.86 (2H, t, J=8 Hz), 6.46 (1H, d, J=16 Hz), 7.55 (1H, d, J=16 Hz), 7.65–7.76 (4H, m)

(8) 4-(Methoxyacetamido)cinnamic acid
mp: 201.5°–229° C.

NMR (CDCl$_3$, δ): 4.02 (2H, s), 6.43 (1H, d, J=16 Hz), 7.52 (1H, d, J=16 Hz), 7.63 (2H, d, J=8 Hz), 7.74 (2H, d, J=8 Hz), 9.97 (1H, s)

(9) 4-[N-(3-Pyridylmethyl)acetamido]cinnamic acid
mp: 184°–186° C.

NMR (DMSO-$d_6$, δ): 1.90 (3H, s), 4.91 (2H, s), 6.52 (1H, d, J=15 Hz), 7.21–7.39 (3H), 7.50–7.79 (4H), 8.39 (1H, d, J=2 Hz), 8.43 (1H, dd, J=5, 2 Hz)

(10) 4-(Isonicotinoylamino)cinnamic acid
mp: 283°–290° C.

NMR (DMSO-$d_6$, δ): 6.46 (1H, d, J=16.2 Hz), 7.53 (1H, d, J=16.2 Hz), 7.68 (2H, d, J=9 Hz), 7.79–7.91 (4H), 8.80 (2H, dd, J=6, 0.5 Hz)

(11) 4-[3-(3-Pyridyl)ureido]cinnamic acid
mp: 219°–221° C.

NMR (DMSO-$d_6$, δ): 6.40 (1H, d, J=15 Hz), 7.37 (1H, dd, J=9, 5 Hz), 7.47–7.70 (5H), 7.98 (1H, dt, J=9, 1 Hz), 8.21 (1H, br d, J=5 Hz), 8.62 (1H, d, J=1 Hz), 9.03 (1H, s), 9.16 (1H, s)

(12) 4-(Morpholinocarbonylamino)cinnamic acid
mp: 219°–221° C.

NMR (DMSO-$d_6$, δ): 3.39–3.49 (4H), 3.58–3.68 (4H), 6.37 (1H, d, J=15 Hz), 7.46–7.60 (5H), 8.76 (1H, br s)

(13) 4-(2-Oxopiperidino)cinnamic acid
mp: 235.7°–243.2° C.

NMR (DMSO-$d_6$, δ): 1.73–1.97 (4H, m), 2.39 (2H, dif-t), 3.61 (2H, dif-t), 6.51 (1H, d, J=16 Hz), 7.34 (2H, d, J=8 Hz), 7.59 (1H, d, J=16 Hz), 7.70 (2H, d, J=8 Hz)

(14) 4-(N-Methyl-2-methoxyacetamido)cinnamic acid
mp: 182.1° C.

NMR (DMSO-$d_6$, δ): 3.17 (3H, s), 3.20 (3H, s), 3.87 (2H, br s), 6.57 (1H, d, J=15 Hz), 7.39 (2H, d, J=9 Hz), 7.60 (1H, d, J=15 Hz), 7.74 (2H, d, J=9 Hz)

(15) 4-(1-Pyrrolyl)cinnamic acid
mp: 236°–240° C.

NMR (DMSO-$d_6$, δ): 6.30 (2H, t, J=1 Hz), 6.54 (1H, d, J=16 Hz), 7.48 (2H, t, J=1 Hz), 7.53–7.71 (3H), 7.80 (2H, d, J=9 Hz)

Preparation 57

To a solution of ethyl 4-aminocinnamate (150 mg) and triethylamine (94 mg) in methylene chloride (3 ml) was added mesyl chloride (0.08 ml) under ice-cooling under nitrogen atmosphere, and the mixture was stirred at ambient temperature for 2 hours. The reaction mixture was poured into water, and extracted with methylene chloride twice. The combined organic layer was washed with water, dried over magnesium sulfate and concentrated to give a residue including ethyl 4-mesylaminocinnamate and ethyl 4-(N,N-dimesylamino)cinnamate. The residue was dissolved in ethanol, and 1N aqueous sodium hydroxide solution (1.5 ml) was added thereto at 40° C. The mixture was stirred at ambient temperature for 2 days, and 1N hydrochloric acid (1.5 ml) was added thereto. The mixture was concentrated in vacuo, and the residue was partitioned between 10% methanol-methylene chloride and water. The organic layer was washed with water, dried over magnesium sulfate and concentrated in vacuo. The residue was purified by preparative thin-layer chromatography (methylene chloride-methanol, 10:1, V/V) to give 4-mesylaminocinnamic acid (49.3 mg).

mp: 218° C.

p NMR (DMSO-$d_6$, δ): 3.05 (3H, s), 6.44 (1H, d, J=16 Hz), 7.21 (2H, d, J=8 Hz), 7.53 (1H, d, J=16 Hz), 7.66 (2H, d, J=8 Hz)

Preparation 58

4-(N,N-Dimethylcarbamoyl)benzaldehyde was obtained by reacting 4-formylbenzoic acid with dimethylamine hydrochloride according to a similar manner to that of Preparation 47.

mp: 60°–67° C.

p NMR (CDCl$_3$, δ): 2.97 (3H, s), 3.15 (3H, s), 7.59 (2H, d, J=7.5 Hz), 7.94 (2H, d, J=7.5 Hz), 10.3 (1H,

Preparation 59

A mixture of 2-acetylamino-5-formylpyridine (241 mg) and malonic acid (168 mg) in pyridine (0.12 ml) and ethanol (0.36 ml) was refluxed for 2 hours. After cooling the mixture, the precipitate was collected by filtration, and washed ethyl acetate to give (E)-3-(6-acetylamino-3-pyridyl)acrylic acid (248 mg) as a colorless powder.

mp: 291°–292° C.

p NMR (DMSO-d$_6$, δ): 2.10 (3H, s), 6.55 (1H, d, J=16 Hz), 7.58 (1H, d, J=16 Hz), 8.07–8.21 (2H), 8.59 (1H, br s)

Preparation 60

The following compounds were obtained according to a similar manner to that of Preparation 59.

(1) (E)-3-(6-Ethoxycarbonyl-3-pyridyl)acrylic acid (from ethyl 5-formyl-2-pyridinecarboxylate)

mp: 201°–202° C.

NMR (DMSO-d$_6$, δ): 1.33 (3H, t, J=7 Hz), 4.36 (2H, q, J=7 Hz), 6.80 (1H, d, J=16 Hz), 7.69 (1H, d, J=16 Hz), 8.07 (1H, d, J=9 Hz), 8.33 (1H, dd, J=9, 2 Hz), 9.00 (1H, d, J=2 Hz)

(2) 4-(N,N-Dimethylcarbamoyl)cinnamic acid

NMR (CDCl$_3$, δ): 2.99 (3H, s), 3.11 (3H, s), 6.49 (1H, d, J=15 Hz), 7.46 (2H, d, J=8 Hz), 7.59 (2H, d, J=8 Hz), 7.76 (1H, d, J=15 Hz)

Preparation 61

To a suspension of sodium hydride (60% active, 124 mg) in dimethylformamide (2 ml) at ambient temperature was added ethyl 4-hydroxycinnamate (500 mg) under nitrogen, and the mixture was stirred for 1 hour. 2-Bromoethyl acetate (522 mg) was added to the mixture at same temperature, and the mixture was allowed to stand for 19 hours. The reaction mixture was poured into water and extracted with ethyl acetate. The organic layer was washed with water and brine, dried over magnesium sulfate and evaporated in vacuo. The residue was chromatographed on silica gel eluting with chloroform to give ethyl 4-(2-acetoxyethoxy)cinnamate (716 mg) as an oil.

p NMR (CDCl$_3$, δ): 1.33 (3H, t, J=7.5 Hz), 2.11 (3H, s), 4.19 (2H, t, J=6 Hz), 4.25 (2H, q, J=7.5 Hz), 4.44 (2H, t, J=6 Hz), 6.31 (1H, d, J=16 Hz), 6.94 (2H, d, J=8 Hz), 7.49 (2H, d, J=8 Hz), 7.64 (1H, d, J=16 Hz)

Preparation 62

4-(2-Hydroxyethoxy)cinnamic acid was obtained from ethyl 4-(2-acetoxyethoxy)cinnamate according to a similar manner to that of Preparation 55.

mp: 194° C.

p NMR (DMSO-d$_6$, δ): 3.64–3.79 (2H, br peak), 4.02 (2H, t, J=6 Hz), 4.90 (1H, br peak), 6.37 (1H, d, J=16 Hz), 6.98 (2H, d, J=8 Hz), 7.54 (1H, d, J=16 Hz), 7.63 (2H, d, J=8 Hz)

Example 74

The following compounds were obtained according to similar manners to those of Examples 53 or 69.

(1) 3-Bromo-8-[2,6-dichloro-3-[N-methyl-N-[(thiomorpholinoacetyl)glycyl]amino]benzyloxy]-2-methylimidazo[1,2-a]pyridine NMR (CDCl$_3$, δ): 2.44 (3H, s), 2.66–2.88 (8H), 3.01 (2H, s), 3.28 (3H, s), 3.55 (1H, dd, J=18, 5 Hz), 3.82 (1H, dd, J=18, 5 Hz), 5.50 (2H, s), 6.71 (1H, d, J=7 Hz), 6.87 (1H, t, J=7 Hz), 7.32 (1H, d, J=9 Hz), 7.50 (1H, d, J=9 Hz), 7.78 (1H, d, J=7 Hz), 7.90 (1H, br s)

(2) 3-Bromo-8-[2,6-dichloro-3-[N-[(N,N-dimethyl-β-alanyl)glycyl]-N-methylamino]benzyloxy]-2-methylimidazo[1,2-a]pyridine NMR (CDCl$_3$, δ): 2.39–2.56 (11H), 2.78 (2H, t, J=6 Hz), 3.24 (3H, s), 3.55 (1H, dd, J=17, 4 Hz), 3.82 (1H, dd, J=17, 5 Hz), 5.50 (2H, s), 6.71 (1H, d, J=7 Hz), 6.87 (1H, t, J=7 Hz), 7.34 (1H, d, J=9 Hz), 7.49 (1H, d, J=9 Hz), 7.79 (1H, d, J=7 Hz), 8.49 (1H, br s)

Example 75

The following compounds were obtained according to similar manners to those of Examples 36 to 39.

(1) 3-Bromo-8-[2,6-dichloro-3-[N-methyl-N-[(2-pyrimidinylthio)acetyl]glycyl]amino]benzyloxy]-2-methylimidazo[1,2-a]pyridine mp: 212°–212.5° C.

p NMR (CDCl$_3$, δ): 2.42 (3H, s), 3.21 (3H, s), 3.52 (1H, dd, J=18, 5 Hz), 3.70–3.89 (3H), 5.49 (2H, s), 6.71 (1H, d, J=7 Hz), 6.87 (1H, t, J=7 Hz), 7.07 (1H, t, J=5 Hz), 7.28 (1H, d, J=9 Hz), 7.47 (1H, d, J=9 Hz), 7.77 (1H, d, J=7 Hz), 8.03 (1H, br s), 8.62 (2H, d, J=5 Hz)

(2) 3-Bromo-8-[2,6-dichloro-3-[N-methyl-N-[(phenoxyacetyl)glycyl]amino]benzyloxy]-2-methylimidazo[1,2-a]pyridine NMR (CDCl$_3$, δ): 2.43 (3H, s), 3.28 (3H, s), 3.62 (1H, dd, J=17, 5 Hz), 3.89 (1H, dd, J=17, 5 Hz), 4.50 (2H, s), 5.50 (2H, s), 6.71 (1H, d, J=7 Hz), 6.80–7.09 (4H), 7.22–7.39 (3H), 7.46–7.60 (2H), 7.78 (1H, d, J=7 Hz)

(3) 3-Bromo-8-[2,6-dichloro-3-[N-[(heptafluorobutanoyl)glycyl]-N-methylamino]benzyloxy]-2-methylimidazo-[1,2-a]pyridine NMR (CDCl$_3$, δ): 2.44 (3H, s), 3.29 (3H, s), 3.62 (1H, dd, J=17, 4 Hz), 3.87 (1H, dd, J=17, 5 Hz), 5.51 (2H, s), 6.71 (1H, d, J=7 Hz), 6.87 (1H, t, J=7 Hz), 7.32 (1H, d, J=9 Hz), 7.41–7.55 (2H), 7.78 (1H, d, J=7 Hz)

(4) 3-Bromo-8-[2,6-dichloro-3-[N-(n-heptanoylglycyl)-N-methylamino]benzyloxy]-2-methylimidazo[1,2-a]pyridine NMR (CDCl$_3$, δ): 0.88 (3H, t, J=7 Hz), 1.16–1.40 (6H), 1.50–1.77 (2H), 2.21 (2H, t, J=7 Hz), 2.42 (3H, s), 3.25 (3H, s), 3.52 (1H, dd, J=18, 4 Hz), 3.80 (1H, dd, J=18, 5 Hz), 5.49 (2H, s), 6.41 (1H, br t, J=5 Hz), 6.72 (1H, d, J=7 Hz), 6.85 (1H, t, J=7 Hz), 7.31 (1H, d, J=9 Hz), 7.48 (1H, d, J=9 Hz), 7.78 (1H, d, J=7 Hz)

(5) 3-Bromo-8-[2,6-dichloro-3-[N-methyl-N-(cinnamoylglycyl)amino]benzyloxy]-2-methylimidazo[1,2-a]pyridine NMR (CDCl$_3$, δ): 2.43 (3H, s), 3.29 (3H, s), 3.69 (1H, dd, J=17, 5 Hz), 3.92 (1H, dd, J=17, 5 Hz), 5.50 (2H, s), 6.49 (1H, d, J=15 Hz), 6.62 (1H, br s), 6.72 (1H, d, J=7 Hz), 6.86 (1H, t, J=7 Hz), 7.30–7.64 (8H), 7.78 (1H, d, J=7 Hz)

(6) 3-Bromo-8-[2,6-dichloro-3-[N-methyl-N-[(trans-3-pentenoyl)glycyl]amino]benzyloxy]-2-methylimidazo[1,2-a]pyridine NMR (CDCl$_3$, δ): 1.72 (3H, d, J=5 Hz), 2.43 (3H, s), 2.95 (2H, d, J=5 Hz), 3.25 (3H, s), 3.51 (1H, dd, J=18, 4 Hz), 3.79 (1H, dd, J=18, 5 Hz), 5.43–5.79 (4H), 6.60 (1H, br s), 6.71 (1H, d, J=7 Hz), 6.87 (1H, t, J=7 Hz), 7.30 (1H, d, J=9 Hz), 7.49 (1H, d, J=9 Hz), 7.78 (1H, d, J=7 Hz)

(7) 3-Bromo-8-[3-[N-[(3-butenoyl)glycyl]-N-methylamino]-2,6-dichlorobenzyloxy]-2-methylimidazo[1,2-a]pyridine NMR (CDCl$_3$, δ): 2.43 (3H, s), 3.02 (2H, d, J=7 Hz), 3.25 (3H, s), 3.52 (1H, dd, J=18, 4 Hz), 3.79 (1H, dd, J=18, 5 Hz), 5.19–5.32 (2H), 5.49 (2H, s), 6.94 (1H, m), 6.59 (1H, br s), 6.72 (1H, d, J=7 Hz), 6.87 (1H, t, J=7 Hz), 7.30 (1H, d, J=9 Hz), 7.48 (1H, d, J=9 Hz), 7.78 (1H, d, J=7 Hz)

(8) 3-Bromo-8-[2,6-dichloro-3-[N-methyl-N-[(4-phenylbutanoyl)glycyl]amino]benzyloxy]-2-methylimidazo[1,2-a]pyridine NMR (CDCl$_3$, δ): 1.86–2.06 (2H), 2.22 (2H, t, J=8 Hz), 2.42 (3H, s), 2.63 (2H, t, J=8 Hz), 3.25 (3H, s), 3.51 (1H, dd, J=17, 5 Hz), 3.79 (1H, dd, J=17, 5 Hz), 5.49 (2H, s), 6.39 (1H, br s), 6.71 (1H, d, J=7 Hz), 6.86 (1H, t, J=7 Hz), 7.11–7.34 (6H), 7.48 (1H, d, J=9 Hz), 7.78 (1H, d, J=7 Hz)

(9) 3-Bromo-8-[2,6-dichloro-3-[N-methyl-N-[4-(methylcarbamoyl)cinnamoylglycyl]amino]benzyloxy]-2-methylimidazo[1,2-a]pyridine NMR (CDCl₃, δ): 2.45 (3H, s), 3.03 (3H, d, J=5 Hz), 3.28 (3H, s), 3.66 (1H, dd, J=4, 18 Hz), 3.92 (1H, dd, J=4, 18 Hz), 5.46 (1H, d, J=10 Hz), 5.53 (1H, d, J=10 Hz), 6.16 (1H, q-like), 6.53 (1H, d, J=16 Hz), 6.62–6.78 (2H, m), 6.85 (1H, t, J=7.5 Hz), 7.33 (1H, d, J=8 Hz), 7.45–7.68 (4H, m), 7.70–7.82 (3H, m)

(10) 3-Bromo-8-[2,6-dichloro-3-[N-[4-(dimethylcarbamoyl)cinnamoylglycyl]-N-methylamino]benzyloxy]-2-methylimidazo[1,2-a]pyridine NMR (CDCl₃, δ): 2.45 (3H, s), 2.99 (3H, br s), 3.10 (3H, br s), 3.29 (3H, s), 3.69 (1H, dd, J=17, 4 Hz), 3.91 (1H, dd, J=17, 5 Hz), 5.47 (1H, d, J=10 Hz), 5.52 (1H, d, J=10 Hz), 6.50 (1H, d, J=15 Hz), 6.65 (1H, br t, J=4 Hz), 6.71 (1H, d, J=7 Hz), 6.86 (1H, t, J=7 Hz), 7.29–7.62 (7H), 7.78 (1H, d, J=7 Hz)

(11) 3-Bromo-8-[2,6-dichloro-3-[N-[4-(2-methoxyethylcarbamoyl)cinnamoylglycyl]-N-methylamino]benzyloxy]-2-methylimidazo[1,2-a]pyridine NMR (CDCl₃, δ): 2.44 (3H, s), 3.29 (3H, s), 3.40 (3H, s), 3.52–3.77 (5H), 3.91 (1H, dd, J=17, 5 Hz), 5.50 (2H, s), 6.48–6.61 (2H), 6.63–6.79 (2H), 6.88 (1H, t, J=7 Hz), 7.33 (1H, d, J=9 Hz), 7.46–7.65 (4H), 7.72–7.83 (3H)

(12) 8-[3-[N-[4-[N,N-Bis(2-methoxyethyl)carbamoyl]-cinnamoylglycyl]-N-methylamino]-2,6-dichlorobenzyloxy]-3-bromo-2-methylimidazo[1,2-a]-pyridine NMR (CDCl₃, δ): 2.44 (3H, s), 3.21–3.82 (15H), 3.92 (1H, dd, J=17, 5 Hz), 5.48 (1H, d, J=10 Hz), 5.56 (1H, d, J=10 Hz), 6.50 (1H, d, J=15 Hz), 6.65 (1H br t, J=4 Hz), 6.73 (1H, d, J=7 Hz), 6.88 (1H, t, J=7 Hz), 7.30–7.62 (7H), 7.78 (1H, d, J=7 Hz)

(13) 3-Bromo-8-[2,6-dichloro-3-[N-methyl-N-[4-(4-pyridylcarbamoyl)cinnamoylglycyl]amino]benzyloxy]-2-methylimidazo[1,2-a]pyridine NMR (CDCl₃, δ): 2.40 (3H, s), 3.25 (3H, s), 3.65 (1H, dd, J=17, 4 Hz), 3.90 (1H, dd, J=17, 5 Hz), 5.42 (1H, d, J=10 Hz), 5.51 (1H, d, J=10 Hz), 6.51 (1H, d, J=15 Hz), 6.69–6.80 (2H), 6.87 (1H, t, J=7 Hz), 7.30 (1H, d, J=9 Hz), 7.41–7.69 (6H), 7.78 (1H, d, J=7 Hz), 7.87 (2H, d, J=8 Hz), 8.43–8.59 (3H)

(14) 3-Bromo-8-[2,6-dichloro-3-[N-methyl-N-[4-(2-oxo-1-pyrrolidinyl)cinnamoylglycyl]amino]benzyloxy]-2-methylimidazo[1,2-a]pyridine NMR (CDCl₃, δ): 2.15 (1H, quint, J=7.5 Hz), 2.41 (3H, s), 2.63 (2H, t, J=7.5 Hz), 3.26 (3H, s), 3.65 (1H, dd, J=4, 18 Hz), 3.80–3.99 (3H, m), 5.43–5.57 (2H, m), 6.43 (1H, d, J=16 Hz), 6.60 (1H, t-like), 6.73 (1H, d, J=8 Hz), 6.85 (1H, t, J=8 Hz), 7.32 (1H, d, J=8 Hz), 7.45–7.61 (4H, m), 7.67 (2H, d, J=8 Hz), 7.78 (1H, d, J=6 Hz)

(15) 3-Bromo-8-[2,6-dichloro-3-[N-[4-(methoxyacetamido)cinnamoylglycyl]-N-methylamino]benzyloxy]-2-methylimidazo[1,2-a]pyridine NMR (CDCl₃, δ): 2.43 (3H, s), 3.26 (3H, s), 3.50 (3H, s), 3.65 (1H, dd, J=4, 18 Hz), 3.90 (1H, dd, J=4, 18 Hz), 4.01 (2H, s), 5.42–5.57 (2H, m), 6.40 (1H, d, J=16 Hz), 6.59 (1H, t-like), 6.72 (1H, d, J=7.5 Hz), 6.85 (1H, t, J=7.5 Hz), 7.32 (1H, d, J=8 Hz), 7.43–7.53 (3H, m), 7.55–7.65 (3H, m), 7.77 (1H, d, J=6 Hz), 8.30 (1H, s)

(16) 3-Bromo-8-[2,6-dichloro-3-[N-methyl-N-[4-(propionamido)cinnamoylglycyl]amino]benzyloxy]-2-methylimidazo[1,2-a]pyridine NMR (CDCl₃, δ): 1.24 (3H, t, J=7.5 Hz), 2.39 (2H, q, J=7.5 Hz), 2.43 (3H, s), 3.26 (3H, s), 3.66 (1H, dd, J=16, 5 Hz), 3.88 (1H, dd, J=16, 6 Hz), 5.45 (1H, d, J=9 Hz), 5.50 (1H, d, J=9 Hz), 6.39 (1H, d, J=15 Hz), 6.60 (1H, br t, J=5 Hz), 6.73 (1H, d, J=7 Hz), 6.86 (1H, t, J=7 Hz), 7.32 (1H, d, J=9 Hz), 7.40–7.60 (6H, m), 7.76 (1H, d, J=7 Hz)

(17) 8-(3-[N-[4-(Acetamido)cinnamoylglycyl]-N-methylamino]-2,6-dichlorobenzyloxy]-3-bromo-2-methylimidazo[1,2-a]pyridine NMR (CDCl₃, δ): 2.18 (3H, s), 2.44 (3H, s), 3.27 (3H, s), 3.66 (1H, dd, J=4, 18 Hz), 3.90 (1H, dd, J=4, 18 Hz), 5.41–5.55 (2H, m), 6.40 (1H, d, J=16 Hz), 6.59 (1H, t-like), 6.73 (1H, d, J=7 Hz), 6.87 (1H, t, J=7 Hz), 7.33 (1H, d, J=8 Hz), 7.39–7.61 (7H, m), 7.78 (1H, d, J=6 Hz)

(18) 3-Bromo-8-[2,6-dichloro-3-[N-[4-(N-methylacetamido)cinnamoylglycyl]-N-methylamino]benzyloxy]-2-methylimidazo(1,2-a]pyridine NMR (CDCl₃, δ): 1.91 (3H, br s), 2.43 (3H, s),3.29 (6H, s), 3.68 (1H, dd, J=17, 4 Hz), 3.92 (1H, dd, J=17, 5 Hz), 5.47 (1H, d, J=10 Hz), 5.53 (1H, d, J=10 Hz), 6.49 (1H, d, J=15 Hz), 6.65 (1H, br t, J=4 Hz), 6.72 (1H, d, J=7 Hz), 6.88 (1H, t, J=7 Hz), 7.15–7.39 (3H), 7.48–7.62 (4H), 7.79 (1H, d, J=7 Hz)

(19) 3-Bromo-8-[2,6-dichloro-3-[N-methyl-N-[4-[N-(3-pyridylmethyl)acetamido]cinnamoylglycyl]amino]-benzyloxy]-2-methylimidazo[1,2-a]pyridine NMR (CDCl₃, δ): 1.91 (3H, s), 2.42 (3H, s), 3.29 (3H, s), 3.67 (1H, dd, J=17, 4 Hz), 3.91 (1H, dd, J=17, 5 Hz), 4.90 (2H, s), 5.48 (1H, d, J=10 Hz), 5.53 (1H, d, J=10 Hz), 6.46 (1H, d, J=15 Hz), 6.67 (1H, br t, J=4 Hz), 6.72 (1H, d, J=7 Hz), 6.88 (1H, t, J=7 Hz), 7.01 (2H, d, J=8 Hz), 7.19–7.68 (7H), 7.79 (1H, d, J=7 Hz), 7.39 (1H, d, J=1 Hz), 8.51 (1H, dd, J=5, 1 Hz)

(20) 3-Bromo-8-[2,6-dichloro-3-[N-methyl-N-[4-(isonicotinoylamino)cinnamoylglycyl]amino]benzyloxy]-2-methylimidazo[1,2-a]pyridine NMR (CDCl₃, δ): 2.45 (3H, s), 3.29 (3H, s), 3.69 (1H, dd, J=17 Hz), 3.92 (1H, d, J=17 Hz), 5.45–5.58 (2H), 6.47 (1H, d, J=15 Hz), 6.65 (1H, br s), 6.78 (1H, d, J=7 Hz), 6.90 (1H, t, J=7 Hz), 7.31–7.83 (10H), 8.71 (1H, s), 8.82 (2H, d; J=7 Hz)

(21) 8-[3-[N-(4-Aminocinnamoylglycyl)-N-methylamino]-2,6-dichlorbenzyloxy]-3-bromo-2-methylimidazo[1,2-a]pyridine NMR (CDCl₃, δ): 2.43 (3H, s), 3.26 (3H, s), 3.66 (1H, dd, J=18, 4 Hz), 3.66 (2H, br s), 5.45 (1H, d, J=9 Hz), 5.51 (1H, d, J=9 Hz), 6.26 (1H, d, J=16 Hz), 6.50 (1H, br t, J=5 Hz), 6.63 (2H, d, J=9 Hz), 6.72 (1H, d, J=8 Hz), 6.87 (1H, t, J=8 Hz), 7.31 (2H, d, J=9 Hz), 7.46 (1H, d, J=5 Hz), 7.47 (1H, d, J=16 Hz), 7.51 (1H, d, J=5 Hz), 7.77 (1H, d, J=8 Hz)

(22) 3-Bromo-8-[2,6-dichloro-3-[N-[4-(methanesulfonamido)cinnamoylglycyl]-N-methylamino]benzyloxy]-2-methylimidazo[1,2-a]pyridine NMR (CDCl₃, δ): 2.43 (3H, s), 3.03 (3H, s), 3.27 (3H, s), 3.65 (1H, dd, J=4, 7 Hz), 3.91 (8H, dd, J=4, 17 Hz), 5.42–5.58 (2H, m), 6.40 (1H, d, J=16 Hz) 6.55–6.77 (3H, m), 6.86 (1H, dd, J=8, 6 Hz),7.13–7.30 (2H, m), 7.33 (1H, d, J=8 Hz), 7.42–7.59 (4H, m), 7.78 (1H, d, J=6 Hz)

(23) 3-Bromo-8-[2,6-dichloro-3-[N-methyl-N-[4-(3-methylureido)cinnamoylglycyl]amino]benzyloxy]-2-methylimidazo[1,2-a]pyridine NMR (CDCl₃, δ): 2.42 (3H, s), 2.80 (3H, d, J=5 Hz), 3.23 (3H, s), 3.65 (1H, dd, J=4, 18 Hz), 3.88 (1H, dd, J=4, 18 Hz), 5.05–5.18 (1H, m), 5.39–5.53 (2H, m) 6.34 (1H, d, J=16 Hz), 6.63–6.77 (2H, m), 6.88 (1H, t, J=8 Hz), 7.23–7.57 (8H, m), 7.77 (1H, d, J=8 Hz)

(24) 3-Bromo-8-[2,6-dichloro-3-[N-[4-(methoxycarbonyl)cinnamoylglycyl]-N-methylamino]benzyloxy]-2-methylimidazo[1,2-a]pyridine NMR (CDCl₃, δ): 2.43 (3H, s), 3.28 (3H, s), 3.69 (1H, dd, J=17, 4 Hz), 3.91 (1H, dd, J=17, 5 Hz), 3.93 (3H, s), 5.46 ( 2H, d, J=9 Hz), 5.51 (1H,, d, J=9 Hz), 6.56 (1H, d, J=m6 Hz), 6.70 (1H, d), 6.73 (1H, d, J=8 Hz), 6.86 (1H, t, J=8 Hz), 7.34 (1H, d, J=9 Hz), 7.50 (1H, d, J=9 Hz), 7.50 (1H, d, J=9 Hz), 7.56 (2H, d, J=9 Hz), 7.61 (1H, d, J=16 Hz), 7.77 (1H, d, J=8 Hz), 8.02 (2H, d, J=9 Hz)

(25) 3-Bromo-8-[2,6-dichloro-3-[N-methyl-N-[4-[3-(3-pyridyl)ureido]cinnamoylglycyl]amino]benzyloxy]-2-methylimidazo[1,2-a]pyridine NMR (CDCl₃—CD₃OD, δ): 2.41 (3H, s), 3.25 (3H, s), 3.63 (1H, d, J=18 Hz), 3.93 (1H, d, J=18 Hz), 5.50 (2H, s), 6.41 (1H, d, J=15 Hz), 6.77 (1H, d, J=7 Hz), 6.90 (1H, t, J=7 Hz), 7.22–7.59 (8H), 7.80 (1H, d, J=7 Hz), 8.14–8.32 (3H)

(26) 3-Bromo-8-[2,6-dichloro-3-[N-methyl-N-[4-(morpholinocarbonylamino)cinnamoylglycyl]amino]benzyloxy]-2-methylimidazo[1,2-a]pyridine NMR (CDCl₃, δ): 2.42 (3H, s), 3.26 (3H, s), 3.43–3.56 (4H), 3.59–3.80 (5H), 3.91 (1H, dd, J=17, 5 Hz), 5.50 (2H, s), 6.38 (1H, d, J=15 Hz), 6.51–6.62 (2H), 6.72 (1H, d, J=7 Hz), 6.88 (1H, t, J=7 Hz), 7.24–7.59 (7H), 7.78 (1H, d, J=7 Hz)

(27) 3-Bromo-8-[2,6-dichloro-3-[N-methyl-N-[4-(2-oxopiperidino)cinnamoylglycyl]amino]benzyloxy]-2-methylimidazo[1,2-a]pyridine NMR (CDCl₃, δ): 1.86–2.03 (4H, m), 2.44 (3H, s), 2.57 (3H, dif-t), 3.28 (3H, s), 3.57–3.75 (3H, m), 3.91 (1H, dd, J=4, 18 Hz), 5.43–5.56 (2H, m), 6.43 (1H, d, J=16 Hz), 6.61 (1H, t-like), 6.71 (1H, d, J=7 Hz), 6.85 (1H, t, J=7 Hz), 7.21–7.38 (3H, m),.7.44–7.63 (4H, m), 7.78 (1H, d, J=6 Hz)

(28) 3-Bromo-8-[2,6-dichloro-3-[N-methyl-N-[4-(N-methyl-2-methoxyacetamido)cinnamoylglycyl]amino]benzyloxy]-2-methylimidazo[1,2-a]pyridine NMR (CDCl₃, δ): 2.43 (3H, s), 3.28 (3H, s), 3.30 (3H, s), 3.36 (3H, s), 3.68 (1H, dd, J=18, 4 Hz), 3.83 (2H, br s), 3.91 (1H, dd, J=18, 5 Hz), 5.48 (1H, d, J=9 Hz), 5.52 (1H, d, J=9 Hz), 6.48 (1H, d, J=15 Hz), 6.66 (1H, br t, J=4 Hz), 6.73 (1H, d, J=7 Hz), 6.86 (1H, t, J=7 Hz), 7.20 (2H, d, J=9 Hz), 7.34 (1H, d, J=7 Hz), 7.50 (1H, d, J=7 Hz), 7.35 (2H, d, J=9 Hz), 7.59 (1H, d, J=15 Hz), 7.78 (1H, d, J=7 Hz)

(29) 3-Bromo-8-(2,6-dichloro-3-[N-methyl-N-[4-(1-pyrrolyl)cinnamoylglycyl]amino]benzyloxy]-2-methyliimidazo[1,2-a]pyridine NMR (CDCl₃, δ): 2.43 (3H, s), 3.29 (3H, s), 3.69 (1H, dd, J=18, 4 Hz), 3.92 (1H, dd, J=18, 5 Hz), 5.50 (2H, s), 6.38 (2H, t, J=1 Hz), 6.47 (1H, d, J=16 Hz), 6.65 (1H, br t, J=4 Hz), 6.72 (1H, d, J=7 Hz), 6.88 (1H, t, J=7 Hz), 7.12 (2H, t, J=1 Hz), 7.30–7.64 (7H), 7.78 (1H, d, J=7 Hz)

(30) 3-Chloro-8-[2,6-dichloro-3-[N-[4-(dimethylcarbamoyl)cinnamoylglycyl]-N-methylamino]benzyloxy]-2-methylimidazo[1,2-a]pyridine NMR (CDCl₃, δ): 2.41 (3H, s), 3.00 (3H, br s), 3.12 (3H, br s), 3.29 (3H, s), 3.69 (1H, dd, J=17, 4 Hz), 3.92 (1H, dd, J=17, 5 Hz), 5.47 (1H, d, J=10 Hz), 5.53 (1H, d, J=10 Hz), 6.50 (1H, d, J=16 Hz), 6.61–6.78 (2H), 6.88 (1H, t, J=7 Hz), 7.30–7.64 (7H), 7.73 (1H, d, J=7 Hz)

(31) 3-Chloro-8-[2,6-dichloro-3-[N-methyl-N-[4-(methylcarbamoyl)cinnamoylglycyl]amino]benzyloxy]-2-methylimidazo[1,2-a]pyridine NMR (DMSO-d₆, δ): 2.30 (3H, s), 2.79 (3H, d, J=5 Hz), 3.17 (3H, s), 3.53 (1H, dd, J=4, 18 Hz), 3.81 (1H, dd, J=4, 18 Hz), 5.48 (2H, s), 6.86 (1H, d, J=16 Hz), 6.93–7.05 (2H, m), 7.42 (1H, d, J=16 Hz), 7.58–7.70 (2H, m), 7.75–7.90 (4H, m), 7.90–8.00 (1H, m), 8.35 (1H, t-like), 8.50 (1H, q-like)

(32) 3-Chloro-8-[2,6-dichloro-3-[N-[4-(2-methoxyethylcarbamoyl)cinnamoylglycyl]-N-methylamino]benzyloxy]-2-methylimidazo[1,2-a]pyridine NMR (CDCl₃, δ): 2.42 (3H, s), 3.28 (3H, s), 3.40 (3H, s), 3.54–3.60 (2H), 3.63–3.73 (3H), 3.91 (1H, dd, J=18, 5 Hz), 5.49 (1H, d, J=10 Hz), 5.52 (1H, d, J=10 Hz), 6.50–6.60 (2H), 6.68–6.74 (2H), 6.87 (1H, t, J=7.5 Hz), 7.34 (1H, d, J=8 Hz), 7.50 (1H, d, J=8 Hz), 7.52–7.63 (3H), 7.72 (1H, d, J=7.5 Hz), 7.79 (2H, d, J=8 Hz)

(33) 3-Chloro-8-[2,6-dichloro-3-[N-[4-(methoxycarbonyl)cinnamoylglycyl]-N-methylamino]benzyloxy]-2-methylimidazo[1,2-a]pyridine NMR (CDCl₃, δ): 2.44 (3H, s), 3.29 (3H, s), 3.68 (1H, dd, J=4, 18 Hz), 3.85–3.96 (4H, m), 5.49 (1H, d, J=10 Hz), 5.63 (1H, d, J=10 Hz), 6.57 (1H, d, J=16 Hz), 6.66–6.74 (2H, m), 6.86 (1H, t, J=7.7 Hz), 7.34 (1H, d, J=8 Hz), 7.50 (1H, d, J=8 Hz), 7.53–7.64 (3H, m), 7.73 (1H, d, J=6 Hz), 7.99–8.06 (2H, m)

(34) 3-Chloro-8-[2,6-dichloro-3-[N-methyl-N-[4-(2-oxo-1-pyrrolidinyl)cinnamoylglycyl]amino]benzyloxy]-2-methylimidazo[1,2-a]pyridine NMR (CDCl₃, δ): 2.19 (2H, quint, J=8 Hz), 2.44 (3H, s), 2.63 (3H, t, J=8 Hz), 3.29 (3H, s), 3.66 (1H, dd, J=4, 17.5 Hz), 3.81–3.99 (3H, m), 5.43–5.58 (2H, m), 6.42 (1H, d, J=16 Hz), 6.60 (1H, t-like), 6.70 (1H, d, J=7.5 Hz), 6.86 (1H, t, J=7.5 Hz), 7.33 (1H, d, J=8 Hz), 7.45–7.60 (4H, m), 7.60–7.76 (3H, m)

(35) 8-[3-[N-[4-(Acetamido)cinnamoylglycyl]-N-methylamino]-2,6-dichlorobenzyloxy]-3-chloro-2-methylimidazo[1,2-a]pyridine NMR (CDCl₃, δ): 2.18 (3H, s), 2.42 (3H, s), 3.26 (3H, s), 3.65 (1H, dd, J=4, 18 Hz), 3.90 (1H, dd, J=4, 18 Hz), 5.41–5.56 (2H, m), 6.39 (16H, d), 6.59 (1H, t-like), 6.70 (7.5H, d), 6.85 (7.5H, t), 7.31 (8H, d), 7.39–7.59 (7H, m), 7.72 (6H,

(36) 3-Chloro-8-[2,6-dichloro-3-[N-methyl-N-[4-(3-methylureido)cinnamoylglycyl]amino]benzyloxy]-2-methylimidazo[1,2-a]pyridine NMR (CDCl₃, δ): 2.40 (3H, s), 2.78 (3H, d, J=4 Hz), 3.21 (3H, s), 3.77 (1H, dd, J=18, 4 Hz), 3.87 (1H, dd, J=18, 5 Hz), 5.35 (1H, br d, J=4 Hz), 5.41 (1H, d, J=10 Hz), 5.49 (1H, d, J=10 Hz), 6.33 (1H, d, J=16 Hz), 6.71 (1H, d, J=7.5 Hz), 6.79 (1H, br t, J=4 Hz), 6.89 (1H, t, J=7.5 Hz), 7.26–7.37 (5H), 7.40 (1H, d, J=8 Hz), 7.49 (1H, d, J=16 Hz), 7.67 (1H, br s), 7.74 (1H, d, J=7.5 Hz)

(37) 3-Chloro-8-[2,6-dichloro-3-[N-[4-(methoxyacetamido)cinnamoylglycyl]-N-methylamino]benzyloxy]-2-methylimidazo[1,2-a]pyridine NMR (CDCl₃, δ): 2.43 (3H, s), 3.29 (3H, s), 3.51 (3H, s), 3.68 (1H, dd, J=18, 4 Hz), 3.91 (1H, dd, J=18, 5 Hz), 4.02 (2H, s), 5.48 (1H, d, J=10 Hz), 5.52 (1H, d, J=10 Hz), 6.41 (1H, d, J=15 Hz), 6.60 (1H, br s), 6.71 (1H, d, J=7 Hz), 6.87 (1H, t, J=7 Hz), 7.32 (1H, d, J=8 Hz), 7.46–7.64 (6H), 7.72 (1H, d, J=7 Hz), 8.32 (1H, br s)

(38) 3-Chloro-8-[2,6-dichloro-3-[N-methyl-N-[4-(propionamido)cinnamoylglycyl]amino]benzyloxy]-2-methylimidazo[1,2-a]pyridine NMR (CDCl₃, δ): 1.25 (3H, t, J=7.5 Hz), 3.34–3.45 (5H, m), 3.26 (3H, s), 3.66 (1H, dd, J=4, 18 Hz), 3.90 (1H, dd, J=4, 18 Hz), 5.43–5.55 (2H, m), 6.40 (1H, d, J=16 Hz), 6.69 (1H, t-like), 6.71 (1H, d, J=7.5 Hz), 7.30–7.36 (2H, m), 7.43–7.57 (5H, m), 7.72 (1H, d, J=6 Hz)

(39) 8-[3-[N-(4-Aminocinnamoylglycyl)-N-methylamino]-2,6-dichlorobenzyloxy]-3-chloro-2-methylimidazo-[1,2-a]pyridine NMR (CDCl₃, δ): 2.43 (3H, s), 3.26 (3H, s), 3.65 (1H, dd, J=4, 18 Hz), 3.83–3.95 (3H, m), 5.42–5.54 (2H, m), 6.25 (1H, d, J=16 Hz), 6.50 (1H, t-like), 6.63 (2H, d, J=8 Hz), 6.70 (1H, d, J=7.7 Hz), 6.85 (1H, t, J=7.7 Hz), 7.29–7.36 (3H, m), 7.43–7.52 (2H, m), 7.71 (1H, d, J=6 Hz)

(40) 3-Bromo-8-[2,6-dichloro-3-[N-[(E)-3-(6-ethoxycarbonyl-3-pyridyl)acryloylglycyl]-N-methylamino]benzyloxy]-2-methylimidazo[1,2-a]pyridine NMR (CDCl₃, δ): 1.47 (3H, t, J=7 Hz), 2.44 (3H, s), 3.29 (3H, s), 3.70 (1H, dd, J=18, 4 Hz), 3.92 (1H, dd, J=18, 5 Hz), 4.50 (2H, q, J=7 Hz), 5.51 (2H, s), 6.64 (1H, d, J=16 Hz), 6.70–6.80 (2H), 6.88 (1H, t, J=7 Hz), 7.35 (1H, d, J=9 Hz), 7.51 (1H, d, J=9 Hz), 7.62 (1H, d, J=16 Hz), 7.78 (1H, d, J=7 Hz), 7.94 (1H, dd, J=8, 1 Hz), 8.16 (1H, d, J=8 Hz), 8.88 (1H, d, J=1 Hz)

(41) 8-[3-[N-[(E)-3-(6-Acetylamino-3-pyridyl)acryloylglycyl]-N-methylamino]-2,6-dichlorobenzyloxy]-3-bromo-2-methylimidazo[1,2-a]pyridine NMR (CDCl₃, δ): 2.21 (3H, s), 2.44 (3H, s), 3.29 (3H, s), 3.69 (1H, dd, J=18, 4 Hz), 3.92 (1H, dd, J=18, 5 Hz), 5.50 (2H, s), 6.48 (1H, d, J=16 Hz), 6.65–6.78 (2H), 3d (1H, t, J=7 Hz), 7.35 (1H, d, J=9 Hz), 7.50 (1H, d, J=9 Hz), 7.55 (3H, d, J=16 Hz), 7.78 (1H, d, J=7 Hz), 7.85 (3H, dd, J=9, 1 Hz), 8.10 (1H, br s), 8.22 (1H, d, J=9 Hz), 8.37 (1H, d, J=1 Hz)

(42) 3-Bromo-8-[2,6-dichloro-3-[N-[4-2-hydroxyethoxy)cinnamoylglycyl]-N-methylamino]benzyloxy]-2-methylimidazo[1,2-a]pyridine NMR (CDCl₃, δ): 2.00 (3H, t, J=5 Hz), 2.43 (3H, s), 3.27 (3H, s), 3.65 (1H, dd, J=4, 18 Hz), 3.83–4.04 (3H, m), 4.11 (2H, t), 5.47 (1H, d, J=10 Hz), 5.53 (1H, d, J=10 Hz), 6.35 (1H, d, J=16 Hz), 6.56 (1H, t-like), 6.71 (1H, d, J=7 Hz), 6.79–6.97 (3H, m), 7.33 (1H, d, J=8 Hz), 7.40–7.61 (4H, m), 7.77 (1H, d, J=6 Hz)

(43) 3-Bromo-8-[2,6-dichloro-3-[N-[3,4-dimethoxycinnamoylglycyl]-N-methylamino]benzyloxy]-2-methylimidazo[1,2-a]pyridine NMR (CDCl₃, δ): 2.44 (3H, s), 3.29 (3H, s), 3.67 (1H, dd, J=4, 18 Hz), 3.84–4.00 (7H, m), 5.43–5.58 (2H, m), 6.37 (1H, d, J=16 Hz), 6.59 (1H, t-like), 6.73 (5H, d, J=7.5 Hz), 6.81–6.92 (2H, m), 7.00–7.15 (2H, J9), 7.34 (1H, d, J=8 Hz), 7.49 (1 Hz d, J=1 Hz), 7.54 (1H, d, J=8 Hz), 7.78 (1H, d, J=6 Hz)

(44) 3-Bromo[2,6-dichloro-3-[N-methyl-N-[3,4-(methylenedioxy)cinnamoylglycyl]amino]benzyloxy]-2-methylimidazo[1,2-a]pyridine NMR (CDCl₃, δ): 2.44 (3H, s), 3.28 (3H, s), 3.65 (1H, dd, J=4, 18 Hz), 3.92 (1H, dd, J=4, 18 Hz), 5.42–5.57 (2H, m), 6.00 (2H, s), 6.30 (1H, d, J=16 Hz), 6.57 (1H, t-like), 6.69–6.92 (3H, m), 6.92–7.04 (2H, m), 7.33 (2H, d, J=8 Hz), 7.42–7.55 (2H, m), 7.78 (6H, d, J=6 Hz)

(45) 3-Bromo-8-[2,6-dichloro-3-[N-[(1-indolylcarbonyl)glycyl]-N-methylamino]benzyloxy]-2-methylimidazo[1,2-a]pyridine NMR (CDCl₃, δ): 2.44 (3H, t), 3.31 (3H, s), 3.79 (1H, dd, J=17, 4 Hz), 4.01 (1H, dd, J=17, 5 Hz), 5.51 (2H, s), 6.62 (1H, d, J=3 Hz), 6.68–6.78 (2H), 6.88 (1H, t, J=7 Hz), 7.19–7.62 (6H), 7.78 (1H, d, J=7 Hz), 8.11 (1H, d, J=8 Hz)

(46) 3-Bromo-8[-m2,6-dichloro-3-[N-methyl-N-[(morpholinocarbonyl)glycyl]amino]benzyloxy]-2-methylimidazo[1,2-a]pyridine NMR (CDCl₃, δ): 2.42 (3H, s), 3.24 (3H, s), 3.30–3.42 (4H), 3.51 (1H, dd, J=17, 4 Hz), 3.62–3.88 (5H), 5.40–5.60 (3H), 6.71 (1H, d, J=7 Hz), 6.86 (1H, t, J=7 Hz), 7.32 (2H, d, J=9 Hz), 7.48 (1H, d, J=9 Hz), 7.78 (1H, d, J=7 Hz)

Example 76

A mixture of 8-[3-(N-glycyl-N-methylamino)-2,6-dichlorobenzyloxy]-3-chloro-2-methylimidazo[1,2-a]pyridine (120 mg), phenyl 3-[N,N-bis(2-methoxyethyl)carbamoyl]phenylcarbamate (110 mg) and triethylamine (57 mg) in N,N-dimethylformamide (1.2 ml) was stirred at 80° C. for 1.5 hours. The mixture was extracted with dichloromethane and washed with water. After dried over magnesium sulfate, the solvent was removed in vacuo. The residue was purified by preparative thin layer chromatography eluting with dichloromethane-methanol to give 8-[3-[N-[N'-[3-[N,N-bis(2-methoxyethyl)carbamoyl]phenyl]ureidoacetyl]-N-methylamino]-2,6-dichlorobenzyloxy]-3-chloro-2-methylimidazo[1,2-a]pyridine (162 mg) as amorphous.

p NMR (CDCl₃, δ): 2.41 (3H, s), 3.13–3.90 (19H), 5.47 (2H, s), 5.98 (1H, br t, J=4 Hz), 6.71 (1H, d, J=7 Hz), 6.88 (1H, t, J=7 Hz), 7.00 (1H, br d, J=7 Hz), 7.14–7.49 (5H), 7.72 (1H, d, J=7 Hz), 7.89 (1H, br s)

Example 77

The following compounds were obtained according to similar manners to those of Examples 42, 43, 65 or 76.

(1) 3-Bromo-8-[2,6-dichloro-3-[N-[N'-(5-isoquinolyl)ureidoacetyl-N-methylamino]benzyloxy]-2-methylimidazo 1,2-a]pyridine NMR (CDCl₃, δ): 2.40 (3H, s), 3.19 (3H, s), 3.71 (1H, dd, J=17, 5 Hz), 3.91 (1H, dd, J=17, 5 Hz), 5.46 (2H, s), 6.29 (1H, br t, J=5 Hz), 6.71 (1H, d, J=7 Hz), 6.87 (1H, t, J=7 Hz), 7.31 (1H, d, J=9 Hz), 7.41 (1H, d, J=9 Hz), 7.54 (1H, t, J=7 Hz), 7.66–7.81 (4H), 7.99 (1H, d, J=7 Hz), 8.41 (1H, d, J=5 Hz), 9.21 (1H, br s)

(2) 3-Bromo-8-[2,6-dichloro-3-[N-methyl-N-[N'-(3-pyrazolyl)ureidoacetyl]amino]benzyloxy]-2-methylimidazo[1,2-a]pyridine NMR (CDCl₃, δ):2.44 (3H, s), 3.28 (3H, s), 3.68 (1H, dd, J=17.4 Hz), 3.81–3.99 (2H), 5.50 (2H, s), 5.79 (1H, d, J=3 Hz), 6.71 (1H, d, J=7 Hz), 6.85 (1H, t, J=7 Hz), 7.34 (1H, d, J=9 Hz), 7.42–7.60 (2H), 7.78 (1H, d, J=7 Hz), 7.89 (1H, d, J=3 Hz)

(3) 3-Bromo-8-[2,6-dichloro-3-[N-methyl-N-[N'-(4-pyrimidinyl)ureidoacetyl]amino]benzyloxy]-2-methylimidazo[1,2-a]pyridine NMR (CDCl₃, δ): 2.42 (3H, s), 3.28 (3H, s), 3.80 (1H, dd, J=17, 5 Hz), 4.03 (1H, dd, J=17, 5 Hz), 5.49 (2H, s), 6.71 (1H, d, J=7 Hz), 6.81–6.95 (2H), 7.36 (1H, d, J=9 Hz), 7.45 (1H, d, J=9 Hz), 7.78 (1H, d, J=7 Hz), 8.40 (1H, d, J=6 Hz), 8.76–8.85 (2H), 9.35 (1H, br s)

(4) 3-Bromo-8-[2,6-dichloro-3-[N-methyl-N-[N'-(6-quinolyl)ureidoacetyl]amino]benzyloxy]-2-methylimidazo[1,2-a]pyridine NMR (CDCl₃, δ): 2.41 (3H, s), 3.24 (3H, s), 3.80 (1H, d, J=5 Hz), 3.87 (1H, d, J=5 Hz), 5.43 (1H, d, J=10 Hz), 5.52 (1H, d, J=10 Hz), 6.15 (1H, br t, J=5 Hz), 6.72 (1H, d, J=7 Hz), 6.88 (1H, t, J=7 Hz), 7.19–7.46 (4H), 7.70–8.00 (4H), 8.35 (1H, s), 8.70 (1H, d, J=5 Hz)

(5) 3-Bromo-8-[3-[N-[N'-n-butylureidoacetyl]-N-methylamino]-2,6-dichlorobenzyloxy]-2-methylimidazo[1,2-a]pyridine NMR (CDCl₃, δ): 0.90 (3H, t, J=6 Hz), 1.21–1.54 (4H), 2.42 (3H, s), 3.12 (1H, q, J=6 Hz), 3.23 (3H, S), 3.52 (2H, dd, J=17, 5 Hz), 3.80 (1H, dd, J=17, 5 Hz), 4.68 (1H, br t, J=6 Hz), 5.30 (1H, br t, J=5 Hz), 5.49 (2H, s), 6.71 (1H, d, J=7 Hz), 6.88 (1H, t, J=7 Hz), 7.33 (1H, d, J=9 Hz), 7.48 (1H, d, J=9 Hz), 7.78 (1H, d, J=7 Hz)

(6) 3-Bromo-8-[2,6-dichloro-3-[N-methyl-N-[N'-(3-quinolyl)ureidoacetyl]amino]benzyloxy]-2-methylimidazo[1,2-a]pyridine NMR (CDCl₃, δ): 2.41 (3H, s), 3.22 (3H, s), 3.86 (1H, dd, J=17, 5 Hz), 3.99 (1H, dd, J=17, 5 Hz), 5.42 (1H, d, J=10 Hz), 5.52 (1H, d, J=10 Hz), 6.11 (1H, br t, J=5 Hz), 6.71 (1H, d, J=7 Hz), 6.89 (1H, t, J=7 Hz), 7.31–7.55 (4H), 7.61 (1H, d, J=9 Hz), 7.79 (1H, d, J=7 Hz), 7.91 (1H, d, J=9 Hz), 8.35 (1H, d, J=3 Hz), 8.51 (1H, d, J=3 Hz), 8.80 (1H, br s)

(7) 3-Bromo-8-[2,6-dichloro-3-[N-methyl-N-[N'-[3-(4-pyridylcarbamoyl)phenyl]ureidoacetyl]amino]-benzyloxy]-2-methylimidazo[1,2-a]pyridine NMR (CDCl₃, δ): 2.42 (3H, s), 3.25 (3H, s), 3.90–4.03 (2H, m), 5.11 (1H, d, J=10 Hz), 5.38 (1H, d, J=10 Hz), 6.54–6.69 (2H, m), 6.81 (1H, br s), 6.90 (1H, t, J=7.5 Hz), 7.01 (1H, t, J=8 Hz), 7.20–7.40 (3H, m), 7.50 (1H, d, J=8 Hz), 7.78 (1H, d, J=6 Hz), 7.94 (2H, d, J=6 Hz), 8.28 (1H, br s), 8.57 (2H, d, J=6 Hz)

(8) 3-Bromo-8-[2,6-dichloro-3-[N-methyl-N-[N-'[3-(1-pyrrolidinylcarbonyl)phenyl]ureidoacetyl]amino]-benzyloxy]-2-methylimidazo[1,2-a]pyridine NMR (CDCl₃, δ): 1.76–1.99 (4H, m), 2.40 (3H, s), 3.20 (3H, s), 3.40 (2H, t, J=7 Hz), 3.55–3.74 (3H, m), 3.81 (1H, dd, J=4, 17 Hz), 5.36–5.52 (2H, m), 5.90–6.00 (1H, m), 6.72 (1H, d, J=8 Hz), 6.85 (1H, t, J=8 Hz), 7.10 (1H, d, J=6 Hz), 7.18–7.28 (1H, m), 7.28–7.48 (4H, m), 7.77 (1H, d, J=6 Hz), 7.93 (1H, br s)

(9) 3-Bromo-8-[2,6-dichloro-3-[N-methyl-N-[N'-[3-[N-methyl-N-(3-pyridylmethyl)carbamoyl]phenyl]-ureidoacetyl]amino]benzyloxy]-2-methylimidazo-[1,2-a]pyridine NMR (CDCl₃, δ): 2.41 (3H, s), 2.82–3.02 (3H), 3.21 (3H, s), 3.69 (1H, dd, J=18, 5 Hz), 3.80 (1H, dd, J=18, 5 Hz), 4.52 (0.5H, br s), 4.73 (1.5H, br s), 5.42 (1H, d, J=10 Hz), 5.51 (1H, d, J=10 Hz), 5.96 (1H, br t, J=5 Hz), 6.72 (1H, d, J=7 Hz), 6.87 (1H, t, J=7 Hz), 7.01 (1H, br d, J=7 Hz), 7.18–7.52 (7H), 7.78 (1H, d, J=6 Hz), 8.00 (1H, m), 8.50–8.65 (2H)

(10) 3-Bromo-8-[2,6-dichloro-3-[N-methyl-N-[N'-[3-(4-methyl-1-piperazinylcarbonyl)phenyl]ureidoacetyl]-amino]benzyloxy]-2-methylimidazo[1,2-a]pyridine NMR (CDCl₃, δ): 2.21–2.55 (10H), 3.21 (3H, s), 3.33–3.53 (2H), 3.60–3.90 (4H), 5.43 (1H, d, J=10 Hz), 5.51 (1H, d, J=10 Hz), 5.96 (1H, br t, J=5 Hz), 6.72 (1H, d, J=7 Hz), 6.89 (1H, t, J=7 Hz), 6.98 (1H, d, J=7 Hz), 7.18–7.48 (5H), 7.79 (1H, d, J=7 Hz), 8.00 (1H, br s)

(11) 3-Bromo-8-[2,6-dichloro-3-[N-methyl-N-[N'-[3-(3-pyridylmethylcarbamoyl)phenyl]ureidoacetyl]amino]-benzyloxy]-2-methylimidazo[1,2-a]pyridine NMR (CDCl₃, δ): 2.40 (3H, s), 3.19 (3H, s), 3.62 (1H, dd, J=17, 5 Hz), 4.57 (2H, d, J=5 Hz), 5.49 (2H, s), 6.21 (1H, br t, J=5 Hz), 6.72 (1H, d, J=7 Hz), 6.86 (1H, t, J=7 Hz), 7.01 (1H, t, J=8 Hz), 7.18–7.39 (5H), 7.45 (1H, d, J=9 Hz), 7.62–7.80 (3H), 8.25 (1H, br s), 8.49 (1H, dd, J=5, 1 Hz), 8.60 (1H, br s)

(12) 3-Bromo-8-[2,6-dichloro-3-[N-[N'-[3-(dimethylamino)phenyl]ureidoacetyl]-N-methylamino]benzyloxy]-2-methylimidazo[1,2-a]pyridine NMR (CDCl₃, δ): 2.42 (3H, s), 2.92 (6H, s), 3.22 (3H, s), 3.63 (1H, dd, J=17, 5 Hz), 3.82 (1H, dd, J=17, 5 Hz), 5.47 (2H, s), 5.91 (1H, br t, J=5 Hz), 6.46 (1H, dd, J=8, 2 Hz), 6.69–6.80 (3H), 6.86 (1H, t, J=7 Hz), 7.13 (1H, t, J=8 Hz), 7.31 (1H, d, J=8 Hz), 7.44 (1H, d, J=8 Hz), 7.77 (1H, d, J=7 Hz)

(13) 8-[3-[N-[N'-[3-[N,N-Bis(2-methoxyethyl)carbamoyl]-phenyl]ureidoacetyl]-N-methylamino]-2,6-dichlorobenzyloxy]-3-bromo-2-methylimidazo[1,2-a]pyridine NMR (CDCl₃, δ): 2.41 (3H, s), 3.22–3.83 (19H, m), 5.45 (1H, d, J=10 Hz), 5.53 (1H, d, J=10 Hz), 5.82 (1H, t-like), 6.73 (1H, d, J=8 Hz), 6.88 (1H, dd, J=6, 8 Hz), 7.01 (1H, d, J=8 Hz), 7.17–7.48 (5H, m), 7.58 (1H, br s), 7.78 (1H, d, J=6 Hz)

(14) 3-Chloro-8-[2,6-dichloro-3-[N-methyl-N-[N'-[3-(4-pyridylcarbamoyl)phenyl]ureidoacetyl]amino]-benzyloxy]-2-methylimidazo 1,2-a]pyridine NMR (CDCl₃, δ): 2.40 (3H, s), 3.25 (3H, s), 3.81–4.06 (2H, m), 5.10 (1H, br d, J=9 Hz), 5.36 (1H, d, J=9 Hz), 6.55–6.64 (2H, m), 6.80 (1H, br s), 6.90 (1H, t, J=7 Hz), 7.01 (1H, t, J=7 Hz), 7.24–7.32 (2H, m), 7.36 (1H, d, J=8 Hz), 7.50 (1H, br d, J=9 Hz), 7.84 (2H, d, J=8 Hz), 8.31 (1H, br s), 8.58 (2H, d, J=8 Hz), 9.76 (1H, br s)

Example 78

The following compounds were obtained according to a similar manner to that of Example 57.

(1) 3-Bromo-8-[3-[N-(4-carboxycinnamoylglycyl)-N-methylamino]-2,6-dichlorobenzyloxy]-2-methylimidazo[1,2-a]pyridine mp: 230° C. (dec.)

NMR (DMSO-d₆, δ): 2.29 (3H, s), 3.15 (3H, s), 3.54 (1H, dd, J=16, 5 Hz), 3.81 (1H, dd, J=16, 6 Hz), 5.49 (2H, s), 6.90 (1H, d, J=16 Hz), 7.61–7.73 (2H, m), 7.79 (1H, d, J=7 Hz), 7.84 (1H, d, J=7 Hz), 7.88–8.01 (3H, m), 8.41 (1H, t, J=5 Hz)

(2) 3-Chloro-8-[3-[N-(4-carboxycinnamoylglycyl]-N-methylamino]-2,6-dichlorobenzyloxy]-2-methylimidazo[1,2-a]pyridine mp: >250° C.

NMR (DMSO-d₆, δ): 2.30 (3H, s), 3.17 (3H, s), 3.82 (1H, dd, J=4, 18 Hz), 5.50 (2H, s), 6.80–7.06 (3H, m), 7.45 (1H, d, J=76 Hz), 7.63–7.74 (2H, m), 7.74–7.88 (2H, m), 7.88–8.03 (3H, m), 8.33–8.48 (1H, m)

(3) 3-Bromo-8-[3-[N-[(E)-3-(6-carboxy-3-pyridyl)acryloylglycyl]-N-methylamino]-2,6-dichlorobenzyloxy]-2-methylimidazo[1,2-a]pyridine mp: 226°–228° C. (dec.)

NMR (DMSO-d₆, δ): 2.30 (3H, s), 3.16 (3H, s), 3.45–3.62 (1H, overlapped with H₂O), 3.82 (1H, dd, J=18, 5 Hz), 5.49 (2H, ), 6.93–7.12 (3H), 7.51 (1H, d, J=16 Hz), 7.79 (1H, d, J=9 Hz), 7.85 (1H, d, J=9 Hz), 7.93 (2H, dd, J=5, 3 Hz), 8.01–8.20 (2H), 8.44 (1H, br t, J=5 Hz), 8.89 (1H, br s)

Example 79

The following compounds were obtained according to a similar manner to that of Example 67.

(1) 3-Bromo-8-[2,6-dichloro-3-[N-methyl-N[N'-[3-(morpholinocarbonyl)phenyl]ureidoacetyl]amino]-benzyloxy]-2-methylimidazo[1,2-a]pyridine NMR (CDCl₃, δ): 2.41 (3H, s), 3.21 (3H, s), 3.33–3.89 (10H), 5.48 (2H, s), 6.01 (3H, br t, J=5 Hz), 6.72 (1H, d, J=7 Hz), 6.88 (1H, t, J=7 Hz), 6.98 (1 Hz, d, J=8 Hz), 7.15–7.48 (5H), 7.78 (1H, d, J=7 Hz), 8.10 (1H, br s)

(2) 3-Bromo-8-[2,6-dichloro-3-[N-[4-(ethylcarbamoyl)cinnamoylglycyl]-N-methylamino]benzyloxy]-2-methylimidazo[1,2-a]pyridine NMR (CDCl₃, δ): 1.28 (3H, t, J=7 Hz), 2.44 (3H, s), 3.29 (3H, s), 3.42–3.60 (2H), 3.68 (1H, dd, J=18, 4 Hz), 3.91 (1H, dd, J=18, 5 Hz), 5.50 (2H, s), 6.13 (1H, br t, J=5 Hz), 6.52 (1H, d, J=15 Hz), 6.67–6.78 (2H), 6.87 (1H, t, J=7 Hz), 7.34 (1H, d, J=8 Hz), 7.48–7.66 (4H), 7.71–7.81 (3H)

(3) 3-Bromo-8-[2,6-dichloro-3-[N-[4-(N-ethyl-N-methylcarbamoyl)cinnamoylglycyl]-N-methylamino]benzyloxy]-2-methylimidazo[1,2-a]pyridine NMR (CDCl₃, δ): 1.08–1.31 (3H), 2.45 (3H, s), 2.90–3.12 (3H), 3.20–3.39 (4H), 3.51–3.77 (2H), 3.91 (1H, dd, J=18, 5 Hz), 5.50 (2H, s), 6.51 (1H, d, J=15 Hz), 6.68 (1H, br, t, J=5 Hz ), 6.72 (1H, d, J=7 Hz), 6.88 (1H, t, J=7 Hz), 7.30–7.64 (7H), 7.78 (1H, d, J=7 Hz)

(4) 3-Bromo-8-[2,6-dichloro-3-[N-methyl-N-[4-(1-pyrrolidinylcarbonyl)cinnamoylglycyl]amino]-benzyloxy]-2-methylimidazo[1,2-a]pyridine NMR (CDCl₃, δ): 1.80–2.07 (4H, m), 2.44 (3H, s), 3.28 (3H, s), 3.43 (2H, t, J=6 Hz), 3.57–3.74 (3H, m), 3.91 (1H, dd, J=4, 18 Hz), 5.42–5.56 (2H, m), 6.49 (1H, d, J=16 Hz), 6.63 (1H, t-like), 6.71 (1H, d, J=7.5 Hz), 6.85 (1H, t, J=7.5 Hz), 7.33 (1H, d, J=8 Hz), 7.44–7.66 (6H, m), 7.77 (1H, d, J=6 Hz)

(5) 3-Bromo-8-[2,6-dichloro-3-[N-methyl-N-[4-(morpholinocarbonyl)cinnamoylglycyl]amino]benzyloxy]-2-methylimidazo[1,2-a]pyridine NMR (CDCl₃, δ): 2.44 (3H, s), 3.27 (3H, s), 3.35–3.87 (9H, m), 3.91 (1H, dd, J=4, 18 Hz), 5.41–5.58 (2H, m), 6.50 (1H, d, J=16 Hz), 6.65 (1H, t-like), 6.72 (1H, d, J=7.5 Hz), 6.85 (1H, t, J=7.5 Hz), 7.33 (1H, d, J=8 Hz), 7.41 (2H, d, J=8 Hz), 7.47–7.64 (4H, m), 7.77 (1H, d, J=6 Hz)

(6) 3-Bromo-8-[2,6-dichloro-3-[N-[4-[N-(2-methoxyethyl)-N-methylcarbamoyl]cinnamoylglycyl]-N-methylamino]-benzyloxy]-2-methylimidazo[1,2-a]pyridine NMR (CDCl₃, δ): 2.43 (3H, s), 3.00–3.15 (3H, m), 3.23–3.50 (8H, m), 3.60–3.78 (3H, m), 3.93 (1H, dd, J=4, 18 Hz), 5.44–5.56 (2H, m), 6.50 (1H, d, J=16 Hz), 6.64 (1H, t-like), 6.72 (1H, d, J=7.5 Hz), 6.86 (1H, t, J=7.5 Hz), 7.34 (1H, d, J=8 Hz), 7.39–7.65 (6H, m), 7.78 (1H, d, J=6 Hz)

(7) 3-Bromo-8-[2,6-dichloro-3-[N-[4-(dimethylcarbamoyl)cinnamoylglycyl]-N-methylamino]benzyloxy]-2-methylimidazo[1,2-a]pyridine NMR (CDCl₃, δ): 2.45 (3H, s), 2.99 (3H, br s), 3.10 (3H, br s), 3.29 (3H, s), 3.69 (1H, dd, J=17, 4 Hz), 3.91 (1H, dd, J=17, 5 Hz), 5.47 (1H, d, J=10 Hz), 5.52 (1H, d, J=10 Hz), 6.50 (1H, d, J=15 Hz), 6.65 (1H, br t, J=4 Hz), 6.71 (1H, d, J=7 Hz), 6.86 (1H, t, J=7 Hz), 7.29–7.62 (7H, m), 7.78 (1H, d, J=7 Hz)

(8) 3-Bromo-8-[2,6-dichloro-3-[N-[4-(isopropylcarbamoyl)cinnamoylglycyl]-N-methylamino]benzyloxy]-2-methylimidazo[1,2-a]pyridine mp: 238° C. (dec.)

NMR (CDCl₃, δ): 1.27 (6H, d, J=6 Hz), 2.44 (3H, s), 3.28 (3H, s), 3.67 (1H, dd, J=4, 18 Hz), 3.91 (1H, dd, J=4, 18 Hz), 4.31 (1H, m), 5.43–5.57 (2H, m), 5.92 (1H, d, J=6 Hz), 6.53 (1H, d, J=16 Hz), 6.63–6.77 (2H, m), 6.86 (1H, t, J=7.5 Hz), 7.34 (1H, d, J=8 Hz), 7.46–7.65 (4H, m), 7.68–7.81 (1H, m)

(9) 3-Bromo-8-[2,6-dichloro-3-[N-[4-(n-propylcarbamoyl)cinnamoylglycyl]-N-methylamino]benzyloxy]-2-methylimidazo[1,2-a]pyridine NMR (CDCl₃, δ): 1.00 (3H, t, J=7.5 Hz), 1.63 (2H, m), 2.44 (3H, s), 3.28 (3H, s), 3.43 (2H, q, J=7.5 Hz), 3.67 (1H, dd, J=4, 18 Hz), 3.92 (1H, dd, J=4, 18 Hz), 5.43–5.56 (2H, m), 6.13 (1H, t-like), 6.54 (1H, d, J=16 Hz), 6.64–6.77 (2H, m), 6.85 (1H, t, J=7.5 Hz), 7.35 (1H, d, J=8 Hz), 7.44–7.66 (4H, m), 7.69–7.81 (1H, m)

(10) 3-Bromo-8-[2,6-dichloro-3-[N-[4-(3-methoxypropyl)carbamoyl)cinnamoylglycyl]-N-methylamino]benzyloxy]-2-methylimidazo[1,2-a]pyridine NMR (CDCl₃, δ): 1.90 (2H, quint, J=6 Hz), 2.45 (3H, s), 3.28 (3H, s), 3.40 (3H, s), 3.51–3.75 (5H, m), 3.91 (1H, dd, J=4, 18 Hz), 5.43–5.57 (2H, m), 6.53 (1H, d, J=16 Hz), 6.62–6.77 (2H, m), 6.86 (1H, t, J=7.5 Hz), 6.99 (1H, t-like), 7.34 (1H, d, J=8 Hz), 7.45–7.67 (4H, m), 7.71–7.81 (3H, m)

(11) 3-Bromo-8-[2,6-dichloro-3-[N-[4-(2-ethoxyethylcarbamoyl)cinnamoylglycyl]-N-methylamino]-benzyloxy]-2-methylimidazo[1,2-a]pyridine NMR (CDCl₃—CD₃OD, δ): 1.23 (3H, t, J=7 Hz), 2.43 (3H, s), 3.28 (3H, s), 3.46–3.77 (7H, m), 3.93 (1H, dd, J=4, 18 Hz), 5.42–5.56 (2H, m), 6.46–6.61 (2H, m), 6.65–6.78 (2H, m), 6.87 (1H, t, J=7.5 Hz), 7.35 (8H, d), 7.46–7.64 (4H, m), 7.72–7.83 (3H, m)

(12) 3-Bromo-8-[2,6-dichloro-3-[N-[4-(2-hydroxyethylcarbamoyl)cinnamoylglycyl]-N-methylamino]benzyloxy]-2-methylimiazo[1,2-a]pyridine NMR (CDCl₃—CD₃OD, δ): 2.41 (3H, s), 3.26 (3H, s), 3.34–3.46 (1H, m), 3.57 (2H, g, J=5 Hz), 3.65–3.81 (3H, m), 3.95 (1H, d, J=17.5 Hz), 5.50 (2H, s), 6.58 (1H, d, J=16 Hz), 6.75 (1H, d, J=7.5 Hz), 6.89 (1H, t, J=7.5 Hz), 7.42 (1H, d, J=8 Hz), 7.48–7.63 (4H, m), 7.73–7.87 (3H, m)

(13) 3-Bromo-8-[2,6-dichloro-3-[N-[4-(diethylcarbamoyl)cinnamoylglycyl]-N-methylamino]-benzyloxy]-2-methylimidazo[1,2-a]pyridine NMR (CDCl₃, δ): 1.00–1.35 (6H, m), 2.43 (3H, s), 3.26 (3H, s), 3.40–3.75 (5H, m), 3.91 (1H, dd, J=4, 18 Hz), 5.47 (1H, d, J=10 Hz), 5.53 (1H, d, J=10 Hz), 6.48 (1H, d, J=16 Hz), 6.65 (1H, t-like), 6.71 (1H, d, J=7.5 Hz), 6.86 (1H, t, J=7.5 Hz), 7.30–7.45 (3H, m), 7.45–7.64 (4H, m), 7.76 (6H, d)

(14) 3-Bromo-8-[2,6-dichloro-3-[N-[N'-[3-(2-methoxyethylcarbamoyl)phenyl]ureidoacetyl]-N-methylamino]benzyloxy]-2-methylimidazo[1,2-a]pyridine NMR (CDCl₃, δ): 2.42 (3H, s), 3.23 (3H, s), 3.35 (3H, s), 3.49–3.79 (5H, m), 3.87 (1H, dd, J=18, 5 Hz), 5.44 (1H, d, J=10 Hz), 5.52 (1H, d, J=10 Hz), 6.07 (1H, t-like), 6.72 (1H, d, J=8 Hz), 6.80–6.93 (2H, m), 7.15–7.60 (6H, m), 7.78 (1H, d, J=6 Hz), 7.92 (1H, s)

(15) 3-Bromo-8-[2,6-dichloro-3-[N-[N'-[3-[N-(2-methoxyethyl)-N-methylcarbamoyl]phenyl]ureidoacetyl]-N-methylamino]benzyloxy]-2-methylimidazo[1,2-a]pyridine NMR (CDCl₃, δ): 2.42 (3H, s), 2.96–3.14 (3H, m), 3.20–3.49 (8H, 3), 3.58–3.90 (4H, M), 5.43 (1H, d, J=10 Hz), 5.51 (1H, d, J=10 Hz), 5.88 (1H, t-like), 6.72 (1H, d, J=7.5 Hz), 6.86 (1H, t, J=7.5 Hz), 7.00 (1H, dif-dd, J=7.5 Hz), 7.18–7.47 (5H, m), 7.72 (1H, s), 7.77 (1H, d, J=6 Hz)

(16) 3-Bromo-8-[2,6-dichloro-3-[N-[N'-[3-[N,N-bis(2-ethoxyethyl)carbamoyl]phenyl]ureidoacetyl]-N-methylamino]benzyloxy]-2-methylimidazo[1,2-a]pyridine NMR (CDCl₃, δ): 1.07–1.28 (6H, m), 2.40 (3H, s), 3.20 (3H, s), 3.28–3.81 (14H, m), 5.45 (1H, d, J=10 Hz), 5.54 (1H, d, J=10 Hz), 5.84 (1H, t-like), 6.73 (1H, d, J=7.5 Hz), 6.89 (1H, t, J=7.5 Hz), 7.03 (1H, d, J=7.5 Hz), 7.18–7.49 (5H, m), 7.58 (1H, s), 7.79 (8H, d, s)

(17) 3-Bromo-[2,6-dichloro-3-[N-[N'-[3-[N,N-bis(2-hydroxyethyl)carbamoyl]phenyl]ureidoacetyl]-N-methylamino]benzyloxy]-2-methylimidazo[1,2-a]pyridine NMR (CDCl₃, δ): 2.40 (3H, m), 3.23 (3H, s), 3.26–4.01 (12H, m), 5.39–5.55 (2H, m), 6.01 (1H, t-like), 3.71 (1H, d, J=7.5 Hz), 6.86 (1H, t, J=7.5 Hz), 7.02 (1H, d, J=7.5 Hz), 7.10–7.53 (5H, m), 7.77 (1H, d, J=6 Hz), 8.36 (1H, s)

(18) 3-Chloro-8-[2,6-dichloro-3-[N-[4-(N-ethyl-N-methylcarbamoyl)cinnamoylglycyl]-N-methylamino]benzyloxy]-2-methylimidazo[1,2-a]pyridine NMR (CDCl₃, δ):1.05–1.32 (3H, m), 2.43 (3H, s), 2.88–3.13 (3H, m), 3.20–3.37 (4H, m), 3.47–3.76 (2H, m), 3.93 (1H, dd, J=4, 18 Hz), 5.41–5.57 (2H, m), 6.50 (1H, d, J=16 Hz), 6.60–6.75 (2H, m), 6.86 (1H, t, J=7.5 Hz), 7.30–7.46 (3H, m), 7.46–7.64 (4H, m), 7.73 (1H, d, J=6 Hz)

(19) 3-Chloro-8-[2,6-dichloro-3-[N-[4-(ethylcarbamoyl)cinnamoylglycyl]-N-methylamino]benzyloxy]-2-methylimidazo[1,2-a]pyridine NMR (CDCl₃, δ): 1.24 (3H, t, J=7.5 Hz), 2.41 (3H, s), 3.26 (3H, s), 3.50 (2H, quint, J=7.5 Hz), 3.65 (1H, dd, J=4, 18 Hz), 3.90 (1H, dd, J=4, 18 Hz), 5.43–5.55 (2H, m), 6.10 (1H, t-like), 6.53 (1H, d, J=16 Hz), 6.63–6.75 (2H, m), 6.85 (1H, t, J=7.5 Hz), 7.33 (1H, d, J=8 Hz), 7.44–7.64 (4H, m), 7.67–7.80 (3H, m)

(20) 3-Bromo-8-[2,6-dichloro-3-[N-methyl-N-[(E)-3-(6-methylcarbamoyl-3-pyridyl)acryloylglycyl]amino]-benzyloxy]-2-methylimidazo[1,2-a]pyridine NMR (CDCl₃, δ): 2.45 (3H, s), 3.05 (3H, d, J=5 Hz), 3.29 (3H, s), 3.70 (1H, dd, J=18, 4 Hz), 3.92 (1H, dd, J=18, 5 Hz), 5.49 (1H, d, J=10 Hz), 5.52 (1H, d, J=10 Hz), 6.61 (1H, d, J=16 Hz), 6.70–6.79 (2H), 6.88 (1H, t, J=7.5 Hz), 7.34 (1H, d, J=7.5 Hz), 7.50 (1H, d, J=7.5 Hz), 7.61 (1H, d, J=16 Hz), 7.78 (1H, d, J=7.5 Hz), 7.92–8.02 (2H), 8.20 (1H, d, J=7.5 Hz), 8.62 (1H, br s)

(21) 3-Bromo-8-[2,6-dichloro-3-[N-[(E)-3-(6-dimethylcarbamoyl-3-pyridyl)acryloylglycyl]-N-methylamino]benzyloxy]-2-methylimidazo[1,2-a]pyridine NMR (CDCl$_3$, δ): 2.43 (3H, s), 3.11 (3H, s), 3.16 (3H, s), 3.29 (3H, s), 3.69 (1H, dd, J=18, 5 Hz), 3.91 (1H, dd, J=18, 5 Hz), 5.49 (1H, d, J=10 Hz), 5.52 (1H, d, J=10 Hz), 6.60 (1H, d, J=16 Hz), 6.70–6.78 (2H), 6.87 (1H, t, J=7.5 Hz), 7.35 (1H, d, J=8 Hz), 7.50 (1H, d, J=8 Hz), 7.60 (1H, d, J=16 Hz), 7.69 (1H, d, J=8 Hz), 7.78 (1H, d, J=7.5 Hz), 7.91 (1H, dd, J=8, 2 Hz), 8.69 (1H, br s)

(22) 3-Bromo-8-[2,6-dichloro-3-[N-[(E)-3-(6ethylcarbamoyl-3-pyridyl)acryloylglycyl]-N-methylamino]benzyloxy]-2-methylimidazo[1,2-a]pyridine NMR (CDCl$_3$, δ): 1.29 (3H, t, J=7 Hz), 2.45 (3H, s), 3.29 (3H, s), 3.48–3.59 (2H), 3.70 (1H, dd, J=18, 4 Hz), 3.92 (1H, dd, J=18, 5 Hz), 5.49 (1H, d, J=10 Hz), 5.53 (1H, d, J=10 Hz), 6.61 (1H, d, J=16 Hz), 6.70–6.79 (2H), 6.87 (1H, t, J=7.5 Hz), 7.36 (1H, d, J=8 Hz), 7.51 (1H, d, J=8 Hz), 7.62 (1H, d, J=16 Hz), 7.68 (1H, d, J=7 Hz), 7.92–8.01 (2H), 8.20 (1H, d, J=7.5 Hz), 8.63 (1H, br s)

(23) 3-Bromo-8-[2,6-dichloro-3-[N-[(E)-3-[6-(3-methoxypropylcarbamoyl)-3-pyridyl]acryloylglycyl]-N-methylamino]benzyloxy]-2-methylimidazo[1,2-a]pyridine NMR (CDCl$_3$, δ): 1.91 (2H, quint, J=6.5 Hz), 2.45 (3H, s), 3.28 (3H, s), 3.38 (3H, s), 3.50–3.63 (4H, m), 3.68 (1H, dd, J=4, 18 Hz), 3.93 (1H, dd, J=4, 18 Hz), 5.48 (1H, d, J=10 Hz), 5.53 (1H, d, J=10 Hz), 6.61 (1H, d, J=16 Hz), 6.70–7.76 (2H, m), 6.86 (1H, t, J=7.3 Hz), 7.35 (1H, d, J=8.7 Hz), 7.50 (1H, d, J=8.3 Hz), 7.62 (1H, d, J=16 Hz), 7.78 (1H, d, J=7.5 Hz), 7.95 (1H, dd, J=8.3, 2.2 Hz), 8.20 (1H, d, J=8.3 Hz), 8.29 (1H, t-like), 8.65 (1H, d, J=2.0 Hz)

Example 80

To a suspension of 3-bromo-8-[2,6-dichloro-3-[N-methyl-N-[N'-(3-nitrophenyl)ureidoacetyl]amino]benzyloxy]-2-methylimidazo[1,2-a]pyridine (800 mg) in ethanol (8 ml) was added tin(II) chloride (954 mg) at ambient temperature. The mixture was refluxed for 1.5 hours. After cooling, the mixture was adjusted to pH 10 with 1N sodium hydroxide solution. To this mixture was added dichloromethane (10 ml) and the precipitate was removed by filtration. The filtrate was extracted with dichloromethane twice. The organic layer was washed with saturated sodium bicarbonate, water and brine. After dried over magnesium sulfate, the solvent was removed in vacuo. The residue was purified by column chromatography eluting with dichloromethane-methanol to give 8-[3-[N-[N'-(3-aminophenyl)ureidoacetyl]-N-methylamino]-2,6-dichlorobenzyloxy]-3-bromo-2-methylimidazo[1,2-a]pyridine (539 mg) as amorphous.

p NMR (CDCl$_3$, δ): 2.42 (3H, s), 3.22 (3H, s), 3.56–3.75 (3H), 3.82 (1H, dd, J=18, 5 Hz), 5.48 (2H, s), 5.92 (1H, br t, J=4 Hz), 6.88 (1H, dd, J=8, 1 Hz), 6.53 (1H, br d, J=7 Hz), 6.72 (1H, d, J=7 Hz), 6.79–6.91 (2H), 7.01 (1H, t, J=8 Hz), 7.09 (1H, br s), 7.33 (1H, d, J=9 Hz), 7.45 (1H, d, J=9 Hz), 7.78 (1H, d, J=7 Hz)

Example 81

3-Bromo-8-[2,6-dichloro-3-[N-[4-(ethoxycarbonylacetamido)cinnamoylglycyl]-N-methylamino]benzyloxy]-2-methylimidazo[1,2-a]pyridine was obtained by reacting 8-[3-[N-(4-aminocinnamoylglycyl)-N-methylamino]-2,6-dichlorobenzyloxy]-3-bromo-2-methylimidazo[1,2-a]pyridine with ethyl chloroformylacetate according to a similar manner to that of Example 37.

p NMR (CDCl$_3$, δ): 1.33 (3H, t, J=7.5 Hz), 2.44 (3H, s), 3.26 (3H, s), 3.47 (2H, s), 3.65 (1H, dd, J=4, 18 Hz), 3.90 (1H, dd, J=4, 18 Hz), 4.26 (2H, q, J=7.5 Hz), 5.42–5.55 (2H, m), 6.41 (1H, d, J=16 Hz), 6.60 (1H, t-like), 6.72 (1H, d, J=7.5 Hz), 6.85 (1H, t, J=7.5 Hz), 7.33 (1H, d, J=8 Hz), 7.43–7.64 (6H, m), 7.78 (1H, d, J=6 Hz), 9.45 (1H, s)

Example 82

8-[3-[N-[4-(Benzamido)cinnamoylglycyl]-N-ethylamino]-2,6-dichlorobenzyloxy]-3-bromo-2-methylimidazo[1,2-a]pyridine was obtained by reacting 8-[3-[N-(4-aminocinnamoylglycyl)-N-methylamino]-2,6-dichlorobenzyloxy]-3-bromo-2-methylimidazo[1,2-a]pyridine with benzoic acid in the presence of N-ethyl-N'-(3-dimethylaminopropyl)carbodiimide hydrochloride and 1-hydroxybenzotriazole according to a similar manner to that of Example 39.

p NMR (CDCl$_3$, δ): 2.41 (3H, s), 3.25 (3H, s), 3.66 (1H, dd, J=18, 4 Hz), 3.90 (1H, dd, J=18, 5 Hz) 5.49 (2H, br s), 6.42 (1H, d, J=16 Hz), 6.60 (1H, br t), 6.72 (1H, d, J=7 Hz), 6.86 (1H, t, J=7 Hz), 7.18–7.80 (9H, m), 7.86 (2H, d, J=9 Hz), 8.01 (1H, br s)

Example 83

The following compounds were obtained according to similar manners to those of Examples 81 or 82.

(1) 3-Bromo-8-[2,6-dichloro-3-[N-methyl-N-[4-(4-pyridylacetamido)cinnamoylglycyl]amino]benzyloxy]-2-methylimidazo[1,2-a]pyridine NMR (CDCl$_3$, δ): 2.40 (3H, s), 3.23 (3H, s), 3.64 (1H, dd, J=18, 5 Hz), 3.67 (2H, br s), 3.86 (1H, dd, J=18, 4 Hz), 5.42 (1H, d, J=9 Hz), 5.48 (1H, d, J=9 Hz), 6.39 (1H, d, J=16 Hz), 6.63 (1H, br t, J=4 Hz), 6.73 (1H, d, J=7.5 Hz), 6.86 (1H, t, J=7.5 Hz), 7.15–7.33 (3H, m), 7.35–7.57 (6H, m), 7.78 (1H, d, J=7.5 Hz), 8.18 (1H br s), 8.58 (2H, dd, J=7, 2 Hz)

(2) 3-Bromo-8-[2,6-dichloro-3-[N-[4-(3-methoxypropionamido)cinnamoylglycyl]-N-methylamino]-benzyloxy]-2-methylimidazo[1,2-a]pyridine NMR (CDCl$_3$, δ): 2.45 (3H, s), 2.65 (2H, t, J=6 Hz), 3.28 (3H, s), 3.46 (3H, s), 3.59–3.79 (3H, m), 3.90 (1H, dd, J=4, 18 Hz), 5.42–5.57 (2H, m), 6.40 (1H, d, J=16 Hz), 6.60 (1H, t-like), 6.73 (1H, d, J=7 Hz), 6.87 (1H, d, J=7 Hz), 7.33 (1H, d, J=8 Hz), 7.40–7.60 (6H, m), 7.77 (1H, d, J=6 Hz), 8.39 (1H, s)

(3) 8-[3-[N-[4-(Acetamidoacetamido)cinnamoylglycyl]-N-methylamino]-2,6-dichlorobenzyloxy]-3-bromo-2-methylimidazo[1,2-a]pyridine NMR (CDCl$_3$, δ): 2.10 (3H, s), 2.44 (3H, s), 3.27 (3H, s), 3.64 (1H, dd, J=4, 17.5 Hz), 3.92 (1H, dd, J=4, 17.5 Hz), 4.06 (2H, d, J=6 Hz), 5.43–5.56 (2H, m), 6.35 (1H, d, J=16 Hz), 6.59 (1H, t-like), 6.66–6.92 (3H, m), 7.30–7.57 (7H, m), 7.76 (1H, d, J=6 Hz), 8.86 (1H, s)

(4) 3-Bromo-8-[2,6-dichloro-3-[N-methyl-N-[4-[2-(dimethylamino)acetamido]cinnamoylglycyl]amino]-benzyloxy]-2-methylimidazo[1,2-a]pyridine NMR (CDCl$_3$, δ): 2.39 (6H, s), 2.43 (3H, s), 3.08 (2H, s), 3.28 (3H, s), 3.68 (1H, dd, J=4, 17.5 Hz), 4.92 (1H, dd, J=4, 17.5 Hz), 5.42–5.56 (2H, m), 6.42 (1H, d, J=16 Hz), 6.59 (1H, t-like), 6.72 (1H, d, J=7.5 Hz), 6.86 (1H, t, J=7.5 Hz), 7.33 (1H, d, J=8 Hz), 7.40–7.68 (6H, m), 7.76 (1H, d, J=6 Hz), 9.23 (1H, s)

(5) 3-Bromo-8-[2,6-dichloro-3-[N-[4-[(E)-3-(ethoxycarbonyl)acrylamido]cinnamoylglycyl]-N-methylamino]benzyloxy]-2-methylimidazo[1,2-a]pyridine NMR (CDCl₃, δ): 1.30 (3H, J=7.5 Hz), 2.41 (3H, s), 3.25 (3H, s), 3.64 (1H, dd, J=17, 4 Hz), 3.88 (1H, dd, J=17, 5 Hz), 4.24 (2H, q, J=7.5 Hz), 5.42 (1H, d, J=9 Hz), 5.49 (1H, d, J=9 Hz), 6.40 (1H, d, J=16 Hz), 6.67 (1H, br t, J=4 Hz), 6.73 (1H, d, J=7 Hz), 6.81–6.97 (2H, m), 7.10 (1H, d, J=15 Hz), 7.20 (2H, d, J=9 Hz), 7.36–7.52 (3H, m), 7.58 (1H, d, J=11 Hz), 7.63 (1H, d, J=7 Hz), 7.78 (1H, d, J=7 Hz), 8.82 (1H, br s)

(6) 3-Bromo-8-[2,6-dichloro-3-[N-[4-(hydroxyacetamido)cinnamoylglycyl]-N-methylamino]benzyloxy)-2-methylimidazo[1,2-a]pyridine NMR (CDCl₃, δ): 2.39 (3H, s), 3.24 (3H, s), 3.67 (1H, dd, J=17, 4 Hz), 3.94 (1H, dd, J=17, 5 Hz), 4.11 (2H, s), 5.48 (2H, s), 6.30 (1H, d, J=15 Hz), 6.66–6.90 (2H, m), 6.86 (1H, t, J=7 Hz), 7.25–7.60 (7H, m), 7.76 (1H, d, J=7 Hz), 8.78 (1H, br s)

(7) 3-Bromo-8-[2,6-dichloro-3-[N-[4-(2-chloroethoxycarbonylamino)cinnamoylglycyl]-N-methylamino]benzyloxy]-2-methylimidazo[1,2-a]pyridine NMR (CDCl₃, δ): 2.44 (3H, s), 3.27 (3H, s), 3.57–3.80 (3H, m), 3.91 (1H, dd, J=4, 18 Hz), 4.45 (2H, t, J=6 Hz), 5.50 (2H, s), 6.40 (1H, d, J=16 Hz), 6.60 (1H, t-like), 6.72 (1H, d, J=7.5 Hz), 6.80–6.91 (2H, m), 7.22–7.60 (7H, m), 7.78 (1H, d, J=6 Hz)

(8) 3-Bromo-8-[2,6-dichloro-3-[N-[N'-[3-(methoxyacetamido)phenyl]ureidoacetyl]-N-methylamino]-benzyloxy]-2-methylimidazo[1,2-a]pyridine mp: 238°–239° C.

NMR (CDCl₃—CD₃OD, δ): 2.40 (3H, s), 3.25 (3H, s), 345–3.68 (4H, overlapped with H₂O), 3.89 (1H, d, J=18 Hz), 4.00 (2H, s), 5.50 (2H, s), 6.78 (1H, d, J=7 Hz), 6.91 (5H, t, J=7 Hz), 7.08–7.38 (3H), 7.44 (1H, d, J=9 Hz), 7.52 (1H, d, J=9 Hz), 7.59 (1H, br s), 7.80 (1H, d, J=7 Hz)

(9) 3-Bromo-8-[2,6-dichloro-3-[N-[N'-[3-(ethoxycarbonylacetamido)phenyl]ureidoacetyl]-N-methylaminobenzyloxy]-2-methylimidazo[1,2-a]pyridine NMR (CDCl₃, δ): 1.27 (3H, t, J=7 Hz), 2.40 (3H, s), 3.19 (3H, s), 3.41 (2H, s), 3.59 (1H, br d, J=18 Hz), 3.89 (1H, br d, J=18 Hz), 4.19 (2H, q, J=7 Hz), 5.40 (2H, s), 6.22 (1H, br s), 6.72 (1H, d, J=7 Hz), 6.88 (1H, t, J=7 Hz), 7.00–7.52 (6H), 7.78 (1H, d, J=7 Hz), 8.18 (7H, br s), 9.62 (1H, br s)

(10) 3-Chloro-8-[2,6-dichloro-3-[N-[4-(3-methoxypropionamido)cinnamoylglycyl]-N-methylamino]benzyloxy]-2-methylimidazo[1,2-a]pyridine NMR (CDCl₃, δ): 2.31 (3H, s), 2.63 (2H, t, J=5 Hz), 3.26 (3H, s), 3.47 (3H, s), 3.61–3.77 (3H) 3.90 (1H, dd, J=18, 5 Hz), 5.48 (1H, d, J=10 Hz), 5.51 (1H, d, J=10 Hz), 6.39 (1H, d, J=15 Hz), 6.60 (1H, br s), 6.71 (1H, d, J=7.5 Hz), 6.87 (1H, t, J=7.5 Hz), 7.32 (1H, d, J=8 Hz), 7.41–7.58 (6H), 7.72 (1H, d, J=7.5 Hz), 8.45 (1H, br s)

(11) 8-[3-[N-[4-(Acetamidoacetamido)cinnamnoylglycyl]-N-methylamino]-2,6-dichlorobenzyloxy]-3-chloro-2-methylimidazo[1,2-a]pyridine NMR (CDCl₃, δ):2.09 (3H, s), 2.42 (3H, s), 3.25 (3H, s), 3.64 (1H, dd, J=4, 18 Hz), 3.90 (1H, dd, J=4, 18 Hz), 4.05 (2H, d, J=5 Hz), 5.43–5.54 (2H, m), 6.39 (1H, d, J=16 Hz), 6.62 (1H, t-like), 6.70 (1H, d, J=7.7 Hz), 6.80 (1H, t-like), 6.86 (1H, t, J=7.7 Hz), 7.32–7.55 (7H, m), 7.72 (2H, d, J=6 Hz), 8.85 (1H, s)

Example 84

A solution of 8-[3-[N-(4-aminocinnamoylglycyl)-N-methylamino]-2,6-dichlorobenzyloxy]-3-bromo-2-methylimidazo[1,2-a]pyridine (150 mg) and succinic anhydride (26 mg) in dioxane (3 ml) was refluxed for 2 hours. After cooling, the solution was removed in vacuo to give 3-bromo-8-[3-[N-[4-(3-carboxypropionamido)cinnamoylglycyl]-N-methylamino]-2,6-dichlorobenzyloxy]-2-methylimidazo[1,2-a]pyridine (175 mg) as amorphous.

p NMR (CDCl₃—CD₃OD, δ): 2.41 (3H, s), 2.59–2.70 (4H), 3.27 (3H, s), 3.64 (1H, d, J=18 Hz), 3.98 (1H, d, J=18 Hz), 5.51 (2H, s), 6.41 (1H, d, J=15 Hz), 6.76 (1H, d, J=7 Hz), 6.90 (1H, t, J=7 Hz), 7.38–7.62 t7H), 7.79 (1H, d, J=7 Hz)

Example 85

A solution of 8-[3-(N-glycyl-N-methylamino)-2,6-dichlorobenzyloxy]-3-bromo-2-methylimidazo[1,2-a]pyridine (300 mg) and dimethyl cyanodithioiminocarbonate (93 mg) in dimethylformamide (3 ml) was heated at 700° C. for 1 hour. After cooling the reacting mixture, to the mixture was added 70% solution of ethylamine in water (0.57 ml) and the mixture was heated at 60° C. for 2 hours. To this mixture was added water (3 ml) in an ice-water bath. The precipitates were collected by vacuum filtration and washed with ethyl acetate to give 3-bromo-8-[3-[N-[(2-cyano-3-ethylguanidino)acetyl]-N-methylamino]-2,6-dichlorobenzyloxy]-2-methylimidazo[1,2-a]pyridine (278 mg) as colorless crystals.

mp: >250° C.

p NMR (CDCl₃—CD₃OD, δ): 1.20 (3H, t, J=7 Hz), 2.39 (3H s), 3.16–3.31 (5H), 3.61 (1H, d, J=17 Hz), 3.73 (1H, d, J=17 Hz), 5.47 (1H, d, J=10 Hz), 5.57 (1H, d, J=10 Hz), 6.79 (1H, d, J=7 Hz), 6.91 (1H, t, J=7 Hz), 7.42 (1H, d, J=9 Hz), 7.56 (1H, d, J=9 Hz), 7.80 (1H, d, J=7 Hz)

Example 86

A suspension of 3-bromo-8-[3-[N-[4-(3-carboxypropionamido)cinnamoylglycyl]-N-methylamino]-2,6-dichlorobenzyloxy]-2-methylimidazo[1,2-a]pyridine (110 mg) and anhydrous sodium acetate (16 mg) in acetic anhydride (1.1 ml) was refluxed for 5 hours. After cooling, the solvent was removed in vacuo. The residue was dissolved in dichloromethane (5 ml) and washed with water, saturated sodium bicarbonate twice and brine. After dried over magnesium s the solvent was removed in vacuo. The residue was purified by preparative thin-layer chromatography (ethyl acetate-methanol) to give 3-bromo-8-[2,6-dichloro-3-[N-[4-(succinimido)cinnamoylglycyl]-N-methylamino]benzyloxy]-2-methylimidazo[1,2-a]pyridine (12 mg) as amorphous.

p NMR (CDCl₃, δ): 2.43 (3H, s), 2.91 (4H, s), 3.29 (3H, s), 3.68 (1H, dd, J=18, 4 Hz), 3.91 (1H, dd, J=18, 5 Hz), 5.48 (1H, d, J=10 Hz), 5.53 (1H, d, J=10 Hz), 6.50 (1H, d, J=16 Hz), 6.68 (1H, br t, J=4 Hz), 6.72 (1H, d, J=7 Hz), 6.88 (1H, t, J=7 Hz), 7.22–7.39 (3H), 7.48–7.67 (4H), 7.78 (1H, d, J=7 Hz)

Example 87

To a solution of 3-bromo-8-[2,6-dichloro-3-[N-[4-(2-chloroethoxycarbonylamino)cinnamoylglycyl]-N-methylamino]benzyloxy]-2-methylimidazo[1,2-a]pyridine (128 mg) in methanol was added dropwise sodium methanolate (28% in methanol, 37 mg) under nitrogen in ice-water bath and the mixture was stirred for 1 hour at same temperature and then at ambient temperature for 2 hours. The reaction mixture was poured into water and extracted with dichloromethane. The organic layer was washed with water and brine, dried over magnesium sulfate and evaporated in vacuo. The residue was purified by preparative thin layer chromatography(ethyl acetate) to give 3-bromo-8-[2,6-dichloro-3-[N-[4-(2-oxo-3-oxazolidinyl)cinnamoylglycyl]-N-methylamino]benzyloxy]-2-methylimidazo[1,2-a]pyridine (77 mg) as an amorphous powder.

p NMR (CDCl$_3$, δ): 2.44 (3H, s), 3.28 (3H, s), 3.66 (1H, dd, J=4, 18 Hz), 3.91 (1H, dd, J=4, 18 Hz), 4.10 (2H, dd, J=6, 8 Hz), 4.53 (2H, dd, J=6, 8 Hz), 5.45–5.57 (2H, m), 6.43 (1H, d, J=16 Hz), 6.60 (1H, t-like), 6.72 (1H, d, J=7.5 Hz), 6.85 (1H t, J=7.5 Hz), 7.34 (1H, d, J=8 Hz), 7.45–7.62 (6H, m), 7.76 (6H, d)

Example 88

(1) 3-Bromo-8-[3-[N-[N'-[3-(4-bromobutyramido)phenyl]-ureidoacetyl]-N-methylamino]-2,6-dichlorobenzyloxy]-2-methylimidazo[1,2-a]pyridine was obtained according to a similar manner to that of Example 82.

(2) 3-Bromo-8-[2,6-dichloro-3-[N-methyl-N-[N'-[3-(2-oxo-1-pyrrolidinyl)phenyl]ureidoacetyl]amino]benzyloxy]-2-methylimidazo[1,2-a]pyridine was obtained according to a similar manner to that of Example 87.

NMR (CDCl$_3$, δ): 2.01–2.27 (2H), 2.41 (3H, s), 2.59 (2H, t, J=8 Hz), 3.23 (3H, s), 3.63 (1H, dd, J=17, 5 Hz), 3.74–3.92 (3H), 4.58 (1H, br t, J=6 Hz), 5.46 (2H, s), 5.99 (1H, br t, J=5 Hz), 6.72 (1H, d, J=7 Hz), 6.88 (1H, t, J=8 Hz), 7.02–7.50 (5H), 7.60 (1H, d, J=9 Hz), 7.77 (1H, d, J=7 Hz)

Example 89

A mixture of 3-bromo-8-[2,6-dichloro-3-[N-[4-(3-carboxypropionamido)cinnamoylglycyl]-N-methylamino]benzyloxy]-2-methylimidazo[1,2-a]pyridine (60 mg), ethanol (12 mg), N-ethyl-N'-(3-dimethylaminopropyl) carbodiimide hydrochloride (21 mg), 1-hydroxybenzotriazole (17 mg) and N,N-dimethylformamide (0.6 ml) was stirred for 3 hours at ambient temperature. Ethyl acetate was added thereto, and the mixture was washed with water four times, dried over magnesium sulfate and concentrated in vacuo. The residue was purified by preparative thin layer chromatography (methylene chloride:methanol=10:1, V/V) to give 3-bromo-8-[2,6-dichloro-3-[N-[4-(3-ethoxycarbonylpropionamido)cinnamoylglycyl]-N-methylamino]benzyloxy]-2-methylimidazo[1,2-a]pyridine (7 mg) as an amorphous.

p NMR (CDCl$_3$, δ): 1.28 (3H, t, J=7 Hz), 2.44 (3H, s), 2.60–2.82 (4H), 3.28 (3H, s), 3.66 (1H, dd, J=18, 4 Hz), 3.91 (1H, dd, J=18, 5 Hz), 4.18 (2H, q, J=7 Hz), 5.49 (2H, s), 6.39 (1H, d, J=15 Hz), 6.61–6.79 (2H), 6.87 (1H, t, J=7 Hz), 7.30–7.60 (7H), 7.78 (1H, d, J=7 Hz), 8.12 (1H, br s)

Example 90

To a solution of 8-[3-[N-[N'-(3-acetylphenyl)ureidoacetyl]-N-methylamino]-2,6-dichlorobenzyloxy]-3-bromo-2-methylimidazo[1,2-a]pyridine (200 mg) in methanol (2 ml) was added sodium borohydride (24 mg) under ice-bath cooling, and the mixture was stirred for 1 hour at ambient temperature. To the reaction mixture was added 1N hydrochloric acid, and the mixture was stirred for 30 minutes. Saturated aqueous solution of sodium bicarbonate was added thereto, and the mixture was extracted with methylene chloride three times. The combined organic layer was washed with water and brine, dried over magnesium sulfate, and concentrated in vacuo. The residue was purified by silica gel column chromatography (methylene chloride:methanol=30:1, V/V) to give 3-bromo-8-[2,6-dichloro-3-[N-[N'-[3-(1-hydroxyethyl)phenyl]ureidoacetyl]-N-methylamino]benzyloxy]-2-methylimidazo[1,2-a]pyridine (160 mg) as an amorphous.

p NMR (CDCl$_3$, δ): 1.41 (3H, d, J=6 Hz), 2.41 (3H, 8), 3.22 (3H, s), 3.61 (1H, br dt, J=17, 3 Hz), 3.88 (1H, dd, J=17, 5 Hz), 4.79 (1H, m), 5.49 (2H, s), 6.09 (1H, br t, J=5 Hz), 6.72 (1H, d, J=7 Hz), 6.87 (1H, t, J=7 Hz), 6.96 (1H, m), 7.10–7.49 (4H), 7.59 (1H, br d, J=7 Hz), 7.78 (1H, d, J=7 Hz)

Example 91

To a solution of 3-bromo-8-[2,6-dichloro-3-[N-methyl-N-[(thiomorpholinoacetyl)glycyl]amino]benzyloxy]-2-methylimidazo[1,2-a]pyridine (200 mg) in methylene chloride (2 ml) was added m-chloroperbenzoic acid (80% purity, 76 mg) under ice-bath cooling, and the mixture was stirred for 1 hour at the same temperature. The reaction mixture was washed with water twice and brine, dried over magnesium sulfate, and concentrated in vacuo. The residue was purified by preparative thin layer chromatography (methylene chloride:methanol=5:1, V/V) to give 3-bromo-8-[2,6-dichloro-3-[N-methyl-N-[[(1-oxothiomorpholino)acetyl]glycyl]amino]benzyloxy]-2-methylimidazo[1,2-a]-pyridine (96 mg) as an amorphous.

p NMR (CDCl$_3$, δ): 2.44 (3H, d), 2.70–3.02 (6H), 3.11 (2H, s), 3.15–3.36 (5H), 3.57 (1H, dd, J=17, 5 Hz), 3.85 (1H, dd, J=17, 5 Hz), 5.47 (1H, dd, J=10 Hz), 5.52 (1H, d, J=10 Hz ), 6.71 (1H, d, J=7 Hz), 6.86 (1H, t, J=7 Hz), 7.31 (1H, d, J=9 Hz), 7.50 (1H, d, J=9 Hz), 7.79 (1H, d, J=7 Hz), 7.84 (1H, br t, J=5 Hz)

Example 92

To a solution of 3-bromo-8-[2,6-dichloro-3-[N-methyl-N-[(thiomorpholinoacetyl)glycyl]amino]benzyloxy]-2-methylimidazo[1,2-a]pyridine (200 mg) in methylene chloride (2 ml) was added m-chloroperbenzoic acid (80% purity, 190 mg) under ice-bath cooling, and the mixture was stirred for 2 hours at the same temperature. The reaction mixture was washed with water twice and brine, dried over magnesium sulfate, and concentrated in vacuo. The residue was purified by preparative thin layer chromatography (methylene chloride:methanol=3:1, V/V) to give 3-bromo-8-[2,6-dichloro-3-[N-[[(1,1-dioxothiomorpholino)acetyl]glycyl]-N-methylamino]benzyloxy]-2-methylimidazo[1,2-a]pyridine (99 mg) as an amorphous.

p NMR (CDCl$_3$, δ): 2.43 (3H, s), 2.81–3.01 (2H), 3.21 (3H, s), 3.48–4.20 (10H), 5.50 (2H, s), 6.71 (1H, d, J=7 Hz), 6.86 (1H, t, J=7 Hz), 7.40 (1H, d, J=9 Hz), 7.50 (1H, d, J=9 Hz), 7.77 (1H, d, J=7 Hz)

Example 93

The following compounds were obtained according to a similar manner to that of Example 60.

(1) 3-Bromo-8-[2,6-dichloro-3-[N-methyl-N-[(thiomorpholinoacetyl)glycyl]amino]benzyloxy]-2-methylimidazo[1,2-a]pyridine dihydrochloride NMR (CDCl$_3$—CD$_3$OD, δ): 2.61 (3H, s), 2.70–4.30 (15H), 5.65 (1H, d, J=10 Hz), 5.75 (1H, d, J=10 Hz), 7.52–7.70 (4H), 8.22 (1H, dd, J=5, 3 Hz)

(2) 3-Bromo-8-[2,6-dichloro-3-[N-methyl-N-[[(1-oxothiomorpholino)acetyl]glycyl]amino]benzyloxy]-2-methylimidazo[1,2-a]pyridine dihydrochloride NMR (CDCl$_3$—CD$_3$OD, δ): 2.67 (3H, s), 3.00–3.19 (2H), 3.22 (3H, s), 3.57–4.24 (10H), 5.60 (1H, d, J=10 Hz), 5.70 (1H, d, J=10 Hz), 7.39–7.66 (4H), 8.10 (1H, d, J=6 Hz)

(3) 3-Bromo-8-[2,6-dichloro-3-[N-[[(1,1-dioxothiomorpholino)acetyl]glycyl]-N-methylamino]benzyloxy]-2-methylimidazo[1,2-a]pyridine dihydrochloride NMR (CDCl₃—CD₃OD, δ): 2.63 (3H, s), 3.00–3.19 (2H), 3.24 (3H, s), 3.35–3.57 (2H), 3.72 (1H, d, J=16 Hz), 3.93 (1H, d, J=16 Hz), 4.20–4.41 (2H), 4.62–4.98 (4H), 5.67 (2H, s), 7.38–7.67 (4H), 8.09 (1H, d, J=6 Hz)

(4) 3-Bromo-8-[2,6-dichloro-3-[N-methyl-N-[[(2-pyrimidinylthio)acetyl]glycyl]amino]benzyloxy]-2-methylimidazo[1,2-a]pyridine dihydrochloride NMR (CDCl₃—CD₃OD, δ): 2.57 (3H, s), 3.26 (3H, s), 3.67 (2H, s), 3.86 (2H, s), 5.64 (1H, d, J=10 Hz), 5.73 (1H, d, J=10 Hz), 7.19 (1H, t, J=5 Hz), 7.48–7.69 (4H), 8.21 (1H, dd, J=5, 1 Hz), 8.66 (2H, d, J=5 Hz)

(5) 3-Bromo-8-2,6-dichloro-3-[N-methyl-N-[(phenoxyacetyl)glycyl]amino]benzyloxy]-2-methylimidazo[1,2-a]pyridine hydrochloride NMR (CDCl₃—CD₃OD, δ): 2.58 (3H, s), 3.30 (3H, s), 3.78 (2H, s), 4.51 (2H, s), 5.67 (1H, d, J=10 Hz), 5.77 (1H, d, J=10 Hz), 6.90–7.10 (3H), 7.25–7.42 (2H), 7.51–7.70 (4H), 8.21 (1H, dd, J=5, 2 Hz)

(6) 3-Bromo-8-[2,6-dichloro-3-[N-[(heptafluorobutanoyl)glycyl]-N-methylamino]benzyloxy]-2-methylimidazo-[1,2-a]pyridine hydrochloride NMR (CDCl₃—CD₃OD, δ): 2.62 (3H, s), 3.28 (3H, s), 3.77 (1H, d, J=17 Hz), 3.89 (1H, d, J=17 Hz), 5.62 (1H, d, J=10 Hz), 5.71 (1H, d, J=10 Hz), 7.39–7.63 (4H), 8.09 (1H, dd, J=6, 1 Hz)

(7) 3-Bromo-8-[2,6-dichloro-3-[N-(n-heptanoylglycyl)-N-methylamino]benzyloxy]-2-methylimidazo[1,2-a]pyridine hydrochloride NMR (CDCl₃—CD₃OD, δ): 0.89 (3H, t, J=7 Hz), 1.21–1.40 (6H), 1.51–1.70 (2H), 2.26 (2H, t, J=7 Hz), 2.58 (3H, s), 3.29 (3H, s), 3.68 (2H, s), 5.67 (1H, d, J=10 Hz), 5.77 (1H, d, J=10 Hz), 7.52–7.70 (4H), 8.24 (1H, dd, J=5, 2 Hz)

(8) 2-Bromo-8-[2,6-dichloro-3-[N-methyl-N-(cinnamoylglycyl)amino]benzyloxy]-2-methylimidazo[1,2-a]pyridine hydrochloride NMR (CDCl₃—CD₃OD, δ): 2.60 (3H, s), 3.30 (3H, s), 3.81 (2H, s), 5.67 (1H, d, J=10 Hz), 5.78 (1H, d, J=10 Hz), 6.60 (1H, d, J=15 Hz), 7.32–7.69 (10H), 8.20 (1H, dd, J=5, 2 Hz)

(9) 3-Bromo-8-[2,6-dichloro-3-[N-methyl-N-[(trans-3-pentenoyl)glycyl]amino]benzyloxy]-2-methylimidazo[1,2-a]pyridine hydrochloride NMR (CDCl₃—CD₃OD, δ): 1.73 (3H, d, J=6 Hz), 2.58 (3H, s), 2.99 (2H, d, J=6 Hz), 3.29 (3H, s), 3.68 (2H, s), 5.40–5.80 (4H), 7.52–7.70 (4H), 8.25 (1H, dd, J=5, 1 Hz)

(10) 3-Bromo-8-[3-[N-[(3-butenoyl)glycyl]-N-methylamino]-2,6-dichlorobenzyloxy]-2-methylimidazo[1,2-a]pyridine hydrochloride NMR (CDCl₃—CD₃OD, δ): 2.59 (3H, s), 3.06 (2H, d, J=7 Hz), 3.28 (3H, s), 3.68 ( 2H, s), 5.18–5.31 (2H), 5.61–6.01 (3H), 7.50–7.69 (4H), 8.21 (1H, dd, J=5, 3 Hz)

(11) 3-Bromo-8-[2,6-dichloro-3-[N-methyl-N-[(4-phenylbutanoyl) glycyl]amino]benzyloxy]-2-methylimidazo[1,2-a]pyridine hydrochloride NMR (CDCl₃—CD₃OD, δ):1.83–2.02 (2H), 2.29 (2H, t, J=8 Hz), 2.57 (3H, s), 2.66 (2H, t, J=8 Hz), 3.28 (3H, s), 3.68 (2H, s), 5.65 (1H, d, J=10 Hz), 5.77 (1H, d, J=10 Hz), 7.10–7.32 (5H), 7.51–7.69 (4H), 8.22 (1H, dd, J=5, 2 Hz)

(12) 3-Bromo-8-[2,6-dichloro-3-[N-[(N,N-dimethyl-β-alanyl)glycyl]-N-methylamino]benzyloxy]-2-methylimidazo-1,2-a]pyridine hydrochloride NMR (CDCl₃—CD₃OD, δ): 2.60 (3H, s), 2.79–2.95 (8H), 3.25 (2H, s), 3.36–3.49 (2H), 3.60 (1H, d, J=17 Hz), 3.82 (1H, d, J=17 Hz), 5.67 (1H, d, J=10 Hz), 5.77 (1H, d, J=10 Hz), 7.53–7.70 (4H), 8.24 (1H, d, J=6 Hz)

(13) 3-Bromo-8-[2,6-dichloro-3-[N-[N'-(5-isoquinolyl)ureidoacetyl]-N-methylamino]benzyloxy]-2-methylimidazo[1,2-a]pyridine dihydrochloride NMR (CDCl₃—CD₃OD, δ): 2.58 (3H, s), 3.29 (3H, s), 3.75 (1H, d, J=(17 Hz), 3.90 (2H, d, J=17 Hz), 5.66 (1H, d, J=10 Hz), 5.78 (1H, d, J=10 Hz), 7.52–7.66 (4H), 7.91 (1H, t, J=8 Hz), 8.10 (1H, d, J=8 Hz), 8.20 (1H, br s), 8.50 (1H, d, J=6 Hz), 8.60 (1H, d, J=8 Hz), 8.88 (3H, d, J=6 Hz), 9.60 (1H, s)

(14) 3-Bromo-8-[2,6-dichloro-3-[N-methyl-N-[N'-(3-pyrazolyl)ureidoacetyl]amino]benzyloxy]-2-methylimidazo[1,2-a]pyridine dihydrochloride NMR (CDCl₃—CD₃OD, δ): 2.59 (3H, s), 3.30 (3H, s), 3.79 (1H, d, J=17 Hz), 3.93 (1H, d, J=17 Hz), 5.67 (1H, d, J=10 Hz), 5.76 (1H, d, J=10 Hz), 6.40 (1H, d, J=3 Hz), 7.50–7.70 (4H), 8.12 (1H, d, J=3 Hz), 8.21 (1H, dd, J=5, 3 Hz)

(15) 3-Bromo-8-[2,6-dichloro-3-[N-methyl-N-[N'-(4-pyrimidinyl)ureidoacetyl]amino]benzyloxy]-2-methylimidazo[1,2-a]pyridine dihydrochloride NMR (CDCl₃—CD₃OD, δ): 2.60 (3H, s), 3.29 (3H, s), 3.71 (1H, d, J=18 Hz), 3.88 (1H, d, J=18 Hz), 5.71 (2H, br s), 7.52–7.71 (4H), 8.07–8.79 (2H), 8.58 (1H, br s), 8.99 (1H, br s)

(16) 3-Bromo-8-[2,6-dichloro-3-[N-methyl-N-[N'-(6-quinolyl)ureidoacetyl]amino]benzyloxy]-2-methylimidazo[1,2-a]pyridine dihydrochloride NMR (CDCl₃—CD₃OD, δ): 2.59 (3H, s), 3.28 (3H, s), 3.70 (1H, d, J=16 Hz), 3.88 (1H, d, J=16 Hz), 5.64 (1H, d, J=10 Hz), 5.76 (1H, d, J=10 Hz), 7.47–7.66 (4H), 7.90 (1H, dd, J=9, 5 Hz), 8.04–8.46 (4H), 8.81 (1H, d, J=9 Hz), 8.90 (1H, d, J=5 Hz)

(17) 3-Bromo-8-[2,6-dichloro-3-[N-[(1-indolylcarbonyl)glycyl]-N-methylamino]benzyloxy]-2-methylimidazo[1,2-a]pyridine hydrochloride mp: 224° C. (dec.)

NMR (CDCl₃—CD₃OD, δ): 2.58 (3H, s), 3.31 (3H, s), 3.83 (1H, d, J=17 Hz), 3.95 (1H, d, J=17 Hz), 5.67 (1H, d, J=10 Hz), 5.74 (1H, d, J=10 Hz), 6.65 (1H, d, J=4 Hz), 7.18–7.38(2H), 7.53–7.70 (6H), 8.12 (1H, d, J=8 Hz), 8.21 (1H, m)

(18) 3-Bromo-8-[2,6-dichloro-3-[N-methyl-N-[(morpholinocarbonyl)glycyl]amino]benzyloxy]-2-methylimidazo[1,2-a]pyridine hydrochloride NMR (CDCl₃—CD₃OD, δ): 2.58 (3H, s), 3.27 (3H, s), 3.31–3.48 (4H), 3.61–3.79 (6H), 5.63 (1H, d, J=10 Hz), 5.78 (1H, d, J=10 Hz), 7.52–7.69 (4H), 8.23 (1H, dd, J=5, 1 Hz)

(19) 3-Bromo-8-[2,6-dichloro-3-[N-methyl-N-[N'-[3-(morpholinocarbonyl)phenyl]ureidoacetyl]amino]-benzyloxy]-2-methylimidazo[1,2-a]pyridine hydrochloride NMR (CDCl₃—CD₃OD, δ): 2.55 (3H, s), 3.29 (3H, s), 3.41–3.86 (10H), 5.69 (1H, d, J=10 Hz), 5.78 (1H, d, J=10 Hz), 7.00 (1H, d, J=7 Hz), 7.27–7.71 (7H), 8.26 (1H, d, J=5 Hz)

(20) 3-Bromo-8-[3-[N-(N'-n-butylureidoacetyl)-N-methylamino]-2,6-dichlorobenzyloxy]-2-methylimidazo[1,2-a]pyridine hydrochloride NMR (CDCl₃—CD₃OD, δ): 0.89 (3H, t, J=6 Hz), 1.20–1.41 (2H), 1.48–1.66 (2H), 2.62 (3H, s), 3.11–3.29 (5H), 3.87 (1H, d, J=17 Hz), 4.00 (1H, d, J=17 Hz), 5.56 (1H, d, J=10 Hz), 5.71 (1H, d, J=10 Hz), 7.36–7.61 (4H), 8.06 (1H, d, J=6 Hz)

(21) 3-Bromo-8-[2,6-dichloro-3-[N-methyl-N-[N'-(3-quinolyl)ureidoacetyl]amino]benzyloxy]-2-methylimidazo[1,2-a]pyridine dihydrochloride NMR (CDCl₃, δ): 2.69 (3H, s), 3.23 (3H, s), 3.94 (2H, s), 5.59 (1H, d, J=10 Hz), 5.69 (1H, d, J=10 Hz), 7.36–7.60 (4H), 7.69–7.79 (2H), 8.00 (1H, d, J=9 Hz), 8.11 (1H, d, J=6 Hz), 8.41 (1H, d, J=9 Hz), 9.07 (1H, br s), 9.28 (1H, br s)

(22) 3-Bromo-8-[2,6-dichloro-3-[N-[N'-[3-(1-hydroxyethyl)phenyl]ureidoacetyl]-N-methylamino]benzyloxy]-2-methylimidazo[1,2-a]pyridine hydrochloride NMR (CDCl₃—CD₃OD, δ): 1.42 (3H, d, J=6 Hz), 2.53 (3H, s), 3.28 (3H, s), 3.73 (2H, s), 4.79 (1H, q, J=6 Hz), 5.62 (1H, d, J=10 Hz), 5.77 (1H, d, J=10 Hz), 6.99 (1H, d, J=6 Hz), 7.13–7.31 (3H), 7.51–7.67 (4H), 8.20 (1H, dd, J=5, 3 Hz)

(23) 3-Bromo-8-[2,6-dichloro-3-[N-methyl-N-[4-(methylcarbamoyl)cinnamoylglycyl]amino]benzyloxy]-2-methylimidazo[1,2-a]pyridine hydrochloride NMR (CDCl₃—CD₃OD, δ): 2.52 (3H, s), 3.29 (3H, s), 3.84 (2H, s), 5.64 (1H, d, J=10 Hz), 5.70 (1H, d, J=10 Hz), 6.65 (1H, d, J=16 Hz), 7.28–7.33 (1H, m), 7.45–7.61 (6H, m), 7.77 (2H, d, J=8 Hz), 8.07–8.14 (1H, m)

(24) 3-Bromo-8-[2,6-dichloro-3-[N-[4-(dimethylcarbamoyl)cinnamoylglycyl]-N-methylamino]benzyloxy]-2-methylimidazo[1,2-a]pyridine hydrochloride NMR (CDCl₃—CD₃OD, δ): 2.60 (3H, s), 3.02 (3H, br s), 3.12 (3H, br s), 3.30 (3H, s), 3.81 (2H, s), 5.66 (1H, d, J=10 Hz), 5.77 (1H, d, J=10 Hz), 6.68 (1H, d, J=15 Hz), 7.37–7.70 (9H), 8.21 (1H, dd, J=5, 2 Hz)

(25) 3-Bromo-8-[2,6-dichloro-3-[N-[4-(2-methoxyethylcarbamoyl)cinnamoylglycyl]-N-methylamino]benzyloxy]-2-methylimidazo[1,2-a]pyridine hydrochloride NMR (CDCl₃—CD₃OD, δ): 2.60 (3H, s), 3.29 (3H, s), 3.42 (3H, s), 3.61 (4H, s), 3.81 (2H, s), 5.67 (1H, d, J=10 Hz), 5.77 (1H, d, J=10 Hz), 6.69 (1H, d, J=15 Hz), 7.50–7.70 (7H), 7.82 (2H, d, J=8 Hz), 8.21 (1H, dd, J=5, 3 Hz)

(26) 8-[3-[N-[4-[N,N-Bis(2-methoxyethyl)carbamoyl]cinnamoylglycyl]-N-methylamino]-2,6-dichlorobenzyloxy]-3-bromo-2-methylimidazo-[1,2-a]pyridine hydrochloride NMR (CDCl₃—CD₃OD, δ): 2.60 (3H, s), 3.21–3.87 (16H), 5.68 (1H, d, J=10 Hz), 5.77 (1H, d, J=10 Hz), 6.65 (1H, d, J=15 Hz), 7.34–7.70 (9H), 3.21 (1H, m)

(27) 3-Bromo-8-[2,6-dichloro-3-[N-methyl-N-[4-(4-pyridylcarbamoyl)cinnamoylglycyl]amino]benzyloxy]-2-methylimidazo[1,2-a]pyridine dihydrochloride NMR (CDCl₃—CD₃OD, δ): 2.60 (3H, s), 3.30 (3H, s), 3.84 (2H, br s), 5.67 (1H, d, J=10 Hz), 5.77 (1H, d, J=10 Hz), 6.72 (1H, d, J=15 Hz), 7.44–7.77 (7H), 8.11 (2H, d, J=8 Hz), 8.21 (1H, t, J=4 Hz), 8.49–8.61 (4H)

(28) 3-Bromo-8-[2,6-dichloro-3-[N-methyl-N-[4-(2-oxo-1-pyrrolidinyl)cinnamoylglycyl]amino]benzyloxy]-2-methylimidazo[1,2-a]pyridine hydrochloride NMR (CDCl₃—CD₃OD, δ): 2.18 (2H, quint, J=7.5 Hz), 2.54–2.68 (5H, m), 3.29 (3H, s), 3.81 (2H, s), 3.89 (2H, t, J=7.5 Hz), 5.65 (1H, d, J=10 Hz), 5.74 (1H, d, J=10 Hz), 6.50 (1H, d, J=16 Hz), 7.44–7.68 (9H, m), 8.11 (1H, t, J=4 Hz)

(29) 3-Bromo-8-[2,6-dichloro-3-[N-[4-(methoxyacetamido)cinnamoylglycyl]-N-methylamino]benzyloxy]-2-methylimidazo[1,2-a]pyridine hydrochloride NMR (CDCl₃—CD₃OD, δ): 2.66 (3H, s), 3.29 (3H, s), 3.51 (3H, s), 3.82 (2H, s), 4.03 (2H, s), 5.60–5.77 (2H, m), 6.50 (1H, d, J=16 Hz), 7.40–7.65 (9H, m), 8.04–8.15 (1H, m)

(30) 3-Bromo-8-[2,6-dichloro-3-[N-methyl-N-[4-(propionamido)cinnamoylglycyl]amino]benzyloxy]-2-methylimidazo[1,2-a]pyridine hydrochloride NMR (CD₃OD, δ): 1.19 (3H, t, J=7.5 Hz), 2.40 (2H, q, J=7.5 Hz), 2.50 (3H, s), 3.24 (3H, s), 3.79 (1H, d, J=16 Hz), 3.86 (1H, d, J=16 Hz), 5.69–5.80 (2H, m), 6.60 (1H, d, J=15 Hz), 7.36–7.80 (9H, m)

(31) 8-[3-[N-[(4-(Acetamido)cinnamoylglycyl]-N-methylamino]-2,6-dichlorobenzyloxy]-3-bromo-2-methylimidazo[1,2-a]pyridine hydrochloride NMR (CDCl₃—CD₃OD, δ): 2.18 (3H, s), 2.58 (3H, s), 3.28 (3H, s), 3.76 (1H, d, J=16 Hz), 3.90 (1H, d, J=16 Hz), 5.65 (2H, s), 6.43 (1H, d, J=16 Hz), 7.25–7.39 (2H, m), 7.39–7.64 (7H, m), 8.03–8.16 (1H, m)

(32) 3-Bromo-8-[2,6-dichloro-3-[N-[4-(N-methylacetamido)cinnamoylglycyl]-N-methylamino]benzyloxy]-2-methylimidazo[1,2-a]pyridine hydrochloride NMR (CDCl₃—CD₃OD, δ): 1.91 (3H, br s), 2.61 (3H, s), 3.28 (3H, br s), 3.31 (3H, s), 3.81 (2H, br s), 5.66 (1H, br d, J=10 Hz), 5.78 (1H, br d, J=10 Hz), 6.63 (1H, d, J=15 Hz), 7.22 (2H, d, J=9 Hz), 7.46–7.70 (7H), 8.20 (1H, br s)

(33) 3-Bromo-8-[2,6-dichloro-3-[N-methyl-N-[4-[N-(3-pyridylmethyl)acetamido]cinnamoylglycyl]amino]benzyloxy]-2-methylimidazo[1,2-a]pyridine dihydrochloride NMR (CDCl₃—CD₃OD, δ): 1.99 (3H, s), 2.60 (3H, s), 3.76 (1H, d, J=18 Hz), 3.88 (1H, d, J=18 Hz), 5.10 (2H, s), 5.68 (1H, d, J=10 Hz), 5.78 (1H, d, J=10 Hz), 6.70 (1H, d, J=15 Hz), 7.20 (2H, d, J=8 Hz), 7.47–7.70 (7H), 8.04 (1H, dd, J=8, 6 Hz), 8.22 (1H, dd, J=6, 1 Hz), 8.51 (1H, br d, J=8 Hz), 8.72–8.84 (2H)

(34) 3-Bromo-8-[2,6-dichloro-3-[N-methyl-N-[4-(isonicotinoylamino)cinnamoylglycyl]amino]-benzyloxy]-2-methylimidazo[1,2-a]pyridine dihydrochloride NMR (CDCl₃—CD₃OD, δ): 2.60 (3H, s), 3.30 (2H, s), 3.82 (2H, s), 5.66 (1H, d, J=10 Hz), 5.75 (1H, d, J=10 Hz), 6.59 (1H, d, J=15 Hz), 7.44–7.69 (7H), 7.40 (2H, d, J=9 Hz), 8.20 (1H, t, J=5 Hz), 8.60 (2H, d, J=6 Hz), 9.00 (2H, d, J=6 Hz)

(35) 3-Bromo-8-[2,6-dichloro-3-[N-[4-(ethoxycarbonylacetamido)cinnamoylglycyl]-N-methylamino]benzyloxy]-2-methylimidazo[1,2-a]pyridine hydrochloride NMR (CDCl₃—CD₃OD, δ):1.34 (3H, t, J=7.5 Hz), 2.55 (3H), 3.28 (3H, s), 3.50 (2H, s), 3.77 (1H, d, J=18 Hz), 3.89 (1H, d, J=18 Hz), 4.26 (2H, J=7.5 Hz), 5.60 (2H, s), 6.45 (1H, d, J=16 Hz), 7.20–7.35 (2H, m), 7.35–7.64 (7H, m), 7.98 (1H, d, J=6 Hz)

(36) 8-[3-[N-[4-(Benzamido)cinnamoylglycyl]-N-methylamino]-2,6-dichlorobenzyloxy]-3-bromo-2-methylimidazo[1,2-a]pyridine hydrochloride NMR (CDCl₃—CD₃OD, δ, 3:1 V/V): 2.60 (3H, s), 3.29 (3H, s), 3.83 (2H, s), 5.66 (1H, d, J=9 Hz), 5.74 (1H, d, J=9 Hz), 6.56 (1H, d, J=15 Hz), 7.36–7.70 (10H, m), 7.78 (2H, d, J=9 Hz), 7.93 (2H, dd, J=9, 0.5 Hz), 8.21 (2H, m)

(37) 3-Bromo-8-[2,6-dichloro-3-[N-methyl-N-[4-(4-pyridylacetamido)cinnamoylglycyl]amino]benzyloxy]-2-methylimidazo[1,2-a]pyridine dihydrochloride NMR (CDCl₃—CD₃OD, δ, 3:1 V/V): 2.59 (3H, s), 3.29 (3H, s), 3.78 (1H, d, J=16 Hz), 3.84 (1H, d, J=16 Hz), 4.19 (2H, s), 5.64 (1H, d, J=10 Hz), 5.72 (1H, d, J=10 Hz), 6.51 (1H, d, J=15 Hz), 7.38–7.77 (9H, m), 8.10–8.29 (3H, m), 8.72 (2H, d, J=7 Hz)

(38) 3-Bromo-8-[2,6-dichloro-3-[N-[4-(methanesulfonamido)cinnamoylglycyl]-N-methylamino]benzyloxy]-2-methylimidazo[1,2-a]pyridine hydrochloride NMR (CDCl₃—CD₃OD, δ): 2.60 (3H, s), 3.00 (3H, s), 3.25 (3H, s), 3.82 (2H, s), 5.63 (1H, d, J=10 Hz), 5.73 (1H, d, J=10 Hz), 6.51 (1H, d, J=16 Hz), 7.22 (2H, d, J=8 Hz), 7.38–7.65 (7H, m), 8.07–8.19 (1H, m)

(39) 3-Bromo-8-[2,6-dichloro-3-[N-methyl-N-[4-(3-methylureido)cinnamoylglycyl]amino]benzyloxy]-2-methylimidazo[1,2-a]pyridine hydrochloride NMR (CDCl₃—CD₃OD, δ): 2.53 (3H, s), 2.80 (3H, s), 3.27 (3H, s), 3.73 (1H, d, J=17 Hz), 3.95 (1H, d, J=17 Hz), 5.63 (2H, s), 6.34 (1H, d, J=16 Hz), 7.19 (2H, d, J=8 Hz), 7.24–7.43 (3H, m), 7.43–7.64 (4H, m), 8.05–8.14 (1H, m)

(40) 3-Bromo-8-[2,6-dichloro-3-[N-methyl-N-[4-[3-(3-pyridyl)ureido]cinnamoylglycyl]amino]benzyloxy]-2-methylimidazo[1,2-a]pyridine dihydrochloride NMR (CDCl₃—CD₃OD, δ): 2.60 (3H, s), 3.30 (3H, s), 3.76 (1H, d, J=17 Hz), 3.91 (1H, d, J=17 Hz), 5.66 (1H, d, J=10 Hz), 5.75 (1H, d, J=10 Hz), 6.50 (1H, d, J=15 Hz), 7.36–7.70 (9H), 7.89 (1H, dd, J=8, 5 Hz), 8.20 (1H, t, J=5 Hz), 8.31 (1H, d, J=6 Hz), 8.63 (1H, br d, J=8 Hz), 9.34 (1H, d, J=1 Hz)

(41) 3-Bromo-8-[2,6-dichloro-3-[N-methyl-N-[4-(morpholinocarbonylamino)cinnamoylglycyl]amino]benzyloxy]-2-methylimidazo[1,2-a]pyridine hydrochloride NMR (CDCl₃—CD₃OD, δ): 2.60 (3H, s), 3.30 (3H, s), 3.50–3.60 (4H), 3.70–3.85 (6H), 5.66 (1H, d, J=10 Hz), 5.76 (3H, d, J=10 Hz), 6.49 (1H, d, J=15 Hz), 7.39–7.70 (9H), 8.21 (1H, dd, J=5, 3 Hz)

(42) 3-Bromo-8-[2,6-dichloro-3-[N-methyl-N-[N'-[3-(4-pyridylcarbamoyl)phenyl]ureidoacetyl]amino]-benzyloxy]1,2-methylimidazo[1,2-a]pyridine dihydrochloride NMR (CDCl₃—CD₃OD, δ): 2.56 (3H, s), 3.27 (3H, s), 3.83 (2H, s), 5.60 (1H, d, J=10 Hz), 5.70 (1H, d, J=10 Hz), 7.22–7.38 (1H, m), 7.38–7.67 (6H, m), 7.80–7.93 (1H, m), 8.05–8.16 (1H, m), 8.45 (2H, d, J=7.5 Hz), 8.53 (2H, d, J=7.5 Hz)

(43) 3-Bromo-8-[2,6-dichloro-3-[N-methyl-N-[N'-[3-(1-pyrrolidinylcarbonyl)phenyl]ureidoacetyl]amino]-benzyloxy]-2-methylimidazo[1,2-a]pyridine hydrochloride NMR (DMSO-d₆, δ): 1.71–1.91 (4H, s), 2.39 (3H, s), 3.13 (3H, s), 5.51–5.65 (2H, m), 6.42–6.51 (1H, m), 7.00 (7H, d, J=7 Hz), 7.19–7.44 (3H, m), 7.51–7.75 (2H, m), 7.79–7.88 (2H, m), 8.24 (1H, d, J=6 Hz), 9.07–9.16 (2 H, m)

(44) 3-Bromo-8-[2,6-dichloro-3-[N-methyl-N-[N'-[3-[N-methyl-N-(3-pyridylmethyl)carbamoyl]phenyl]-ureidoacetyl]amino]benzyloxy]-2-methylimidazo-[1,2-a]pyridine dihydrochloride NMR (CDCl₃—CD₃OD, δ): 2.54 (3H, s), 3.10 (3H, s), 3.25 (3H, s), 3.65–3.98 (2H, overlapped with H₂O), 4.89 (2H, br s), 5.61 (1H, d, J=10 Hz), 5.72 (1H, d, J=10 Hz), 7.02 (1H, d, J=7 Hz), 7.29 (1H, t, J=7 Hz), 7.41–7.62 (6H), 8.09 (1H, dd, J=9, 6 Hz), 8.18 (1H, t, J=5 Hz), 8.60 (1H, br s), 8.80 (1H, d, J=5 Hz), 8.91 (1H, br s)

(45) 3-Bromo-8-[2,6-dichloro-3-[N-methyl-N-[N'-[3-(4-methyl-1-piperazinylcarbonyl)phenyl]ureidoacetyl]-amino]benzyloxy]-2-methylimidazo[1,2-a]pyridine dihydrochloride NMR (CDCl₃—CD₃OD, δ): 2.54 (3H, s), 2.90 (3H, s), 3.00–3.80 (13H), 5.62 (1H, d, J=10 Hz), 5.74 (1H, d, J=10 Hz), 7.01 (1H, d, J=7 Hz), 7.26–7.68 (7H ), 8.20 (1H, m)

(46) 3-Bromo-8-[2,6-dichloro-3-[N-methyl-N-[N'-[3-(3-pyridylmethylcarbamoyl)phenyl]ureidoacetyl]amino]-benzyloxy]-2-methylimidazo[1,2-a]pyridine NMR (CDCl₃—CD₃OD, δ): 2.51 (3H, s), 3.26 (3H, s), 3.76 (2H, s), 4.76 (2H, s), 5.62 (1H, d, J=10 Hz), 5.72 (1H, d, J=10 Hz), 7.29 (1H, t, J=8 Hz), 7.49–7.74 (7H), 7.99 (1H, dd, J=7, 5 Hz), 3.18 (1H, t, J=4 Hz), 8.61–8.72 (2H), 8.90 (1H, br s)

(47) 3-Bromo-8-[2,6-dichloro-3-[N-[N'-[3-(dimethylamino)phenyl]ureidoacetyl]-N-methylamino]benzyloxy]-2-methylimidazo[1,2-a]pyridine dihydrochloride NMR (CDCl₃—CD₃OD, δ): 2.59 (3H, s), 3.21 (6H, s), 3.29 (3H, s), 3.66 (1H, d, J=17 Hz), 3.89 (1H, d, J=17 Hz), 5.64 (1H, d, J=10 Hz), 5.76 (1H, d, J=10 Hz), 7.21–7.68 (7H), 7.89 (1H, br s), 8.21 (1H, t, J=4 Hz)

(48) 3-Bromo-8-[2,6-dichloro-3-[N-[4-(ethylcarbamoyl)cinnamoylglycyl]-N-methylamino]benzyloxy]-2-methylimidazo[1,2-a]pyridine hydrochloride NMR (CDCl₃—CD₃OD, δ): 1.27 (3H, t, J=7 Hz), 2.60 (3H, s), 3.30 (3H, s), 3.47 (2H, q, J=7 Hz), 3.83 (2H, s), 5.68 (1H, d, J=10 Hz), 5.77 (1H, d, J=10 Hz), 6.70 (1H, d, J=15 Hz), 7.49–7.70 (7H), 7.82 (2H, d, J=9 Hz), 3.22 (1H, dd, J=5, 3 Hz)

(49) 3-Bromo-8-[2,6-dichloro-3-[N-[4-(N-ethyl-N-methylcarbamoyl)cinnamoylglycyl]-N-methylamino]-benzyloxy]-2-methylimidazo[1,2-a]pyridine hydrochloride NMR (CDCl₃—CD₃OD, δ): 1.11–1.33 (3H), 2.60 (3H, s), 2.94–3.12 (3H), 3.23–3.42 (4H), 3.59 (1H, m), 3.81 (2H, s), 5.68 (1H, d, J=10 Hz), 5.77 (1H, d, J=10 Hz), 6.68 (1H, d, J=15 Hz), 7.37–7.69 (9H), 8.21 (1H, dd, J=5, 3 Hz)

(50) 3-Bromo-8-[2,6-dichloro-3-[N-methyl-N-[4-(1-pyrrolidinylcarbonyl)cinnamoylglycyl]amino]-benzyloxy]-2-methylimidazo[1,2-a]pyridine hydrochloride NMR (CDCl₃—CD₃OD, δ): 1.78–2.07 (4H, m), 2.63 (3H, s), 3.28 (3H, s), 3.34–3.51 (2H, m), 3.51–3.70 (2H, m), 3.76 (1H, d, J=18 Hz), 3.90 (1H, d, J=18 Hz), 5.63 (1H, d, J=10 Hz), 5.72 (1H, d, J=10 Hz), 6.63 (1H, d, J=16 Hz), 7.38–7.67 (9H, m), 8.03–8.17 (1H, m)

(51) 3-Bromo-8-[2,6-dichloro-3-[N-methyl-N-[4-(morpholinocarbonyl)cinnamoylglycyl]amino]benzyloxy]-2-methylimidazo[1,2-a]pyridine hydrochloride NMR (CDCl₃—CD₃OD, δ): 2.61 (3H, s), 3.30 (3H, s), 3.35–3.95 (10H, m), 5.64 (1H, d, J=10 Hz), 5.74 (1H, d, J=10 Hz), 6.65 (1H, d, J=16 Hz), 7.40 (2H, d, J=8 Hz), 7.46–7.65 (7H, m), 8.09–8.18 (1H, m)

(52) 3-Bromo-8-[2,6-dichloro-3-[N-[4-[N-(2-methoxyethyl)-N-methylcarbamoyl]cinnamoylglycyl]-N-methylamino]-benzyloxy]-2-methylimidazo[1,2-a]pyridine hydrochloride NMR (CDCl₃—CD₃OD, δ): 2.62 (3H, s), 3.00–3.15 (3H, m), 3.60–3.93 (4H, m), 5.63 (1H, d, J=10 Hz), 5.73 (1H, d, J=10 Hz), 6.61 (1H, d, J=16 Hz), 7.41 (2H, d, J=8 Hz), 7.47–7.65 (7H, m), 8.08–8.20 (1H, m)

(53) 3-Bromo-8-[2,6-dichloro-3-[N-[4-(isopropylcarbamoyl)cinnamoylglycyl]-N-methylamino]benzyloxy]-2-methylimidazo[1,2-a]pyridine hydrochloride NMR (CDCl₃—CD₃OD, δ): 1.28 (6H, d, J=6 Hz), 2.63 (3H, s), 3.29 (3H, s), 3.77 (1H, d, J=16 Hz), 3.90 (1H, d, J=16 Hz), 4.25 (1H, m), 5.63 (1H, d, J=10 Hz), 5.72 (1H, d, J=10 Hz), 6.65 (1H, d, J=16 Hz), 7.41–7.63 (7H, m), 7.74 (2H, d, J=8 Hz), 8.04–8.17 (1H, m)

(54) 3-Bromo-8-2,6-dichloro-3-[N-[4-(n-propylcarbamoyl)cinnamoylglycyl]-N-methylamino]benzyloxy]-2-methylimidazo[1,2-a]pyridine hydrochloride NMR (CDCl₃—CD₃OD, δ): 0.99 (3H, t, J=7.5 Hz), 1.65 (2H, m), 2.61 (3H, s), 3.30 (3H, s), 3.34–3.47 (2H, m), 3.84 (2H, s-like), 5.63 (1H, d, J=10 Hz), 5.72 (1H, d, J=10 Hz), 6.66 (1H, d, J=16 Hz), 7.40–7.65 (7H, m), 7.77 (2H, d, J=8 Hz), 8.05–8.16 (1H, m)

(55) 3-Bromo-8-[2,6-dichloro-3-[N-[4-(3-methoxypropylcarbamoyl)cinnamoylglycyl]-N-methylamino]benzyloxy]-2-methylimidazo[1,2-a]pyridine hydrochloride NMR (CDCl₃—CD₃OD, δ): 1.90 (2H, quint, J=6 Hz), 2.64 (3H, s), 3.28 (3H, s), 3.40 (3H, s), 3.55 (4H, q, J=6 Hz), 3.78 (1H, d, J=17.5 Hz), 3.89 (1H, d, J=17.5 Hz), 5.64 (1H, d, J=10 Hz), 5.73 (1H, d, J=10 Hz), 6.74 (1H, d, J=16 Hz), 7.44–7.64 (7H, m), 7.75 (2H, d, J=8 Hz), 8.05–8.16 (1H, m)

(56) 3-Bromo-8-[2,6-dichloro-3-[N-[4-(2-ethoxethylcarbamoyl)cinnamoylglycyl]-N-methylamino]benzyloxy]-2-methylimidazo[1,2-a]pyridine hydrochloride NMR (CDCl₃—CD₃OD, δ): 1.22 (3H, t, J=7 Hz), 3.63 (3H,s), 3.50–3.71 (6H, m) ), 3.88 (1H, d, J=18 Hz), 3.90

(1H, d, J=18 Hz), 5.65 (1H, d, J=1 Hz), 5.72 (1H, d, J=10 Hz), 6.65 (1H, d, J=16 Hz), 7.46–7.65 (7H, m), 7.79 (2H, d, J=8 Hz), 8.05–8.14 (1H, m)

(57) 3-Bromo-8-[2,6-dichloro-3-[N-[4-(2-hydroxyethylcarbamoyl)cinnamoylglycyl]-N-methylamino benzyloxy]-2-methylimidazo[1,2-a]pyridine hydrochloride NMR (CDCl$_3$—CD$_3$OD, δ): 2.60 (3H, s), 3.26 (3H, s), 3.57 (2H, t, J=5 Hz), 3.78 (2H, d, J=5 Hz), 3.85 (2H, s), 5.59–5.74 (2H, m), 6.64 (2H, d, J=10 Hz), 6.40–7.64 (7H, m), 7.32 (2H, d, J=8 Hz), 8.03–8.15 (1H, m)

(58) 3-Bromo-8-[2,6-dichloro-3-[N-[4-(diethylcarbanoyl)cinnamoylglycyl]-N-methyl amino]benzyloxy]-2-methylimidazo[1,2-a]pyridine hydrochloride NMR (CDCl$_3$—CD$_3$OD, δ): 1.03–1.33 (6H, m), 2.65 (3H, s), 3.13–3.35 (5H, m), 3.45–3.63 (2H, m), 3.77 (1H, d, J=18 Hz), 3.90 (1H, d, J=18 Hz), 5.63 (1H, d, J=10 Hz), 5.71 ( (H, d, J=10 Hz), 6.60 (5H, d, J=16 Hz), 7.33 (2H, d, J=8 Hz), 7.41–7.63 (7H, m), 8.02–8.13 (1H, m)

(59) 3-Bromo-8-[2,6-dichloro-3-[N-methyl-N-[4-(2-oxopiperidino)cinnamoylglycyl]amino]benzyloxy]-2-methylimidazo[1,2-a]pyridine hydrochloride NMR (CDCl$_3$—CD$_3$OD, δ): 1.90–2.03 (4H, m), 2.50–2.66 (5H, m), 3.60–3.72 (2H, m), 3.80 (2H, s), 5.65 (1H, d, J=10 Hz), 5.75 (1H, d, J=10 Hz), 6.55 (1H, d, J=16 Hz), 7.27 (2H, d, J=8 Hz), 7.45–7.67 (7H, m), 8.09–8.21 (1H, m)

(60) 3-Bromo-8-[2,6-dichloro-3-[N-methyl-N-[4-(N-methyl-2-methoxyacetamido)cinnamoylglycyl]amino]benzyloxy]-2-methylimidazo[1,2-a]pyridine hydrochloride NMR (CDCl$_3$—CD$_3$OD, δ, 3:1 V/V): 2.60 (3H, s), 3.30 (6H, s), 3.35 (3H, s), 3.76–3.96 (4H, m), 5.68 (1H, d, J=9 Hz), 5.76 (1H, d, J=9 Hz), 6.69 (1H, d, J=15 Hz), 7.26 (2H, br d, J=8 Hz), 7.48–7.73 (7H, m), 8.24 (1H, br d, J=8 Hz)

(61) 3-Bromo-8-[2,6-dichloro-3-[N-methyl-N-[4-(1-pyrrolyl)cinnamoylglycyl]amino]benzyloxy]-2-methylimidazo[1,2-a]pyridine hydrochloride NMR (CDCl$_3$—CD$_3$OD, δ): 2.61 (3H, s), 3.30 (3H, s), 3.81 (2H, s), 5.68 (1H, d, J=10 Hz), 5.78 (1H, d, J=10 Hz), 6.39 (2H, s), 6.60 (1H, d, J=15 Hz), 7.38–7.70 (11H), 8.20 (1H, dd, J=5, 3 Hz)

(62) 3-Bromo-8-[2,6-dichloro-3-[N-[4-(3-methoxypropionamido)cinnamoylglycyl]-N-methylamino]-benzyloxy]-2-methylimidazo[1,2-a]pyridine hydrochloride NMR (CDCl$_3$—CD$_3$OD, δ): 2.55–2.70 (5H, m), 3.30 (3H, s), 3.44 (3H, s), 3.76 (2H, t, J=6 Hz), 3.83 (2H, s), 5.67 (2H, s), 6.46 (1H, d, J=16 Hz), 7.33–7.63 (9H, m), 8.02–8.14 (1H, m)

(63) 8-[3-[N-[4-(Acetamidoacetamido)cinnamoylglycyl]-N-methylamino]-2,6-dichlorobenzyloxy]-3-bromo-2-methylimidazo[1,2-a]pyridine hydrochloride NMR (CDCl$_3$—CD$_3$OD, δ): 2.07 (3H, s), 2.56 (3H, s), 3.27 (3H, s), 3.75 (1H, d, J=17 Hz), 3.88 (1H, d, J=17 Hz), 4.00 (2H, s), 5.59–5.75 (2H, m), 6.48 (1H, d, J=16 Hz), 7.35–7.43 (2H, m), 7.45–7.67 (7H, m), 8.08–8.19 (1H, m)

(64) 3-Bromo-8-[2,6-dichloro-3-[N-methyl-N-[4-[(dimethylamino)acetamido]cinnamoylglycyl]amino] benzyloxy]-2-methylimidazo[1,2-a]pyridine hydrochloride NMR (CDCl$_3$—CD$_3$OD, δ): 2.58 (3H, s), 3.04 (6H, s), 3.27 (3H, s), 3.83 (2H, br s), 4.21 (2H, br s), 5.64 (2H, br s), 6.46 (1H, d, J=16 Hz), 7.26–7.67 (9H, m), 8.06–8.16 (1H, m)

(65) 3-Bromo-8-[2,6-dichloro-3-[N-[4-(succinimido)cinnamoylglycyl]-N-methylamino]benzyloxy]-2-methylimidazo[1,2-a]pyridine hydrochloride NMR (CDCl$_3$—CD$_3$OD, δ): 2.60 (3H, s), 2.95 (4H, s), 3.30 (3H, s), 3.81 (2H, s), 5.68 (1H, br d, J=10 Hz), 5.78 (1H, br d, J=10 Hz), 6.64 (1H, d, J=16 Hz), 7.35 (2H, d, J=9 Hz), 7.50–7.60 (7H), 8.21 (1H, m)

(66) 3-Bromo-8-[2,6-dichloro-3-[N-[4-[(E)-3-(ethoxycarbonyl)acrylamido]cinnamoylglycyl]-N-methylamino]benzyloxy]-2-methylimidazo[1,2-a]pyridine hydrochloride NMR (CDCl$_3$—CD$_3$OD, δ, 3:1, V/V): 1.36 (3H, t, J=7.5 Hz), 2.49 (3H, s), 3.28 (3H, s), 3.37 (2H, q, J=7.5 Hz), 3.81 (2H, s), 5.66 (1H, d, J=9 Hz), 5.75 (1H, d, J=9 Hz), 6.56 (1H, d, J=15 Hz), 6.91 (1H, d, J=15 Hz), 7.17 (1H, d, J=15 Hz), 7.36–7.80 (9H, m), 8.20 (1H, br d, J=4 Hz)

(67) 3-Bromo-8-[2,6-dichloro-3-[N-[4-(2-oxo-3-oxazolidinyl)cinnamoylglycyl]-N-methylamino]benzyloxy]-2-methylimidazo[1,2-a]pyridine hydrochloride NMR (CDCl$_3$—CD$_3$OD, δ): 2.60 (3H, s), 3.28 (3H, s), 3.81 (2H, s), 4.11 (2H, dd, J=6, 8 Hz), 4.52 (2H, dd, J=6, 8 Hz), 5.64 (1H, d, J=10 Hz), 5.74 (1H, d, J=10 Hz), 6.54 (1H, d, J=16 Hz), 7.37–7.69 (9H, m), 8.07–8.20 (1H, m)

(68) 8-[3-[N-[N'-[3-[N,N-Bis(2-methoxyethyl)carbamoyl]phenyl]ureidoacetyl]-N-methylamino]-2,6-dichlorobenzyloxy]-3-bromo-2-methylimidazo-[1,2-a]pyridine hydrochloride NMR (CDCl$_3$—CD$_3$OD, δ): 2.56 (3H, s), 3.22 (3H, s), 3.52–3.73 (4H, m), 3.79 (1H, d, J=18 Hz), 4.01 (1H, d, J=18 Hz), 5.58 (1H, d, J=10 Hz), 5.65 (1H, d, J=10 Hz), 6.88 (1H, d, J=7.5 Hz), 7.20 (1H, t, J=8 Hz), 7.33–7.56 (6H, m), 8.06 (1H, d, J=6 Hz)

(69) 3-Bromo-8-2,6-dichloro-3-[N-[N'-[3-(2-methoxyethylcarbamoyl)phenyl]ureidoacetyl]-N-methylamino]benzyloxy]-2-methylimidazo[1,2-a]pyridine hydrochloride NMR (CDCl$_3$—CD$_3$OD, δ): 2.58 (3H, s), 3.24 (3H, s), 3.38 (3H, s), 3.55 (4H, s-like), 3.88 (2H, s), 5.61 (2H, s), 7.19 (1H, t, J=8 Hz), 7.25–7.40 (1H, m), 7.40–7.54 (5H, m), 7.60–7.66 (1H, m), 8.07 (1H, d, J=6 Hz)

(70) 3-Bromo-8-[2,6-dichloro-3-[N-[N'-[3-[N-(2-methoxyethyl)-N-methylcarbamoyl]phenyl]ureidoacetyl]-N-methylamino]benzyloxy]-2-methylimidazo[1,2-a]-pyridine hydrochloride NMR (CDCl$_3$—CD$_3$OD, δ): 2.53 (3H, s), 2.94–3.07 (3H, m), 3.55–3.69 (2H, br peak), 3.75 (1H, d, J=16 Hz), 3.87 (1H, d, J=16 Hz), 5.58 (1H, d, J=10 Hz), 5.69 (1H, d, J=10 Hz), 6.92 (1H, d, J=7.5 Hz), 7.22 (1H, t, J=7.5 Hz), 7.28–7.59 (6H, m), 8.05–8.15 (1H, m)

(71) 3-Bromo-8-[2,6-dichloro-3-[N-[N'-[3-[N,N-bis(2-ethoxyethyl)carbamoyl]phenyl]ureidoacetyl]-N-methylamino]benzyloxy]-2-methylimidazo[1,2-a]pyridine hydrochloride NMR (CDCl$_3$—CD$_3$OD, δ): 1.05–1.28 (6H, m), 2.54 (3H, s), 3.25 (3H, s), 3.30–3.80 (13H, m), 3.86 (1H, d, J=17.5 Hz), 5.58 (1H, d, J=10 Hz), 5.67 (1H, d, J=10 Hz), 6.94 (1H, d, J=7.5 Hz), 7.15–7.35 (2H, m), 7.35–7.60 (5H, m), 8.07 (1H, d, J=6 Hz)

(72) 3-Bromo-8-[2,6-dichloro-3-[N-[N'-[3-[N,N-bis(2-hydroxyethyl)carbamoyl]phenyl]ueidoacetyl]-N-methylamino]benzyloxy]-2-methylimidazo[1,2-a]pyridine hydrochloride NMR (CDCl$_3$—CD$_3$OD, δ): 2.55 (3H, s), 3.23 (3H, s), 3.53–3.75 (4H, br peak), 3.75–3.94 (4H, br peak), 5.57 (1H, d, J=10 Hz), 5.67 (1H, d, J=10 Hz), 6.99 (1H, d, J=7.5 Hz), 7.21 (1H, t, J=7.5 Hz), 7.25–7.60 (6H, m), 8.08 (1H, d, J=6 Hz)

(73) 3-Bromo-8-[2,6-dichloro-3-[N-[N'-[3-(methoxyacetamido)phenyl]ureidoacetyl]-N-methylamino] benzyloxy]-2-methylimidazo[1,2-a]-pyridine hydrochloride NMR (CDCl$_3$—CD$_3$OD, δ): 2.54 (3H, s), 3.28 (3H, s), 3.51 (3H, s), 3.74 (2H, s), 3.92–4.09 (2H, overlapped with H$_2$O), 5.63 (1H, d, J=10 Hz), 5.74 (1H, d, J=10 Hz), 7.13–7.20 (3H), 7.51–7.66 (5H), 8.19 (1H, t, J=3 Hz)

(74) 3-Bromo-8-[2,6-dichloro-3-[N-[N'- N[3-] (ethoxycarbonyl)acetamido]phenyl]ureidoacetyl]-N-methylamino]benzyloxy]-2-methylimidazo[1,2-a]pyridine hydrochloride NMR (CDCl₃—CD₃OD, δ): 1.31 (3H, t, J=7 Hz), 2.52 (3H, s), 3.28 (3H, s), 3.47 (2H, s), 3.75 (2H, br s), 4.23 (2H, q, J=7 Hz), 5.63 (1H, br d, J=10 Hz), 5.73 (1H, br d, J=10 Hz), 7.11–7.20 (3H), 7.49–7.66 (5H), 8.18 (1H, br t, J=4 Hz)

(75) 3-Chloro-8-[2,6-dichloro-3-[N-[4-(dimethylcarbamoyl)cinnamoylglycyl]-N-methylamino]benzyloxy]-2-methylimidazo[1,2-a]pyridine hydrochloride NMR (CDCl₃—CD₃OD, δ): 2.60 (3H, s), 3.02 (3H, br s), 3.12 (3H, br s), 3.30 (3H, s), 3.81 (2H, s), 5.68 (1H, d, J=10 Hz), 5.78 (1H, d, J=10 Hz), 6.69 (1H, d, J=16 Hz), 7.41–7.70 (9H), 8.20 (1H, t, J=4 Hz)

(76) 3-Chloro-8-[2,6-dichloro-3-[N-methyl-N-[4-(methylcarbamoyl)cinnamoylglycyl]amino]benzyloxy]-2-methylimidazo[1,2-a]pyridine hydrochloride NMR (CDCl₃—CD₃OD, δ): 2.61 (3H, s), 3.98 (3H, s), 3.29 (3H, s), 3.84 (2H, s), 5.62 (1H, d, J=10 Hz), 5.70 (2H, d, J=10 Hz), 6.64 (1H, d, J=16 Hz), 7.42–7.66 (7H, m), 7.77 (2H, d, J=8 Hz), 8.02–8.14 (9H, m)

(77) 3-Chloro-8-[2,6-dichloro-3-[N-[4-[(2-methoxyethyl)carbamoyl]cinnamoylglycyl]-N-methylamino]benzyloxy]-2-methylimidazo[1,2-a]pyridine hydrochloride NMR (CDCl₃—CD₃OD, δ): 2.61 (3H, s), 3.29 (3H, s), 3.41 (3H, s), 3.47–3.73 (4H, overlapped with H₂O), 3.82 (2H, br s), 5.65 (1H, d, J=10 Hz), 5.74 (1H, d, J=10 Hz), 6.68 (1H, d, J=15 Hz), 7.48–7.66 (7H), 7.80 (2H, br d, J=9 Hz), 8.14 (1H, t, J=4 Hz)

(78) 3-Chloro-8-[2,6-dichloro-3-[N-[4-(N-ethyl-N-methylcarbamoyl)cinnamoylglycyl]-N-methylamino]benzyloxy]-2-methylimidazo[1,2-a]pyridine hydrochloride NMR (CDCl₃—CD₃OD, δ): 1.07–1.33 (3H, m), 2.61 (3H, s), 3.27 (3H, s), 3.44–3.66 (2H, m), 3.76 (1H, d, J=18 Hz), 3.88 (1H, d, J=18 Hz), 5.63 (1H, d, J=10 Hz), 5.73 (1H, d, J=10 Hz), 6.61 (1H, d, J=16 Hz), 7.23–7.44 (2H, m), 7.44–7.63 (7H, m), 8.01–8.15 (1H, m)

(79) 3-Chloro-8-[2,6-dichloro-3-[N-[4-(ethylcarbamoyl)cinnanoylglycyl]-N-methylamino]benzyloxy]-2-methylimidazo[1,2-a]pyridine hydrochloride NMR (CDCl₃—CD₃OD, δ): 1.25 (3H, t, J=7.5 Hz), 2.61 (3H, s), 3.26 (3H, s), 3.45 (2H, q, J=7.5 Hz), 3.78 (1H, d, J=17.5 Hz), 3.90 (1H, d, J=17.5 Hz), 5.63 (1H, d, J=10 Hz), 5.70 (1H, d, J=10 Hz), 6.64 (1H, d, J=16 Hz), 7.41–7.64 (7H, m), 7.76 (2H, d, J=8 Hz), 8.00–8.13 (1H, m)

(80) 3-Chloro-8-[2,6-dichloro-3-[N-methyl-N-[4-(2-oxo-1-pyrrolidinyl)cinnamoylglycyl]amino]benzyloxy]-2-methylimidazo[1,2-a]pyridine hydrochloride NMR (CDCl₃, δ): 2.20 (2H, quint, J=7 Hz), 2.55–2.70 (5H, m), 3.28 (3H, s), 3.80 (3H, s), 3.90 (2H, t, J=7.5 Hz), 5.65 (1H, d, J=10 Hz), 5.74 (1H, d, J=10 Hz), 6.51 (1H, d, J=16 Hz), 7.40–7.58 (9H, m), 8.04–8.15 (1H, m)

(81) 8-[3-[N-[4-(Acetamido)cinnamoylglycyl]-N-methylamino]-2,6-dichlorobenzyloxy]-3-chloro-2-methylimidazo[1,2-a]pyridine hydrochloride NMR (CDCl₃—CD₃OD, δ): 2.19 (3H, s), 2.60 (3H, s), 3.28 (3H, s), 3.78 (1H, d, J=18 Hz), 3.89 (1H, d, J=18 Hz), 5.67 (2H, s), 6.46 (1H, d, J=16 Hz), 7.24–7.64 (9H, m), 8.02–8.13 (1H, m)

(82) 3-Chloro-8-[2,6-dichloro-3-[N-methyl-N-[4-(3-methylureido)cinnamoylglycyl]amino]benzyloxy]-2-methylimidazo[1,2-a]pyridine hydrochloride NMR (CDCl₃—CD₃OD, δ): 2.58 (3H, s), 2.81 (3H, s), 3.29 (3H, s), 3.74 (1H, d, J=17 Hz), 3.83–4.00 (1H, overlapped with H₂O), 5.63 (1H, d, J=10 Hz), 5.71 (1H, d, J=10 Hz), 6.40 (1H, d, J=16 Hz), 7.28–7.46 (5H), 7.51–7.68 (4H), 8.18 (1H, dd, J=5.1 Hz)

(83) 3-Chloro-8-[2,6-dichloro-3-[N-[4-(methoxyacetamido)cinnamoylglycyl]-N-methylamino]benzyloxy]-2-methylimidazo[1,2-a]pyridine hydrochloride NMR (CDCl₃—CD₃OD, δ): 2.60 (3H, s), 3.29 (3H, s), 3.52 (3H, s), 3.64–3.98 (2H, overlapped with H₂O), 4.03 (2H, s), 5.66 (1H, d, J=10 Hz), 5.77 (1H, d, J=10 Hz), 6.52 (1H, d, J=16 Hz), 7.42–7.68 (9H), 8.19 (1H, t, J=4 Hz)

(84) 3-Chloro-8-[2,6-dichloro-3-[N-methyl-N-[4-(propionamido)cinnamoylglycyl]amino]benzyloxy]-2-methylimidazo[1,2-a]pyridine hydrochloride NMR (CDCl₃—CD₃OD, δ): 1.23 (3H, t, J=7.5 Hz), 2.42 (2H, q, J=7.5 Hz), 2.59 (3H, s), 3.28 (3H, s), 3.76 (1H, d, J=17.5 Hz), 3.88 (1H, d, J=17.5 Hz), 5.66 (2H, s), 6.43 (1H, d, J=16 Hz), 7.32–7.63 (9H, m), 8.01–8.12 (1H, m)

(85) 3-Chloro-8-[2,6-dichloro-3-[N-[4-(3-methoxypropionamido)cinnamoylglycyl]-N-methylamino]benzyloxy]-2-methylimidazo[1,2-a]pyridine hydrochloride NMR (CDCl₃—CD₃OD, δ): 2.55–2.70 (5H), 3.29 (3H, s), 3.92 (3H, s), 3.70–4.00 (4H, overlapped with H₂O), 5.61–5.69 (2H), 6.50 (1H, d J=16 Hz), 7.39–7.68 (9H), 8.18 (1H, br s)

(86) 8-[3-[N-[4-(Acetamidoacetamido)cinnamoylglycyl]-N-methylamino]-2,6-dichlorobenzyloxy]-3-chloro-2-methylimidazo[1,2-a]pyridine hydrochloride NMR (CDCl₃—CD₃OD, δ): 2.09 (3H, s), 2.59 (3H, s), 3.82 (2H, d, J=6 Hz), 4.00 (2H, s), 5.68 (2H, s-like), 6.47 (2H, d, J=16 Hz), 7.35–7.69 (9H, m), 8.06–8.15 (1H, m)

(87) 8-[3-[N-[N'-[3-[N,N-Bis(2-methoxyethyl)carbamoyl]phenyl]ureidoacetyl]-N-methylamino]-2,6-dichlorobenzyloxy]-3-chloro-2-methylimidazo[1,2-a]pyridine hydrochloride NMR (CDCl₃—CD₃OD, δ): 2.54 (3H, s), 3.28 (3H, s), 3.31–3.79 (16 Hz), 5.63 (1H, d, J=10 Hz), 5.75 (1H, d, J=10 Hz), 6.99 (1H, d, J=7 Hz), 7.20–7.48 (3H), 7.51–7.67 (4H), 8.18 (1H, t, J=4 Hz)

(88) 3-Chloro-8-[2,6-dichloro-3-[N-methyl-N-[N'-[3-(4-pyridylcarbamoyl)phenyl]ureidoacetyl]amino]benzyloxy]-2- methylimidazo[1,2-a]pyridine dihydrochloride NMR (CDCl₃—CD₃OD, δ, 3:1 V/V): 2.55 (3H, s), 3.27 (3H, s), 3.70 (4H, d, J=15 Hz), 3.79 (1H, d, J=15 Hz), 5.65 (1H, d, J=9 Hz), 5.75 (1H, d, J=9 Hz), 7.39 (1H, d, J=8 Hz), 7.51–7.75 (6H, m), 7.98 (1H, m), 8.15–8.26 (1H, m), 8.50 (2H, d, J=8 Hz), 8.56 (1H, d, J=8 Hz)

(89) 3-Bromo-8-[2,6-dichloro-3-[N-methyl-N-[(E)-3-(6-methylcarbamoyl-3-pyridyl)acryloylglycyl]amino]-benzyloxy]-2-methylimidazo[1,2-a]pyridine dihydrochloride NMR (CDl₃—CD₃OD, δ): 2.62 (3H, s), 3.05 (3H, s), 3.29 (3H, s), 3.70–3.85 (1H, overlapped with H₂O), 3.91 (1H, d, J=18 Hz), 5.64 (1H, d, J=10 Hz), 5.73 (1H, d, J=10 Hz), 6.90 (1H, d, J=16 Hz), 7.50–7.67 (5H), 8.11–8.27 (2H), 8.32 (1H, br d, J=8 Hz), 8.82 (1H, br s)

(90) 8-[3-[N-[(E)-3-(6-Acetamido-3-pyridyl)acryloylglycyl]-N-methylamino]-2,6-dichlorobenzyloxy]-3-bromo-2-methylimidazo[1,2-a]pyridine dihydrochloride NMR (CDCl₃—CD₃OD, δ): 2.41 (3H, s), 2.60 (3H, s), 3.28 (3H, s), 3.75 (1H, d, J=18 Hz), 3.91 (1H, d, J=18 Hz), 5.63 (1H, d, J=10 Hz), 5.75 (1H, d, J=10 Hz), 6.92 (1H, d, J=16 Hz), 7.40–7.65 (5H), 8.00 (1H, d, J=9 Hz), 8.20 (1H, t, J=5 Hz), 8.46–8.61 (2H)

(91) 3-Bromo-8-[2,6-dichloro-3-[N-[4-(2-hydroxyethoxy)cinnamoylglycyl]-N-methylamino]benzyloxy]-2-methylimidazo[1,2-a]pyridine hydrochloride NMR (CDCl₃—CD₃OD): 2.63 (3H, s), 3.29 (3H, s), 3.80 (2H, s), 3.94 (2H, t, J=5 Hz), 4.10 (2H, t, J=5 Hz), 5.60–5.77 (2H, m), 6.43 (1H, d, J=16 Hz), 6.90 (2H, d, J=8 Hz), 7.40–7.64 (7H, m), 8.07–8.17 (1H, m)

(92) 3-Bromo-8-[2,6-dichloro-3-[N-(3,4-dimethoxycinnamoylglycyl)-N-methylamino]benzyloxy]-2-methylimidazo[1,2-a]pyridine hydrochloride NMR (CDCl₃—CD₃OD, δ): 2.64 (3H, s), 3.30 (3H, s), 3.80 (2H, s), 3.91 (3H, s), 3.94 (3H, s), 5.65 (1H, d, J=10 Hz), 5.75 (1H, d, J=10 Hz), 6.44 (1H, d, J=16 Hz), 6.87 (1H, d, J=8 Hz), 7.03–7.15 (2H, m), 7.39–7.65 (5H, m), 8.05–8.19 (1H, m)

(93) 3-Bromo-8-[2,6-dichloro-3-[N-methyl-N-[3,4-(methylenedioxy)cinnamoylglycyl]amino]benzyloxy]-2-methylimidazo[1,2-a]pyridine hydrochloride NMR (CDCl₃, δ): 2.60 (3H, s), 3.80 (3H, s), 5.65 (1H, d, J=10 Hz)) 5.74 (1H, d, J=10 Hz), 6.00 (2H, s), 6.40 (7H, d, J=16 Hz), 6.80 (1H 1 d, J=8 Hz), 6.94–7.04 (2H, m), 7.37–7.66 (5H, m), 8.09–8.19 (8H, m)

(94) 3-Bromo-8-[2,6-dichloro-3-[N-[(E)-3-(6-dimethylcarbamoyl-3-pyridyl)acryloylglycyl]-N-methylamino]benzyloxy]-2-methylimidazo[1,2a]pyridine dihydrochloride NMR (CDCl₃—CD₃OD, δ): 2.53 (3H, s), 3.02 (3H, br s), 3.10 (3H, br s), 3.20 (3H, s), 3.70 (1H, d, J=17 Hz), 3.86 (1H, d, J=17 Hz), 5.56 (1H, d, J=10 Hz), 5.67 (1H, d, J=10 Hz), 6.85 (1H, d, J=16 Hz) 7.38–7.59 (5H), 7.71 (1H, br d, J=8 Hz), 8.09 (1H, t, J=4 Hz), 8.21 (1H, br d, J=8 Hz), 8.80 (1H, br s)

(95) 3-Bromo-8-[2,6-dichloro-3-[N-[(E)-3-(6-ethylcarbamoyl-3 -pyridyl)acryloylglycyl]-N-methylamino]benzyloxy]-2-methylimidazo[1,2-a]pyridine dihydrochloride NMR (CDCl₃—CD₃OD, δ): 1.22 (3H, t, J=7 Hz), 2.57 (3H, s), 3.46 (1H, q, J=7 Hz), 3.73 (1H, d, J=17 Hz), 3.89 (1H, d, J=17 Hz), 5.58 (1H, d, J=10 Hz), 5.68 (1H, d, J=16 Hz), 6.81 (1H, d, J=16 Hz), 7.38–7.59 (5H), 8.00–8.19 (2H), 8.26 (1H, d, J=8 Hz), 8.75 (1H, br s)

(96) 3-Bromo-8-[2,6-dichloro-3-[N-[(E)-3-[6-(3-methoxypropylcarbamoyl)-3-pyridyl]acryloylglycyl]-N-methylamino]benzyloxy]-2-methylimidazo[1,2-a]pyridine dihydrochloride NMR (CDCl₃—CD₃OD, δ): 1.85 (2H, quint, J=6 Hz), 2.58 (3H, s), 3.23 (3H, s), 3.41–3.60 (4H, m), 3.73 (1H, d, J=17.5 Hz), 3.88 (1H, d, J=17.5 Hz), 5.57 (1H, d, J=10 Hz), 5.67 (1H, d, J=10 Hz), 6.78 (1H, d, J=16 Hz), 7.37–7.60 (5H, m), 7.98–8.11 (2H, m), 8.17 (1H, d, J=8 Hz), 8.66–8.74 (1H, m)

Example 94

3-Chloro-8-(2,6-dichlorophenyl)methylamino-2-methylimidazo[1,2-a]pyridine was obtained according to a similar manner to that of Example 2.

mp: 142.9° C. (dec.)

Example 95

Sulfuric acid salt of 3-bromo-8-[2,6-dichloro-3-[N-methyl-N-(butyrylglycyl)amino]benzyloxy]-2-methylimidazo[1,2-a]pyridine was obtained by mixing 3-bromo-8-[2,6-dichloro-3-[N-methyl-N-(butyrylglycyl)amino]benzyl-2-methylimidazo[1,2-a]pyridine with sulfuric acid.

mp: 154°–156° C.

Example 96

Maleic acid salt of 3-chloro-8-[2,6-dichloro-3-(N-methyl-N-acetylamino)benzyloxy]-2-methylimidazo[1,2-a]pyridine was obtained by mixing 3-chloro-8-[2,6-dichloro-3-(N-methyl-N-acetylamino)benzyloxy]-2-methylimidazo-[1,2-a]pyridine with maleic acid.

mp: 193°–195° C.

Example 97

Methanesulfonic acid salt of 3-chloro-8-[2,6 -dichloro-3-(N-methyl-N-acetylamino)benzyloxy]-2-methylimidazo[1,2-a]pyridine was obtained by mixing 3-chloro-8-[2,6-dichloro-3-(N-methyl-N-acetylamino)benzyloxy]-2-methylimidazo[1,2-a]pyridine with methanesulfonic acid.

mp: 165° C. (dec.)

Example 98

Oxalic acid salt of 3-chloro-8-[2,6-dichloro-3-(N-methyl-N-acetylamino)benzyloxy]-2-methylimidazo[1,2-a]-pyridine was obtained by mixing 3-chloro-8-[2,6-dichloro-3-(N-methyl-N-acetylamino)benzyloxy]-2-methylimidazo-1,2-a]pyridine with oxalic acid.

mp: 180°–181° C.

Example 99

Methanesulfonic acid salt of 3-bromo-8-[2,6-dichloro-3-[N-[4-(dimethylcarbamoyl)cinnamoylglycyl]-N-methylamino]benzyloxy]-2-methylimidazo[1,2-a]pyridine was obtained by mixing 3-bromo-8-[2,6-dichloro-3-[N-[4-(dimethylcarbamoyl)cinnamoylglycyl]-N-methylamino] benzyloxy]-2-methylimidazo[1,2-a]pyridine with methanesulfonic acid.

mp: 195.5° C.

p NMR (DMSO-d₆, δ): 2.30 (3H, s), 2.38 (3H, s), 2.90 (3H, br s), 2.98 (3H, br s), 3.15 (3H, s), 3.52 (1H, dd, J=17, 4 Hz), 3.83 (1H, dd, J=17, 5 Hz), 5.56 (1H, d, J=9 Hz), 5.61 (1H, d, J=9 Hz), 6.84 (1H, d, J=15 Hz), 7.34–7.48 (3H, m), 7.50–7.75 (3H, m), 7.81 (1H, d, J=8 Hz), 7.86 (1H, d, J=8 Hz), 8.24 (1H, d, J=7.5 Hz), 8.36 (1H, t, J=7.5 Hz)

Example 100

The following compounds were obtained according to a similar manner to that of Example 67.

(1) 3-Bromo-8-[2,6-dichloro-3-[N-methyl-N-[4-[(2-pyridylmethyl)carbamoyl]cinnamoylglycyl]amino]-benzyloxy]-2-methylimidazo[1,2-a]pyridine NMR (CDCl₃, δ): 2.44 (3H, s), 3.28 (3H, s), 3.68 (1H, dd, J=4, 16 Hz), 3.91 (1H, dd, J=4, 16 Hz), 4.76 (2H, d, J=4 Hz), 5.49 (1H, d, J=10 Hz), 5.53 (1H, d, J=10 Hz), 6.53 (1H, d, J=16 Hz), 6.70 (1H, t-like), 6.73 (1H, d, J=7.5 Hz), 6.86 (1H, t, J=7.5 Hz), 7.20–7.29 (1H, m), 7.29–7.37 (2H, m), 7.50 (1H, d, J=8 Hz), 7.54–7.61 (2H, m), 7.61–7.74 (2H, m), 7.77 (1H, d, J=6 Hz), 7.89 (2H, d, J=8 Hz), 8.59 (1H, d, J=4 Hz) its dihydrochloride NMR (CDCl₃—CD₃OD, δ): 2.60 (3H, s), 3.24 (3H, s), 3.72–3.89 (2H, m), 4.95 (3H, s), 5.61 (1H, d, J=10 Hz), 5.68 (1H, d, J=10 Hz), 6.60 (1H, d, J=16 Hz), 7.41–7.60 (7H, m), 7.82 (1H, t, J=7.5 Hz), 7.93 (2H, d, J=8 Hz), 8.02–8.09 (1H, m), 8.11 (1H, d, J=8 Hz), 8.40 (1H, t, J=7.5 Hz), 8.68 (1H, d, J=6 Hz)

(2) 3-Bromo-8-[2,6-dichloro-3-[N-methyl-N-[4-[(3-pyridylmethyl)carbamoyl]cinnamoylglycyl]amino]-benzyloxy]-2-methylimidazo[1,2-a]pyridine NMR (CDCl₃, δ): 2.43 (3H, s), 3.26 (3H, s), 3.66 (1H, dd, J=4, 16 Hz), 3.91 (1H, dd, J=4, 16 Hz), 4.67 (2H, d, J=6 Hz), 5.46 (1H, d, J=10 Hz), 5.52 (1H, d, J=10 Hz), 6.53 (1H, d, J=15 Hz), 6.61 (1H, t-like), 6.20 (1H, t-like), 6.72 (1H, d, J=7.5 Hz), 6.85 (1H, t, J=7.5 Hz), 7.25–7.36 (2H, m), 7.49 (1H, d, J=7.5 Hz), 7.52–7.62 (3H, m), 7.71 (1H, d, J=7.5 Hz), 7.74–7.83 (3H, m), 8.55 (1H, d, J=6 Hz), 8.60 (1H, s-like) its dihydrochloride NMR (CDCl₃—CD₃OD, δ): 2.55 (3H, s), 3.22 (3H, s), 3.81 (2H, s), 4.74 (2H, s), 5.60 (1H, d, J=10 Hz), 5.66 (1H, d, J=10 Hz), 6.60 (1H, d, J=16 Hz), 7.35–7.58 (7H, m), 7.84–7.93 (3H, m), 8.06 (1H, d, J=6 Hz), 8.59–8.70 (2H, m), 8.93 (1H, s-like)

(3) 3-Bromo-8-[2,6-dichloro-3-[N-methyl-N-[4-[(4-pyridylmethyl)carbamoyl]cinnamoylglycyl]amino]-benzyloxy]-2-methylimidazo[1,2-a]pyridine NMR (CDCl₃, δ): 2.42 (3H, s), 3.26 (3H, s), 3.65 (1H, dd, J=17, 4 Hz), 3.90 (1H, dd, J=17, 5 Hz), 4.65 (2H, d, J=7 Hz), 5.47 (1H, d, J=9 Hz), 5.51 (1H, d, J=9 Hz), 6.54 (1H, d, J=15 Hz), 6.67–6.81 (3H, m), 6.86 (1H, t, J=7 Hz), 7.25 (2H, d, J=7 Hz), 7.32 (1H, d, J=8 Hz), 7.47 (1H, d, J=7 Hz), 7.51–7.62 (3H, m), 7.76 (1H, d, J=7 Hz), 7.81 (2H, d, J=9 Hz), 8.52–8.60 (2H, m) its dihydrochloride NMR (CDCl₃—CD₃OD, δ): 2.54 (3H, s), 3.20 (3H, s), 3.80 (2H, br s), 4.79 (2H, br s), 5.58 (1H, d, J=9 Hz), 5.65 (1H, d, J=9 Hz), 6.63 (1H, d, J=15 Hz), 7.33–7.60 (7H, m), 7.94 (2H, br d, J=7.5 Hz), 7.99 (2H, br d, J=7 Hz), 8.07 (1H, br s), 8.56–8.66 (2H, m)

(4) 3-Bromo-8-[2,6-dichloro-3-[N-methyl-N-[4-(allylcarbamoyl)cinnamoylglycyl]amino]benzyloxy]-2-methylimidazo[1,2-a]pyridine NMR (CDCl₃, δ): 2.43 (3H, s), 3.27 (3H, s), 3.66 (1H, dd, J=17, 4 Hz), 3.90 (1H, dd, J=17, 5 Hz), 4.04–4.14 (2H, m), 5.18 (1H, d, J=10 Hz), 5.26 (1H, d, J=17 Hz), 5.46 (1H, d, J=9 Hz), 5.51 (1H, d, J=9 Hz), 5.86–6.02 (1H, m), 6.23 (1H, br t, J=6 Hz), 6.53 (1H, d, J=17 Hz), 6.69 (1H, br t, J=6 Hz), 6.72 (1H, d, J=7 Hz), 6.85 (1H, d, J=7 Hz), 7.33 (1H, d, J=7.5 Hz), 7.49 (1H, d, J=7.5 Hz), 7.52–7.64 (3H, m), 7.72–7.83 (3H, m) its hydrochloride NMR (CDCl₃—CD₃OD, δ): 2.55 (3H, s), 3.21 (3H, s), 3.73 (1H, d, J=17 Hz), 3.81 (1H, d, J=17 Hz), 3.99 (2H, d, J=5 Hz), 5.11 (1H, d, J=10 Hz), 5.20 (1H, d, J=15 Hz), 5.57 (1H, d, J=9 Hz), 5.64 (1H, d, J=9 Hz), 5.80–5.96 (1H, m), 6.60 (1H, d, J=15 Hz), 7.40–7.55 (9H, m), 7.72 (2H, d, J=9 Hz), 8.05 (1H, m)

(5) 3-Bromo-8-[2,6-dichloro-3-[N-methyl-N-[4-(2-propynylcarbamoyl)cinnamoylglycyl]amino]benzyloxy]-2-methylimidazo[1,2-a]pyridine NMR (CDCl₃, δ): 2.26–2.30 (1H, m), 2.42 (3H, s), 3.26 (3H, s), 3.67 (1H, dd, J=17, 4 Hz), 3.90 (1H, dd, J=17, 5 Hz), 4.20–4.30 (2H, m), 5.47 (1H, d, J=9 Hz), 5.51 (1H, d, J=9 Hz), 6.37 (1H, br t, J=5 Hz), 6.53 (1H, d, J=15 Hz), 6.69 (1H, br s), 6.71 (1H, d, J=7 Hz), 6.85 (1H, t, J=7 Hz), 7.33 (1H, d, J=7.5 Hz), 7.48 (1H, d, J=7.5 Hz), 7.50–7.64 (3H, m), 7.72–7.84 (3H, m) its hydrochloride NMR (CDCl₃—CD₃OD, δ): 2.24 (1H, t, J=3 Hz), 2.56 (3H, s), 3.22 (3H, s), 3.76 (1H, d, J=17 Hz), 3.82 (1H, d, J=17 Hz), 4.15 (2H, d, J=3 Hz), 5.58 (1H, d, J=9 Hz), 5.63 (1H, d, J=9 Hz), 6.60 (1H, d, J=15 Hz), 7.39–7.56 (7H, m), 7.74 (2H, d, J=9 Hz), 8.05 (1H, br d, J=7 Hz)

(6) 3-Bromo-8-[2,6-dichloro-3-[N-methyl-N-[4-[(methylcarbamoylmethyl)carbamoyl]cinnamoylglycyl]-amino]benzyloxy]-2-methylimidazo[1,2-a]pyridine NMR (CDCl₃, δ): 2.43 (3H, s), 2.87 (3H, d, J=5 Hz), 3.28 (3H, s), 3.67 (1H, dd, J=4, 16 Hz), 3.92 (1H, dd, J=4, 16 Hz), 4.10 (2H, d, J=5 Hz), 5.48 (1H, d, J=10 Hz), 5.53 (1H, d, J=10 Hz), 6.10 (1H, br), 6.54 (1H, d, J=16 Hz), 6.70–6.80 (2H, m), 6.86 (1H, t, J=7.5 Hz), 7.09 (1H, t-like), 7.35 (1H, d, J=8 Hz), 7.50 (1H, d, J=8 Hz), 7.52–7.63 (3H, m), 7.77 (1H, d, J=7 Hz), 7.82 (2H, d, J=8 Hz) its hydrochloride NMR (CDCl₃—CD₃OD, δ): 2.60 (3H, s), 2.80 (3H, s), 3.23 (3H, s), 3.73 (1H, d, J=18 Hz), 7.86 (1H, d, J=18 Hz), 4.03 (2H, s), 5.57–5.69 (2H, m), 6.60 (1H, d, J=16 Hz), 7.36–7.56 (7H, m), 7.80 (2H, d, J=8 Hz), 8.05 (1H, d, J=6 Hz)

Example 101

The following compounds were obtained according to similar manners to those of Examples 81 or 82.

(1) 8-[3-[N-[4-(Acryloylamino)cinnamoylglycyl]-N-methylamino]-2,6-dichlorobenzyloxy]-3-bromo-2-methylimidazo[1,2-a]pyridine NMR (CDCl₃, δ): 2.43 (3H, s), 3.26 (3H, s), 3.65 (1H, dd, J=4, 18 Hz), 3.89 (1H, dd, J=5, 18 Hz), 5.45 (1H, d, J=10 Hz), 5.50 (1H, d, J=10 Hz), 5.78 (1H, d, J=10 Hz), 6.25 (1H, dd, J=10, 17 Hz), 6.40 (1H, d, J=15 Hz), 6.45 (1H, d, J=17 Hz), 6.60 (1H, t-like), 6.73 (1H, d, J=7.5 Hz), 6.87 (1H, t, J=7.5 Hz), 7.32 (1H, d, J=8 Hz), 7.42–7.50 (3H, m), 7.53 (1H, d, J=15 Hz), 7.58–7.72 (3H, m), 7.77 (1H, d, J=7.5 Hz) its hydrochloride NMR (CDCl₃—CD₃OD, δ): 2.53 (3H, s), 3.25 (3H, s), 3.76 (1H, d, J=16 Hz), 3.85 (1H, d, J=16 Hz), 5.61 (2H, s), 5.70 (1H, dd, J=2, 10 Hz), 6.31–6.46 (3H, m), 7.25–7.56 (7H, m), 7.61 (2H, d, J=8 Hz), 8.03 (1H, d, J=6 Hz)

(2) 3-Bromo-8-[2,6-dichloro-3-[N-[4-[(2-furylcarbonyl)amino]cinnamoylglycyl]-N-methylamino]benzyloxy]-2-methylimidazo[1,2-a]pyridine NMR (CDCl₃, δ):2.45 (3H, s), 3.30 (3H, s), 3.70 (1H, dd, J=4, 18 Hz), 3.93 (1H, dd, J=5, 18 Hz), 5.50 (1H, d, J=10 Hz), 5.54 (1H, d, J=10 Hz), 6.43 (1H, d, J=16 Hz), 6.56–6.65 (2H, m), 6.75 (1H, d, J=7.5 Hz), 6.88 (1H, t, J=7.5 Hz), 7.26–7.31 (1H, m), 7.35 (1H, d, J=7.5 Hz), 7.47–7.63 (5H, m), 7.70 (2H, d, J=8 Hz), 7.79 (1H, d, J=7.5 Hz), 8.17 (1H, s) its hydrochloride NMR (CDCl₃—CD₃OD, δ): 2.59 (3H, s), 3.26 (3H, s), 3.80 (2H, s), 5.59–5.70 (2H, m), 6.46 (1H, d, J=16 Hz), 6.55 (1H, d, J=2 Hz), 7.38–7.58 (8H, m), 7.60–7.67 (3H, m), 8.01–8.09 (1H, m)

(3) 3-Bromo-8-[2,6-dichloro-3-[N-methyl-N-[4-[2-(2-thienyl)acetamido]cinnamoylglycyl]amino]benzyloxy]-2-methylimidazo[1,2-a]pyridine NMR (CDCl₃, δ): 2.43 (3H, s), 3.26 (3H, s), 3.66 (1H, dd, J=16, 4 Hz), 3.90 (1H, dd, J=16, 4 Hz), 3.96 (2H, s), 5.66 (1H, d, J=10 Hz), 5.51 (1H, d, J=10 Hz), 6.39 (1H, d, J=16 Hz), 6.59 (1H, t-like), 6.72 (1H, d, J=7.5 Hz), 6.86 (1H, t, J=7.5 Hz), 7.01–7.10 (2H, m), 7.32 (2H, d, J=8 Hz), 7.40–7.56 (7H, m), 7.77 (1H, d, J=6 Hz) its hydrochloride NMR (CDCl₃—CD₃OD, δ): 2.52 (3H, s), 3.23 (3H, s), 3.76 (1H, d, J=17 Hz), 3.85 (1H, d, J=17 Hz), 3.95 (2H, s), 5.60 (2H, s), 6.39 (1H, d, J=16 Hz), 6.93–7.00 (1H, m), 7.04 (1H, d, J=3 Hz), 7.20–7.26 (1H, m), 7.33 (1H, d, J=16 Hz), 7.38–7.56 (8H, m), 7.98 (1H, d, J=6 Hz)

(4) 3-Bromo-8-[2,6-dichloro-3-[N-methyl-N-[4-[2-(1-methyl-1H-pyrrol-2-yl)acetamido]cinnamoylglycyl]-amino]benzyloxy]-2-methylimidazo[1,2-a]pyridine NMR (CDCl₃, δ): 2.43 (3H, s), 3.26 (3H, s), 3.56 (3H, s), 3.66 (1H, dd, J=4, 18 Hz), 3.73 (2H, s), 3.90 (1H, dd, J=4, 18 Hz), 5.47 (1H, d, J=10 Hz), 5.52 (1H, d, J=10 Hz), 6.13–6.20 (2H, m), 6.40 (1H, d, J=16 Hz), 6.58 (1H, t-like), 6.66–6.79 (2H, m), 6.82–6.90 (1H, m), 7.29–7.38 (2H, m), 7.42–7.57 (6H, m), 7.77 (1H, d, J=6 Hz)

What we claim is:

1. A process for preparing a compound of the formula:

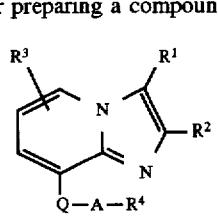

wherein R¹ is halogen, $R^2$ and $R^3$ are each hydrogen, lower alkyl, halo(lower)alkyl or acyl, $R^4$ is aryl substituted with at least two substituents selected from the group consisting of:
halogen;
halo(lower)alkyl;
acyl;
aryl;
aryl substituted with halogen or cyano;
ar(lower)alkyl substituted with hydroxy;
lower alkoxy;
nitro;
amino;
amino substituted with substituents selected from the group consisting of lower alkyl, acyl, ar(lower)alkyl, heterocyclic(lower)alkyl, carboxy(lower)alkyl, lower alkylaminomethylene and N-methylpyrrolidinylidene;
a heterocyclic group and
a heterocyclic group substituted with oxo; or $R^4$ is a heterocyclic group substituted with at least two substituents selected from the group consisting of:
halogen;
lower alkyl;
halo(lower)alkyl;
acyl;
aryl;
aryl substituted with halogen or cyano; ar(lower)alkyl substituted with hydroxy;
lower alkoxy;
oxo;
nitro;
amino;
amino substituted with substituent(s) selected from the group consisting of lower alkyl, acyl, ar(lower)alkyl, heterocyclic(lower)alkyl, carboxy(lower)alkyl, lower alkylaminomethylene and N-methylpyrrolidinylidene;
a heterocyclic group and
a heterocyclic group substituted with oxo;

Q is O or N—$R^{11}$,
in which $R^{11}$ is hydrogen or acyl, and A is lower alkylene, or salt thereof, which comprises:
halogenating a compound of the formula:

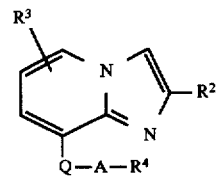

wherein $R^2$, $R^3$, $R^4$, Q and A are each as defined above, or salt thereof thereof.

* * * * *